(12) United States Patent
Bryant et al.

(10) Patent No.: US 7,026,323 B2
(45) Date of Patent: Apr. 11, 2006

(54) PLATELET ADENOSINE DIPHOSPHATE RECEPTOR ANTAGONISTS

(75) Inventors: Judi A. Bryant, Mill Valley, CA (US); Brad O. Buckman, Oakland, CA (US); Imadul Islam, Hercules, CA (US); Raju Mohan, Encinitas, CA (US); Michael M. Morrissey, Danville, CA (US); Guo Ping Wei, San Ramon, CA (US); Wei Xu, Danville, CA (US); Shendong Yuan, Hercules, CA (US)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/947,579

(22) Filed: Sep. 22, 2004

(65) Prior Publication Data

US 2005/0038037 A1    Feb. 17, 2005

Related U.S. Application Data

(62) Division of application No. 10/163,742, filed on Jun. 5, 2002, now Pat. No. 6,861,424.

(60) Provisional application No. 60/296,498, filed on Jun. 6, 2001.

(51) Int. Cl.
*A61K 31/497* (2006.01)

(52) U.S. Cl. .............................. 514/254.1; 514/254.01; 544/374; 544/388; 544/383; 544/387; 544/393; 544/400

(58) Field of Classification Search ................ 544/374, 544/388; 514/254.1, 255.01
See application file for complete search history.

(56) References Cited

U.S. PATENT DOCUMENTS

| | | | |
|---|---|---|---|
| 4,258,192 A | 3/1981 | Okamoto et al. | ............ 546/166 |
| 5,346,907 A | 9/1994 | Kerwin, Jr. et al. | ......... 514/312 |
| 5,607,937 A | 3/1997 | Stuerzebecher et al. | .... 514/255 |

FOREIGN PATENT DOCUMENTS

| | | |
|---|---|---|
| EP | 739 886 A2 | 10/1996 |
| GB | 1334705 | 10/1973 |
| WO | WO 92/08709 | 5/1992 |
| WO | WO 94/18185 | 8/1994 |
| WO | WO 98/56771 | 12/1998 |

OTHER PUBLICATIONS

CAS Registry Numbers, p. 1-18 obtained from Com Genex Product List, published Jun. 26, 2003.*
ComGenex Product List (2001), Supplementary information concerning Ten Products available for sale.*

Dullweber, F. et al., "Factorising Ligand Affinity: A Combined Thermodynamic and Crystallographic Study of Trypsin and Thrombin Inhibition," *J. Mol. Biol. 313*: 593-614, 2001.
Folts et al., "Platelet Aggregation in Partially Obstructed Vessels and its Elimination with Aspirin," *Circulation 54* (3):365-370, 1976.
Gachet et al., "Purinoceptors on Blood Platelets: Further Pharmacological and Clinical Evidence to Suggest the Presence of Two ADP Receptors," *British Journal Haematology 91*(2):434-444, Oct. 1995.
Herbert et al., "Clopidogrel, A Novel Antiplatelet and Antithrombotic Agent," *Cardiovascular Drug Reviews 11* (2):180-198, 1993.
Humphries et al., "Pharmacological Profile of the Novel P2T-Purinoceptor Antagonist, FPL 67085 in vitro and in the Anaesthetized Rat in vivo," *British Journal of Pharmacology 115*(6):1110-1116, Jul. 1995.
Kamm, W. et al., "Transport of Peptidomimetic Thrombin Inhibitors with a 3-Amidino-Phenylalnine Structure: Permeability and Efflux Mechanism in Monolayers of a Human Intestinal Cell Line (Caco-2)," *Pharmaceutical Research 18*(8): 1110-1118, 2001.
Kaslow and Marsh, "Substituted Bromoquinolines" J. Organic Chemistry 12(3):456-458, May 1947.
Mills, "ADP Receptors on Platelets," *Thrombosis Haemostasis 76*(6):835-856, Dec. 1996.
Mustard, et al., "Isolation of Human Platelets from Plasma by Centrifugation and Washing," *Methods Enzymology 169*: 3-11, 1989.

(Continued)

*Primary Examiner*—Emily Bernhardt
(74) *Attorney, Agent, or Firm*—Seed IP Law Group PLLC

(57) ABSTRACT

Compounds of the following formula (I):

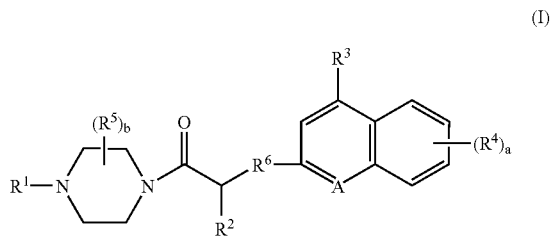

(I)

where a, b, $R^1$, $R^2$, $R^3$, $R^4$ and $R^6$ are described herein, are useful as inhibitors of platelet adenosine diphosphate. Pharmaceutical compositions containing these compounds, methods of using these compounds as antithrombotic agents and processes for synthesizing these compounds are also described herein.

7 Claims, No Drawings

OTHER PUBLICATIONS

Pierce, A.C. and Jorgenson, W.L., "Estimation of Binding Affinities for Selective Thrombin Inhibitors via Monte Carlo Simulations," *J. Med. Chem. 44*: 1043-1050, 2001.

Späth, "Zur Konstitution der Kyurensäure," *Monatshefte für Chimie 42*:89-95, 1921.

* cited by examiner

PLATELET ADENOSINE DIPHOSPHATE RECEPTOR ANTAGONISTS

CROSS-REFERENCE TO RELATED APPLICATION

This application is a divisional of U.S. patent application Ser. No. 10/163,742, filed Jun. 5, 2002 now U.S. Pat. No. 6,861,424; which claims the benefit of U.S. Provisional Patent Application No. 60/296,498, filed Jun. 6, 2001, where these applications are incorporated herein by reference in their entireties.

FIELD OF THE INVENTION

The invention relates to piperazine derivatives, their use as platelet adenosine diphosphate receptor antagonists, pharmaceutical compositions containing them and processes for their preparation.

BACKGROUND OF THE INVENTION

Platelets interact with the coagulation and fibrinolysis systems in the maintenance of hemostasis and in the pathogenesis of thrombosis and thromboembolism. Platelets rapidly adhere to damaged vascular tissue, and release a variety of prothrombotic, chemotactic, and mitogenic factors, aimed at prompting hemostasis and wound healing. Platelets also play an important role in arterial thrombosis, a common cause of death and disability in patients with cardiovascular disease. Platelet inhibitors have been successfully used for secondary prevention of arterial thrombosis in patients with coronary, cerebral, and peripheral vascular disease.

Platelets adhere to exposed subendothelium after vessel wall injury by binding to von Willebrand factor (vWf) and collagen. This induces platelets to change shape from a disc shape to a round form with pseudopodia, which enforces platelet adhesion and aggregation. The final common pathway for platelet aggregation is the activation of the fibrinogen receptor (GPIIb-IIIa). As a result, dimeric fibrinogen molecules present in plasma can bind and link platelets together to form aggregates.

Activated platelets secrete their granule contents, many of which act directly on blood cells, including platelets themselves, and endothelium. Platelets contain several kinds of secretory granules. The dense-granules contain adenosine diphosphate ("ADP"), adenosine triphosphate ("ATP") and serotonin. The α-granules contain several platelet-specific proteins (platelet factor 4 and β-thromboglobulin), growth factors (PDGF, TGF-β, EGF and ECGF) and coagulation factors (fibrinogen, Factor V and vWf. Platelets also secrete biologically active arachidonic acid products. Well known is $TxA_2$ which is inhibited by aspirin through irreversible inactivation of the cyclooxygenase producing $TxA_2$.

Many stimuli, such as thrombin, collagen, ADP and thromboxane A2 (TxA2), activate platelets by binding to their cell surface receptors. Most of these receptors are G-protein-coupled receptors. Activation of G-proteins has been shown to be an essential event in platelet activation. For example, platelets from Gq-/- mice do not aggregate in response to thrombin, collagen, ADP or TxA2 (Offermans, S. et al., Nature (1998), Vol. 389, No. 11, pp. 183–185). Many down-stream signaling events have been elucidated, including activation of phospholipase-C (PLC) and protein kinase C, increase in intracellular calcium concentration, decrease in cAMP level and tyrosine phosphorylation.

ADP plays a pivotal role in platelet activation. ADP not only causes primary aggregation of platelets but is also responsible for the secondary aggregation following activation by other agonists such as thrombin and collagen. Contained at very high concentrations in the platelet dense-granules, ADP is released when platelets are activated to reinforce platelet aggregation. ADP-induced platelet activation plays an important role in maintaining normal hemostasis. Several congenital bleeding disorders have been linked to the decreased number of platelet ADP receptors and deficiency of ADP-induced platelet aggregation. Patients having "storage pool disease", which is due to defects in the storage of nucleotides and/or their secretion from the platelet dense-granules, have impaired platelet aggregation in response to collagen and other stimuli due to the absence of the amplification effects by ADP.

ADP-induced platelet activation also plays a key role in the initiation and propagation of thrombosis. Administration of ADP has been shown to induce thrombus formation in rat and mice mesenteric venules. In contrast, ADP-removing enzymes have been shown to dramatically reduce platelet deposition on collagen and to inhibit laser-induced thrombosis in rat mesenteric arterioles and venules, supporting the theory that ADP plays a role in mediating platelet recruitment in thrombus formation. Several ADP-induced early signaling events in platelets have been described. These include a transient rise in free cytoplasmic calcium, an inhibition of adenylate cyclase through activation of $G_{i2}$, an increase in cytosolic pH by activating the Na+/H+-exchange, and exposure of the platelet binding sites for fibrinogen independent of protein kinase C. While these signaling events collectively contribute to platelet aggregation, the specific role of each remains the subject of on-going investigations.

The current model of ADP-induced platelet activation involves two G-protein coupled purinergic receptors, one of which is coupled to the activation of the phospholipase-C pathway ($P2Y_1$) and the other is coupled to the inhibition of adenylate cyclase ($P2Y_{AC}$). $P2Y_{AC}$ is the best target for a platelet ADP receptor antagonist for several reasons. First, $P2Y_{AC}$ is predominately platelet specific. Secondly, it is required for ADP-induced aggregation. Thirdly, it plays an important role in sustaining thrombin or collagen-induced aggregation. Finally, it is the molecular target for anti-aggregate drugs such as Clopidogrel and Ticlopidine. Both of these drugs have been shown to be efficacious in various thrombosis models. However, Clopidogrel has been shown to be an irreversible inhibitor of platelet aggregation with a slow onset of action. Similarly, the ATP analogues, AR-C67085 and AR-C69931MX, which are potent antagonists for ADP-induced platelet aggregation, have also been shown to be effective in thrombosis models and are currently under clinical investigation. All these findings indicate that ADP is a critical mediator of arterial thrombus formation and hence an excellent target for antithrombotic intervention.

When the properties of current oral platelet inhibitors, such as aspirin, Clopidogrel and Ticlopidine are compared, it becomes clear that, while relatively safe, current oral platelet inhibitors are only modestly effective in preventing thrombotic complications in patients with underlying vascular disease. It is clear that there is a need in this field for a potent, selective, reversible, orally active platelet ADP receptor ($P2Y_{AC}$) inhibitor.

SUMMARY OF THE INVENTION

The compounds of the invention are antagonists of the platelet ADP receptor, $P2Y_{AC}$, and are therefore useful in treating disease-states characterized by thrombotic activity and in so doing are useful as antithrombotic agents in the treatment and prevention of thrombosis. Accordingly, in one aspect, the invention is directed to compounds selected from the group consisting of the following formula (I):

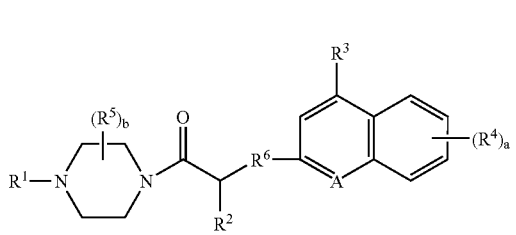

wherein:

a and b are independently 1 to 4;

is =CH— or =N—;

$R^1$ is hydrogen, alkyl, carboxyalkyl, aryl, aralkyl, alkylcarbonyl, alkoxyalkoxyalkylcarbonyl, aryloxyalkylcarbonyl, carboxyalkylcarbonyl, alkoxycarbonylalkylcarbonyl, alkoxycarbonylalkyl, alkoxycarbonyl, arylcarbonyl, aryloxycarbonyl, aralkoxycarbonyl, cycloalkylcarbonyl, haloalkoxycarbonyl, aminocarbonyl, monoalkylaminocarbonyl, alkoxycarbonylaminocarbonyl, alkylsulfonyl, arylsulfonyl, heterocyclyl, or heterocyclylcarbonyl;

$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, tetrahydrofuranonyl, or heterocyclylalkyl;

$R^3$ is hydrogen, alkyl, hydroxy, halo, carboxyalkenyl, alkoxy, alkoxycarbonyl, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono(alkoxycarbonylalkyl)aminocarbonyl, mono(carboxyalkyl)aminocarbonyl, mono(di(alkoxycarbonyl)alkyl)aminocarbonyl, mono((alkoxycarbonyl)(carboxy)alkyl)aminocarbonyl, mono(dicarboxyalkyl)aminocarbonyl, aminocarbonylalkoxy, dialkylaminocarbonylalkoxy, monoaralkylaminocarbonylalkoxy, mono(carboxyalkyl)aminocarbonylalkoxy, mono(alkoxycarbonylalkyl)aminocarbonylalkoxy, carboxycycloalkoxy, alkoxycarbonylcycloalkoxy, aminocarbonylcycloalkoxy, heterocyclyl, tetrahydrofuranonyloxy, or heterocyclylalkoxy;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

$R^6$ is —N($R^7$)—C(O)— or —C(O)—N($R^7$)—;

$R^7$ is hydrogen, alkyl, carboxyalkyl, or alkoxycarbonylalkyl;

as a single stereoisomer, a mixture of individual stereoisomers, or a racemic mixture;

or a pharmaceutically acceptable salt thereof.

In another aspect, this invention is directed to pharmaceutical compositions useful in treating a mammal having a disease-state characterized by thrombotic activity, which composition comprises a pharmaceutically acceptable excipient and a compound of formula (I) as defined above.

In another aspect, this invention is directed to methods of treating disease-states characterized by thrombotic activity, which methods comprise administering to a mammal having a disease-state characterized by thrombotic activity a therapeutically effective amount of a compound of formula (I) as defined above.

DETAILED DESCRIPTION OF THE INVENTION

Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, it is understood that for radicals, as defined below, that contain a substituted alkyl or alkenyl group that the substitution can occur on any carbon of the alkyl group.

"Alkylcarbonyl" refers to a radical of the formula —C(O)—$R_a$ where $R_a$ is an alkyl radical as defined above, e.g., acetyl, ethylcarbonyl, n-propylcarbonyl, and the like.

"Alkylcarbonylamino" refers to a radical of the formula —N(H)—C(O)—$R_a$ where $R_a$ is an alkyl radical as defined above, e.g., acetylamino, ethylcarbonylamino, n-propylcarbonylamino, and the like.

"Alkylthio" refers to a radical of the formula —S—$R_a$ where $R_a$ is an alkyl radical as defined above, e.g., methylthio, ethylthio, n-propylthio, and the like.

"Alkylsulfonyl" refers to a radical of the formula —S(O)$_2R_a$ where $R_a$ is an alkyl radical as defined above, e.g., methylsulfonyl, ethylsulfonyl, n-propylsulfonyl, and the like.

"Alkylsulfonylalkyl" refers to a radical of the formula —$R_a$—S(O)$_2$—$R_a$ where each $R_a$ is independently an alkyl radical as defined above, e.g., methylsulfonylmethyl, 2-methylsulfonylethyl, 2-ethylsulfonylpropyl, and the like.

"Alkenyl" refers to a straight or branched chain monovalent or divalent radical consisting solely of carbon and hydrogen, containing at least one double bond and having from two to eight carbon atoms, e.g., ethenyl, prop-1-enyl, but-1-enyl, pent-1-enyl, penta-1,4-dienyl, and the like.

"Alkoxy" refers to a radical of the formula —OR$_a$ where R$_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like.

"Alkoxycarbonyl" refers to a radical of the formula —C(O)OR$_a$ where R$_a$ is an alkyl radical as defined above, e.g., methoxycarbonyl, ethoxycarbonyl, n-propoxycarbonyl, and the like.

"Alkoxycarbonylalkyl" refers to a radical of the formula —R$_a$—C(O)OR$_a$ where each R$_a$ is independently an alkyl radical as defined above, e.g., methoxycarbonylmethyl, (1,1-dimethylethoxy)carbonylmethyl, 2-(methoxycarbonyl)ethyl, and the like.

"Alkoxycarbonylaminocarbonyl" refers to a radical of the formula —C(O)—N(H)—C(O)OR$_a$ where R$_a$ is an alkyl radical as defined above, e.g., methoxycarbonylaminocarbonyl, ethoxycarbonylaminocarbonyl, n-propoxycarbonylaminocarbonyl, and the like.

"Alkoxycarbonylcycloalkoxy" refers to a radical of the formula —O—R$_c$—C(O)OR$_a$ where R$_a$ is an alkyl radical as defined above and R$_c$ is a cycloalkyl radical as defined below, e.g., 1-methoxycarbonylcyclobut-1-oxy, 1-ethoxycarbonylcyclobut-1-oxy, 1-n-propoxycarbonylcyclobutoxy, and the like.

"Alkoxyalkoxyalkylcarbonyl" refers to a radical of the formula —C(O)—R$_a$—O—R$_a$—O—R$_a$ where each R$_a$ is independently an alkyl radical as defined above, e.g., 2-(ethoxy)ethoxymethylcarbonyl, 3-(2-(n-butoxy)ethoxy)propylcarbonyl, and the like.

"Alkoxycarbonylalkyl" refers to a radical of the formula —R$_a$—C(O)OR$_a$ where each R$_a$ is independently an alkyl radical as defined above, e.g., methoxycarbonylmethyl, 2-(ethoxycarbonyl)ethyl, 2-(methoxycarbonyl)propyl, and the like.

"Alkoxycarbonylalkoxy" refers to a radical of the formula —O—R$_a$—C(O)OR$_a$ where each R$_a$ is independently an alkyl radical as defined above, e.g., methoxycarbonylmethoxy, 2-(ethoxycarbonyl)ethoxy, 2-(methoxycarbonyl)propoxy, and the like.

"Alkoxycarbonylalkenyloxy" refers to a radical of the formula —O—R$_d$—C(O)OR$_a$ where R$_a$ is an alkyl radical as defined above and R$_d$ is an alkenyl radical as defined above, e.g., 2-(methoxycarbonyl)ethenyloxy, 3-(ethoxycarbonyl)prop-1-enyloxy, and the like.

"Alkoxycarbonylalkylcarbonyl" refers to a radical of the formula —C(O)—R$_a$—C(O)OR$_a$ where each R$_a$ is independently an alkyl radical as defined above, e.g., methoxycarbonylmethylcarbonyl, 2-(ethoxycarbonyl)ethylcarbonyl, 2-(methoxycarbonyl)propylcarbonyl, and the like.

"Alkoxycarbonylalkylaminocarbonylalkyl" refers to a radical of the formula —R$_a$—C(O)—N(H)—R$_a$—C(O)OR$_a$ where each R$_a$ is independently an alkyl radical as defined above, e.g., methoxycarbonylmethyl, 2-(ethoxycarbonyl)ethylaminocarbonylmethyl, 2-(2-(methoxycarbonyl)propylaminocarbonyl)propyl, and the like.

"Alkoxycarbonylalkylthioalkyl" refers to a radical of the formula —R$_a$—S—R$_a$—C(O)OR$_a$ where each R$_a$ is independently an alkyl radical as defined above, e.g., methoxycarbonylmethylthiomethyl, 2-(ethoxycarbonyl)ethylthiomethyl, 2-(2-(methoxycarbonyl)propylthio)propyl, and the like.

"Alkoxycarbonylalkoxycarbonylalkyl" refers to a radical of the formula —R$_a$—C(O)—O—R$_a$—C(O)OR$_a$ where each R$_a$ is independently an alkyl radical as defined above,
e.g., methoxycarbonylmethoxy, 2-(ethoxycarbonyl)ethoxycarbonylmethyl, 3-(2-(methoxycarbonyl)propoxycarbonyl)propyl, and the like.

"(Alkoxycarbonylalkyl)(alkyl)aminocarbonylalkyl" refers to a radical of the formula —R$_a$—C(O)—N(R$_a$)—R$_a$—C(O)OR$_a$ where each R$_a$ is independently an alkyl radical as defined above, e.g., (methoxycarbonylmethyl)(methyl)aminocarbonylmethyl, 2-((ethoxycarbonylmethyl)(methyl)aminocarbonyl)ethyl, and the like.

"Amino" refers to the —NH$_2$ radical.

"Aminoalkyl" refers to a radical of the formula —R$_a$—NH$_2$, e.g., aminomethyl, 2-aminomethyl, 2-aminopropyl, and the like.

"Aminocarbonyl" refers to the —C(O)NH$_2$ radical.

"Aminocarbonylalkoxy" refers to a radical of the formula —O—R$_a$—C(O)NH$_2$, e.g., aminocarbonylmethoxy, 2-(aminocarbonyl)ethoxy, 2-(aminocarbonyl)propoxy, and the like.

"Aminocarbonylalkyl" refers to a radical of the formula —R$_a$—C(O)NH$_2$, e.g., aminocarbonylmethyl, 2-(aminocarbonyl)ethyl, 2-(aminocarbonyl)propyl, and the like.

"Aminocarbonylcycloalkoxy" refers to a radical of the formula —O—R$_c$—C(O)NH$_2$ where R$_c$ is a cycloalkyl radical as defined below, e.g., 1-(aminocarbonyl)cyclobutoxy, 2-(aminocarbonyl)cyclohexyl, and the like.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of hydroxy, hydroxyalkyl, halo, haloalkyl, haloalkoxy, alkyl, alkoxy, carboxy, alkoxycarbonyl, carboxyalkyl, alkoxycarbonylalkyl, carboxyalkoxy, alkoxycarbonylalkoxy, aminocarbonyl, monoalkylaminocarbonyl, dialkylaminocarbonyl, formyl, alkylcarbonylamino, nitro, cyano, amino, monoalkylamino, dialkylamino, and aminoalkyl, as defined herein. For R$^1$, preferred aryl radicals are those radicals which are optionally substituted by one or more substituents selected from the group consisting of halo and alkyl. For R$^2$, preferred aryl radicals are those radicals which are optionally substituted by one or more substituents independently selected from the group consisting of hydroxy, carboxyalkoxy and alkoxycarbonylalkoxy.

"Aralkyl" refers to a radical of the formula —R$_a$R$_b$ where R$_a$ is an alkyl radical as defined above, substituted by R$_b$, an aryl radical, as defined above, e.g., benzyl. For R$^1$, preferred aralkyl radicals are those radicals wherein the R$_b$ group is optionally substituted by one or more substituents independently selected from the group consisting of halo and alkyl. For R$^2$, preferred aralkyl radicals are those radicals wherein the R$_b$ group is optionally substituted by one or more substitutents independently selected from the group consisting of alkoxycarbonyl, carboxy, alkoxycarbonylalkoxy, carboxyalkoxy, and hydroxy. For R$^5$, preferred aralkyl radicals are those radicals wherein the R$_b$ group is optionally substituted by one or more hydroxy radicals.

"Aryloxy" refers to a radical of the formula —OR$_b$ where R$_b$ is an aryl radical as defined above, e.g., phenoxy.

"Arylcarbonyl" refers to a radical of the formula —C(O)—R$_b$ where R$_b$ is an aryl radical as defined above, e.g., phenylcarbonyl, (4-acetylaminophenyl)carbonyl, (2-methoxyphenyl)carbonyl, and the like. For R$^1$, preferred arylcarbonyl radicals are those radicals wherein the R$_b$ group is optionally substituted by by one or more substituents independently selected from the group consisting of acetylamino, carboxy, aminocarbonyl, alkoxycarbonyl, haloalkoxy, alkoxy, and alkyl.

"Arylsulfonyl" refers to a radical of the formula —S(O)$_2$—R$_b$ where R$_b$ is an aryl radical as defined above, e.g., phenylsulfonyl, 4-chlorophenylsulfonyl, 4-methylphenylsulfonyl, and the like. For R$^1$, preferred arylsulfonyl radicals are those radicals wherein the R$_b$ group is optionally substituted by one or more substituents independently selected from the group consisting of halo and alkyl.

"Aryloxycarbonyl" refers to a radical of the formula —C(O)OR$_b$ where R$_b$ is an aryl radical as defined above, e.g., phenoxycarbonyl.

"Aryloxyalkylcarbonyl" refers to a radical of the formula —C(O)OR$_b$R$_a$ where R$_a$ is an alkyl radical, as defined above, substituted by R$_b$, an aryl radical, as defined above, e.g., phenoxymethylcarbonyl, (2-phenoxyethyl)carbonyl, and the like.

"Aralkoxy" refers to a radical of the formula —OR$_e$ where R$_e$ is an aralkyl radical as defined above, e.g., benzyloxy, 3-phenylpropoxy, and the like.

"Aralkoxyalkyl" refers to a radical of the formula —R$_a$—OR$_e$ where R$_a$ is an alkyl radical as defined above and R$_e$ is an aralkyl radical as defined above, e.g., benzyloxymethyl, 2-(benzyloxy)ethyl, 2-(benzyloxy)propyl, and the like.

"Aralkoxycarbonyl" refers to a radical of the formula —C(O)OR$_e$ where R$_e$ is an aralkyl radical as defined above, e.g., benzyloxycarbonyl, and the like.

"Aralkoxycarbonylalkyl" refers to a radical of the formula —R$_a$—C(O)OR$_e$ where R$_a$ is an alkyl radical as defined above and R$_e$ is an aralkyl radical as defined above, e.g., benzyloxycarbonylmethyl, 2-(benzyloxycarbonyl)ethyl, 3-((naphthalen-2-yl)oxy)carbonyl)propyl, and the like.

"Aralkoxycarbonylaminoalkyl" refers to a radical of the formula —R$_a$—N(H)—C(O)OR$_e$ where R$_a$ is an alkyl radical as defined above and R$_e$ is an aralkyl radical as defined above, e.g., benzyloxycarbonylaminomethyl, 2-(benzyloxycarbonylamino)ethyl, 2-(benzyloxycarbonylamino)propyl, and the like.

"Carboxy" refers to the —C(O)OH radical.

"Carboxyalkyl" refers to a radical of the formula —R$_a$—C(O)OH, where R$_a$ is an alkyl radical as defined above, e.g., carboxymethyl, 2-carboxyethyl, 2-carboxypropyl and the like.

"Carboxyalkoxy" refers to a radical of the formula —O—R$_a$—C(O)OH, where R$_a$ is an alkyl radical as defined above, e.g., carboxymethoxy, 2-carboxyethoxy, 2-carboxypropoxy, and the like.

"Carboxyalkylcarbonyl" refers to a radical of the formula —C(O)—R$_a$—C(O)OH, where R$_a$ is an alkyl radical as defined above, e.g., 2-carboxyethylcarbonyl, carboxymethylcarbonyl, 3-carboxypropylcarbonyl, and the like.

"Carboxyalkylamino" refers to a radical of the formula —N(H)—R$_a$—C(O)OH where R$_a$ is an alkyl radical as defined above, e.g., carboxymethylamino, 2-carboxyethylamino, 3-carboxypropylamino, and the like.

"Carboxyalkylaminocarbonylalkyl" refers to a radical of the formula —R$_a$—C(O)—N(H)—R$_a$—C(O)OH where each R$_a$ is independently an alkyl radical as defined above, e.g., carboxymethylaminocarbonylmethyl, 2-(carboxymethylaminocarbonyl)ethyl, 2-(2-carboxyethyl)aminocarbonyl)ethyl, 3-(2-carboxyethyl)aminocarbonyl)butyl, and the like.

"Carboxyalkylthioalkyl" refers to a radical of the formula —R$_a$S—R$_a$—C(O)OH were each R$_a$ is independently an alkyl radical as defined above, e.g., carboxymethylthiomethyl, (1-carboxyethyl)thiomethyl, 2-((1-carboxypropyl)thio)ethyl, and the like.

"Carboxyalkoxyalkyl" refers to a radical of the formula —R$_a$—O—R$_a$—C(O)OH where each R$_a$ is independently an alkyl radical as defined above, e.g., 2-(carboxymethoxy)ethyl, (2-carboxyethoxy)methyl, 3-(2-carboxypropoxy)propyl, and the like.

"Carboxyalkoxycarbonylalkyl" refers to a radical of the formula —R$_a$—C(O)—O—R$_a$—C(O)OH where each R$_a$ is independently an alkyl radical as defined above, e.g., carboxymethoxycarbonylmethyl, 2-(carboxymethoxycarbonyl)ethyl, 2-((2-carboxyethoxy)carbonyl)propyl, and the like.

"Carboxyalkenyl" refers to a radical of the formula —R$_d$—C(O)OH where R$_d$ is an alkenyl radical as defined above, e.g., 2-carboxyethenyl, 3-carboxyprop-1-enyl, 3-carboxybut-1-enyl and the like.

"Carboxyalkenyloxy" refers to a radical of the formula —O—R$_d$—C(O)OH where R$_d$ is an alkenyl radical as defined above, e.g., 2-carboxyethenyloxy, 3-carboxyprop-1-enyloxy, 3-carboxybut-1-enyloxy, and the like.

"Cycloalkyl" refers to a stable 3- to 10-membered monocyclic or bicyclic radical which is saturated, and which consist solely of carbon and hydrogen atoms, e.g., cyclopropyl, cyclobutyl, cyclobutyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, halo, hydroxy, amino, nitro, alkoxy, carboxy, phenyl and alkoxycarbonyl.

"Cycloalkylcarbonyl" refers to a radical of the formula —C(O)—R$_c$ where R$_c$ is a cycloalkyl radical as defined above, e.g., cyclobutylcarbonyl, cyclopropylcarbonyl, and the like. For R$^1$, a preferred cycloalkylcarbonyl radical is that radical wherein the R$_c$ group is optionally substituted by a phenyl group.

"(Cycloalkyl)(alkoxycarbonyl)alkoxy" refers to a radical of the formula —OR$_a$(R$_c$)—C(O)OR$_a$ where each R$_a$ is independently an alkyl radical as defined above and R$_c$ is a cycloalkyl radical as defined above, e.g., (cyclohexyl)(methoxycarbonyl)methoxy, (cyclobutyl)(ethoxycarbonyl)methoxy, and the like.

"(Cycloalkyl)(carboxy)alkoxy" refers to a radical of the formula —OR$_a$(R$_c$)—C(O)OH where R$_a$ is an alkyl radical as defined above and R$_c$ is a cycloalkyl radical as defined above, e.g., (cyclohexyl)(carboxy)methoxy, (cyclobutyl)(carboxy)methoxy, and the like.

"Carboxycycloalkoxy" refers to a radical of the formula —O—R$_c$—C(O)OH where R$_c$ is a cycloalkyl radical as defined above, e.g., 1-carboxycyclobut-1-oxy, 1-carboxycyclohex-1-oxy, and the like.

"(Carboxy)(hydroxy)alkoxy" refers to a radical of the formula —O—R$_a$(OH)—C(O)OH wherein R$_a$ is an alkyl radical defined above substituted by an hydroxy radical and a carboxy radical, as defined herein, e.g., 1-carboxy-3-hydroxypropoxy, 2-carboxy-4-hydroxybutoxy, 1-carboxy-5-hydroxypent-2-oxy, and the like.

"(Carboxy)(hydroxy)alkyl" refers to a radical of the formula —R$_a$(OH)—C(O)OH wherein R$_a$ is an alkyl radical defined above substituted by an hydroxy radical and a carboxy radical, as defined herein, e.g., 1-carboxy-3-hydroxypropyl, 2-carboxy-4-hydroxybutyl, 1-carboxy-5-hydroxypent-2-yl, and the like.

"(Carboxyalkyl)(alkyl)amino" refers to a radical of the formula —N(R$_a$)—R$_a$—C(O)OH wherein each R$_a$ is independently an alkyl radical as defined above, and wherein the nitrogen atom is substituted by the R$_a$ group and the —R$_a$—C(O)OH group, e.g., (carboxyethyl)(ethyl)amino, (2-carboxyethyl)(methyl)amino, and the like.

"(Carboxyalkyl)(alkyl)aminocarbonylalkyl" refers to a radical of the formula —R$_a$—C(O)—N(R$_a$)—R$_a$—C(O)OH wherein each $R_a$ is independently an alkyl radical as defined above, and wherein the nitrogen atom is substituted by the $R_a$ group and the —$R_a$—C(O)OH group, e.g., (carboxyethyl)(ethyl)aminocarbonylmethyl, 2-((2-carboxyethyl)(methyl)aminocarbonyl)ethyl, and the like.

"Cyano" refers to the —C≡N radical.

"Cyanoalkoxy" refers to a radical of the formula —O—$R_a$—C≡N where $R_a$ is an alkyl radical as defined above, e.g., 2-cyanoethoxy, 2-cyanopropoxy, 4-cyanobut-2-oxy, and the like.

"Dialkylamino" refers to a radical of the formula —N($R_a$)—$R_a$ where each $R_a$ is independently an alkyl radical, e.g., dimethylamino, diethylamino, methylethylamino, and the like.

"Dialkylaminocarbonyl" refers to a radical of the formula —C(O)—N($R_a$)—$R_a$ where each $R_a$ is independently an alkyl radical, e.g., dimethylaminocarbonyl, diethylaminocarbonyl, methyl(ethyl)aminocarbonyl, and the like.

"Dialkylaminoalkyl" refers to a radical of the formula —$R_a$—N($R_a$)—$R_a$ where each $R_a$ is independently an alkyl radical as defined above, e.g., dimethylaminomethyl, 2-(diethylamino)ethyl, 3-(methyl(ethyl)amino)propyl, and the like.

"Dialkylaminoalkoxy" refers to a radical of the formula —O—$R_a$—N($R_a$)—$R_a$ where each $R_a$ is independently an alkyl radical as defined above, e.g., dimethylaminomethoxy, 2-(diethylamino)ethoxy, 3-(methyl(ethyl)amino)propoxy, and the like.

"Dialkylaminocarbonylalkoxy" refers to a radical of the formula —O$R_a$—C(O)—N($R_a$)—$R_a$ where each $R_a$ is independently an alkyl radical, e.g., dimethylaminocarbonylmethoxy, diethylaminocarbonylmethoxy, 2-(methyl(ethyl)aminocarbonyl)ethoxy, and the like.

"Di(alkoxycarbonyl)alkoxy" refers to a radical of the formula —O—$R_a$(C(O)O—$R_a$)—C(O)O—$R_a$ where each $R_a$ is independently an alkyl radical as defined above, e.g., di(methoxycarbonyl)methoxy, di(ethoxycarbonyl)methoxy, 2,2-di(ethoxycarbonyl)ethoxy, and the like.

"Di(carboxy)alkoxy" refers to a radical of the formula —O—$R_a$(C(O)OH)—C(O)OH where each $R_a$ is independently an alkyl radical as defined above, e.g., di(carboxy)methoxy, di(carboxy)methoxy, 2,2-di(carboxy)ethoxy, and the like.

"Di(alkylcarbonyl)amino" refers to a radical of the formula —N(C(O)—$R_a$)—C(O)—$R_a$ where each $R_a$ is independently an alkyl radical as defined above, e.g., di(acetyl)amino, di(ethylcarbonyl)amino, and the like.

"(Dialkylaminoalkyl)(alkyl)amino" refers to a radical of the formula —N($R_a$)—$R_a$—N($R_a$)$R_a$, where each $R_a$ is independently an alkyl radical as defined above and where each nitrogen atom is disubstituted, e.g., (dimethylaminomethyl)(methyl)amino, (diethylaminomethyl)(methyl)amino, (2-(dimethylamino)ethyl)(ethyl)amino, and the like.

"(Dialkylamino)(carboxy)alkoxy" refers to a radical of the formula —O—$R_a$(C(O)OH)—N($R_a$)$R_a$, where each $R_a$ is independently an alkyl radical as defined above and where the first $R_a$ group is substituted by a —C(O)OH group and a —N($R_a$)$R_a$ group, e.g., 3-dimethylamino-1-carboxymethoxy, 4-diethylamino-1-carboxymethoxy, and the like.

"(Dialkylaminocarbonylalkyl)(alkyl)amino" refers to a radical of the formula —N($R_a$)—$R_a$—C(O)—N($R_a$)$R_a$ where each $R_a$ is independently an alkyl radical as defined above and where each nitrogen atom is disubstituted, e.g., (dimethylaminocarbonylmethyl)(methyl)amino, (diethylaminocarbonylmethyl)(methyl)amino, (2-(diethylaminocarbonyl)ethyl)(ethyl)amino, and the like.

"Formyl" refers to the radical —C(O)H.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkylsulfonylaminoalkyl" refers to a radical of the formula —$R_a$—N(H)—S(O)$_2$$R_f$ where $R_a$ is an alkyl radical as defined above and $R_f$ is a haloalkyl radical as defined above, e.g., 2-(trifluoromethoxysulfonylamino)ethyl, 3-(trifluoromethoxysulfonylamino)propyl, and the like.

"Haloalkenyl" refers to an alkenyl radical, as defined above, that is substituted by one or more halo radicals, as defined above, e.g., 1,2-difluoroethenyl, 3-bromo-2-fluoroprop-1-enyl, 1,2-dibromoethenyl, and the like.

"Haloalkoxy" refers to a radical of the formula —O$R_f$ where $R_f$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Haloalkenyloxy" refers to a radical of the formula —O$R_g$ where $R_g$ is an haloalkenyl radical as defined above, as defined above, e.g., 1,2-difluoroethenyloxy, 3-bromo-2-fluoroprop-1-enyloxy, 1,2-dibromoethenyloxy, and the like.

"Haloalkoxycarbonyl" refers to a radical of the formula —C(O)O$R_f$ where $R_f$ is an haloalkyl radical as defined above, e.g., trifluoromethoxycarbonyl, difluoromethoxycarbonyl, trichloromethoxycarbonyl, 2,2,2-trifluoroethoxycarbonyl, 1-fluoromethyl-2-fluoroethoxycarbonyl, 3-bromo-2-fluoropropoxycarbonyl, 1-bromomethyl-2-bromoethoxycarbonyl, and the like.

"Hydroxy" refers to the —OH radical.

"Hydroxyalkyl" refers to a alkyl radical as defined above that is substituted by a hydroxy radical, e.g., hydroxymethyl, 2-hydroxyethyl, 2-hydroxypropyl, 3-hydroxypropyl, 4-hydroxybutyl, 3-hydroxybutyl, and the like.

"Hydroxyalkoxy" refers to a radical of the formula —O$R_a$—OH where $R_a$ is an alkyl radical as defined above, e.g., 2-hydroxyethoxy, 2-hydroxypropoxy, 4-hydroxybutoxy, 3-hydroxybutoxy, and the like.

"(Hydroxyalkyl)(alkyl)amino" refers to a radical of the formula —N($R_a$)—$R_a$—OH where each $R_a$ is independently an alkyl radical as defined above, e.g., (2-hydroxyethyl)(methyl)amino, (2-hydroxyethyl)(ethyl)amino, (3-hydroxypropyl)(ethyl)amino, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may be attached to the main structure at any heteroatom or carbon atom which results in the creation of a stable compound. Examples of such heterocyclyl radicals include, but are not limited to, azepinyl, acridinyl, benzimidazolyl, benzthiazolyl, benzoxazolyl, benzopyranyl, benzopyranonyl, benzofuranyl, benzofuranonyl, benzothienyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, isoindolyl, indolinyl, isoindolinyl, indanyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of hydroxy, halo, alkyl, alkoxy, phenoxy, haloalkyl, haloalkoxy, formyl, nitro, cyano, amino, monoalkylamino, dialkylamino, carboxy, alkoxycarbonyl, benzylcarbonyl, alkylcarbonyl, carboxyalkyl, alkoxycarbonylalkyl, aminocarbonyl, monoalkylaminocarbonyl, dialkylaminocarbonyl, aminocarbonylalkyl, monoalkylaminocarbonylalkyl, dialkylaminocarbonylalkyl, as defined herein.

For $R^1$, preferred heterocyclyl radicals are those radicals selected from the group consisting of benzoxazolyl, benzthiazolyl, pyridinyl, and pyrimidinyl. For $R^3$, preferred heterocyclyl radicals are those radicals selected from the group consisting of morpholinyl, piperidinyl (optionally substituted by one or more substituents selected from the group consisting of aminocarbonyl, alkoxycarbonyl, carboxy and hydroxy), pyrrolidinyl (optionally substituted by hydroxy), and piperazinyl (optionally substituted by one or more substituents selected from the group consisting of alkyl and carboxyalkyl).

"Heterocyclylalkyl" refers to a radical of the formula —$R_a$—$R_h$ where $R_a$ is an alkyl radical as defined above and $R_h$ is an heterocyclyl radical as defined above, e.g., imidazol-3-ylmethyl, triazol-3-ylmethyl, 2-tetrazolylethyl, and the like. For $R^2$, preferred heterocyclylalkylradicals are those radicals where $R_h$ is selected from the group consisting of imidazolyl (optionally substituted by carboxyalkyl), indolyl, triazolyl and tetrazolyl.

"Heterocyclylalkoxy" refers to a radical of the formula —O—$R_a$—$R_h$ where $R_a$ is an alkyl radical as defined above and $R_h$ is an heterocyclyl radical as defined above, e.g., 1-tetrazolylethoxy, oxiranylmethoxy, and the like. For $R^3$, preferred heterocyclylalkoxy radicals are those radicals where $R_h$ is selected from the group consisting of oxiranyl or tetrazolyl. For $R^4$, preferred heterocyclylalkoxy radicals are those radicals where $R_h$ is pyrrolidinyl (optionally substituted by one or more substituents independently selected from the group consisting of hydroxy and carboxy).

"Heterocyclylcarbonyl" refers to a radical of the formula —C(O)—$R_h$ where $R_h$ is a heterocyclyl radical as defined above, e.g., furan-2-ylcarbonyl, piperidin-4-ylcarbonyl, thien-2-ylcarbonyl, morpholin-4-ylcarbonyl, and the like. For $R^1$, preferred heterocyclylcarbonyl radicals are those radicals wherein $R_h$ is selected from the group consisting of furanyl, thienyl, piperidinyl, morpholinyl and pyridinyl (optionally substituted by one or more substitutents independently selected from the group consisting of hydroxy, halo and alkyl).

"Monoalkylamino" refers to a radical of the formula —N(H)—$R_a$ where $R_a$ is an alkyl radical as defined above, e.g., methylamino, ethylamino, n-propylamino, and the like.

"Monoalkylaminocarbonyl" refers to a radical of the formula —C(O)—N(H)—$R_a$ where $R_a$ is an alkyl radical as defined above, e.g., methylaminocarbonyl, ethylaminocarbonyl, n-propylaminocarbonyl, and the like.

"Monoaralkylaminocarbonylalkoxy" refers to a radical of the formula —O—$R_a$—C(O)—N(H)—$R_e$ where $R_a$ is an alkyl radical as defined above and $R_e$ is an aralkyl radical as defined above, e.g., benzylaminocarbonylmethoxy, 2-(benzylaminocarbonyl)ethoxy, 2-(4-hydroxybenzylaminocarbonyl)propoxy, and the like.

"Mono(carboxyalkyl)aminocarbonyl" refers to a radical of the formula —C(O)—N(H)—$R_a$—C(O)OH where $R_a$ is an alkyl radical as defined above, e.g., (2-carboxyethyl)aminocarbonyl, carboxymethylaminocarbonyl, and the like.

"Mono(carboxyalkyl)aminocarbonylalkoxy" refers to a radical of the formula —O—$R_a$—C(O)—N(H)—$R_a$—C(O)OH where each $R_a$ is independently an alkyl radical as defined above, e.g., (2-carboxyethyl)aminocarbonylmethoxy, 2-(carboxymethylaminocarbonyl)propoxy, and the like.

"Mono(alkoxycarbonylalkyl)aminocarbonylalkoxy" refers to a radical of the formula —O—$R_a$—C(O)—N(H)—$R_a$—C(O)O$R_a$ where each $R_a$ is independently an alkyl radical as defined above, e.g., (2-ethoxycarbonylethyl)aminocarbonylmethoxy, 2-(ethoxycarbonylmethylaminocarbonyl)propoxy, and the like.

"Mono(alkoxycarbonylalkyl)aminocarbonyl" refers to a radical of the formula —C(O)—N(H)—$R_a$—C(O)O$R_a$ where each $R_a$ is independently an alkyl radical as defined above, e.g., (2-methoxycarbonylethyl)aminocarbonyl, ethoxycarbonylmethylaminocarbonyl, and the like.

"Mono((alkoxycarbonyl)(carboxy)alkyl)aminocarbonyl" refers to a radical of the formula —C(O)—N(H)—$R_a$(C(O)OH)—C(O)O$R_a$ where each $R_a$ is independently an alkyl radical as defined above, e.g., (1-carboxy-3-(1,1-dimethylethoxycarbonyl)propyl)aminocarbonyl, and the like.

"Mono(di(alkoxycarbonyl)alkyl)aminocarbonyl" refers to a radical of the formula —C(O)—N(H)—$R_a$(C(O)O$R_a$)—C(O)O$R_a$ where each $R_a$ is independently an alkyl radical as defined above, e.g., (1-methoxycarbonyl-3-(1,1-dimethylethoxycarbonyl)propyl)aminocarbonyl, and the like.

"Mono(dicarboxyalkyl)aminocarbonyl" refers to a radical of the formula —C(O)—N(H)—$R_a$(C(O)OH)—C(O)OH where $R_a$ is an alkyl radical as defined above, e.g., (1,3-dicarboxypropyl)aminocarbonyl, and the like.

"Mammal" includes humans and domesticated animals, such as cats, dogs, swine, cattle, sheep, goats, horses, rabbits, and the like.

"Nitro" refers to the —$NO_2$ radical.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7–9, 21–24 (Elsevier, Amsterdam).

A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" refers to that amount of a compound of the invention which, when administered to a human in need thereof, is sufficient to effect treatment, as defined below, for a disease-state characterized by thrombotic activity. The amount of a compound of the invention which constitutes a "therapeutically effective amount" will vary depending on the compound, the condition and its severity, and the age of the human to be treated, but can be determined routinely by one of ordinary skill in the art having regard to his own knowledge and to this disclosure.

"Treating" or "treatment" as used herein covers the treatment of a disease-state in a mammal, preferably a human, which disease-stated is characterized by thrombotic activity, and includes:

(i) preventing the condition from occurring in a human, in particular, when such human is predisposed to the condition but has not yet been diagnosed as having it;

(ii) inhibiting the condition, i.e., arresting its development; or (iii) relieving the condition, i.e., causing regression of the condition.

In the above definitions, the use of parentheses in a formula is used to conserve space. Accordingly, the use of parenthesis in a formula indicates that the group enclosed within the parentheses is attached directly to the atom preceding the parenthesis. For example, the term "di(carboxy)alkoxy" is defined as a radical of the formula —O—R$_a$(C(O)OH)—C(O)OH. This formula can be drawn as follows:

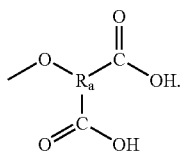

It will also be appreciated that certain compounds of the invention or pharmaceutically acceptable salts thereof, may exist in, and be isolated in, isomeric forms, including tautomeric forms, cis- or trans-isomers. In addition, certain compounds of the invention or pharmaceutically acceptable salts thereof may contain one or more asymmetric centers and may thus give rise to enantiomers, diastereomers, and other stereoisomeric forms that may be defined, in terms of absolute stereochemistry, such as (R)— or (S)—. The present invention is meant to include all such possible isomers, as well as their racemic and optically pure forms. Optically active (R)— and (S)— isomers may be prepared using chiral synthons or chiral reagents by methods known to those of ordinary skill in the art, or resolved using conventional techniques. When the compounds described herein contain olefinic double bonds or other centers of geometric asymmetry, and unless specified otherwise, it is intended that the compounds include both E and Z geometric isomers.

The nomenclature used herein is a modified form of the I.U.P.A.C. nomenclature system wherein the compounds of the invention are named herein as derivatives of the quinoline or naphthalene moiety.

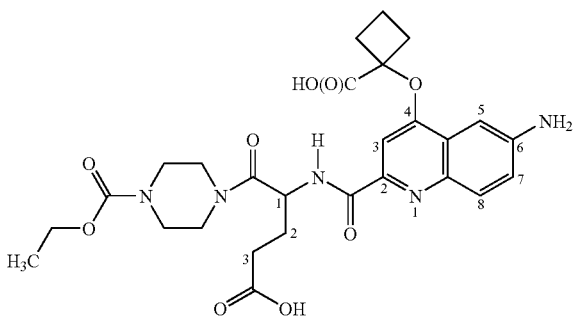

is named herein as 2-[1-(4-(ethoxycarbonyl)piperazin-1-yl)carbonyl-3-carboxypropyl]aminocarbonyl-6-amino-4-(1-carboxycyclobut-1-oxy)quinoline. Unless otherwise indicated, compound names are intended to include any single stereoisomer, enantiomer, diastereomer, racemate or mixtures thereof.

Utility of the Compounds of the Invention

The compounds of the invention act as selective antagonists of the platelet ADP receptor, P2Y$_{AC}$. Accordingly, the compounds are useful in treating disease-states which are characterized as having thrombotic activity. In particular, the compounds are useful as inhibitors of platelet activation, aggregation and degranulation, anti-thrombotic agents or in the treatment or prophylaxis of unstable angina, coronary angioplasty (PTCA), myocardial infarction, perithrombolysis, primary arterial thrombotic I complications of atherosclerosis such as thrombotic or embolic stroke, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopenic purpura, hemolytic uremic syndrome, thrombotic complications of septicernia, adult respiratory distress syndrome, anti-phospholipid syndrome, heparin-induced thrombocytopaenia and pre-eclampsia/eclampsia, or venous thrombosis such as deep vein thrombosis, venoocclusive disease, hematological conditions such as myeloproliferative disease, including thrombocythemia; or in the prevention of mechanically-induced platelet activation in vivo, such as cardiopulmonary bypass (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, atheromatous plaque formation/progression, vascular stenosis/restenosis and asthma, in which platelet-derived factors are implicated in the disease process.

The compounds of formula (I) are also useful as standard or reference compounds, for example, as a quality standard or control, in tests or assays involving the inhibition of the platelet ADP receptor, P2Y$_{AC}$. Such compounds may be provided in a commercial kit, for example, for use in pharmaceutical research involving the platelet ADP receptor, P2Y$_{AC}$. For example, a compound of formula (I) could be used as a reference in an assay to compare its known activity to a compound with an unknown activity. This would ensure that the experimenter that the assay was being performed properly and provide a basis for comparison, especially if the test compound was a derivative of the reference compound. When developing new assays or protocols, compounds of formula (I) could be used to test their effectiveness.

Testing of the Compounds of the Invention

The ability of the compounds to inhibit the platelet adenosine diphosphate receptor known as the P2Y$_{AC}$ receptor, and its biological effects may be tested in a variety of in vitro, ex vivo and in vivo assays. For example, the ability of the compounds to bind to the P2Y$_{AC}$ receptor may be measured by methods similar to those described in Gachet, C. et al., *Br. J. Haemotol.* (1995), Vol. 91, pp. 434–444 and Mills, D. C. B., *Thromb. Haemost.* (1996), Vol. 76, No. 6, pp. 835–856, and by the method described below in Example 17. The ability of the compounds to inhibit ADP-induced aggregation of platelets may be measured by methods similar to those described in R. G. Humphries, *Br. J. Pharm.* (1995), Vol. 115, pp. 1110–1116 and *Methods in Enzymology*, Vol. 169, p. 3 and by the method described below in Example 18. The ability of the compounds to inhibit thrombus formation in vivo or ex vivo may be measured by methods similar to those described in J. M. Herbert, *Cardiovasc. Drug Reviews* (1993), Vol. 11, No. 2, pp. 180–198 or J. D. Folts, *Circulation* (1976), Vol. 54, No. 3, p. 365, or by the methods described below in Example 19. The results of these assays clearly demonstrate that the compounds of the invention are functional antagonists of the platelet adenosine diphosphate receptor and are thereful useful in inhibiting platelet aggregation and thrombus formation.

Administration of the Compounds of the Invention

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state characterized by thrombotic activity in accordance with the teachings of this invention.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

Preferred Embodiments

Of the compounds of formula (I) as set forth above in the Summary of the Invention, several groups of compounds are particularly preferred.

One preferred group is that group of compounds wherein:
a is 1 or 2;
b is 1;
A is =N—;
$R^1$ is alkoxycarbonyl;
$R^2$ is carboxyalkyl, alkoxycarbonylalkyl, carboxyalkoxycarbonylalkyl or heterocyclylalkyl;
$R^3$ is alkoxy, alkoxycarbonylalkoxy, alkoxycarbonylcycloalkoxy, carboxyalkoxy, carboxycycloalkoxy, aminocarbonylcycloalkoxy, heterocyclyl, tetrahydrofuranonyloxy or heterocyclylalkoxy;

each R⁴ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;
R⁵ is hydrogen, alkyl or hydroxalkyl;
R⁶ is —N(R⁷)—C(O)—; and
R⁷ is hydrogen or alkyl.

A preferred subgroup of this group of compounds is that subgroup of compounds wherein:
a is 1 or 2;
b is 1;
A is =N—;
R¹ is alkoxycarbonyl;
R² is carboxyalkyl, alkoxycarbonylalkyl or heterocyclylalkyl;
R³ is alkoxy, alkoxycarbonylcycloalkoxy, carboxycycloalkoxy, tetrahydrofuranonyloxy, aminocarbonylcycloalkoxy, heterocyclyl, or heterocyclylalkoxy;
each R⁴ is independently selected from the group consisting of hydrogen, alkyl and heterocyclylalkoxy;
R⁵ is hydrogen, alkyl or hydroxyalkyl;
R⁶ is —N(R⁷)—C(O)—; and
R⁷ is hydrogen.

A preferred class of this subgroup of compounds is that class of compounds wherein R² is carboxyalkyl.

Preferred compounds of this class of compounds are those compounds selected from the group consisting of the following:
2-[1-(4-(ethoxycarbonyl)piperazin-1-yl)carbonyl-3-carboxypropyl]aminocarbonyl-4-(oxiranyl)methoxyquinoline;
2-[1-(4-(ethoxycarbonyl)piperazin-1-yl)carbonyl-3-carboxypropyl]aminocarbonyl-4-(morpholin-4-yl)quinoline;
2-[1-(4-(ethoxycarbonyl)piperazin-1-yl)carbonyl-3-carboxypropyl]aminocarbonyl-4-(1-tetrazol-5-ylethoxy)quinoline;
2-[1-(4-(ethoxycarbonyl)piperazin-1-yl)carbonyl-3-carboxypropyl]aminocarbonyl-4-(tetrazol-5-yl)methoxyquinoline;
2-[1-(4-(ethoxycarbonyl)piperazin-1-yl)carbonyl-3-carboxypropyl]aminocarbonyl-4-(4-aminocarbonylpiperidin-1-yl)quinoline;
2-[1-(4-(ethoxycarbonyl)piperazin-1-yl)carbonyl-3-carboxypropyl]aminocarbonyl-4-(3-carboxypiperidin-1-yl)quinoline;
2-[1-(4-(ethoxycarbonyl)piperazin-1-yl)carbonyl-3-carboxypropyl]aminocarbonyl-4-(3-ethoxycarbonylpiperidin-1-yl)quinoline;
2-[1-(4-(ethoxycarbonyl)piperazin-1-yl)carbonyl-3-carboxypropyl]aminocarbonyl-4-(4-methylpiperazin-1-yl)quinoline;
2-[1-(4-(ethoxycarbonyl)piperazin-1-yl)carbonyl-3-carboxypropyl]aminocarbonyl-4-(3-hydroxypyrrolidin-1-yl)quinoline;
2-[1-(4-(ethoxycarbonyl)piperazin-1-yl)carbonyl-3-carboxypropyl]aminocarbonyl-4-(4-hydroxypiperidin-1-yl)quinoline;
2-[1-(4-(ethoxycarbonyl)piperazin-1-yl)carbonyl-3-carboxypropyl]aminocarbonyl-4-(4-(carboxymethyl)piperazin-1-yl)quinoline;
2-[1-(4-(ethoxycarbonyl)piperazin-1-yl)carbonyl-3-carboxypropyl]aminocarbonyl-4-(3-(carboxymethyl)piperazin-1-yl)quinoline;
2-[1-(4-(ethoxycarbonyl)piperazin-1-yl)carbonyl-3-carboxypropyl]aminocarbonyl-7-(2-carboxy-4-hydroxypyrrolidin-1-yl)ethoxy-4-(1-carboxycyclobut-1-oxy)quinoline;
2-[1-(4-(ethoxycarbonyl)piperazin-1-yl)carbonyl-3-carboxypropyl]aminocarbonyl-7-methyl-4 -(tetrazol-5-yl)methoxyquinoline; and
2-[1-(4-(ethoxycarbonyl)piperazin-1-yl)carbonyl-3-carboxypropyl]aminocarbonyl-7-methyl-4-(1-tetrazol-5-ylethoxy)quinoline.

Particularly preferred of these preferred compounds is 2-[1-(4-(ethoxycarbonyl)piperazin-1-yl)carbonyl-3-carboxypropyl]aminocarbonyl-7-methyl-4-(1-tetrazol-5-ylethoxy) quinoline.

Another preferred class of this subgroup of compounds is that class of compounds wherein R² is alkoxycarbonylalkyl.

Preferred compounds of this class of compounds are those compounds selected from the group consisting of the following:
2-[1-(4-(ethoxycarbonyl)piperazin-1-yl)carbonyl-3-(methoxycarbonyl)propyl]aminocarbonyl-4-(tetrahydro-2-oxofuran-3-yl)oxyquinoline;
2-[1-(4-(ethoxycarbonyl)piperazin-1-yl)carbonyl-3-(methoxycarbonyl)propyl]aminocarbonyl-4-(oxiranyl)methoxyquinoline;
2-[1-(4-(ethoxycarbonyl)piperazin-1-yl)carbonyl-3-(methoxycarbonyl)propyl]aminocarbonyl-4-(3-ethoxycarbonylpiperidin-1-yl)quinoline; and;
2-[1-(4-(ethoxycarbonyl)piperazin-1-yl)carbonyl-3-(ethoxycarbonyl)propyl]aminocarbonyl-4-(1-tetrazol-5-ylethoxy)quinoline.

Another preferred class of this subgroup of compounds is that class of compounds wherein R² is heterocyclylalkyl.

Preferred compounds of this class of compounds are those compounds selected from the group consisting of the following:
2-[1-(4-(ethoxycarbonyl)piperazin-1-yl)carbonyl-2-(imidazol-4-yl)ethyl]aminocarbonyl-4-methoxyquinoline;
2-[1-(4-(ethoxycarbonyl)piperazin-1-yl)carbonyl-2-(indol-3-yl)ethyl]aminocarbonyl-4-methoxyquinoline;
2-[1-(4-(ethoxycarbonyl)piperazin-1-yl)carbonyl-2-(1-(carboxymethyl)imidazol-4-yl)ethyl]aminocarbonyl-4-methoxyquinoline;
2-[1-(4-(ethoxycarbonyl)piperazin-1-yl)carbonyl-2-(1,2,4-triazol-3-yl)ethyl]aminocarbonyl-4-methoxyquinoline;
2-[1-(4-(ethoxycarbonyl)piperazin-1-yl)carbonyl-3-(tetrazol-1-yl)propyl]aminocarbonyl-4-(1-carboxycyclobut-1-oxy)quinoline;
2-[1-(4-(ethoxycarbonyl)piperazin-1-yl)carbonyl-3-(tetrazol-1-yl)propyl]aminocarbonyl-4 -(1-(ethoxycarbonyl)cyclobut-1-oxy)quinoline;
2-[1-(4-(ethoxycarbonyl)piperazin-1-yl)carbonyl-3-(tetrazol-1-yl)propyl]aminocarbonyl-7-methyl-4-(1-carboxycyclobut-1-oxy)quinoline; and
2-[1-(4-(ethoxycarbonyl)piperazin-1-yl)carbonyl-2-(tetrazol-5-yl)ethyl]aminocarbonyl-7-methyl-4-(1-carboxycyclobut-1-oxy)quinoline.

Particularly preferred of these preferred compounds are the following compounds:
2-[1-(4-(ethoxycarbonyl)piperazin-1-yl)carbonyl-3-(tetrazol-1-yl)propyl]aminocarbonyl-7-methyl-4-(1-carboxycyclobut-1-oxy)quinoline; and
2-[1-(4-(ethoxycarbonyl)piperazin-1-yl)carbonyl-2-(tetrazol-5-yl)ethyl]aminocarbonyl-7-methyl-4-(1-carboxycyclobut-1-oxy)quinoline.

Another preferred subgroup of this group of compounds is that subgroup of compounds wherein:

a is 1 or 2;
b is 1;
A is =N—;
R¹ is alkoxycarbonyl;
R² is carboxyalkyl, carboxyalkoxycarbonylalkyl or alkoxycarbonylalkyl;
R³ is alkoxy, alkoxycarbonylalkoxy, alkoxycarbonylcycloalkoxy, aminocarbonylcycloalkoxy, carboxyalkoxy or carboxycycloalkoxy;
each R⁴ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, and dialkylaminoalkoxy;
R⁵ is hydrogen, alkyl or hydroxyalkyl;
R⁶ is —N(R⁷)—C(O)—; and
R⁷ is hydrogen or alkyl.

A preferred class of this subgroup of compounds is that class of compounds wherein:
R³ is alkoxycarbonylalkoxy;
each R⁴ is independently selected from the group consisting of hydrogen, alkyl or halo; and
R⁵ is hydrogen.

Preferred compounds of this class of compounds are those compounds selected from the group consisting of the following:
2-[1-(4-(ethoxycarbonyl)piperazin-1-yl)carbonyl-3-(methoxycarbonyl)propyl]aminocarbonyl-4-(methoxycarbonyl)methoxyquinoline;
2-[1-(4-(ethoxycarbonyl)piperazin-1-yl)carbonyl-3-(methoxycarbonyl)propyl]aminocarbonyl-4-(1-methyl-1-(methoxycarbonyl)ethoxy)quinoline;
2-[1-(4-(ethoxycarbonyl)piperazin-1-yl)carbonyl-3-(1,1-dimethylethoxycarbonylpropyl]aminocarbonyl-4-(1-(ethoxycarbonyl)ethoxy)quinoline;
2-[1-(4-(ethoxycarbonyl)piperazin-1-yl)carbonyl-3-carboxypropyl]aminocarbonyl-4-(1-(ethoxycarbonyl)ethoxy)quinoline;
2-[1-(4-(ethoxycarbonyl)piperazin-1-yl)carbonyl-3-(methoxycarbonyl)propyl]aminocarbonyl-4-(1-(ethoxycarbonyl)ethoxy)quinoline;
2-[1-(4-(ethoxycarbonyl)piperazin-1-yl)carbonyl-3-(methoxycarbonyl)propyl]aminocarbonyl-4-(1-(ethoxycarbonyl)-2-methylpropoxy)quinoline;
2-[1-(4-(ethoxycarbonyl)piperazin-1-yl)carbonyl-3-(1,1-dimethylethoxycarbonyl)propyl]aminocarbonyl-4-(1-methyl-1-(methoxycarbonyl)ethoxy)quinoline;
2-[1-(4-(ethoxycarbonyl)piperazin-1-yl)carbonyl-3-carboxypropyl]aminocarbonyl-4-(1-methyl-1-(methoxycarbonyl)ethoxy)quinoline;
2-[1-(4-(ethoxycarbonyl)piperazin-1-yl)carbonyl-3-(methoxycarbonyl)propyl]aminocarbonyl-4-(1-(methoxycarbonyl)ethoxy)quinoline;
2-[1-(4-(ethoxycarbonyl)piperazin-1-yl)carbonyl-3-carboxypropyl]aminocarbonyl-7-methyl-4-(1-(ethoxycarbonyl)propoxy)quinoline;
2-[1-(4-(ethoxycarbonyl)piperazin-1-yl)carbonyl-3-carboxypropyl]aminocarbonyl-7-methyl-4-(1-(ethoxycarbonyl)-2-methylpropoxy)quinoline;
2-[1-(4-(ethoxycarbonyl)piperazin-1-yl)carbonyl-3-carboxypropyl]aminocarbonyl-6-chloro-7-methyl-4-(1-methyl-1-(ethoxycarbonyl)ethoxy)quinoline; and
2-[1-(4-(ethoxycarbonyl)piperazin-1-yl)carbonyl-3-carboxypropyl]aminocarbonyl-7-methyl-4-(1-methyl-1-(ethoxycarbonyl)ethoxy)quinoline.

Particularly preferred of these preferred compounds are the following compounds:
2-[1-(4-(ethoxycarbonyl)piperazin-1-yl)carbonyl-3-carboxypropyl]aminocarbonyl-7-methyl-4-(1-(ethoxycarbonyl)propoxy)quinoline;
2-[1-(4-(ethoxycarbonyl)piperazin-1-yl)carbonyl-3-carboxypropyl]aminocarbonyl-7-methyl-4-(1-(ethoxycarbonyl)-2-methylpropoxy)quinoline;
2-[1-(4-(ethoxycarbonyl)piperazin-1-yl)carbonyl-3-carboxypropyl]aminocarbonyl-6-chloro-7-methyl-4-(1-methyl-1-(ethoxycarbonyl)ethoxy)quinoline; and
2-[1-(4-(ethoxycarbonyl)piperazin-1-yl)carbonyl-3-carboxypropyl]aminocarbonyl-7-methyl-4-(1-methyl-1-(ethoxycarbonyl)ethoxy)quinoline.

Another preferred class of this subgroup of compounds is that class of compounds wherein:
R³ is alkoxycarbonylcycloalkoxy or aminocarbonylcycloalkoxy; and
R⁵ is hydrogen.

Preferred compounds of this class of compounds are those compounds selected from the group consisting of the following:
2-[1-(4-(ethoxycarbonyl)piperazin-1-yl)carbonyl-3-(1,1-dimethylethoxycarbonyl)propyl]aminocarbonyl-4-(1-(ethoxycarbonyl)cyclobut-1-oxy)quinoline;
2-[1-(4-(ethoxycarbonyl)piperazin-1-yl)carbonyl-3-carboxypropyl]aminocarbonyl-4-(1-(ethoxycarbonyl)cyclobut-1-oxy)quinoline;
2-[1-(4-(ethoxycarbonyl)piperazin-1-yl)carbonyl-3-(methoxycarbonyl)propyl]aminocarbonyl-4-(1-(ethoxycarbonyl)cyclobut-1-oxy)quinoline;
2-[1-(4-(ethoxycarbonyl)piperazin-1-yl)carbonyl-3-(1,1-dimethylethoxycarbonyl)propyl]aminocarbonyl-7-chloro-4-(1-(ethoxycarbonyl)cyclobut-1-oxy)quinoline;
2-[1-(4-(ethoxycarbonyl)piperazin-1-yl)carbonyl-3-(ethoxycarbonyl)propyl]aminocarbonyl-4-(1-(ethoxycarbonyl)cyclobut-1-oxy)quinoline;
2-[1-(4-(ethoxycarbonyl)piperazin-1-yl)carbonyl-3-(1,1-dimethylethoxycarbonyl)propyl]aminocarbonyl-7-(benzyloxy)-4-(1-(ethoxycarbonyl)cyclobut-1-oxy)quinoline;
2-[1-(4-(ethoxycarbonyl)piperazin-1-yl)carbonyl-3-(1,1dimethylethoxycarbonyl)propyl]aminocarbonyl-7-hydroxy-4-(1-(ethoxycarbonyl)cyclobut-1-oxy)quinoline;
2-[1-(4-(ethoxycarbonyl)piperazin-1-yl)carbonyl-3-carboxypropyl]aminocarbonyl-7-chloro-4-(1-(aminocarbonyl)cyclobut-1-oxy)quinoline;
2-[1-(4-(ethoxycarbonyl)piperazin-1-yl)carbonyl-3-carboxypropyl]aminocarbonyl-7-chloro-6-fluoro-4-(1-(ethoxycarbonyl)cyclobut-1-oxy)quinoline;
2-[1-(4-(ethoxycarbonyl)piperazin-1-yl)carbonyl-3-carboxypropyl]aminocarbonyl-7-methoxy-4-(1-(ethoxycarbonyl)cyclobut-1-oxy)quinoline;
2-[1-(4-(ethoxycarbonyl)piperazin-1-yl)carbonyl-3-carboxypropyl]aminocarbonyl-7-hydroxy-4-(1-(ethoxycarbonyl)cyclobut-1-oxy)quinoline;
2-[1-(4-(ethoxycarbonyl)piperazin-1-yl)carbonyl-3-carboxypropyl]aminocarbonyl-5-fluoro-6-methyl-4-(1-(ethoxycarbonyl)cyclobut-1-oxy)quinoline;
2-[1-(4-(ethoxycarbonyl)piperazin-1-yl)carbonyl-3-carboxypropyl]aminocarbonyl-7-methyl-4-(1-(1-methylethoxycarbonyl)cyclobut-1-oxy)quinoline;
2-[1-(4-(ethoxycarbonyl)piperazin-1-yl)carbonyl-3-carboxypropyl]aminocarbonyl-7-chloro-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-7-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-7-chloro-6-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6,7-dimethoxy-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6-fluoro-7-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6-chloro-7-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6,7-dimethyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-7-chloro-6-methoxy-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6,7-dichloro-4-(1-(ethoxycarbonyl)cyclobut-1-oxy)quinoline;

2-[1-(4-(ethoxycarbonyl)piperazin-1-yl)carbonyl-3-(ethoxycarbonyl)propyl]aminocarbonyl-7-methyl-4-(1-(ethoxycarbonyl)cyclobut-1-oxy)quinoline;

2-[1-(4-(ethoxycarbonyl)piperazin-1-yl)carbonyl-3-(1-methylethoxycarbonyl)propyl]aminocarbonyl-7-methyl-4-(1-(ethoxycarbonyl)cyclobut-1-oxy)quinoline;

2-[1-(4-(ethoxycarbonyl)piperazin-1-yl)carbonyl-3-(ethoxycarbonyl)propyl]aminocarbonyl-6-fluoro-7-methyl-4-(1-(ethoxycarbonyl)cyclobut-1-oxy)quinoline;

2-[1-(4-(ethoxycarbonyl)piperazin-1-yl)carbonyl-3-(ethoxycarbonyl)propyl]aminocarbonyl-6-chloro-7-methyl-4-(1-(ethoxycarbonyl)cyclobut-1-oxy)quinoline;

2-[1-(4-(ethoxycarbonyl)piperazin-1-yl)carbonyl-3-(ethoxycarbonyl)propyl]aminocarbonyl-7-chloro-4-(1-(ethoxycarbonyl)cyclobut-1-oxy)quinoline;

2-[1-(4-(ethoxycarbonyl)piperazin-1-yl)carbonyl-3-(ethoxycarbonyl)propyl]aminocarbonyl-6,7-dimethyl-4-(1-(ethoxycarbonyl)cyclobut-1-oxy)quinoline;

2-[1-(4-(ethoxycarbonyl)piperazin-1-yl)carbonyl-3-(ethoxycarbonyl)propyl]aminocarbonyl-6,7-dichloro-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6-methylthio-4-(1-(ethoxycarbonyl)cyclobut-1-oxy)quinoline; and 2-[1-(4-(ethoxycarbonyl)piperazin-1-yl)carbonyl-3-carboxypropyl]aminocarbonyl-7-methyl-4-(1-(methoxycarbonyl)cyclobut-1-oxy)quinoline.

Particularly preferred of these preferred compounds are the following compounds:

2-[1-(4-(ethoxycarbonyl)piperazin-1-yl)carbonyl-3-carboxypropyl]aminocarbonyl-7-chloro-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-7-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-7-chloro-6-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6-fluoro-7-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6-chloro-7-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6,7-dimethyl-4-(1-(ethoxycarbonyl)cyclobut-1-oxy)quinoline; and 2-[1-(4-(ethoxycarbonyl)piperazin-1-yl)carbonyl-3-carboxypropyl]aminocarbonyl-6,7-dichloro-4-(1-(ethoxycarbonyl)cyclobut-1-oxy)quinoline.

Another preferred class of this subgroup of compounds is that class of compounds wherein:

$R^3$ is carboxyalkoxycarbonylalkyl or carboxyalkoxy; and $R^5$ is hydrogen.

Preferred compounds of this class of compounds are those compounds selected from the group consisting of the following:

2-[1-(4-(ethoxycarbonyl)piperazin-1-yl)carbonyl-3-((carboxy)methoxycarbonyl)propyl]aminocarbonyl-4-(carboxy)methoxyquinoline 2-[1-(4-(ethoxycarbonyl)piperazin-1-yl)carbonyl-3-carboxypropyl]aminocarbonyl-4-(carboxy)methoxyquinoline;

2-[1-(4-(ethoxycarbonyl)piperazin-1-yl)carbonyl-3-carboxypropyl]aminocarbonyl-4-(1-methyl-1-carboxyethoxy)quinoline;

2-[1-(4-(ethoxycarbonyl)piperazin-1-yl)carbonyl-3-carboxypropyl]aminocarbonyl-4-(1-carboxy-2,2-dimethylpropoxy)quinoline;

2-[1-(4-(ethoxycarbonyl)piperazin-1-yl)carbonyl-3-carboxypropyl]aminocarbonyl-4-(1-carboxyethoxy)quinoline;

2-[1-(4-(ethoxycarbonyl)piperazin-1-yl)carbonyl-3-(methoxycarbonyl)propyl]aminocarbonyl-4-(carboxy)methoxyquinoline;

2-[1-(4-(ethoxycarbonyl)piperazin-1-yl)carbonyl-3-carboxypropyl]aminocarbonyl-4-(1-(carboxy)ethoxy)quinoline;

2-[1-(4-(ethoxycarbonyl)piperazin-1-yl)carbonyl-3-(ethoxycarbonyl)propyl]aminocarbonyl-7-methyl-4-(1-methyl-1-carboxyethoxy)quinoline;

2-[1-(4-(ethoxycarbonyl)piperazin-1-yl)carbonyl-3-carboxypropyl]aminocarbonyl-7-methyl-4-(1-methyl-1-carboxyethoxy)quinoline;

2-[1-(4-(ethoxycarbonyl)piperazin-1-yl)carbonyl-3-carboxypropyl]aminocarbonyl-7-methyl-4-(1-(carboxy)ethoxy)quinoline;

2-[1-(4-(ethoxycarbonyl)piperazin-1-yl)carbonyl-3-carboxypropyl]aminocarbonyl-7-methyl-4-(1-carboxypropoxy)quinoline;

2-[1-(4-(ethoxycarbonyl)piperazin-1-yl)carbonyl-3-carboxypropyl]aminocarbonyl-7-methyl-4-(1-carboxy-2-methylpropoxy)quinoline; and 2-[1-(4-(ethoxycarbonyl)piperazin-1-yl)carbonyl-3-carboxypropyl]aminocarbonyl-6-chloro-7-methyl-4-(1-methyl-1-carboxyethoxy)quinoline.

Particularly preferred of these preferred compounds are the following compounds:

2-[1-(4-(ethoxycarbonyl)piperazin-1-yl)carbonyl-3-carboxypropyl]aminocarbonyl-7-methyl-4-(1-methyl-1-carboxyethoxy)quinoline;

2-[1-(4-(ethoxycarbonyl)piperazin-1-yl)carbonyl-3-carboxypropyl]aminocarbonyl-7-methyl-4-(1-(carboxy)ethoxy)quinoline;

2-[1-(4-(ethoxycarbonyl)piperazin-1-yl)carbonyl-3-carboxypropyl]aminocarbonyl-7-methyl-4-(1-carboxypropoxy)quinoline;

2-[1-(4-(ethoxycarbonyl)piperazin-1-yl)carbonyl-3-carboxypropyl]aminocarbonyl-7-methyl-4-(1-carboxy-2-methylpropoxy)quinoline; and 2-[1-(4-(ethoxycarbonyl)piperazin-1-yl)carbonyl-3-carboxypropyl]aminocarbonyl-6-chloro-7-methyl-4-(1-methyl-1-carboxyethoxy)quinoline.

Another preferred class of this subgroup of compounds is that class of compounds wherein:
$R^3$ is carboxycycloalkoxy; and
$R^5$ is hydrogen.

A preferred subclass of this class of compounds is that subclass of compounds wherein each $R^4$ is independently selected from the group consisting of alkyl, hydroxyalkyl, alkoxy, halo, haloalkyl, and dialkylaminoalkyl.

Preferred compounds of this subclass of compounds are those compounds selected from the group consisting of the following:

2-[1-(4-(ethoxycarbonyl)piperazin-1-yl)carbonyl-3-carboxypropyl]aminocarbonyl-5,7-dichloro-4-(1-carboxycyclobut-1-oxy)quinoline;

2-[1-(4-(ethoxycarbonyl)piperazin-1-yl)carbonyl-3-carboxypropyl]aminocarbonyl-6-chloro-4-(1-carboxycyclobut-1-oxy)quinoline;

2-[1-(4-(ethoxycarbonyl)piperazin-1-yl)carbonyl-3-carboxypropyl]aminocarbonyl-6-methyl-4-(1-carboxycyclobut-1-oxy)quinoline;

2-[1-(4-(ethoxycarbonyl)piperazin-1-yl)carbonyl-3-carboxypropyl]aminocarbonyl-5-methyl-4-(1-carboxycyclobut-1-oxy)quinoline;

2-[1-(4-(ethoxycarbonyl)piperazin-1-yl)carbonyl-3-carboxypropyl]aminocarbonyl-8-methyl-4-(1-carboxycyclobut-1-oxy)quinoline;

2-[1-(4-(ethoxycarbonyl)piperazin-1-yl)carbonyl-3-carboxypropyl]aminocarbonyl-6-(diethylamino)methyl-4-(1-carboxycyclobut-1-oxy)quinoline;

2-[1-(4-(ethoxycarbonyl)piperazin-1-yl)carbonyl-3-carboxypropyl]aminocarbonyl-7-(diethylamino)methyl-4-(1-carboxycyclobut-1-oxy)quinoline;

2-[1-(4-(ethoxycarbonyl)piperazin-1-yl)carbonyl-3-carboxypropyl]aminocarbonyl-7-fluoro-4-(1-carboxycyclobut-1-oxy)quinoline;

2-[1-(4-(ethoxycarbonyl)piperazin-1-yl)carbonyl-3-carboxypropyl]aminocarbonyl-7-(trifluoromethyl)-4-(1-carboxycyclobut-1-oxy)quinoline;

2-[1-(4-(ethoxycarbonyl)piperazin-1-yl)carbonyl-3-carboxypropyl]aminocarbonyl-7-(hydroxymethyl)-4-(1-carboxycyclobut-1-oxy)quinoline;

2-[1-(4-(ethoxycarbonyl)piperazin-1-yl)carbonyl-3-carboxypropyl]aminocarbonyl-7-ethyl-4-(1-carboxycyclobut-1-oxy)quinoline;

2-[1-(4-(ethoxycarbonyl)piperazin-1-yl)carbonyl-3-carboxypropyl]aminocarbonyl-6-ethyl-4-(1-carboxycyclobut-1-oxy)quinoline;

2-[1-(4-(ethoxycarbonyl)piperazin-1-yl)carbonyl-3-carboxypropyl]aminocarbonyl-6-fluoro-4-(1-carboxycyclobut-1-oxy)quinoline;

2-[1-(4-(ethoxycarbonyl)piperazin-1-yl)carbonyl-3-carboxypropyl]aminocarbonyl-7-chloro-6-fluoro-4-(1-carboxycyclobut-1-oxy)quinoline;

2-[1-(4-(ethoxycarbonyl)piperazin-1-yl)carbonyl-3-carboxypropyl]aminocarbonyl-7-bromo-4-(1-carboxycyclobut-1-oxy)quinoline;

2-[1-(4-(ethoxycarbonyl)piperazin-1-yl)carbonyl-3-carboxypropyl]aminocarbonyl-7-chloro-6-methoxy-4-(1-carboxycyclobut-1-oxy)quinoline;

2-[1-(4-(ethoxycarbonyl)piperazin-1-yl)carbonyl-3-carboxypropyl]aminocarbonyl-6,7-difluoro-4-(1-carboxycyclobut-1-oxy)quinoline;

2-[1-(4-(ethoxycarbonyl)piperazin-1-yl)carbonyl-3-carboxypropyl]aminocarbonyl-5-fluoro-6-methyl-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-6-fluoro-7-methyl-4-(1-carboxycyclobut-1-oxy)quinoline;

2-[1-(4-(ethoxycarbonyl)piperazin-1-yl)carbonyl-3-(1-methylethoxycarbonyl)propyl]aminocarbonyl-6-fluoro-7-methyl-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-7-methyl-4-(1-carboxycyclobut-1-oxy)quinoline;

2-[1-(4-(ethoxycarbonyl)piperazin-1-yl)carbonyl-3-(1-methylethoxycarbonyl)propyl]aminocarbonyl-7-methyl-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-6-chloro-7-methyl-4-(1-carboxycyclobut-1-oxy)quinoline;

2-[1-(4-(ethoxycarbonyl)piperazin-1-yl)carbonyl-3-(1-methylethoxycarbonyl)propyl]aminocarbonyl-6-chloro-7-methyl-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-7-chloro-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-6,7-dimethyl-4-(1-carboxycyclobut-1-oxy)quinoline;

2-[1-(4-(ethoxycarbonyl)piperazin-1-yl)carbonyl-3-(1-methylethoxycarbonyl)propyl]aminocarbonyl-6,7-dimethyl-4-(1-carboxycyclobut-1-oxy)quinoline;

2-[1-(4-(ethoxycarbonyl)piperazin-1-yl)carbonyl-3-(1-methylethoxycarbonyl)propyl]aminocarbonyl-7-chloro-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-6,7-dichloro-4-(1-carboxycyclobut-1-oxy)quinoline;

2-[1-(4-(ethoxycarbonyl)piperazin-1-yl)carbonyl-3-(1-methylethoxycarbonyl)propyl]aminocarbonyl-6,7-dichloro-4-(1-carboxycyclobut-1-oxy)quinoline;

2-[1-(4-(ethoxycarbonyl)piperazin-1-yl)carbonyl-3-carboxypropyl]aminocarbonyl-7-chloro-4-(1-carboxycyclobut-1-oxy)quinoline;

2-[1-(4-(ethoxycarbonyl)piperazin-1-yl)carbonyl-3-carboxypropyl]aminocarbonyl-7-methyl-4-(1-carboxycyclobut-1-oxy)quinoline;

2-[1-(4-(ethoxycarbonyl)piperazin-1-yl)carbonyl-3-carboxypropyl]aminocarbonyl-7-chloro-6-methyl-4-(1-carboxycyclobut-1-oxy)quinoline;

2-[1-(4-(ethoxycarbonyl)piperazin-1-yl)carbonyl-3-carboxypropyl]aminocarbonyl-6-chloro-7-methyl-4-(1-carboxycyclobut-1-oxy)quinoline;

2-[1-(4-(ethoxycarbonyl)piperazin-1-yl)carbonyl-3-carboxypropyl]aminocarbonyl-6-fluoro-7-methyl-4-(1-carboxycyclobut-1-oxy)quinoline;

2-[1-(4-(ethoxycarbonyl)piperazin-1-yl)carbonyl-3-carboxypropyl]aminocarbonyl-6,7-dimethyl-4-(1-carboxycyclobut-1-oxy)quinoline; and 2-[1-(4-(ethoxycarbonyl)piperazin-1-yl)carbonyl-3-carboxypropyl]aminocarbonyl-6,7-dichloro-4-(1-carboxycyclobut-1-oxy)quinoline.

Particularly preferred of these preferred compounds are the following compounds:

2-[1-(4-(ethoxycarbonyl)piperazin-1-yl)carbonyl-3-carboxypropyl]aminocarbonyl-7-chloro-6-fluoro-4-(1-carboxycyclobut-1-oxy)quinoline;

2-[1-(4-(ethoxycarbonyl)piperazin-1-yl)carbonyl-3-carboxypropyl]aminocarbonyl-7-chloro-4-(1-carboxycyclobut-1-oxy)quinoline;
2-[1-(4-(ethoxycarbonyl)piperazin-1-yl)carbonyl-3-carboxypropyl]aminocarbonyl-7-methyl-4-(1-carboxycyclobut-1-oxy)quinoline;
2-[1-(4-(ethoxycarbonyl)piperazin-1-yl)carbonyl-3-carboxypropyl]aminocarbonyl-7-chloro-6-methyl-4-(1-carboxycyclobut-1-oxy)quinoline;
2-[1-(4-(ethoxycarbonyl)piperazin-1-yl)carbonyl-3-carboxypropyl]aminocarbonyl-6-chloro-7-methyl-4-(1-carboxycyclobut-1-oxy)quinoline;
2-[1-(4-(ethoxycarbonyl)piperazin-1-yl)carbonyl-3-carboxypropyl]aminocarbonyl-6-fluoro-7-methyl-4-(1-carboxycyclobut-1-oxy)quinoline;
2-[1-(4-(ethoxycarbonyl)piperazin-1-yl)carbonyl-3-carboxypropyl]aminocarbonyl-6,7-dimethyl-4-(1-carboxycyclobut-1-oxy)quinoline; and
2-[1-(4-(ethoxycarbonyl)piperazin-1-yl)carbonyl-3-carboxypropyl]aminocarbonyl-6,7-dichloro-4-(1-carboxycyclobut-1-oxy)quinoline.

Another preferred subclass of this class of compounds is that subclass of compounds wherein each $R^4$ is independently selected from the group consisting of cyano, nitro, amino, monoalkylamino, and dialkylamino.

Preferred compounds of this subclass of compounds are those compounds selected from the group consisting of the following:
2-[1-(4-(ethoxycarbonyl)piperazin-1-yl)carbonyl-3-carboxypropyl]aminocarbonyl-6-nitro-4-(1-carboxycyclobut-1-oxy)quinoline;
2-[1-(4-(ethoxycarbonyl)piperazin-1-yl)carbonyl-3-carboxypropyl]aminocarbonyl-6-amino-4-(1-carboxycyclobut-1-oxy)quinoline;
2-[1-(4-(ethoxycarbonyl)piperazin-1-yl)carbonyl-3-carboxypropyl]aminocarbonyl-7-cyano-4-(1-carboxycyclobut-1-oxy)quinoline;
2-[1-(4-(ethoxycarbonyl)piperazin-1-yl)carbonyl-3-carboxypropyl]aminocarbonyl-5-cyano-4-(1-carboxycyclobut-1-oxy)quinoline;
2-[1-(4-(ethoxycarbonyl)piperazin-1-yl)carbonyl-3-carboxypropyl]aminocarbonyl-7-nitro-4-(1-carboxycyclobut-1-oxy)quinoline; and
2-[1-(4-(ethoxycarbonyl)piperazin-1-yl)carbonyl-3-carboxypropyl]aminocarbonyl-7-amino-4-(1-carboxycyclobut-1-oxy)quinoline.

Another preferred subclass of this class of compounds is that subclass of compounds wherein each $R^4$ is independently selected from the group consisting of alkoxy, aralkoxy, haloalkoxy, hydroxy, alkylthio, carboxyalkoxy, alkoxycarbonylalkoxy and dialkylaminoalkoxy.

Preferred compounds of this subclass of compounds are those compounds selected from the group consisting of the following:
2-[1-(4-(ethoxycarbonyl)piperazin-1-yl)carbonyl-3-carboxypropyl]aminocarbonyl-7-(benzyloxy)-4-(1-carboxycyclobut-1-oxy)quinoline;
2-[1-(4-(ethoxycarbonyl)piperazin-1-yl)carbonyl-3-carboxypropyl]aminocarbonyl-7-hydroxy-4-(1-carboxycyclobut-1-oxy)quinoline;
2-[1-(4-(ethoxycarbonyl)piperazin-1-yl)carbonyl-3-carboxypropyl]aminocarbonyl-7-n-propoxy-4-(1-carboxycyclobut-1-oxy)quinoline;
2-[1-(4-(ethoxycarbonyl)piperazin-1-yl)carbonyl-3-carboxypropyl]aminocarbonyl-7-(carboxy)methoxy-4-(1-carboxycyclobut-1-oxy)quinoline;
2-[1-(4-(ethoxycarbonyl)piperazin-1-yl)carbonyl-3-carboxypropyl]aminocarbonyl-7-(diethylamino)ethoxy-4-(1-carboxycyclobut-1-oxy)quinoline;
2-[1-(4-(ethoxycarbonyl)piperazin-1-yl)carbonyl-3-carboxypropyl]aminocarbonyl-7-methoxy-4-(1-carboxycyclobut-1-oxy)quinoline;
2-[1-(4-(ethoxycarbonyl)piperazin-1-yl)carbonyl-3-carboxypropyl]aminocarbonyl-6-(benzyloxy)-4-(1-carboxycyclobut-1-oxy)quinoline;
2-[1-(4-(ethoxycarbonyl)piperazin-1-yl)carbonyl-3-carboxypropyl]aminocarbonyl-6-hydroxy-4-(1-carboxycyclobut-1-oxy)quinoline;
2-[1-(4-(ethoxycarbonyl)piperazin-1-yl)carbonyl-3-carboxypropyl]aminocarbonyl-6-(carboxy)methoxy-4-(1-carboxycyclobut-1-oxy)quinoline;
2-[1-(4-(ethoxycarbonyl)piperazin-1-yl)carbonyl-3-carboxypropyl]aminocarbonyl-6-ethoxy-4-(1-carboxycyclobut-1-oxy)quinoline;
2-[1-(4-(ethoxycarbonyl)piperazin-1-yl)carbonyl-3-carboxypropyl]aminocarbonyl-6-methoxy-4-(1-carboxycyclobut-1-oxy)quinoline;
2-[1-(4-(ethoxycarbonyl)piperazin-1-yl)carbonyl-3-carboxypropyl]aminocarbonyl-6-(1-methylethoxy)-4-(1-carboxycyclobut-1-oxy)quinoline;
2-[1-(4-(ethoxycarbonyl)piperazin-1-yl)carbonyl-3-carboxypropyl]aminocarbonyl-7-(trifluoromethoxy)-4-(1-carboxycyclobut-1-oxy)quinoline;
2-[1-(4-(ethoxycarbonyl)piperazin-1-yl)carbonyl-3-carboxypropyl]aminocarbonyl-6-trifluoromethoxy-4-(1-carboxycyclobut-1-oxy)quinoline;
2-[1-(4-(ethoxycarbonyl)piperazin-1-yl)carbonyl-3-carboxypropyl]aminocarbonyl-6,7-dimethoxy-4-(1-carboxycyclobut-1-oxy)quinoline;
2-[1-(4-(ethoxycarbonyl)piperazin-1-yl)carbonyl-3-carboxypropyl]aminocarbonyl-7-hydroxy-4-(1-carboxycyclobut-1-oxy)quinoline; and
2-[1-(4-(ethoxycarbonyl)piperazin-1-yl)carbonyl-3-carboxypropyl]aminocarbonyl-6-methylthio-4-(1-carboxycyclobut-1-oxy)quinoline.

Another preferred subclass of this class of compounds is that subclass of compounds wherein each $R^4$ is independently selected from the group consisting of hydrogen, carboxy, alkoxycarbonyl, aminocarbonyl and alkylcarbonyl.

Preferred compounds of this subclass of compounds are those compounds selected from the group consisting of the following:
2-[1-(4-(ethoxycarbonyl)piperazin-1-yl)carbonyl-3-carboxypropyl]aminocarbonyl-4-(1-carboxycyclobut-1-oxy)quinoline;
2-[1-(4-(ethoxycarbonyl)piperazin-1-yl)carbonyl-2-carboxyethyl]aminocarbonyl-4-(1-carboxycyclobut-1-oxy)quinoline;
2-[1-(4-(ethoxycarbonyl)piperazin-1-yl)carbonyl-3-carboxybutyl]aminocarbonyl-4-(1-carboxycyclobut-1-oxy)quinoline;
2-[1-(4-(ethoxycarbonyl)piperazin-1-yl)carbonyl-3-carboxypropyl]aminocarbonyl-6-carboxy-4-(1-carboxycyclobut-1-oxy)quinoline;
2-[1-(4-(ethoxycarbonyl)piperazin-1-yl)carbonyl-3-carboxypropyl]aminocarbonyl-7-acetyl-4-(1-carboxycyclobut-1-oxy)quinoline;
2-[1-(4-(ethoxycarbonyl)piperazin-1-yl)carbonyl-3-carboxypropyl]aminocarbonyl-5-ethoxycarbonyl-4-(1-carboxycyclobut-1-oxy)quinoline;
2-[1-(4-(ethoxycarbonyl)piperazin-1-yl)carbonyl-3-carboxypropyl]aminocarbonyl-6-acetyl-4-(1-carboxycyclobut-1-oxy)quinoline;

2-[1-(4-(ethoxycarbonyl)piperazin-1-yl)carbonyl-3-carboxypropyl]aminocarbonyl-7-carboxy-4-(1-carboxycyclobut-1-oxy)quinoline; and 2-[1-(4-(ethoxycarbonyl)piperazin-1-yl)carbonyl-3-carboxypropyl]aminocarbonyl-6-aminocarbonyl-4-(1-carboxycyclobut-1-oxy)quinoline.

Another preferred class of this subgroup of compounds is that class of compounds wherein:

$R^3$ is alkoxy; and $R^5$ is hydrogen.

Preferred compounds of this class of compounds are those compounds selected from the group consisting of the following:

2-[1-(4-(ethoxycarbonyl)piperazin-1-yl)carbonyl-2-carboxyethyl]aminocarbonyl-4-methoxyquinoline;

2-[1-(4-(ethoxycarbonyl)piperazin-1-yl)carbonyl-3-carboxypropyl]aminocarbonyl-4-methoxyquinoline;

2-[1-(4-(ethoxycarbonyl)piperazin-1-yl)carbonyl-4-(1,1-dimethylethoxy)carbonylbutyl]aminocarbonyl-4-methoxyquinoline;

2-[1-(4-(ethoxycarbonyl)piperazin-1-yl)carbonyl-4-carboxybutyl]aminocarbonyl-4-methoxyquinoline;

2-[1-(4-(ethoxycarbonyl)piperazin-1-yl)carbonyl-2-carboxyethyl]aminocarbonyl-4-methoxyquinoline;

2-[1-(4-(ethoxycarbonyl)piperazin-1-yl)carbonyl-3-carboxypropyl]aminocarbonyl-4-ethoxyquinoline;

2-[1-(4-(ethoxycarbonyl)piperazin-1-yl)carbonyl-3-carboxypropyl]aminocarbonyl-4-methoxyquinoline;

2-[1-(4-(ethoxycarbonyl)piperazin-1-yl)carbonyl-2-((1,1-dimethylethoxy)carbonyl)ethyl]aminocarbonyl-4-methoxyquinoline;

2-[1-(4-(ethoxycarbonyl)piperazin-1-yl)carbonyl-3-carboxypropyl][methyl]aminocarbonyl-4-methoxyquinoline;

2-[1-(4-((1,1-dimethylethoxy)carbonyl)piperazin-1-yl)carbonyl-3-(methoxycarbonyl)propyl]aminocarbonyl-4-methoxyquinoline;

2-[1-(4-(ethoxycarbonyl)piperazin-1-yl)carbonyl-3-(methoxycarbonyl)propyl]aminocarbonyl-4-methoxyquinoline;

2-[1-(4-(ethoxycarbonyl)piperazin-1-yl)carbonyl-5-(methoxycarbonyl)pentyl]aminocarbonyl-4-methoxyquinoline;

2-[1-(4-(ethoxycarbonyl)piperazin-1-yl)carbonyl-5-(carboxy)pentyl]aminocarbonyl-4-methoxyquinoline;

2-[1-(4-(ethoxycarbonyl)piperazin-1-yl)carbonyl-3-(1,1-dimethylethoxycarbonyl)propyl]aminocarbonyl-7-chloro-4-methoxyquinoline;

2-[1-(4-(ethoxycarbonyl)piperazin-1-yl)carbonyl-3-carboxypropyl]aminocarbonyl-7-chloro-4-methoxyquinoline; and 2-[1-(4-(ethoxycarbonyl)piperazin-1-yl)carbonyl-3-carboxypropyl]aminocarbonyl-5,7-dichloro-4-methoxyquinoline.

Another preferred class of this subgroup of compounds is that class of compounds wherein:

$R^3$ is alkoxy; and $R^5$ is alkyl or hydroxyalkyl.

Preferred compounds of this class of compounds are those compounds selected from the group consisting of the following:

2-[1-(2-methyl-4-(ethoxycarbonyl)piperazin-1-yl)carbonyl-3-(methoxycarbonyl)propyl]aminocarbonyl-4-methoxyquinoline;

2-[1-(2-methyl-4-(ethoxycarbonyl)piperazin-1-yl)carbonyl-3-carboxypropyl]aminocarbonyl-4-methoxyquinoline;

2-[1-(3-(1-methylethyl)-4-(ethoxycarbonyl)piperazin-1-yl)carbonyl-3-(1,1-dimethylethoxycarbonyl)propyl]aminocarbonyl-4-methoxyquinoline;

2-[1-(3-(2-methylpropyl)-4-(ethoxycarbonyl)piperazin-1-yl)carbonyl-3-carboxypropyl]aminocarbonyl-4-methoxyquinoline;

2-[1-(2-(2-methylpropyl)-4-(ethoxycarbonyl)piperazin-1-yl)carbonyl-3-(1,1-dimethylethoxycarbonyl)propyl]aminocarbonyl-4-methoxyquinoline;

2-[1-(2-(2-methylpropyl)-4-(ethoxycarbonyl)piperazin-1-yl)carbonyl-3-carboxypropyl]aminocarbonyl-4-methoxyquinoline;

2-[1-(3-(1-methylethyl)-4-(ethoxycarbonyl)piperazin-1-yl)carbonyl-3-carboxypropyl]aminocarbonyl-4-methoxyquinoline;

2-[1-(3-(1-hydroxyethyl)-4-(ethoxycarbonyl)piperazin-1-yl)carbonyl-3-(1,1-dimethylethoxycarbonyl)propyl]aminocarbonyl-4-methoxyquinoline; and 2-[1-(3-(1-hydroxyethyl)-4-(ethoxycarbonyl)piperazin-1-yl)carbonyl-3-carboxypropyl]aminocarbonyl-4-methoxyquinoline.

Another preferred group of compounds of formula (I) as set forth above in the Summary of the Invention is that group of compounds wherein:

a is 1 or 2;

b is 1;

A is =N—;

$R^1$ is hydrogen, alkyl, carboxyalkyl, aryl, aralkyl, alkylcarbonyl, alkoxyalkoxyalkylcarbonyl, aryloxyalkylcarbonyl, carboxyalkylcarbonyl, alkoxycarbonylalkylcarbonyl, alkoxycarbonylalkyl, arylcarbonyl, aryloxycarbonyl, aralkoxycarbonyl, cycloalkylcarbonyl, haloalkoxycarbonyl, aminocarbonyl, monoalkylaminocarbonyl, alkoxycarbonylaminocarbonyl, alkylsulfonyl, arylsulfonyl, heterocyclyl, or heterocyclylcarbonyl;

$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, and (carboxyalkyl)(alkyl)aminocarbonylalkyl;

$R^3$ is hydrogen, alkyl, hydroxy, halo, carboxyalkenyl, alkoxy, alkoxycarbonyl, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono(alkoxycarbonylalkyl)aminocarbonyl, mono(carboxyalkyl)aminocarbonyl, mono(di(alkoxycarbonyl)alkyl)aminocarbonyl, mono((alkoxycarbonyl)(carboxy)alkyl)aminocarbonyl, mono(dicarboxyalkyl)aminocarbonyl, aminocarbonylalkoxy, dialkylaminocarbonylalkoxy, monoaralkylaminocarbonylalkoxy, mono(carboxyalkyl)aminocarbonylalkoxy, mono(alkoxycarbonylalkyl)aminocarbonylalkoxy, carboxycycloalkoxy, alkoxycarbonylcycloalkoxy, and aminocarbonylcycloalkoxy;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, or heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, or alkoxycarbonylalkyl;

$R^6$ is —N($R^7$)—C(O)—; and $R^7$ is hydrogen, alkyl, carboxyalkyl, or alkoxycarbonylalkyl.

A preferred subgroup of this group of compounds is that subgroup of compounds wherein:

$R^3$ is hydrogen or alkoxy;

each $R^4$ is independently hydrogen, halo or carboxyalkylamino;

$R^5$ is hydrogen or alkyl; and $R^7$ is hydrogen or alkyl.

A preferred class of this subgroup of compounds is that class of compounds wherein $R^1$ is hydrogen, alkyl, aralkyl, carboxyalkyl or alkoxycarbonylalkyl.

Preferred compounds of this class of compounds are those compounds selected from the group consisting of the following:

2-[(piperazin-1-yl)carbonylmethyl]aminocarbonyl-4-methoxyquinoline;

2-[(2-methyl-4-(4-fluorobenzyl)piperazin-1-yl)carbonylmethyl]aminocarbonyl-4-methoxyquinoline;

2-[(2-methyl-4-benzylpiperazin-1-yl)carbonylmethyl]aminocarbonyl-4-methoxyquinoline;

2-[(4-benzylpiperazin-1-yl)carbonylmethyl]aminocarbonyl-4-methoxyquinoline;

2-[(4-ethylpiperazin-1-yl)carbonylmethyl]aminocarbonyl-4-methoxyquinoline;

2-[(4-(1,1-dimethylethoxy)carbonylmethylpiperazin-1-yl)carbonylmethyl]aminocarbonyl-4-methoxyquinoline;

2-[(4-(carboxymethyl)piperazin-1-yl)carbonylmethyl]aminocarbonyl-4-methoxyquinoline;

2-[(4-methylpiperazin-1-yl)carbonylmethyl]aminocarbonyl-4-methoxyquinoline;

2-[1-(piperazin-1-yl)carbonyl-3-(methoxycarbonyl)propyl]aminocarbonyl-4-methoxyquinoline; and 2-[1-(2-methyl-4-(benzyl)piperazin-1-yl)carbonyl-3-(1,1-dimethylethoxycarbonyl)propyl]aminocarbonyl-4-methoxyquinoline.

Another preferred class of this subgroup of compounds is that class of compounds wherein $R^1$ is aryl.

Preferred compounds of this class of compounds are those compounds selected from the group consisting of the following:

2-[(4-(2-methyl-5-chlorophenyl)piperazin-1-yl)carbonylmethyl]aminocarbonyl-4-methoxyquinoline;

2-[1-(4-(3-methylphenyl)piperazin-1-yl)carbonyl-3-(1,1-dimethylethoxycarbonyl)propyl]aminocarbonyl-4-methoxyquinoline;

2-[1-(4-(3-methylphenyl)piperazin-1-yl)carbonyl-3-carboxypropyl]aminocarbonyl-4-methoxyquinoline;

2-[1-(4-(3-chlorophenyl)piperazin-1-yl)carbonyl-3-(1,1-dimethylethoxycarbonyl)propyl]aminocarbonyl-4-methoxyquinoline;

2-[1-(4-(3-methylphenyl)-3-methylpiperazin-1-yl)carbonyl-3-(1,1-dimethylethoxycarbonyl)propyl]aminocarbonyl-4-methoxyquinoline;

2-[1-(4-(3-chlorophenyl)piperazin-1-yl)carbonyl-3-carboxypropyl]aminocarbonyl-4-methoxyquinoline;

2-[1-(3-methyl-4-(3-methylphenyl)piperazin-1-yl)carbonyl-3-carboxypropyl]aminocarbonyl-4-methoxyquinoline;

2-[(4-(3-chlorophenyl)piperazin-1-yl)carbonylmethyl]aminocarbonyl-4-methoxyquinoline;

2-[(3-methyl-4-(3-methylphenyl)piperazin-1-yl)carbonylmethyl]aminocarbonyl-4-methoxyquinoline; and 2-[(4-(3-methylphenyl)piperazin-1-yl)carbonylmethyl]aminocarbonyl-4-methoxyquinoline.

Another preferred class of this subgroup of compounds is that class of compounds wherein $R^1$ is heterocyclyl or heterocyclylcarbonyl.

Preferred compounds of this class of compounds are those compounds selected from the group consisting of the following:

2-[1-(4-(pyrimidin-2-yl)piperazin-1-yl)carbonyl-3-(methoxycarbonyl)propyl]aminocarbonyl-4-methoxyquinoline;

2-[1-(4-(benzoxazol-2-yl)piperazin-1-yl)carbonyl-3-(methoxycarbonyl)propyl]aminocarbonyl-4-methoxyquinoline;

2-[1-(4-(benzthiazol-2-yl)piperazin-1-yl)carbonyl-3-(methoxycarbonyl)propyl]aminocarbonyl-4-methoxyquinoline;

2-[1-(4-(pyrimidin-2-yl)piperazin-1-yl)carbonyl-3-carboxypropyl]aminocarbonyl-4-methoxyquinoline;

2-[1-(4-(benzoxazol-2-yl)piperazin-1-yl)carbonyl-3-carboxypropyl]aminocarbonyl-4-methoxyquinoline;

2-[1-(4-(benzthiazol-2-yl)piperazin-1-yl)carbonyl-3-carboxypropyl]aminocarbonyl-4-methoxyquinoline;

2-[(4-(2-hydroxy-3-chloropyridin-5-yl)carbonylpiperazin-1-yl)carbonylmethyl]aminocarbonyl-4-methoxyquinoline;

2-[1-(3-(2-methylpropyl)-4-(furan-2-ylcarbonyl)piperazin-1-yl)carbonyl-3-carboxypropyl]aminocarbonyl-4-methoxyquinoline;

2-[1-(3-(1-methylethyl)-4-(furan-2-ylcarbonyl)piperazin-1-yl)carbonyl-3-carboxypropyl]aminocarbonyl-4-methoxyquinoline;

2-[1-(3-benzyl-4-(furan-2-ylcarbonyl)piperazin-1-yl)carbonyl-3-carboxypropyl]aminocarbonyl-4-methoxyquinoline;

2-[1-(3-(4-hydroxybenzyl)-4-(furan-2-ylcarbonyl)piperazin-1-yl)carbonyl-3-carboxypropyl]aminocarbonyl-4-methoxyquinoline;

2-[1-(4-(furan-2-ylcarbonyl)piperazin-1-yl)carbonyl-3-carboxypropyl]aminocarbonyl-4-methoxyquinoline;

2-[1-(4-(pyridin-2-yl)piperazin-1-yl)carbonyl-3-(1,1-dimethylethoxycarbonyl)propyl]aminocarbonyl-4-methoxyquinoline;

2-[1-(4-(pyridin-2-yl)piperazin-1-yl)carbonyl-3-carboxypropyl]aminocarbonyl-4-methoxyquinoline;

2-[1-(4-(piperidin-4-ylcarbonyl)piperazin-1-yl)carbonyl-3-carboxypropyl]aminocarbonyl-4-methoxyquinoline;

2-[(4-(furan-2-yl)carbonylpiperazin-1-yl)carbonylmethyl]aminocarbonyl-4-methoxyquinoline;

2-[(4-(thien-2-yl)carbonylpiperazin-1-yl)carbonylmethyl]aminocarbonyl-4-methoxyquinoline;

2-[(4-(morpholin-4-yl)carbonylpiperazin-1-yl)carbonylmethyl]aminocarbonyl-4-methoxyquinoline; and 2-[(4-(pyridin-2-yl)piperazin-1-yl)carbonylmethyl]aminocarbonyl-4-methoxyquinoline.

Another preferred class of this subgroup of compounds is that class of compounds wherein $R^1$ is aminocarbonyl, monoalkylaminocarbonyl or alkoxycarbonylaminocarbonyl.

Preferred compounds of this class of compounds are those compounds selected from the group consisting of the following:

2-[1-(4-((1,1-dimethylethyl)aminocarbonyl)piperazin-1-yl)carbonyl-3-(methoxycarbonyl)propyl]aminocarbonyl-4-methoxyquinoline;

2-[1-(4-((1,1-dimethylethyl)aminocarbonyl)piperazin-1-yl)
carbonyl-3-carboxypropyl]aminocarbonyl-4-methoxyquinoline;

2-[1-(4-(aminocarbonyl)piperazin-1-yl)carbonyl-3-(methoxycarbonyl)propyl]aminocarbonyl-4-methoxyquinoline;

2-[1-(4-(aminocarbonyl)piperazin-1-yl)carbonyl-3-carboxypropyl]aminocarbonyl-4-methoxyquinoline;

2-[(4-((1,1-dimethylethyl)aminocarbonyl)piperazin-1-yl)carbonylmethyl]aminocarbonyl-4-methoxyquinoline;

2-[(4-((1-methylethyl)aminocarbonyl)piperazin-1-yl)carbonylmethyl]aminocarbonyl-4-methoxyquinoline;

2-[(4-((n-propyl)aminocarbonyl)piperazin-1-yl)carbonylmethyl]aminocarbonyl-4-methoxyquinoline;

2-[(4-((n-butyl)aminocarbonyl)piperazin-1-yl)carbonylmethyl]aminocarbonyl-4-methoxyquinoline;

2-[(4-((n-hexyl)aminocarbonyl)piperazin-1-yl)carbonylmethyl]aminocarbonyl-4-methoxyquinoline;

2-[(4-((n-pentyl)aminocarbonyl)piperazin-1-yl)carbonylmethyl]aminocarbonyl-4-methoxyquinoline; and 2-[(4-((ethoxycarbonyl)aminocarbonyl)piperazin-1-yl)carbonylmethyl]aminocarbonyl-4-methoxyquinoline.

Another preferred class of this subgroup of compounds is that class of compounds wherein $R^1$ is alkylcarbonyl, alkoxyalkoxyalkylcarbonyl, aryloxyalkylcarbonyl, carboxyalkylcarbonyl, alkoxycarbonylalkylcarbonyl, arylcarbonyl, aryloxycarbonyl, aralkoxycarbonyl, cycloalkylcarbonyl, or haloalkoxycarbonyl.

Preferred compounds of this class of compounds are those compounds selected from the group consisting of the following:

2-[(4-(trichloromethoxycarbonyl)piperazin-1-yl)carbonylmethyl]aminocarbonyl-4-methoxyquinoline;

2-[(4-(benzyloxycarbonyl)piperazin-1-yl)carbonylmethyl]aminocarbonyl-4-methoxyquinoline;

2-[(4-(1-chloroethoxycarbonyl)piperazin-1-yl)carbonylmethyl]aminocarbonyl-4-methoxyquinoline;

2-[(4-(phenoxycarbonyl)piperazin-1-yl)carbonylmethyl]aminocarbonyl-4-methoxyquinoline;

2-[(4-(2-carboxyethyl)carbonylpiperazin-1-yl)carbonylmethyl]aminocarbonyl-4-methoxyquinoline;

2-[(4-(5-(ethoxycarbonyl)pentyl)carbonylpiperazin-1-yl)carbonylmethyl]aminocarbonyl-4-methoxyquinoline;

2-[(4-(5-carboxypentyl)carbonylpiperazin-1-yl)carbonylmethyl]aminocarbonyl-4-methoxyquinoline;

2-[(4-(4-acetamidophenyl)carbonylpiperazin-1-yl)carbonylmethyl]aminocarbonyl-4-methoxyquinoline;

2-[(4-((2-methoxyethoxy)methyl)carbonylpiperazin-1-yl)carbonylmethyl]aminocarbonyl-4-methoxyquinoline;

2-[(4-(2-methoxycarbonylphenyl)carbonylpiperazin-1-yl)carbonylmethyl]aminocarbonyl-4-methoxyquinoline;

2-[(4-(n-propylsulfonyl)piperazin-1-yl)carbonylmethyl]aminocarbonyl-4-methoxyquinoline;

2-[(4-(2,5-dibromophenyl)sulfonylpiperazin-1-yl)carbonylmethyl]aminocarbonyl-4-methoxyquinoline;

2-[(4-(2,6-diflourophenyl)sulfonylpiperazin-1-yl)carbonylmethyl]aminocarbonyl-4-methoxyquinoline;

2-[(4-(3-bromophenyl)carbonylpiperazin-1-yl)carbonylmethyl]aminocarbonyl-4-methoxyquinoline;

2-[(4-(4-ethylphenyl)carbonylpiperazin-1-yl)carbonylmethyl]aminocarbonyl-4-methoxyquinoline;

2-[(4-(4-n-propylphenyl)carbonylpiperazin-1-yl)carbonylmethyl]aminocarbonyl-4-methoxyquinoline;

2-[(4-(4-n-butylphenyl)carbonylpiperazin-1-yl)carbonylmethyl]aminocarbonyl-4-methoxyquinoline;

2-[(4-(phenoxymethyl)carbonylpiperazin-1-yl)carbonylmethyl]aminocarbonyl-4-methoxyquinoline;

2-[(4-(2,2-dimethylpropyl)carbonylpiperazin-1-yl)carbonylmethyl]aminocarbonyl-4-methoxyquinoline;

2-[(4-(2-ethoxycarbonylethyl)carbonylpiperazin-1-yl)carbonylmethyl]aminocarbonyl-4-methoxyquinoline;

2-[(4-(n-propyl)carbonylpiperazin-1-yl)carbonylmethyl]aminocarbonyl-4-methoxyquinoline;

2-[(4-(n-pentyl)carbonylpiperazin-1-yl)carbonylmethyl]aminocarbonyl-4-methoxyquinoline;

2-[(4-(2-phenylcyclopropyl)carbonylpiperazin-1-yl)carbonylmethyl]aminocarbonyl-4-methoxyquinoline;

2-[(4-(2-bromo-5-methoxyphenyl)carbonylpiperazin-1-yl)carbonylmethyl]aminocarbonyl-4-methoxyquinoline; and 2-[(4-(n-butyl)carbonylpiperazin-1-yl)carbonylmethyl]aminocarbonyl-4-methoxyquinoline;

2-[(4-(3-trifluoromethoxyphenyl)carbonylpiperazin-1-yl)carbonylmethyl]aminocarbonyl-4-methoxyquinoline.

Another preferred group of compounds of formula (I) as set forth above in the Summary of the Invention is that group of compounds wherein:

a is 1 or 2;

b is 1;

A is =N—;

$R^1$ is alkoxycarbonyl;

$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, (carboxy)(hydroxy)alkyl, carboxyalkoxyalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, or (carboxyalkyl)(alkyl)aminocarbonylalkyl;

$R^3$ is hydrogen, alkyl, hydroxy, halo, carboxyalkenyl, alkoxy, alkoxycarbonyl, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono(alkoxycarbonylalkyl)aminocarbonyl, mono(carboxyalkyl)aminocarbonyl, mono(di(alkoxycarbonyl)alkyl)aminocarbonyl, mono((alkoxycarbonyl)(carboxy)alkyl)aminocarbonyl, mono(dicarboxyalkyl)aminocarbonyl, aminocarbonylalkoxy, dialkylaminocarbonylalkoxy, monoaralkylaminocarbonylalkoxy, mono(carboxyalkyl)aminocarbonylalkoxy, mono(alkoxycarbonylalkyl)aminocarbonylalkoxy, carboxycycloalkoxy, alkoxycarbonylcycloalkoxy, aminocarbonylcycloalkoxy or tetrahydrofuranonlyloxy;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

$R^6$ is —N($R^7$)—C(O)—; and $R^7$ is hydrogen, alkyl, carboxyalkyl, or alkoxycarbonylalkyl.

A preferred subgroup of this group of compounds is that subgroup of compounds wherein:

$R^2$ is hydrogen, alkyl, aryl, aralkyl, hydroxyalkyl, haloalkylsulfonylaminoalkyl, or alkoxycarbonylalkoxycarbonylalkyl; and $R^3$ is alkyl, halo, carboxyalkenyl, alkoxycarbonyl, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono (alkoxycarbonylalkyl)aminocarbonyl, mono (carboxyalkyl)aminocarbonyl, mono(di(alkoxycarbonyl) alkyl)aminocarbonyl, mono((alkoxycarbonyl)(carboxy) alkyl)aminocarbonyl, mono(dicarboxyalkyl) aminocarbonyl, aminocarbonylalkoxy, dialkylaminocarbonylalkoxy, monoaralkylaminocarbonylalkoxy, mono(carboxyalkyl)aminocarbonylalkoxy, mono (alkoxycarbonylalkyl)aminocarbonylalkoxy, carboxycycloalkoxy, alkoxycarbonylcycloalkoxy, aminocarbonylcycloalkoxy, or tetrahydrofuranonyloxy.

Preferred compounds of this subgroup of compounds are those compounds selected from the group consisting of the following:

2-[(4-(ethoxycarbonyl)piperazin-1-yl)carbonylmethyl]aminocarbonyl-4-(ethoxycarbonyl)methoxyquinoline;

2-[(4-(ethoxycarbonyl)piperazin-1-yl)carbonylmethyl]aminocarbonyl-4-(carboxy)methoxyquinoline;

2-[(4-(ethoxycarbonyl)piperazin-1-yl)carbonylmethyl]aminocarbonyl-4-(aminocarbonyl)methoxyquinoline;

2-[1-(4-(ethoxycarbonyl)piperazin-1-yl)carbonyl-3-(((1,1-dimethylethoxy)carbonyl)methoxy)carbonylpropyl]aminocarbonyl-4-((1,1-dimethylethoxy)carbonyl)methoxyquinoline;

2-[(4-(ethoxycarbonyl)piperazin-1-yl)carbonylmethyl]aminocarbonyl-4-(3-(ethoxycarbonyl)propoxy)quinoline;

2-[(4-(ethoxycarbonyl)piperazin-1-yl)carbonylmethyl]aminocarbonyl-4-(3-carboxypropoxy)quinoline;

2-[(4-(ethoxycarbonyl)piperazin-1-yl)carbonylmethyl]aminocarbonyl-4-(3-(ethoxycarbonyl)prop-2-en-1-oxy) quinoline;

2-[(4-(ethoxycarbonyl)piperazin-1-yl)carbonylmethyl]aminocarbonyl-4-(tetrahydro-2-oxofuran-3-yl)oxyquinoline;

2-[(4-(ethoxycarbonyl)piperazin-1-yl)carbonylmethyl]aminocarbonyl-4-(1-carboxy-3-hydroxypropoxy)quinoline;

2-[(4-(ethoxycarbonyl)piperazin-1-yl)carbonylmethyl]aminocarbonyl-4-(1,1-di(ethoxycarbonyl)methoxy)quinoline;

2-[(4-(ethoxycarbonyl)piperazin-1-yl)carbonylmethyl]aminocarbonyl-4-(1,1-di(carboxy)methoxy)quinoline;

2-[(4-(ethoxycarbonyl)piperazin-1-yl)carbonylmethyl]aminocarbonyl-4-(1-(ethoxycarbonyl)ethoxy)quinoline;

2-[(4-(ethoxycarbonyl)piperazin-1-yl)carbonylmethyl]aminocarbonyl-4-(1-carboxyethoxy)quinoline;

2-[(4-(ethoxycarbonyl)piperazin-1-yl)carbonylmethyl]aminocarbonyl-4-(3-(carboxy)prop-1-en-1-oxy)quinoline;

2-[(4-(ethoxycarbonyl)piperazin-1-yl)carbonylmethyl]aminocarbonyl-4-(1-(methoxycarbonyl)propoxy)quinoline;

2-[(4-(ethoxycarbonyl)piperazin-1-yl)carbonylmethyl]aminocarbonyl-4-(1-(carboxy)propoxy)quinoline;

2-[(4-(ethoxycarbonyl)piperazin-1-yl)carbonylmethyl]aminocarbonyl-4-(1-methyl-1-(ethoxycarbonyl)ethoxy) quinoline;

2-[(4-(ethoxycarbonyl)piperazin-1-yl)carbonylmethyl]aminocarbonyl-4-(1-methyl-1-(carboxy)ethoxy)quinoline;

2-[(4-(ethoxycarbonyl)piperazin-1-yl)carbonylmethyl]aminocarbonyl-4-(1-(ethoxycarbonyl)cyclobut-1-oxy)quinoline;

2-[(4-(ethoxycarbonyl)piperazin-1-yl)carbonylmethyl]aminocarbonyl-4-(1-(carboxy)cyclobut-1-oxy)quinoline;

2-[1-(4-(ethoxycarbonyl)piperazin-1-yl)carbonyl-3-((trifluoromethyl)sulfonylamino)propyl]aminocarbonyl-7-methyl-4-(1-(ethoxycarbonyl)cyclobut-1-oxy)quinoline; and 2-[1-(4-(ethoxycarbonyl)piperazin-1-yl)carbonyl-3-((trifluoromethyl)sulfonylamino)propyl]aminocarbonyl-7-methyl-4-(1-carboxycyclobut-1-oxy)quinoline.

Another preferred subgroup of this group of compounds is that subgroup of compounds wherein:

$R^2$ is alkylsulfonylalkyl, aralkoxyalkyl, aminoalkyl, haloalkylsulfonylaminoalkyl, carboxyalkylthioalkyl, alkoxycarbonylalkylthioalkyl, (carboxy)(hydroxy)alkyl, carboxyalkoxyalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl; and $R^3$ is hydrogen, hydroxy or alkoxy.

Preferred compounds of this subgroup of compounds are those compounds selected from the group consisting of the following:

2-[1-(4-(ethoxycarbonyl)piperazin-1-yl)carbonyl-5-((2-chlorobenzyloxy)carbonyl)aminopentyl]aminocarbonyl-4-methoxyquinoline;

2-[1-(4-(ethoxycarbonyl)piperazin-1-yl)carbonyl-2-(benzyloxycarbonyl)ethyl]aminocarbonyl-4-methoxyquinoline;

2-[1-(4-(ethoxycarbonyl)piperazin-1-yl)carbonyl-3-(benzyloxycarbonyl)propyl]aminocarbonyl-4-methoxyquinoline;

2-[1-(4-(ethoxycarbonyl)piperazin-1-yl)carbonyl-2-(benzyloxy)ethyl]aminocarbonyl-4-methoxyquinoline;

2-[1-(4-(ethoxycarbonyl)piperazin-1-yl)carbonyl-5-aminopentyl]aminocarbonyl-4-methoxyquinoline;

2-[1-(4-(ethoxycarbonyl)piperazin-1-yl)carbonyl-2-(aminocarbonyl)ethyl]aminocarbonyl-4-methoxyquinoline;

2-[1-(4-(ethoxycarbonyl)piperazin-1-yl)carbonyl-3-(aminocarbonyl)propyl]aminocarbonyl-4-methoxyquinoline;

2-[1-(4-(ethoxycarbonyl)piperazin-1-yl)carbonyl-2-(benzyloxycarbonyl)ethyl]aminocarbonyl-4-methoxyquinoline;

2-[1-(4-(ethoxycarbonyl)piperazin-1-yl)carbonyl-2-(((carboxy)methyl)aminocarbonyl)ethyl]aminocarbonyl-4-methoxyquinoline;

2-[1-(4-(ethoxycarbonyl)piperazin-1-yl)carbonyl-3-(benzyloxycarbonyl)propyl]aminocarbonyl-4-ethoxyquinoline;

2-[1-(4-(ethoxycarbonyl)piperazin-1-yl)carbonyl-3-(benzyloxycarbonyl)propyl]aminocarbonyl-4-methoxyquinoline;

2-[1-(4-(ethoxycarbonyl)piperazin-1-yl)carbonyl-3-(benzyloxycarbonyl)propyl]aminocarbonyl-4-methoxyquinoline;

2-[1-(4-(ethoxycarbonyl)piperazin-1-yl)carbonyl-2-(4-(1,1-dimethylethoxy)carbonylphenyl)ethyl]aminocarbonyl-4-methoxyquinoline;

2-[1-(4-(ethoxycarbonyl)piperazin-1-yl)carbonyl-2-((methoxycarbonyl)methyl)thioethyl]aminocarbonyl-4-methoxyquinoline;

2-[1-(4-(ethoxycarbonyl)piperazin-1-yl)carbonyl-2-(carboxymethyl)thioethyl]aminocarbonyl-4-methoxyquinoline;
2-[1-(4-(ethoxycarbonyl)piperazin-1-yl)carbonyl-3-((carboxymethyl)aminocarbonyl)propyl]aminocarbonyl-4-methoxyquinoline;
2-[1-(4-(ethoxycarbonyl)piperazin-1-yl)carbonyl-3-(((1,1-dimethylethoxycarbonyl)methyl)aminocarbonyl)propyl]aminocarbonyl-4-methoxyquinoline;
2-[1-(4-(ethoxycarbonyl)piperazin-1-yl)carbonyl-2-(((1,1-dimethylethoxycarbonyl)methyl)(methyl)aminocarbonyl)ethyl]aminocarbonyl-4-methoxyquinoline;
2-[1-(4-(ethoxycarbonyl)piperazin-1-yl)carbonyl-2-(((carboxy)methyl)(methyl)aminocarbonyl)ethyl]aminocarbonyl-4-methoxyquinoline;
2-[1-(4-(ethoxycarbonyl)piperazin-1-yl)carbonyl-2-(carboxy)methoxyethyl]aminocarbonyl-4-methoxyquinoline;
2-[1-(4-(ethoxycarbonyl)piperazin-1-yl)carbonyl-3-(benzyloxycarbonyl)propyl]aminocarbonyl-5-nitroquinoline;
2-[1-(4-(ethoxycarbonyl)piperazin-1-yl)carbonyl-3-((ethoxycarbonyl)methoxycarbonyl)propyl]aminocarbonyl-5-aminoquinoline; and
2-[1-(4-(ethoxycarbonyl)piperazin-1-yl)carbonyl-3-(methylsulfonyl)propyl]aminocarbonyl-4-methoxyquinoline.

Another preferred subgroup of this group of compounds is that subgroup of compounds wherein:
$R^2$ is hydrogen, alkyl, aryl, aralkyl or hydroxyalkyl; and
$R^3$ is hydrogen, hydroxy, or alkoxy.

Preferred compounds of this subgroup of compounds are those compounds selected from the group consisting of the following:
2-[(4-(1-dimethylethoxycarbonyl)piperazin-1-yl)carbonylmethyl]aminocarbonyl-4-methoxyquinoline;
2-[(3-methyl-4-(ethoxycarbonyl)piperazin-1-yl)carbonylmethyl]aminocarbonyl-4-methoxyquinoline;
2-[(2-methyl-4-(ethoxycarbonyl)piperazin-1-yl)carbonylmethyl]aminocarbonyl-4-methoxyquinoline;
2-[(4-(2-methylpropoxycarbonyl)piperazin-1-yl)carbonylmethyl]aminocarbonyl-4-methoxyquinoline;
2-[(4-(methoxycarbonyl)piperazin-1-yl)carbonylmethyl]aminocarbonyl-4-methoxyquinoline;
2-[1-(4-(ethoxycarbonyl)piperazin-1-yl)carbonylethyl]aminocarbonyl-4-methoxyquinoline;
2-[(2-methyl-4-(ethoxycarbonyl)piperazin-1-yl)carbonylmethyl]aminocarbonyl-4-methoxyquinoline;
2-[1-(4-(ethoxycarbonyl)piperazin-1-yl)carbonyl-2-phenylethyl]aminocarbonyl-4-methoxyquinoline;
2-[1-(4-(ethoxycarbonyl)piperazin-1-yl)carbonyl-2-methylpropyl]aminocarbonyl-4-methoxyquinoline;
2-[(4-(methoxycarbonyl)piperazin-1-yl)carbonylmethyl]aminocarbonyl-4-methoxyquinoline;
2-[1-(4-(ethoxycarbonyl)piperazin-1-yl)carbonyl-2-hydroxyethyl]aminocarbonyl-4-methoxyquinoline;
2-[(4-(ethoxycarbonyl)piperazin-1-yl)carbonylmethyl]aminocarbonyl-4-ethoxyquinoline;
2-[(3-(benzyloxy)carbonyl-4-(ethoxycarbonyl)piperazin-1-yl)carbonylmethyl]aminocarbonyl-4-methoxyquinoline;
2-[(3-carboxy-4-(ethoxycarbonyl)piperazin-1-yl)carbonylmethyl]aminocarbonyl-4-methoxyquinoline;
2-[(4-(ethoxycarbonyl)piperazin-1-yl)carbonylmethyl](carboxymethyl)aminocarbonyl-4-methoxyquinoline;
2-[1-(4-(ethoxycarbonyl)piperazin-1-yl)carbonyl-2-(4-carboxyphenyl)ethyl]aminocarbonyl-4-methoxyquinoline;
2-[(2,4-di(ethoxycarbonyl)piperazin-1-yl)carbonylmethyl]aminocarbonyl-4-methoxyquinoline;
2-[(2-carboxy-4-(ethoxycarbonyl)piperazin-1-yl)carbonylmethyl]aminocarbonyl-4-methoxyquinoline;
2-[(4-(ethoxycarbonyl)piperazin-1-yl)carbonylmethyl]aminocarbonyl-4-n-propoxyquinoline;
2-[(3-(methoxycarbonyl)methyl-4-(ethoxycarbonyl)piperazin-1-yl)carbonylmethyl]aminocarbonyl-4-methoxyquinoline;
2-[(3-(carboxy)methyl-4-(ethoxycarbonyl)piperazin-1-yl)carbonylmethyl]aminocarbonyl-4-methoxyquinoline;
2-[1-(4-(ethoxycarbonyl)piperazin-1-yl)carbonyl-1-(4-hydroxyphenyl)methyl]aminocarbonyl-4-methoxyquinoline;
2-[1-(4-(ethoxycarbonyl)piperazin-1-yl)carbonyl-1-(4-carboxyphenyl)methyl]aminocarbonyl-4-methoxyquinoline;
2-[(2-(methoxycarbonyl)methyl-4-(ethoxycarbonyl)piperazin-1-yl)carbonylmethyl]aminocarbonyl-4-methoxyquinoline;
2-[(2-(carboxy)methyl-4-(ethoxycarbonyl)piperazin-1-yl)carbonylmethyl]aminocarbonyl-4-methoxyquinoline;
2-[1-(4-(ethoxycarbonyl)piperazin-1-yl)carbonyl-1-(4-(carboxymethoxy)phenyl)methyl]aminocarbonyl-4-methoxyquinoline;
2-[1-(4-(ethoxycarbonyl)piperazin-1-yl)carbonyl-2-(2-(ethoxycarbonyl)methoxyphenyl)ethyl]aminocarbonyl-4-methoxyquinoline;
2-[1-(4-(ethoxycarbonyl)piperazin-1-yl)carbonyl-2-(2-carboxyphenyl)ethyl]aminocarbonyl-4-methoxyquinoline;
2-[1-(4-(ethoxycarbonyl)piperazin-1-yl)carbonyl-2-(2-(carboxy)methoxyphenyl)ethyl]aminocarbonyl-4-methoxyquinoline;
2-[1-(4-(ethoxycarbonyl)piperazin-1-yl)carbonyl-2-(2-hydroxyphenyl)ethyl]aminocarbonyl-4-methoxyquinoline;
2-[1-(4-(ethoxycarbonyl)piperazin-1-yl)carbonyl-2-(3-hydroxyphenyl)ethyl]aminocarbonyl-4-methoxyquinoline;
2-[1-(4-(ethoxycarbonyl)piperazin-1-yl)carbonyl-2-(3-(ethoxycarbonyl)methoxyphenyl)ethyl]aminocarbonyl-4-methoxyquinoline;
2-[1-(4-(ethoxycarbonyl)piperazin-1-yl)carbonyl-2-(3-(carboxy)methoxyphenyl)ethyl]aminocarbonyl-4-methoxyquinoline;
2-[1-(4-(ethoxycarbonyl)piperazin-1-yl)carbonyl-2-(3-carboxyphenyl)ethyl]aminocarbonyl-4-methoxyquinoline;
2-[((4-(ethoxycarbonyl)piperazin-1-yl)carbonylmethyl)carbonyl]amino-4-hydroxyquinoline;
2-[(4-(ethoxycarbonyl)piperazin-1-yl)carbonylmethyl]aminocarbonylquinoline;
2-[(4-(ethoxycarbonyl)piperazin-1-yl)carbonylmethyl]aminocarbonyl-4-hydroxyquinoline; and
2-[(4-(ethoxycarbonyl)piperazin-1-yl)carbonylmethyl]aminocarbonyl-4-methoxyquinoline.

Another preferred group of compounds of formula (I) as set forth above in the Summary of the Invention is that group of compounds wherein:
a is 1 or 2;
b is 1;
A is =N—;
$R^1$ is hydrogen or alkoxycarbonyl;
$R^2$ is carboxyalkyl or alkoxycarbonylalkyl;
$R^3$ is hydrogen, hydroxy, halo, carboxyalkenyl, alkoxy, alkoxycarbonyl, di(alkoxycarbonyl)alkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono(alkoxycarbonylalkyl)aminocarbonyl, mono(carboxyalkyl)aminocarbonyl, mono(di(alkoxycarbonyl)

alkyl)aminocarbonyl, mono((alkoxycarbonyl)(carboxy)alkyl)aminocarbonyl, mono(dicarboxyalkyl)aminocarbonyl, dialkylaminocarbonylalkoxy, monoaralkylaminocarbonylalkoxy, mono(carboxyalkyl)aminocarbonylalkoxy, or mono(alkoxycarbonylalkyl)aminocarbonylalkoxy;

each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;

$R^6$ is —N($R^7$)—C(O)—; and $R^7$ is hydrogen, alkyl, carboxyalkyl, or alkoxycarbonylalkyl.

A preferred subgroup of this group of compounds is that subgroup of compounds wherein $R^3$ is hydrogen, hydroxy, halo, alkoxy, hydroxyalkoxy, haloalkoxy, haloalkenyloxy or alkylthio.

Preferred compounds of this subgroup of compounds are those compounds selected from the group consisting of the following:

2-[1-(piperazin-1-yl)carbonyl-3-carboxypropyl]aminocarbonyl-4-methoxyquinoline;

2-[1-(4-(ethoxycarbonyl)piperazin-1-yl)carbonyl-3-carboxypropyl]aminocarbonyl-4-hydroxyquinoline;

2-[1-(4-(ethoxycarbonyl)piperazin-1-yl)carbonyl-3-carboxypropyl]aminocarbonyl-8-methoxy-4-hydroxyquinoline;

2-[1-(4-(ethoxycarbonyl)piperazin-1-yl)carbonyl-3-methoxycarbonylpropyl]aminocarbonyl-5-nitroquinoline;

2-[1-(4-(ethoxycarbonyl)piperazin-1-yl)carbonyl-3-(methoxycarbonyl)propyl]aminocarbonyl-4-(2,2,2-trifluoroethoxy)quinoline;

2-[1-(4-(ethoxycarbonyl)piperazin-1-yl)carbonyl-3-(methoxycarbonyl)propyl]aminocarbonyl-4-(3,3,3-trifluoropropoxy)quinoline;

2-[1-(4-(ethoxycarbonyl)piperazin-1-yl)carbonyl-3-carboxypropyl]aminocarbonyl-4-(3,3,3-trifluoropropoxy)quinoline;

2-[1-(4-(ethoxycarbonyl)piperazin-1-yl)carbonyl-3-(methoxycarbonyl)propyl]aminocarbonyl-4-(3,4,4-trifluorobut-3-en-1-oxy)quinoline;

2-[1-(4-(ethoxycarbonyl)piperazin-1-yl)carbonyl-3-carboxypropyl]aminocarbonyl-4-(3,4,4-trifluorobut-3-en-1-oxy)quinoline;

2-[1-(4-(ethoxycarbonyl)piperazin-1-yl)carbonyl-3-carboxypropyl]aminocarbonyl-4-(2-hydroxyethoxy)quinoline;

2-[1-(4-(ethoxycarbonyl)piperazin-1-yl)carbonyl-3-carboxypropyl]aminocarbonyl-7-chloro-4-(methylthio)quinoline; and 2-[1-(4-(ethoxycarbonyl)piperazin-1-yl)carbonyl-3-carboxypropyl]aminocarbonyl-5,7-dichloro-4-(methylthio)quinoline.

Another preferred subgroup of this group of compounds is that subgroup of compounds wherein $R^3$ is carboxyalkenyl, alkoxycarbonyl, di(alkoxycarbonyl)alkoxy, di(carboxy)alkoxy, (carboxy)(hydroxy)alkoxy, (dialkylamino)(carboxy)alkoxy, cyanoalkoxy, (cycloalkyl)(alkoxycarbonyl)alkoxy, (cycloalkyl)(carboxy)alkoxy, carboxy, dialkylaminocarbonylalkoxy, monoaralkylaminocarbonylalkoxy, mono(carboxyalkyl)aminocarbonylalkoxy, or mono(alkoxycarbonylalkyl)aminocarbonylalkoxy.

Preferred compounds of this subgroup of compounds are those compounds selected from the group consisting of the following:

2-[1-(4-(ethoxycarbonyl)piperazin-1-yl)carbonyl-3-carboxypropyl]aminocarbonyl-4-(3-hydroxy-1-carboxypropoxy)quinoline;

2-[1-(4-(ethoxycarbonyl)piperazin-1-yl)carbonyl-3-(methoxycarbonyl)propyl]aminocarbonyl-4-(cyanomethoxy)quinoline;

2-[1-(4-(ethoxycarbonyl)piperazin-1-yl)carbonyl-3-(methoxycarbonyl)propyl]aminocarbonyl-4-(dimethylaminocarbonyl)methoxyquinoline;

2-[1-(4-(ethoxycarbonyl)piperazin-1-yl)carbonyl-3-carboxypropyl]aminocarbonyl-4-(dimethylaminocarbonyl)methoxyquinoline;

2-[1-(4-(ethoxycarbonyl)piperazin-1-yl)carbonyl-3-(methoxycarbonyl)propyl]aminocarbonyl-4-(ethoxycarbonylmethylaminocarbonyl)methoxyquinoline;

2-[1-(4-(ethoxycarbonyl)piperazin-1-yl)carbonyl-3-(methoxycarbonyl)propyl]aminocarbonyl-4-(1-cyanoethoxy)quinoline;

2-[1-(4-(ethoxycarbonyl)piperazin-1-yl)carbonyl-3-(methoxycarbonyl)propyl]aminocarbonyl-4-(benzylaminocarbonyl)methoxyquinoline;

2-[1-(4-(ethoxycarbonyl)piperazin-1-yl)carbonyl-3-carboxypropyl]aminocarbonyl-4-(benzylaminocarbonyl)methoxyquinoline;

2-[1-(4-(ethoxycarbonyl)piperazin-1-yl)carbonyl-3-carboxypropyl]aminocarbonyl-4-((carboxy)methylamino)carbonylmethoxyquinoline;

2-[1-(4-(ethoxycarbonyl)piperazin-1-yl)carbonyl-3-carboxypropyl]aminocarbonyl-4-(1-carboxy-3-(diethylamino)propoxy)quinoline;

2-[1-(4-(ethoxycarbonyl)piperazin-1-yl)carbonyl-3-(1,1-dimethylethoxycarbonyl)propyl]aminocarbonyl-4-(methoxycarbonyl)quinoline;

2-[1-(4-(ethoxycarbonyl)piperazin-1-yl)carbonyl-3-carboxypropyl]aminocarbonyl-4-(methoxycarbonyl)quinoline;

2-[1-(4-(ethoxycarbonyl)piperazin-1-yl)carbonyl-3-carboxypropyl]aminocarbonyl-4-carboxyquinoline;

2-[1-(4-(ethoxycarbonyl)piperazin-1-yl)carbonyl-3-(methoxycarbonyl)propyl]aminocarbonyl-4-(1,1-di(ethoxycarbonyl)methoxy)quinoline;

2-[1-(4-(ethoxycarbonyl)piperazin-1-yl)carbonyl-3-carboxypropyl]aminocarbonyl-4-(1,1-di(carboxy)methoxy)quinoline;

2-[1-(4-(ethoxycarbonyl)piperazin-1-yl)carbonyl-3-carboxypropyl]aminocarbonyl-4-(2-carboxyethenyl)quinoline (34 mg);

2-[1-(4-(ethoxycarbonyl)piperazin-1-yl)carbonyl-3-carboxypropyl]aminocarbonyl-7-methyl-4-(1-cyclohexyl-1-carboxymethoxy)quinoline; and 2-[1-(4-(ethoxycarbonyl)piperazin-1-yl)carbonyl-3-carboxypropyl]aminocarbonyl-7-methyl-4-(1-cyclohexyl-1-(methoxycarbonyl)methoxy)quinoline.

Another preferred subgroup of this group of compounds is that subgroup of compounds wherein $R^3$ is mono(alkoxycarbonylalkyl)aminocarbonyl, mono(carboxyalkyl)aminocarbonyl, mono(di(alkoxycarbonyl)alkyl)aminocarbonyl, mono((alkoxycarbonyl)(carboxy)alkyl)aminocarbonyl, or mono(dicarboxyalkyl)aminocarbonyl.

Preferred compounds of this subgroup of compounds are those compounds selected from the group consisting of the following:

2-[1-(4-(ethoxycarbonyl)piperazin-1-yl)carbonyl-3-(1,1-dimethylethoxycarbonyl)propyl]aminocarbonyl-4-(methoxycarbonylmethyl)aminocarbonylquinoline;

2-[1-(4-(ethoxycarbonyl)piperazin-1-yl)carbonyl-3-(1,1-dimethylethoxycarbonyl)propyl]aminocarbonyl-4-(carboxymethyl)aminocarbonylquinoline;

2-[1-(4-(ethoxycarbonyl)piperazin-1-yl)carbonyl-3-carboxypropyl]aminocarbonyl-4-(carboxymethyl)aminocarbonylquinoline;

2-[1-(4-(ethoxycarbonyl)piperazin-1-yl)carbonyl-3-(1,1-dimethylethoxycarbonyl)propyl]aminocarbonyl-4-[(1-(methoxycarbonyl)-3-(1,1-dimethylethoxycarbonyl)propyl)aminocarbonyl]quinoline;

2-[1-(4-(ethoxycarbonyl)piperazin-1-yl)carbonyl-3-(1,1-dimethylethoxycarbonyl)propyl]aminocarbonyl-4-[(1-carboxy-3-(1,1-dimethylethoxycarbonyl)propyl)aminocarbonyl]quinoline;

2-[1-(4-(ethoxycarbonyl)piperazin-1-yl)carbonyl-3-carboxypropyl]aminocarbonyl-4-[(1-(methoxycarbonyl)-3-carboxypropyl)aminocarbonyl]quinoline; and 2-[1-(4-(ethoxycarbonyl)piperazin-1-yl)carbonyl-3-carboxypropyl]aminocarbonyl-4-[(1,3-dicarboxypropyl)aminocarbonyl]quinoline.

Another preferred subgroup of this group of compounds is that subgroup of compounds wherein $R^3$ is (dialkylaminocarbonylalkyl)(alkyl)amino, (carboxyalkyl)(alkyl)amino, (hydroxyalkyl)(alkyl)amino, (dialkylaminoalkyl)(alkyl)amino, or carboxyalkylamino.

Preferred compounds of this subgroup of compounds are those compounds selected from the group consisting of the following:

2-[1-(4-(ethoxycarbonyl)piperazin-1-yl)carbonyl-3-carboxypropyl]aminocarbonyl-5-(carboxymethyl)aminoquinoline;

2-[1-(4-(ethoxycarbonyl)piperazin-1-yl)carbonyl-3-carboxypropyl]aminocarbonyl-4-((dimethylamino)carbonylmethyl)(methyl)aminoquinoline;

2-[1-(4-(ethoxycarbonyl)piperazin-1-yl)carbonyl-3-carboxypropyl]aminocarbonyl-4-(carboxymethyl)(methyl)aminoquinoline;

2-[1-(4-(ethoxycarbonyl)piperazin-1-yl)carbonyl-3-carboxypropyl]aminocarbonyl-5-di(acetyl)aminoquinoline;

2-[1-(4-(ethoxycarbonyl)piperazin-1-yl)carbonyl-3-carboxypropyl]aminocarbonyl-5-acetamidoquinoline;

2-[1-(4-(ethoxycarbonyl)piperazin-1-yl)carbonyl-3-carboxypropyl]aminocarbonyl-4-(methyl)(2-hydroxyethyl)aminoquinoline;

2-[1-(4-(ethoxycarbonyl)piperazin-1-yl)carbonyl-3-carboxypropyl]aminocarbonyl-4-(methyl)(2-(dimethylamino)ethyl)aminoquinoline; and 2-[1-(4-(ethoxycarbonyl)piperazin-1-yl)carbonyl-3-carboxypropyl]aminocarbonyl-4-(carboxymethyl)aminoquinoline.

Another preferred group of compounds of formula (I) as set forth above in the Summary of the Invention is that group of compounds wherein:
a is 1 or 2;
b is 1;
A is =CH—;
$R^1$ is alkoxycarbonyl;
$R^2$ is hydrogen, carboxyalkyl, or aralkoxycarbonylalkyl;
$R^3$ is hydrogen;
each $R^4$ is independently selected from the group consisting of hydrogen, alkyl, alkoxy, halo, haloalkyl, haloalkoxy, and hydroxy;
$R^5$ is hydrogen;
$R^6$ is —N($R^7$)—C(O)—; and
$R^7$ is hydrogen or alkyl.

Preferred compounds of this group of compounds are those compounds selected from the group consisting of the following:

2-[1-(4-(ethoxycarbonyl)piperazin-1-yl)carbonyl-3-(benzyloxycarbonyl)propyl]aminocarbonylnaphthalene;

2-[1-(4-(ethoxycarbonyl)piperazin-1-yl)carbonyl-3-carboxypropyl]aminocarbonylnaphthalene; and 2-[(4-(ethoxycarbonyl)piperazin-1-yl)carbonylmethyl]aminocarbonylnaphthalene.

Another preferred group of compounds of formula (I) as set forth above in the Summary of the Invention is that group of compounds wherein:
a is 1;
b is 1;
A is =CH— or =N—;
$R^1$ is alkoxycarbonyl;
$R^2$ is hydrogen, aralkyl, carboxyalkyl, (carboxy)(hydroxy)alkyl, alkoxycarbonylalkyl, or tetrahydrofuranonyl;
$R^3$ is hydrogen, alkoxy, or carboxyalkoxy;
$R^4$ is hydrogen, hydroxy, carboxyalkoxy, or alkoxycarbonylalkoxy;
$R^5$ is hydrogen;
$R^6$ is —C(O)—N($R^7$)—; and
$R^7$ is hydrogen, alkyl or carboxyalkyl.

Preferred compounds of this group of compounds are those compounds selected from the group consisting of the following:

2-[((4-(ethoxycarbonyl)piperazin-1-yl)carbonylmethyl)carbonyl]aminonaphthalene;

2-[(1-(4-(ethoxycarbonyl)piperazin-1-yl)carbonyl-2-(ethoxycarbonyl)ethyl)carbonyl]aminonaphthalene;

2-[(1-(4-(ethoxycarbonyl)piperazin-1-yl)carbonyl-2-carboxyethyl)carbonyl]aminonaphthalene;

2-[(1-(4-(ethoxycarbonyl)piperazin-1-yl)carbonyl-2-(3-(methoxycarbonyl)phenyl)ethyl)carbonyl]aminonaphthalene;

2-[(1-(4-(ethoxycarbonyl)piperazin-1-yl)carbonyl-2-(3-carboxyphenyl)ethyl)carbonyl]aminonaphthalene;

2-[(1-(4-(ethoxycarbonyl)piperazin-1-yl)carbonyl-2-(4-(methoxycarbonyl)phenyl)ethyl)carbonyl]aminonaphthalene;

2-[(1-(4-(ethoxycarbonyl)piperazin-1-yl)carbonyl-1-(tetrahydro-2-oxofuran-3-yl)methyl)carbonyl]aminonaphthalene;

2-[(1-(4-(ethoxycarbonyl)piperazin-1-yl)carbonyl-2-carboxy-4-hydroxybutyl)carbonyl]aminonaphthalene;

2-[(1-(4-(ethoxycarbonyl)piperazin-1-yl)carbonyl-2-(4-carboxyphenyl)ethyl)carbonyl]aminonaphthalene;

2-[((4-(ethoxycarbonyl)piperazin-1-yl)carbonylmethyl)carbonyl]amino-5-hydroxynaphthalene;

2-[((4-(ethoxycarbonyl)piperazin-1-yl)carbonylmethyl)carbonyl]amino-4-methoxynaphthalene;

2-[((4-(ethoxycarbonyl)piperazin-1-yl)carbonylmethyl)carbonyl]amino-5-(carboxymethoxy)naphthalene;

2-[((4-(ethoxycarbonyl)piperazin-1-yl)carbonylmethyl)carbonyl]amino-5-(3-(ethoxycarbonyl)propoxy)naphthalene;

2-[((4-(ethoxycarbonyl)piperazin-1-yl)carbonylmethyl)carbonyl]amino-5-(3-carboxypropoxy)naphthalene;

2-[((4-(ethoxycarbonyl)piperazin-1-yl)carbonylmethyl)carbonyl]amino-4-(carboxymethoxy)naphthalene;

2-[((4-(ethoxycarbonyl)piperazin-1-yl)carbonylmethyl)carbonyl][carboxymethyl]aminonaphthalene; and 2-[((4-(ethoxycarbonyl)piperazin-1-yl)carbonylmethyl)carbonyl][carboxymethyl]amino-4-methoxynaphthalene.

Of the pharmaceutical compositions of the invention as set forth above in the Summary of the Invention, preferred pharmaceutical compositions comprise a pharmaceutically acceptable excipient and a preferred compound of formula (I) as set forth above.

Of the methods of using the compounds of formula (I) as set forth above in the Summary of the Invention, preferred methods are those methods of using the preferred compounds of formula (I) as set forth above.

Preparation of the Compounds of the Invention

The compounds of the invention are prepared according to the methods described below in the following Reaction Schemes. It is understood that those compounds of the invention which are not specifically prepared in the following Reaction Schemes may be prepared by similar synthetic processes with the appropriately substituted starting materials and reagents by methods known to one of ordinary skill in the art. It is also understood that during the preparation of the compounds of the invention, as described below, additional reactive groups (for example, hydroxy, amino or carboxy groups) on the intermediate compounds utilized in the preparation may be protected as needed by the appropriate protecting group by treating the intermediate compound prior to the desired reaction with the appropriate protecting group precursor by methods known to those of ordinary skill in the art. The protecting groups may then be removed as desired by methods known to those of ordinary skill in the art, for example, by acidic or basic hydrolysis. Such protecting groups and methods are described in detail in Greene, T. W. and Wuts, P. G. M., *Protective Groups in Organic Synthesis*, 2nd Edition, 1991, John Wiley & Sons. Preferred nitrogen-protecting groups are "Boc" (t-butoxycarbonyl) and "CBZ" (benzyloxycarbonyl).

It will also be appreciated by those skilled in the art, although such protected derivatives of compounds of formula (I) as described above in the Summary of the Invention may not possess pharmacological activity as such, they may be administered to a mammal having a disease-state characterized by thrombotic activity and thereafter metabolized in the body to form compounds of the invention which are pharmacologically active. Such derivatives may therefore be described as "prodrugs". All prodrugs of compounds of formula (I) are included within the scope of the invention.

It is understood that in the following description, combinations of substituents and/or variables of the depicted formulae are permissible only if such conbinations result in stable compounds which can be isolated by methods known to those of ordinary skill in the art. Transient compounds are indicated by brackets.

A. Preparation of Compounds of Formula (D)

Compounds of formula (D) are intermediates used in the preparation of the compounds of the invention. They may be prepared as described below in Reaction Scheme 1 wherein b, $R^1$, $R^5$, and $R^7$ are as described above in the Summary of the Invention; PG is a nitrogen-protecting group; $R^{1a}$ is hydrogen or a nitrogen protecting group and $R^{2a}$ is hydrogen, alkyl, aryl, aralkyl, hydroxyalkyl, aminoalkyl, haloalkylsulfonylaminoalkyl, carboxyalkylthioalkyl, alkoxycarbonylalkylthioalkyl, alkoxycarbonylalkyl, aralkoxycarbonylalkyl, aminocarbonylalkyl, aralkoxycarbonylaminoalkyl, heterocyclkylalkyl or cyanoalkyl:

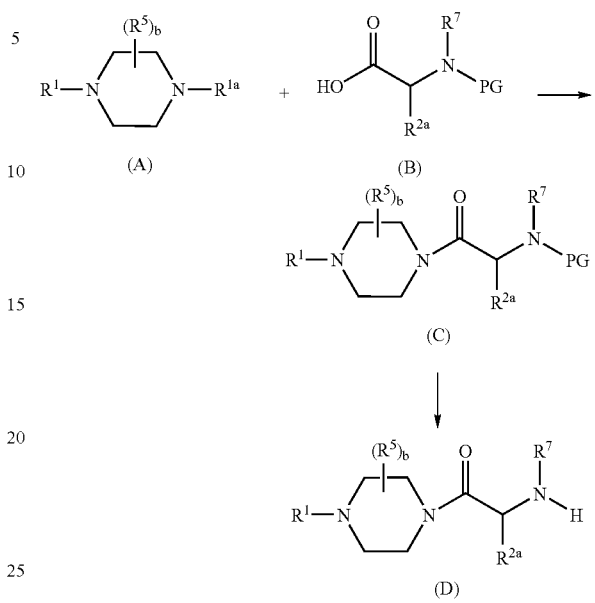

Compounds of formulae (A) and (B) are commercially available, for example, from Aldrich, or may be prepared according to methods known to those of ordinary skill in the art, or by methods as described herein.

In general, compounds of formula (D) are prepared by first treating a compound of formula (B) in an aprotic solvent mixture, such as tetrahydrofuran (THF) and methylene chloride, with a slightly excess equimolar amount of a peptide coupling reaction additive, such as 1-hydroxybenzotriazole (HOBT) and a slightly excess equimolar amount of coupling agent for amide formation, such as 1-(3-dimethylaminopropyl)-3-ethylcarbodiimide (EDCI) at ambient temperature. To this mixture is added a slightly excess equimolar amount of a compound of formula (A) where $R^{1a}$ is hydrogen and the resulting reaction mixture is allowed to stir overnight at ambient temperature. The compound of formula (C) is isolated from the reaction mixture by standard isolation techniques, such as evaporation and extraction.

Depending on what PG is, the compound of formla (C) is then reduced under standard hydrogenation conditions, such as treatment with pladium over carbon under hydrogen or treated under standard hydrolysis conditions to form a compound of formula (D), which is isolated form the reaction mixture by filtration.

Alternatively, compounds of formula (A) where R1 is hydrogen and R1a is a nitrogen protecting group can be treated with the appropriately subsituted acid halide, sulfonyl halide, carbamoyl halide or isocyanate to yield the corresponding appropriately substituted compounds of formula (A), which can then be deprotected under standard deprotecting conditions prior to being reacted with the compound of formula (B) to form compounds of formula (C) and (D) wherein R1 is as described above in the Summary of the Invention.

B. Preparation of Compounds of Formula (Ia) and (Ib)

Compounds of formula (Ia) and (Ib) are compounds of formula (I) and are prepared as described below in Reaction Scheme 2 wherein A is =N— and $R^6$ is —N($R^7$)—C(O)—; a and b are as described as above in the Summary of the Invention; $R^1$ is a nitrogen protecting group or is described as above in the Summary of the Invention; $R^{2a}$ is hydrogen, alkyl, aryl, aralkyl, hydroxyalkyl, aminoalkyl, haloalkylsulfonylaminoalkyl, alkoxycarbonylalkyl, aralkoxycarbonylalkyl, aminocarbonylalkyl, aralkoxycarbonylaminoalkyl, heterocyclylalkyl or cyanoalkyl; $R^{3a}$ is alkyl, alkoxycarbonylalkyl, di(alkoxycarbonyl)alkyl, carboxyalkyl, di(carboxy)alkyl, (carboxy)(hydroxy)alkyl, (dialkylamino)(carboxy)alkyl, hydroxyalkyl, cyanoalkyl, haloalkyl, haloalkenyl, carboxyalkenyl, alkoxycarbonylalkenyl, (cycloalkyl)(alkoxycarbonyl)alkyl, (cycloalkyl)(carboxy)alkyl, aminocarbonylalkyl, dialkylaminocarbonylalkyl, monoaralkylaminocarbonylalkyl, mono(carboxyalkyl) aminocarbonylalkyl, mono(alkoxycarbonylalkyl) aminocarbonylalkyl, carboxycycloalkyl, alkoxycarbonylcycloalkyl, aminocarbonylcycloalkyl, tetrahydrofuranonyl, or heterocyclylalkyl; $R^{3b}$ is alkoxy, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, aminocarbonylalkoxy, dialkylaminocarbonylalkoxy, monoaralkylaminocarbonylalkoxy, mono(carboxyalkyl)aminocarbonylalkoxy, mono(alkoxycarbonylalkyl)aminocarbonylalkoxy, carboxycycloalkoxy, alkoxycarbonylcycloalkoxy, aminocarbonylcycloalkoxy, tetrahydrofuranonyloxy, or heterocyclylalkoxy; $R^4$, $R^5$ and $R^7$ are as described above in the Summary of the Invention; $R^8$ is alkyl or aralkyl, and X is halo:

REACTION SCHEME 2

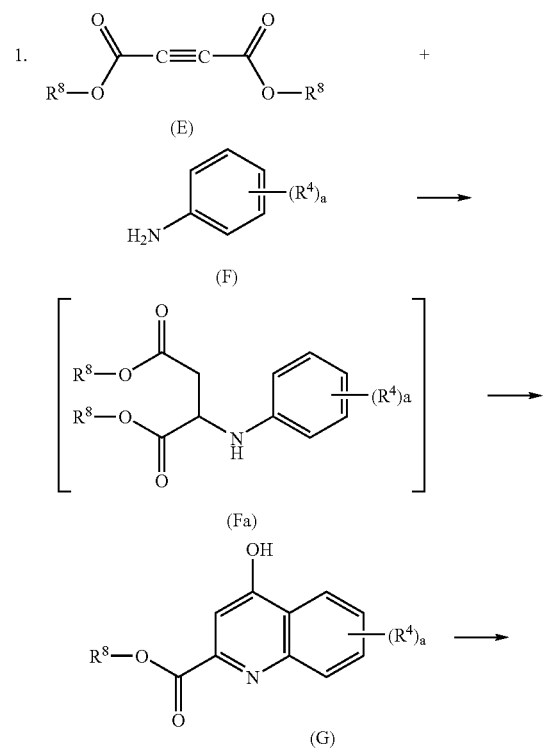

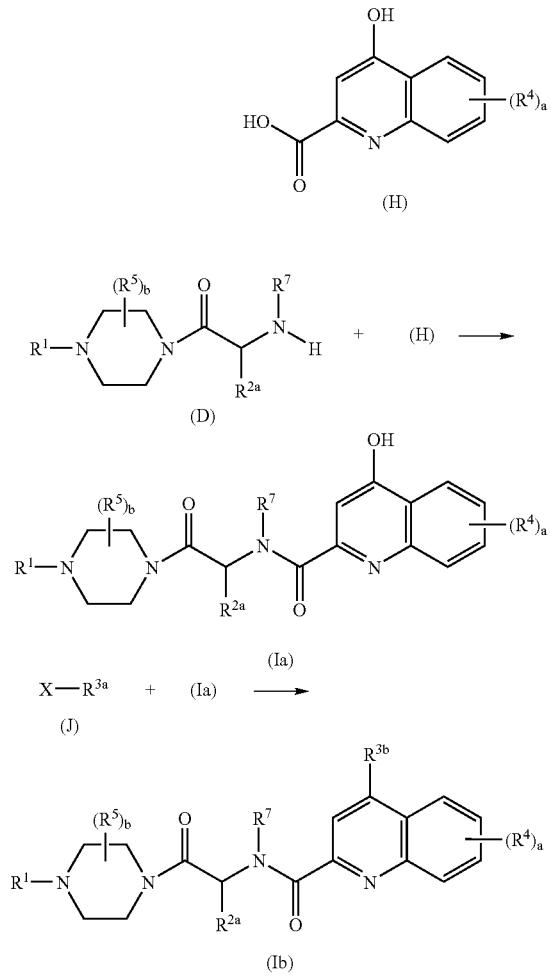

Compounds of formulae (E), (F), and (J) are commercially available, for example, from Aldrich, or may be prepared according to methods known to those of ordinary skill in the art. Compounds of formula (G) and formula (H) may alternatively be prepared by methods disclosed in Great Britain Patent No. 1,334,705.

In general, compounds of formulae (Ia) and (Ib) are prepared by first treating a compound of formula (F) in a protic solvent, such as methanol, with an equimolar amount of a compound of formula (E) with stirring at ambient temperature for about 30 minutes to about an hour, preferably for about 30 minutes. The solvent is removed by evaporation to form a residue.

To an aprotic polar solvent, such as diphenyl ether, heated to between about 200° C. and about 250° C., preferably to about 250° C. is then added the residue and the temperature of the reaction mixture is maintained at the high temperature for about 30 minutes to an hour, preferably for about 30 minutes, at which point the reaction mixture is allowed to cool to ambient temperature. The resulting precipitate is collected and washed with a aprotic polar solvent, such as ether, which is previously heated to below boiling temperature, to give compounds of formula (G). Further purification, for example, by dissolving the mixture in a protic solvent at boiling temperature, such as methanol, and then allowing the mixture to cool to ambient temperature for a period of about 1 to about 2 days, preferably for about 2 days, yields a compound of formula (H), which is isolated from the reaction mixture by standard techniques.

Compound of formula (H) in an aprotic solvent mixture, for example, methylene choride and N,N-dimethylformamide (DMF), is then treated with a slightly excess equimolar amount of a peptide coupling reaction additive, such as 1-hydroxybenzotriazole (HOBT) and a slightly excess equimolar amount of coupling agent for amide formation, such as 1-(3-dimethylaminopropyl)-3-ethylcarbodiimide (EDCI) at ambient temperature. An equimolar amount of a compound of formula (D) in an aprotic solvent, such as methylene chloride, is then added to the reaction mixture. The reaction mixture is stirred at ambient temperature for about 4 to 6 hours, preferably for about 6 hours. The compound of formula (Ia) is then isolated from the reaction mixture by standard isolation techniques, such as evaporation of the solvents, extraction, and concentration.

The compound of formula (Ia) is then treated under standard Williamson synthesis conditions, such as in the presence of a base in an aprotic solvent, for example, cesium carbonate in DMF, with an equimolar amount of a compound of formula (J) at temperatures between about ambient temperature and 100° C. The reaction mixture is stirred from about 2 hours to about 10 hours, preferably for about 10 hours. The compound of formula (Ib) is then isolated from the reaction mixture by standard isolation techniques, such as preparative HPLC.

In addition, compounds of formula (Ib) where $R^{2a}$ is alkoxycarbonylalkyl or aralkoxycarbonylalkyl may be treated under appropriate standard hydrolysis conditions known to those of ordinary skill in the art to form compounds of formula (Ib) where $R^{2a}$ is carboxyalkyl.

In addition, compounds of formula (Ib) where $R^{3b}$ is alkoxycarbonylalkoxy, di(alkoxycarbonyl)alkoxy, alkoxycarbonylalkenyloxy, (cycloalkyl)(alkoxycarbonyl)alkoxy, mono(alkoxycarbonylalkyl)aminocarbonylalkoxy, or alkoxycarbonylcycloalkoxy may be treated under appropriate standard hydrolysis conditions known to those of ordinary skill in the art to form compounds of formula (Ib) where $R^{3a}$ is carboxyalkyl, di(carboxy)alkoxy, carboxyalkenyloxy, (cycloalkyl)(carboxy)alkoxy, mono(carboxyalkyl) aminocarbonylalkoxy or carboxycycloalkoxy.

In addition, compounds of formula (Ib) where $R^4$ is nitro can be reduced under standard reducing conditions to form compounds of formula (Ib) where $R^4$ is amino. Such compounds can be further treated with an alkylating agent or an acylating agent to form compounds of formula (Ib) where $R^4$ is monoalkylamino, dialkylamino, carboxyalkylamino, alkylcarbonylamino, or di(alkylcarbonyl)amino.

In addition, compounds of formula (Ib) where $R^4$ is a halo may be treated with a compound of formula $HR^{3c}$ wherein $R^{3c}$ is amino, monoalkylamino, dialkylamino, carboxyalkylamiono or optionally substituted N-heterocyclyl (where the hydrogen in $HR^{3c}$ is attached to the nitrogen in the N-heterocyclyl) in a similar manner as described below for compounds of formula (Iw) to form compounds of formula (Ib) wherein $R^4$ is amino, monoalkylamino, dialkylamino, carboxyalkylamino or optionally substituted N-heterocyclyl (where the N-heterocyclyl is attached to the quinoline ring via the nitrogen atom in the N-heterocyclyl). These compounds may be further treated with an appropriate acylating agent under standard acylation conditions to form compounds of formula (Ib) wherein $R^4$ is alkylcarbonylamino or di(alkylcarbonyl)amino.

In addition, compounds of formula (Ib) where $R^{2a}$ is cyanoalkyl and/or $R^{3b}$ is cyanoalkoxy can be treated under standard conditions, such as sodium azide, tributyl tin chloride in refluxing toluene, to form compounds of formula (Ib) where $R^{2a}$ is tetrazolylalkyl and/or $R^{3b}$ is tetrazolylalkoxy.

In addition, compounds of formula (Ib) where $R^{2a}$ is aminoalkyl can be treated under standard acylation conditions, such as treatment with a haloalkylsulfonyl halide in the presence of a base, such as triethylamine, in an aprotic solvent, to form compounds of formula (Ib) where $R^{2a}$ is haloalkylsulfonylaminoalkyl.

In addition, compounds of formula (Ib) where $R^4$ is alkyl can be treated under standard bromination conditions, such as treatment wih N-bromosuccinimde carbon tetrachloride and azobisisobutyronitrile (AIBN) to form compounds of formula (Ib) where $R^4$ is bromoalkyl. These compounds may be further treated with a nucleophile, such as a dialkylamine group, to form compounds of formula (Ib) where $R^4$ is dialkylaminoalkyl.

In addition, compounds of formula (Ib) where $R^4$ is hydroxy may be treated with the appropriate group under standard ether synthesis conditions, such as Williamson ether synthesis conditions, to form compounds of formula (Ib) where $R^4$ is alkoxy, aralkoxy, haloalkoxy, carboxyalkoxy, alkoxycarbonylalkoxy, dialkylaminoalkoxy or heterocyclylalkoxy.

In addition, compounds of formula (Ib) where $R^{2a}$ and/or $R^{3b}$ contain a carboxy group may be esterified under standard esterification conditions, such as Fischer esterification conditions, to form compounds of formula (Ib) where $R^{2a}$ and/or $R^{3b}$ contain a corresponding alkoxycarbonyl group.

Alternatively, compounds of formula (D) as prepared above in Reaction Scheme 1 can be reacted with compounds of the following structure:

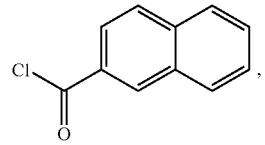

which are commercially avaible or prepared by methods known to one of ordinary skill in the art, under standard acylation conditions to form additional compounds of the invention.

A preferred method of making intermediates used in the preparation of the compounds of the invention which avoids the formation of undesired regiosiomers with respect to the substitution on the quinoline ring is illustrated below in Reaction Scheme 2a wherein $R^{4b}$ is alkyl, alkoxy, aralkoxy, carboxy, alkoxycarbonyl, aminocarbonyl, alkylcarbonylamino, di(alkylcarbonyl)amino, carboxyalkoxy, alkoxycarbonylalkoxy or heterocyclylalkoxy; X is ioido, chloro or bromo; and $R^8$ is alkyl or aralkyl:

REACTION SCHEME 2a

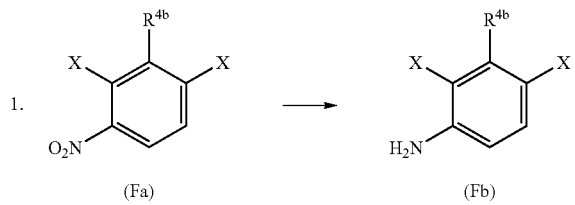

hydroxyalkyl, aminoalkyl, haloalkylsulfonylaminoalkyl, alkoxycarbonylalkylthioalkyl, alkoxycarbonylalkyl, aralkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, (alkoxycarbonylalkyl)(alkyl)aminocarbonylalkyl, tetrahydrofuranonyl, or heterocyclylalkyl; $R^8$ is alkyl or aralkyl; and each X is independently halo:

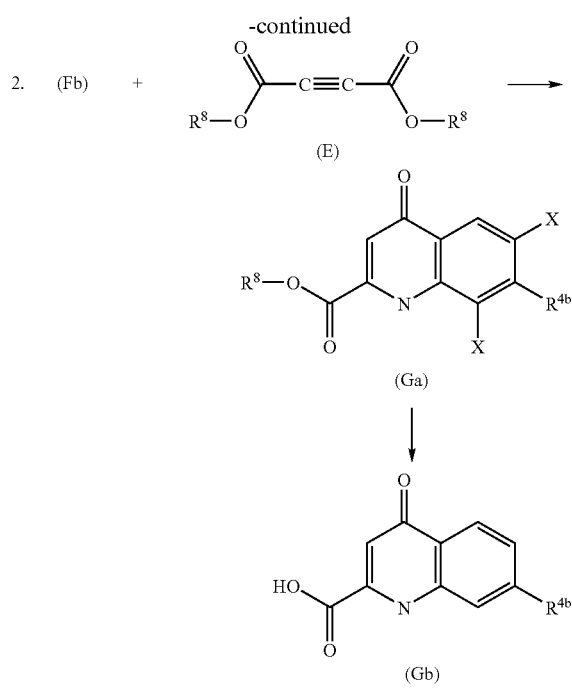

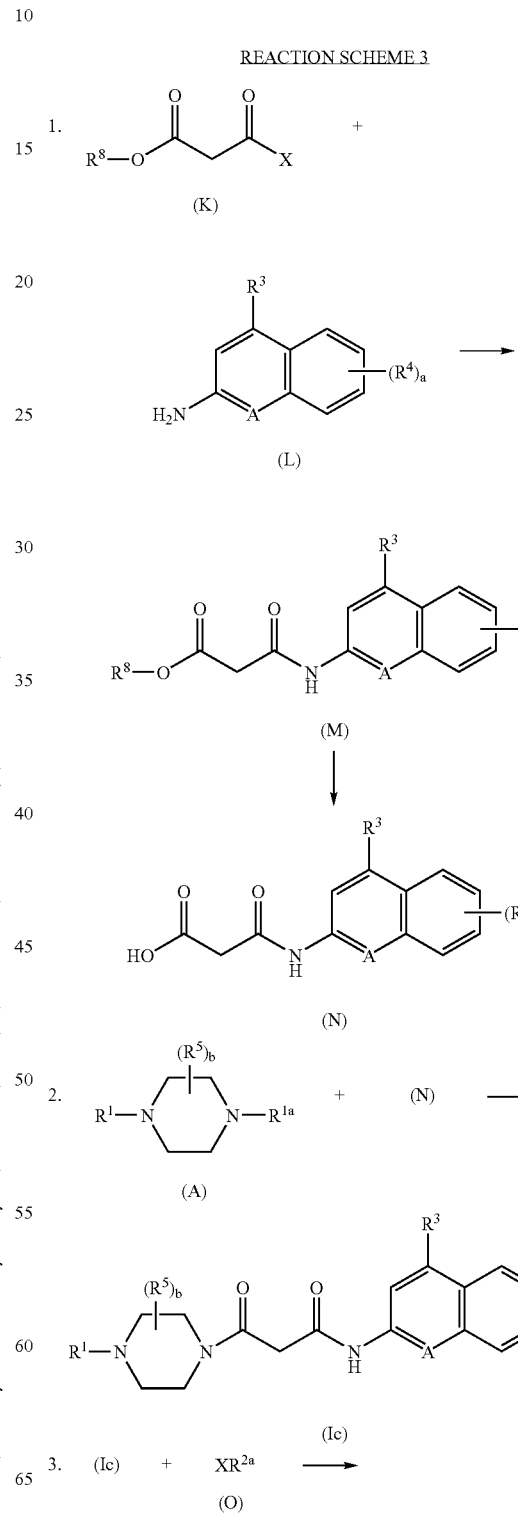

Compounds of formula (Fa) and formula (E) are commercially available, or can prepared according to methods known to those of ordinary skill in the art.

In general, compounds of formula (Gb) are prepared by first treating a compound of formula (Fa) with a reducing agent, such as tin (II) chloride dihydrate, under standard chemical reduction conditions, such as in a protic solvent, to form the compound of formula (Fb), which is isolated from the reaction mixture by standard isolation techniques.

The compound of formula (Fb) in a protic solvent, such as methanol, is then treated with a slightly excess equimolar amount of a compound of formula (E) at reflux temperatures for about 2 to about 4 hours, preferably for about 4 hours. The reaction mixture is then concentrated. An organic solvent is heated to a non-boiling point temperature of between about 240° C. and about 260° C., and the concentrate is then added to the solvent. The temperature of the mixture is maintained at the non-boiling point temperature for about 10 to 20 minutes, preferably for about 20 minutes. The reaction mixture is then cooled slowly to ambient temperature and diluted with an organic solvent. The compound of formula (Ga) is isolated from the reaction mixture by standard isolation techniques, such as filtration.

The compound of formula (Ga) is treated with a hydrolyzing agent under standard hydrolysis conditions and then treated under standard reducing conditions, such as hydrogen gas and palladium over carbon, to form a compound of formula (Gb).

Compounds of formula (Gb) may then be used in place of compounds of formula (G) in Reaction Scheme 1 to prepare compounds of formula (Ia) and formula (Ib).

C. Preparation of Compounds of Formulae (Ic) and (Id)

Compounds of formula (Ic) and (Id) are compounds of formula (I) wherein $R^6$ are —C(O)—N($R^7$)— where $R^7$ is hydrogen and are prepared as described below in Reaction Scheme 3 wherein A, a, b, $R^1$, $R^3$, $R^4$ and $R^5$ are as described above in the Summary of the Invention; $R^{1a}$ is hydrogen; $R^{2a}$ is alkyl, aralkyl, alkylsulfonylalkyl, aralkoxyalkyl,

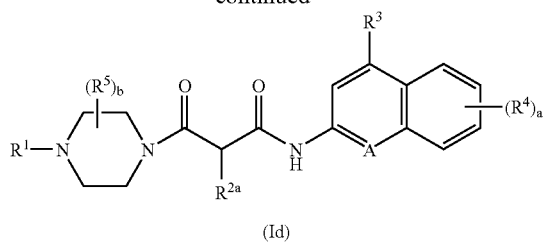

(Id)

Compounds of formulae (A), (K), (L) and (O) are commercially available, for example, from Aldrich, or may be prepared according to methods known to those of ordinary skill in the art.

In general, compounds of formulae (Ic) and (Id) are prepared by first treating a compound of formula (L) in an aprotic solvent, such as methylene chloride, with a slightly excess equimolar amount of a compound of formula (K) in an aprotic solvent, such as methylene choride, in the presence of a base, such as triethylamine, at a temperature of between about 5° C. to about 10° C., preferably at about 5° C. The reaction mixture is stirred from about 30 minutes to about an hour, preferably for about an hour, at a temperature of between about 5° C. to about 15° C., preferably at about 10° C. The compound of formula (M) is then isolated from the reaction mixture by standard isolation techniques, such as organic solvent extraction, and evaporation.

The compound of formula (M) is then hydrolyzed under standard hydrolysis conditions, such as treatment with lithium hydroxide in a protic solvent, such as methanol, to form a compound of formula (N), which is isolated from the reaction mixture by standard isolation techniques, such as acidifying the reaction mixture, organic solvent extraction and evaporation. Compounds of formula (N) wherein the $R^3$ substituent contains a carboxy group are protected accordingly prior to the next step.

The compound of formula (N) in an aprotic solvent, such as methylene chloride, in the presence of a base, such as triethylamine, and a slightly excess equimolar amount of a peptide coupling agent, such as HOBT and/or EDCI, at ambient temperature, is treated with a compound of formula (A). The resulting reaction mixture is stirred from about 6 hours to about 12 hours, preferably for about 12 hours, at ambient temperature. The compound of formula (Ic) is isolated from the reaction mixture by standard isolation techniques.

A compound of formula (Ic) in an aprotic solvent, such as DMF, was slowly added to a suspension of a strong base in an aprotic solvent, such as sodium hydride in DMF. The resulting reaction mixture was stirred at ambient temperature for a few minutes, preferably for about 5 minutes. An equimolar amount of a compound of formula (O) in an aprotic solvent, such as DMF, was then added to the reaction mixture. After quenching the reaction with the addition of water after about 10 to about 20 minutes, preferably after about 10 minutes, the compound of formula (Id) was isolated from the reaction mixture by standard isolation techniques, such as organic solvent extraction, evaporation and purification by flash chromatography.

Compounds of formula (Id) wherein $R^{2a}$ is aryl (substituted by alkoxycarbonyl), aralkyl (substituted by alkoxycarbonyl), alkoxycarbonylalkylthioalkyl, alkoxycarbonylalkyl, aralkoxycarbonylalkyl, alkoxycarbonylalkoxycarbonylalkyl, aralkoxycarbonylaminoalkyl, alkoxycarbonylalkylaminocarbonylalkyl, (alkoxycarbonylalkyl)(alkyl)aminocarbonylalkyl, heterocyclylalkyl (wherein the heterocyclyl radical is substituted by alkoxycarbonyl); may be further treated under standard hydrolysis or de-protecting conditions to form compounds of formula (Id) wherein $R^{2a}$ is aryl (substituted by carboxy), aralkyl (substituted by carboxy), carboxyalkylthioalkyl, carboxyalkyl, carboxyalkoxycarbonylalkyl, aminoalkyl, aminocarbonylalkyl, (carboxyalkyl)(alkyl)aminocarbonylalkyl, heterocyclylalkyl (wherein the heterocyclyl radical is substituted by carboxy).

In a similar manner, compounds of formula (Ic) or (Id) wherein the $R^3$ substituent contains a protected carboxy group may be treated to form the corresponding compounds of formula (Ic) and (Id) wherein the $R^3$ substituent contains a free carboxy group.

Compounds of formula (Ic) and (Id) may further be treated with an appropriate alkylating agent under standard conditions to form compounds of formula (Ic) and (Id) wherein $R^7$ is alkyl, carboxyalkyl or alkoxycarboxyalkyl ($R^7$).

D. Preparation of Compounds of Formulae (If) and (Ig)

Compounds of formulae (If) and (Ig) are compounds of formula (I) and are prepared as described below in Reaction Scheme 4 from compounds of formula (Ie), which are compounds of formula (I) synthesized as described above in Reaction Scheme 2 and Reaction Scheme 3 where $R^{2a}$ is hydroxybenzyl. In the following Reaction Scheme 4, $R^6$ and A are as described above in the Summary of the Invention; $R^1$, $R^3$, $R^4$, $R^5$, a, and b are as described above in Reaction Scheme 2 and Reaction Scheme 3; and $R^8$ is alkyl or aralkyl:

REACTION SCHEME 4

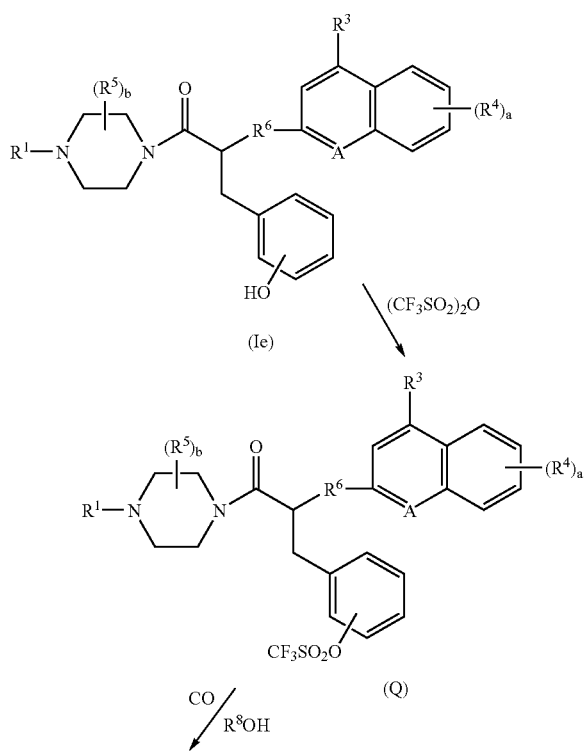

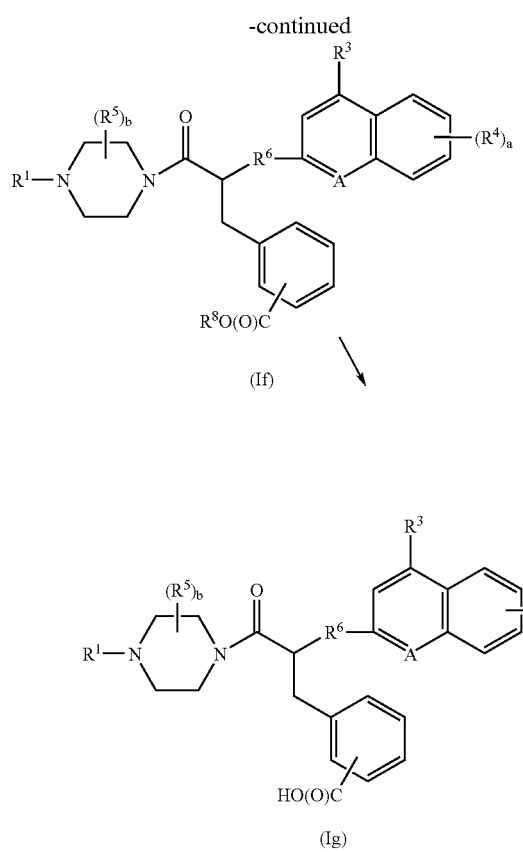

(If)

(Ig)

Compounds of formula (Ie) are prepared as disclosed herein. (CF$_3$SO$_2$)$_2$O is commercially available or may be prepared according to methods known to those skilled in the art.

In general, compounds of formulae (If) and (Ig) are prepared by first treating a compound of formula (Ie) in an aprotic solvent, such as methylene chloride, at a temperature of between –40° C. and –30° C., preferably at –30° C., in the presence of a base, such as triethylamine and/or dimethylaminopyridine, with a excess equimolar amount of (CF$_3$SO$_2$)$_2$O. The resulting reaction mixture is allowed to warm to ambient temperature. The compound of formula (Q) is then isolated from the reaction mixture by standard isolation techniques, such as evaporation and purification by flash chromatography.

The compound of formula (Q) in an aprotic solvent and base is treated with carbon monoxide in the presence of a compound of formula R$^8$OH and a palladium (II) catalyst at ambient temperature. The reaction mixture is heated to between about 50° C. and about 100° C. for about 30 minutes to about one hour. The reaction mixture is cooled to ambient temperature and a compound of formula (If) is isolated from the reaction mixture by standard isolation techniques, such as filtration, concentration and flash column chromatography.

The compound of formula (If) is hydrolyzed under standard hydrolysis conditions to form the compound of formula (Ig).

E. Preparation of Compounds of Formula (Ih)

Compounds of formula (Ih) are compounds of formula (I) and are prepared as described below from compounds of formula (Ie), which are compounds of formula (I) prepared as described herein. In particular, in the following Reaction Scheme 5, R$^1$, R$^3$, R$^4$, R$^5$, R$^6$, A, a and b are as described above in the Summary of the Invention; each R$_a$ is independently an alkyl radical; and X is halo:

REACTION SCHEME 5

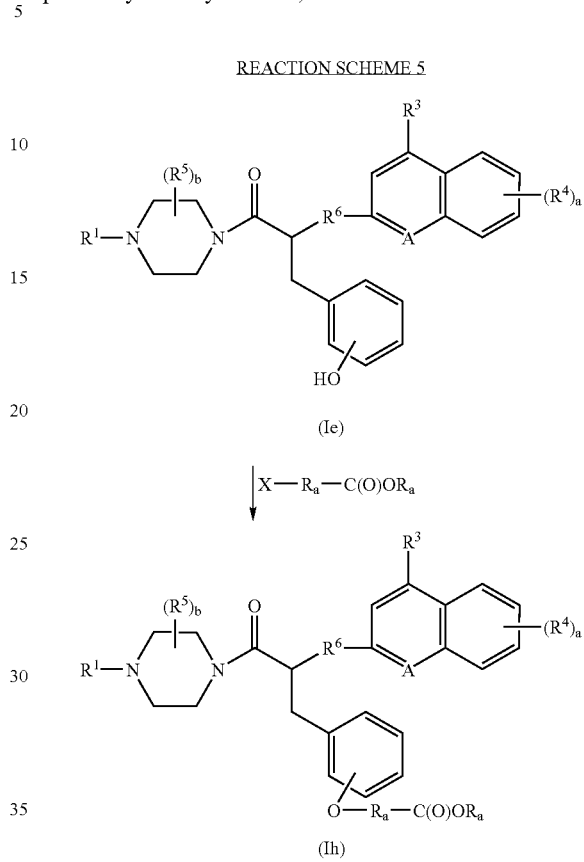

Compounds of formula (Ie) are prepared by methods disclosed herein. Compounds of the formula X—R$_a$—C(O)R$_a$ where each R$_a$ is independently an alkyl radical are commercially available or may be prepared according to methods known to those of ordinary skill in the art.

In general, compounds of formula (Ih) are prepared by treating a compound of formula (Ie) in an aprotic solvent, such as DMF, in the presence of a base, preferably cesium carbonate, with a compound having the formula X—R$_a$—C(O)OR$_a$ where X is halo, preferably bromo or chloro, and each R$_a$ is independently an alkyl radical. The resulting reaction mixture is stirred at ambient temperature for about 4 hours to about 8 hours, preferably for about 6 hours. The compound of formula (Ih) is isolated from the reaction mixture by standard isolation techniques, such as organic solvent extraction, evaporation and purification by HPLC.

Compounds of formula (Ih) may be further hydrolyzed under standard hydrolysis conditions to form compounds having the corresponding acid subsitutents.

F. Preparation of Compounds of Formula (Ij)

Compounds of formula (Ij) are compounds of invention and are prepared as described below in Reaction Scheme 6 from compounds of formula (Ii), which are compounds of formula (I) prepared as described herein. In the following Reaction Scheme 6, R$^1$, R$^3$, R$^4$, R$^5$, R$^6$, A, a and b are as described above in the Summary of the Invention; each $R_a$ is independently an alkyl radical; and X is halo:

REACTION SCHEME 6

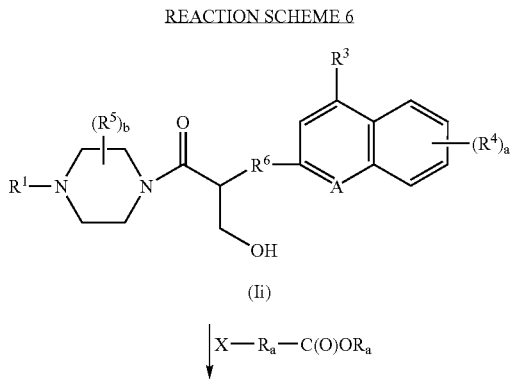

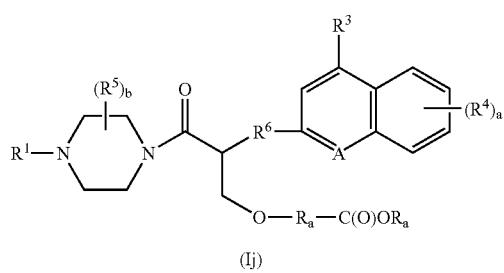

Compounds of formula (Ii) are prepared by methods disclosed herein. Compounds of formula $X-R_a-C(O)OR_a$ are commercially available or may be prepared according to methods known to those skilled in the art.

In general, compounds of formula (Ij) are prepared by treating a compound of formula (Ii) in an aprotic solvent, such as tetrahydrofuran, at a temperature of between about −5° C. and about 5° C., preferably at 0° C., in the presence of a base, such as potassium hexamethyldisilazide, with a compound having the formula $X-R_a-C(O)OR_a$ where X is halo, preferably bromo, and each Ra is independently an alkyl radical. The resulting reaction mixture is stirred from about 30 minutes to 2 hours, preferably for an hour, at a temperature of between about −5° C. and about 5° C., preferably at 0° C. The reaction is quenched with the addition of water. The compound of formula (Ij) is isolated from the reaction mixture by standard isolation techniques, such as organic solvent extraction, concentration and purification by elution through silica gel.

Compounds of formula (Ij) may be further hydrolyzed under standard hydrolysis conditions to form compounds having the corresponding acid subsitutents.

G. Preparation of Compounds of Formulae (Il), (Im) and (In)

Compounds of formulae (Il), (Im) and (In) are compounds of formula (I) and are prepared as described below in Reaction Scheme 7 from compounds of formula (Ik), which are compounds of formula (I) prepared as described herein. In the following Reaction Scheme 7, A, a, b, $R^1$, $R^3$, $R^4$, $R^5$ and $R^6$ are as described above in the Summary of the Invention; each $R_a$ is independently an alkyl radical; $R^9$ is hydrogen or alkyl; and X is halo:

REACTION SCHEME 7

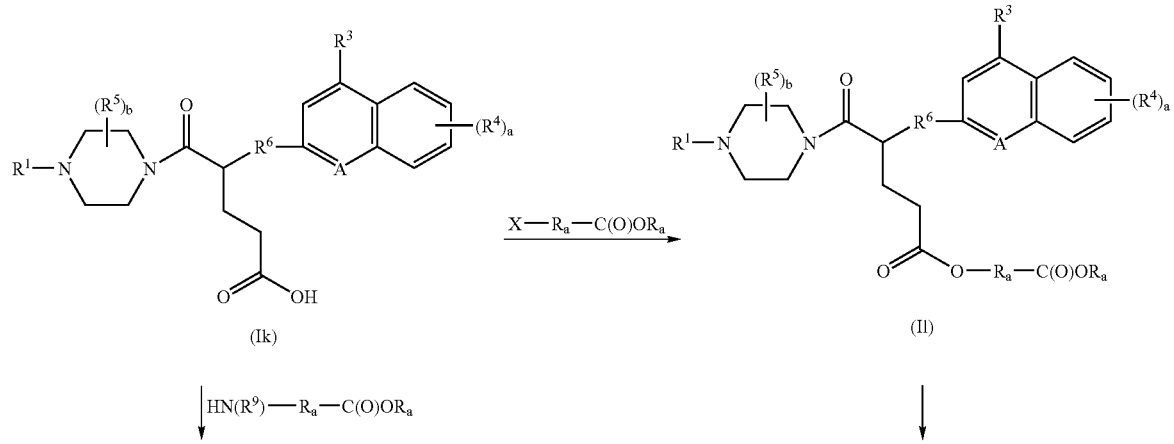

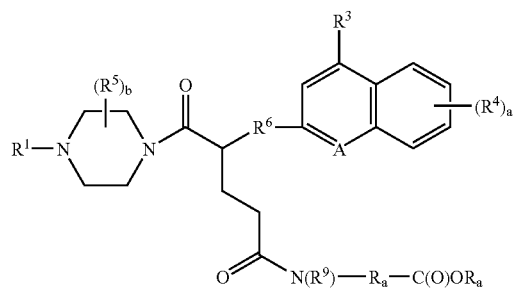

(In)

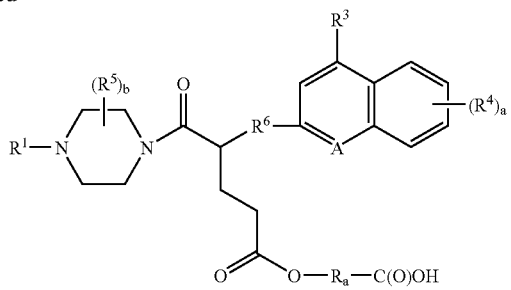

(Im)

Compounds of formula (Ik) are prepared according to methods disclosed herein. Compounds of the formula HN(R9)—R$_a$—C(O)OR$_a$ and formula X—R$_a$—C(O)OR$_a$ are commercially available or may be prepared according to methods known to those of ordinary skill in the art. If desired, compounds of formula (Ik) wherein R$^3$ is hydroxy or contains a hydroxy group may be protected by an appropriate oxygen-protecting group to avoid undesired side reactions.

In general, compounds of formula (Il) and (Im) are prepared by treating a compound of formula (Ik) in an aprotic solvent, such as DMF, with an excess equimolar amount of a compound having the formula X—R$_a$—C(O)OR$_a$ where X is halo, preferably bromo, and each R$_a$ is 2-[(4-(n-butyl)carbonylpiperazin-1-yl)carbonylmethyl]aminocarbonyl-4-methoxyquinoline reaction mixture is heated to a temperature of between about 45° C. and about 55° C., preferably at about 50° C., for about 30 minutes to about an hour, preferably for about an hour. The compound of formula (Il) is then isolated from the reaction mixture by standard isolation techniques, such as organic solvent extraction and evaporation.

The compound of formula (Il) in an aprotic solvent, such as methylene chloride, is treated under standard hydrolysis conditions to form a compound of formula (Im).

In general, compounds of formula (In) are prepared by treating a compound of formula (Ik) in an aprotic solvent, such as tetrahydrofuran, with a slightly excess equimolar amount of a compound having the formula HN(R9)—R$_a$—C(O)OR$_a$ where R$^9$ is hydrogen or alkyl and each R$_a$ is independently an alkyl radical, in the presence of equimolar amounts of a peptide coupling agent, such as EDCI and/or HOBT and a proton scavenger, such as diisopropylethylamine (DIEA). The reaction mixture is stirred from about 6 hours to about 16 hours, preferably for about 12 hours. The compound of formula (In) is isolated from the reaction mixture by standard isolation techniques, such as organic solvent extraction, concentration and purification by elution through silica gel.

Compounds of formula (In) may be further hydrolyzed under standard hydrolysis conditions to form compounds having the corresponding acid subsitutents.

H. Preparation of Compounds of Formula (Ip)

Compounds of formula (Ip) are compounds of formula (I) and are prepared as described below in Reaction Scheme 8 from compounds of formula (Io), which are compounds of formula (I) prepared as described above in Reaction Scheme 2. In the following Reaction Scheme 8, A, a, b, R$^1$, R$^3$, R$^4$, R$^5$ and R$^6$ are as described above in the Summary of the Invention; each R$_a$ is independently an alkyl radical and R$_9$ is hydrogen or alkyl:

REACTION SCHEME 8

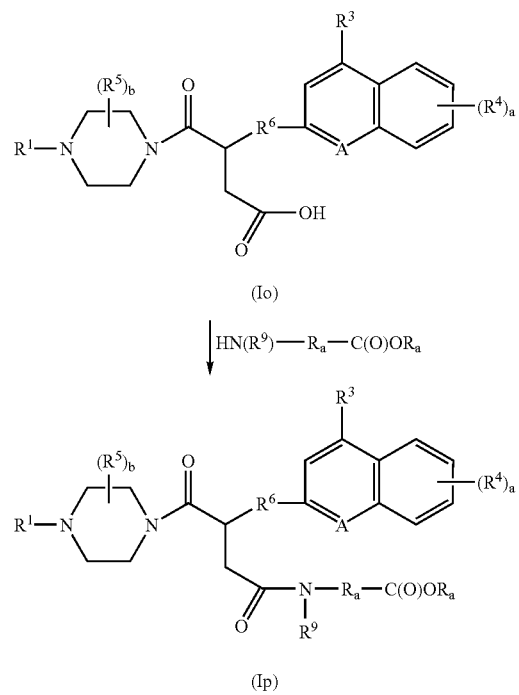

Compounds of formula (Io) are prepared as described herein. Compounds of formula HN(9R)—R$_a$—C(O)OR$_a$ are commercially available or may be prepared according to methods known to those of ordinary skill in the art.

In general, compounds of formula (Ip) are prepared by treating a compound of formula (Io) in an aprotic solvent, such as tetrahydrofuran, with an slight excess equimolar amount of a compound having the formula HN(R9)—R$_a$—C(O)OR$_a$ where R$^9$ is hydrogen or alkyl and each R$_a$ is independently an alkyl radical, in the presence of an equimolar amounts of a peptide coupling agent, such as HOBT and EDCI and a proton scavenger, such as DIEA. The resulting reaction mixture is stirred at ambient temperature for between about 6 hours and about 16 hours, preferably for about 12 hours. The compound of formula (Ip) is isolated from the reaction mixture by standard isolation techniques, such as organic solvent extraction and concentration.

If desired, compounds of formula (Ip) may be further hydrolyzed under standard conditions to form compounds having the corresponding acid subsitutents.

I. Preparation of Compounds of Formula (Ir) and (Is)

Compounds of formula (Ir) and (Is) are compounds of formula (I) and are prepared as described below in Reaction Scheme 9 from compounds of formula (Iq), which are compounds of formula (I) prepared as described above in Reaction Scheme 2. In the following Reaction Scheme 9, A, a, b, $R^1$, $R^3$, $R^4$, $R^5$ and $R^6$ are as described above in the Summary of the Invention; each $R_a$ is independently an alkyl radical; and X is halo:

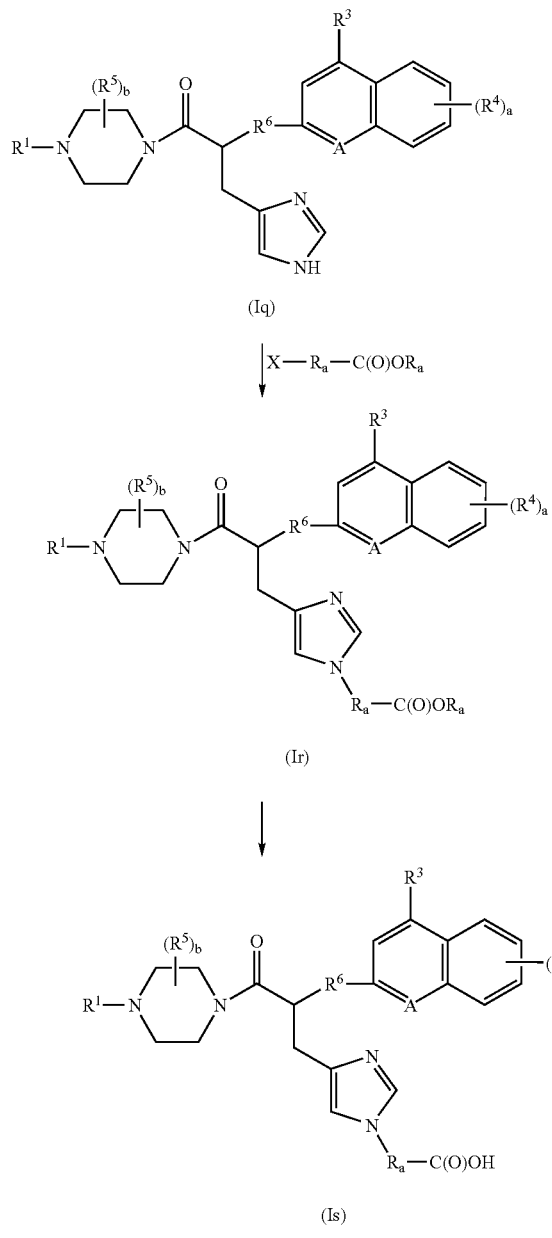

Compounds of formula (Iq) are prepared by methods described herein or according to methods known to those of ordinary skill in the art. Compounds of formula $X-R_a-C(O)OR_a$ are commercially available or may be prepared by methods known to those of ordinary skill in the art.

In general, compounds of formula (Ir) and (Is) are prepared by first treating a compound of formula (Iq) in an aprotic solvent, such as DMF, with a slightly excess equimolar amount of a compound of formula $X-R_a-C(O)OR_a$ where X is halo, preferably bromo, and each $R_a$ is independently an alkyl radical, in the presence of a base, such as potassium carbonate, and a metal halide, such as sodium iodide. The reaction mixture is heated at between about 40° C. and about 60° C., preferably at about 50° C., for about 30 minutes to about an hour, preferably for about an hour. The compound of formula (Ir) is isolated from the reaction mixture by standard techniques, such as evaporation and flash column chromatography.

The compound of formula (Ir) is the hydrolyzed under standard hydrolysis conditions to form the compound of formula (Is).

J. Preparation of Compounds of Formula (It)

Compounds of formula (It) are compounds of formula (I) wherein A is =N— and $R^6$ is —N($R^7$)—C(O)— and are prepared as described below in Reaction Scheme 10 wherein a, b, $R^1$, $R^2$, $R^3$, $R^4$, and $R^5$ are as described above in the Summary of the Invention; $R^{7a}$ is carboxyalkyl or alkoxycarbonylalkyl; and each X is independently halo:

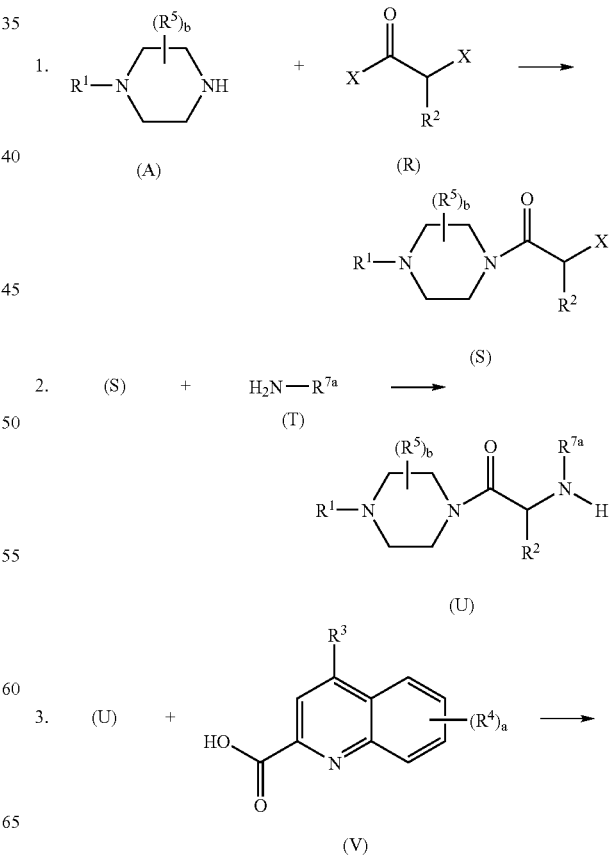

-continued

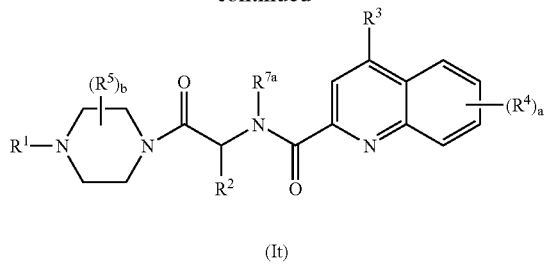

(It)

Compounds of formula (A), formula (R), and formula (T) are commercially available or may be prepared according to methods known to those of ordinary skill in the art. Compounds of formula (V) may be prepared according to methods disclosed herein.

In general, compounds of formula (It) are prepared by first treating a compound of formula (A) in an aprotic solvent, such as methylene chloride, with an one-half equimolar amount of a compound of formula (R) in the presence of a base, such as triethylamine, at a temperature of about −10° C. to about 10° C., preferably at about 0° C. The resulting reaction is stirred at ambient temperature for about 2 hours to about 6 hours, preferably for about 2 hours. The compound of formula (S) is isolated from the reaction mixture by standard isolation techniques.

The compound of formula (S) is then treated with an equimolar amount of a compound of formula (T) in the presence of a base, such as cesium carbonate. The resulting reaction mixture is stirred at a temperature of about 40° C. to about 60° C., preferably at about 50° C., for about 30 minutes to about 2 hours, preferably for about an hour. The compound of formula (U) is isolated from the reaction mixture by standard isolation techniques, such as organic solvent extraction and evaporation.

To a compound of formula (V) in an aprotic solvent, such as methylene chloride, in the presence of a base, such as triethylamine, and a slightly excess equimolar amount of a peptide coupling agent, such as HOBT and/or EDCI, is then added the compound of formula (U). The reaction mixture is stirred at ambient temperature for about 6 hours to about 16 hours, preferably for about 12 hours. The compound of formula (It) is isolated from the reaction mixture by standard isolation techniques, such as evaporation of the solvents and purification by flash column chromatography.

The compound of formula (It) may then be hydrolyzed under standard hydrolysis conditions to form compounds having the corresponding acid subsitutents.

K. Preparation of Compounds of Formula (Iu)

Compounds of formula (Iu) are compounds of formula (I) wherein A is =CH— and $R^6$ is —C(O)—N($R^7$)— and are prepared as described in Reaction Scheme 11 below wherein a, b, $R^1$, $R^3$, $R^4$ and $R^5$ are as described above in the Summary of the Invention; $R^{2b}$ is hydrogen; $R^{7b}$ is alkoxycarbonylalkyl; $R^8$ is alkyl or aralkyl; and each X is independently halo:

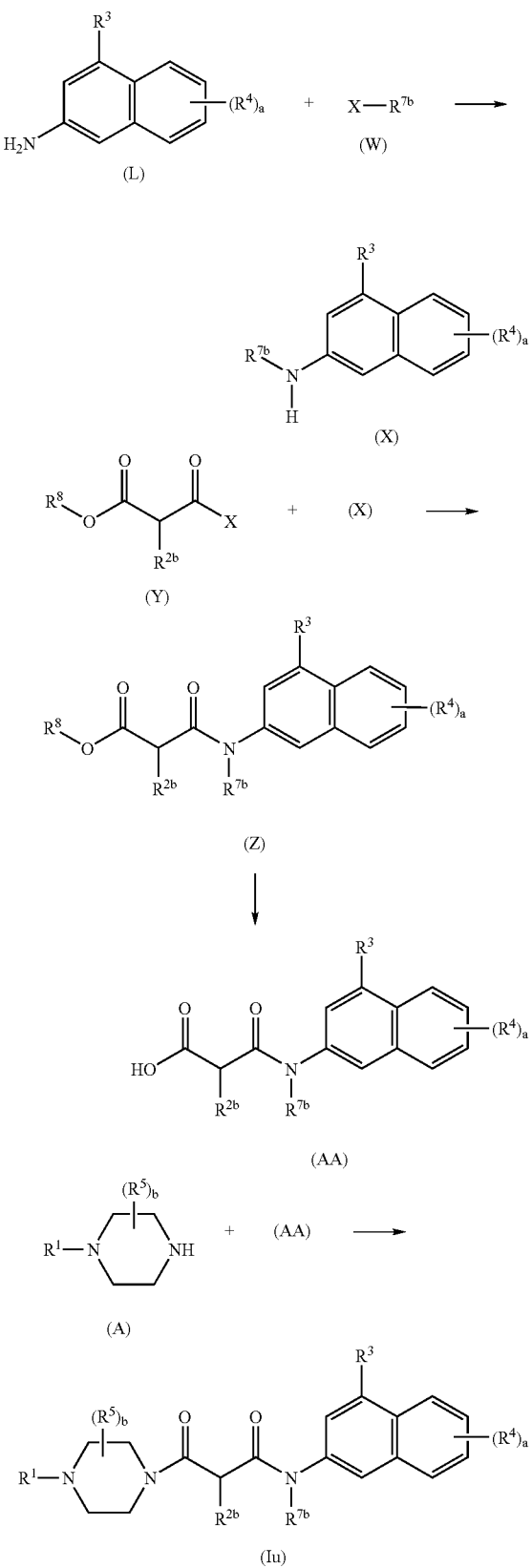

Compounds of formula (L), formula (W), formula (Y) and formula (A) are commercially available, or may be prepared according to methods known to those of ordinary skill in the art.

In general, compounds of formula (Iu) are prepared by first treating a compound of formula (L) in an aprotic solvent, such as DMF, with an excess equimolar amount of a compound of formula (W) in the presence of a base, such as potassium carbonate. The resulting reaction mixture was stirred at ambient temperature for about 6 hours to about 24 hours, preferably for about 24 hours. The compound of formula (X) is isolated from the reaction mixture by standard isolation techniques, such as organic solvent extraction and evaporation.

The compound of formula (X) in an aprotic solvent, such as methylene chloride, was treated with an excess equimolar amount of a compound of formula (Y) in the presence of a base, such as triethylamine. The resulting reaction mixture was stirred at ambient temperature for about 6 hours to about 2 days, preferably for about 12 hours. The compound of formula (Z) is isolated from the reaction mixture by standard isolation techniques, such as evaporation of the solvents and purification by flash chromatography. The compound of formula (Z) is then hydrolyzed under standard hydrolyis conditions to form a compound of formula (AA).

The compound of formula (AA) in an aprotic solvent, such as methylene chloride, in the presence of a base, such as triethylamine, and in the presence of an equimolar amount of peptide coupling reagent, such as HOBT and/or EDCI, is treated with an equimolar amount of a compound of formula (A). The reaction mixture is stirred from about 6 hours to about 16 hours, preferably for about 16 hours. The compound of formula (Iu) is isolated from the reaction mixture by standard isolation techniques, such as concentration, organic solvent extraction, evaporation of the solvents and purification by flash column chromatography.

The compound of formula (Iu) may then be hydrolyzed under standard hydrolysis conditions to form compounds having the corresponding acid subsitutents.

L. Preparation of Compounds of Formula (Iv) and Formula (Iw)

Compounds of formula (Iv) and compounds of formula (Iw) are compounds of formula (I) wherein A is =N— and $R^6$ is —N($R^7$)—C(O)— and are prepared as described below in Reaction Scheme 12 wherein a, b, $R^1$, $R^2$, $R^4$ and $R^5$ are as described above in the Summary of the Invention; $R^{2a}$ is alkoxycarbonylalkyl or carboxyalkyl; $R^{3b}$ is halo; $R^{3c}$ is optionally substituted N-heterocyclyl, (carboxyalkyl)(alkyl)amino, or carboxyalkenyl; and $R^{7a}$ is hydrogen or alkyl:

REACTION SCHEME 12

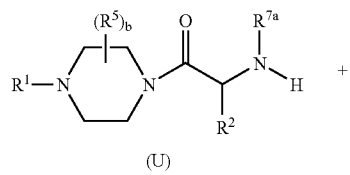

(U)

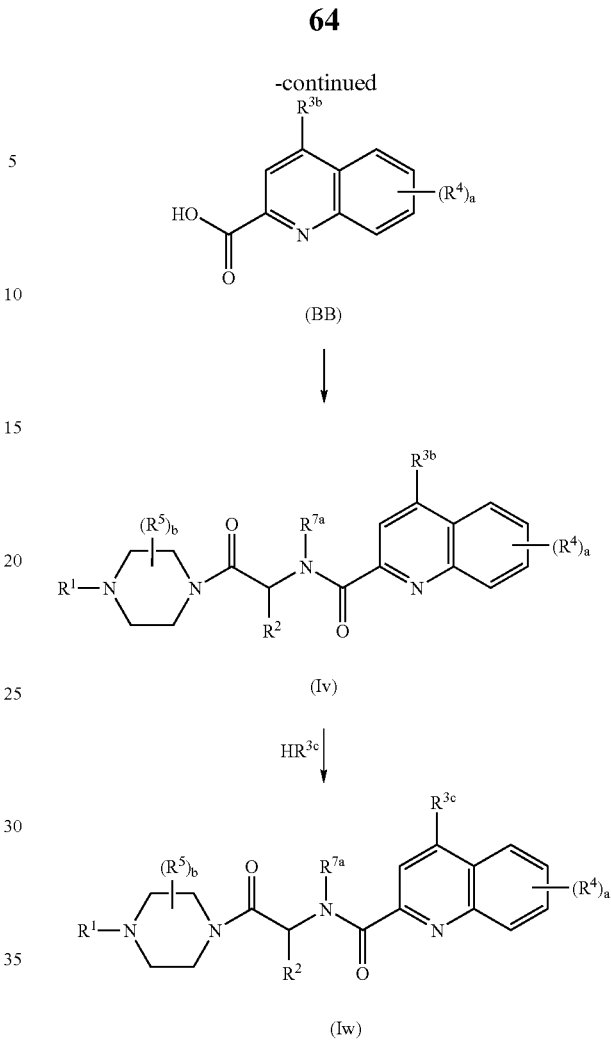

Compounds of formula (U) are prepared by methods disclosed herein. Compounds of formula (BB) are commercially available, or may be prepared according to methods disclosed in *Monatsh. Chem.* (1921), Vol. 42, p. 89, or in *J. Org. Chem.* (1947), Vol. 12, p. 456. Compounds of the formula $HR^{3c}$ are commercially available or may be prepared according to methods known to those of ordinary skill in the art.

In general, compounds of formula (Iv) and formula (Iw) are prepared by treating a compound of formula (BB) in an aprotic solvent, such as tetrahydrofuran, with an equimolar amount of a compound of formula (U) in the presence of a base, such as triethylamine and in the presence of a slightly excess equimolar amount of a peptide coupling agent, such as HOBT and/or EDCI. The resulting reaction mixture is stirred at ambient temperature for about 6 hours to about 16 hours, preferably for about 16 hours. The compound of formula (Iv) is isolated from the reaction mixture by standard isolation techniques, such as organic solvent extraction and purification by flash column chromatography. The compound of formula (Iv) may be further treated under standard hydrolysis conditions to form additional compounds of formula (Iv).

The compound of formula (Iv) in an aprotic solvent, such as dimethyl sulfoxide, is then treated with an excess equimolar amount of a compound of formula $HR^{3c}$ in the presence of a base, such as DIEA. The resulting reaction mixture is heated to about 100° C. to about 110° C., preferably to about 110° C. for about 6 hours to about 24 hours, preferably for about 18 hours. The resulting reaction mixture is then treated with a strong base, such as lithium hydroxide, for about 2 hours to about 4 hours, preferably for about 4 hours, to form the compound of formula (Iw), which is isolated from the reaction mixture by preparative HPLC.

Alternatively, the compound of formula (Iv) is treated with a compound of formula HR$^{3c}$ where R$^{3c}$ is carboxyalkenyl under standard palladium catalyzed conditions to form compounds of formula (Iw) where R$^{3c}$ is carboxyalkenyl.

Alternatively, compounds of formula (Iv) and formula (Iw) wherein the R$^2$ group contains an ester radical, such as alkoxycarbonyl, may be hydrolyzed under standard hydrolysis conditions to form compounds of formula (Iv) and formula (Iw) wherein the R$^2$ group contains the corresponding carboxy radical.

M. Preparation of Compounds of Formula (Ix) and Formula (Iy)

Compounds of formula (Ix) and Formula (Iy) are compounds of formula (I) wherein A is =N— and R$^6$ is —N(R$^7$)—C(O)— and are prepared as described below in Reaction Scheme 13 wherein a, b, R$^1$, R$^2$, R$^4$, and R$^5$ are as described above in the Summary of the Invention; R$^{7a}$ is hydrogen or alkyl; and R$^8$ is alkyl or aralkyl:

REACTION SCHEME 13

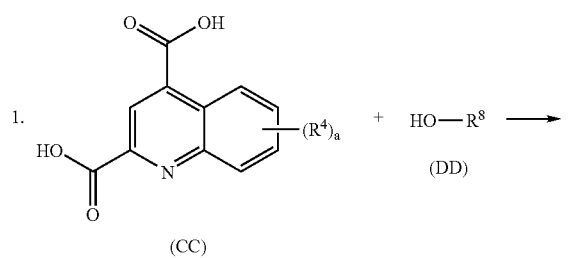

(CC)     (DD)

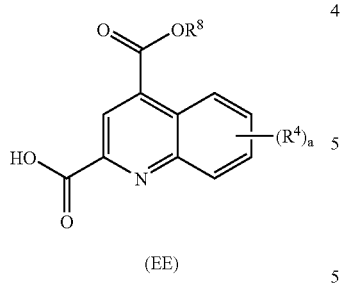

(EE)

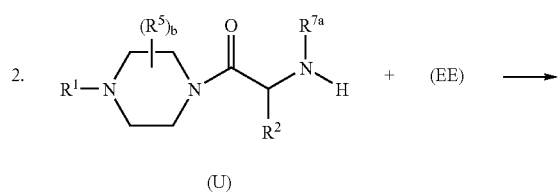

(U)

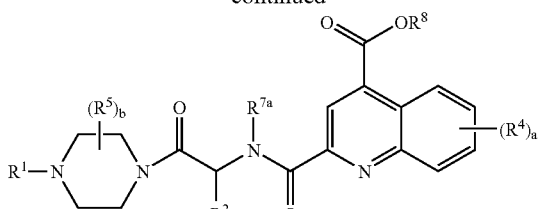

(Ix)

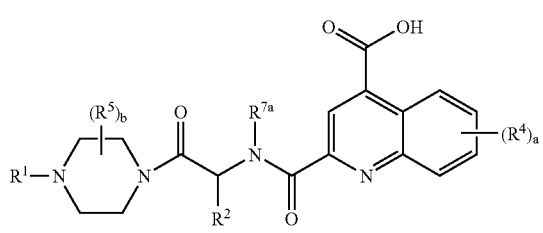

(Iy)

Compounds of formula (CC) are commercially available, for example, from Aldrich Co. Compounds of formula (DD) are commercially available or may be prepared according to methods known to those of ordinary skill in the art. Compounds of formula (U) are prepared by methods disclosed herein or by methods known to those of ordinary skill in the art.

In general, compounds of formula (Ix) and formula (Iy) are prepared by first treating a compound of formula (CC) with a halogenating agent, such as chlorotrimethylsilane (TMSCl) to form the corresponding acid halide, preferably the corresponding acid chloride, which is then treated with an excess molar amount of a compound of formula (DD) to form the compound of formula (EE).

The compound of formula (EE) in an aprotic solvent, such as tetrahydrofuran, is then treated with a slightly excess equimolar amount of a compound of formula (U) in the presence of a slightly excess equimolar amount of a peptide coupling agent, such as HOBT and/or EDCI. The resulting solution is stirred from about 6 hours to about 18 hours, preferably for about 16 hours. The compound of formula (Ix) is isolated from the reaction mixture by standard isolation techniques, such as concentration of the product, organic solvent extraction, evaporation and purification by flash column chromatography. Compounds of formula (Ix) may be treated under standard hydrolysis conditions to form compounds of formula (Iy).

Compounds of formula (Iy) can be further treated with compounds such as a substituted amine, a mono(alkoxycarbonylalkyl)amine, or a mono(dialkoxycarbonylalkyl)amine under standard peptide coupling reaction conditions, such as in the presence of standard peptide coupling agents such as HOBT and EDCI to form compounds of formula (Iy) wherein R$^4$ is aminocarbonyl, mono(alkoxycarbonylalkyl)

aminocarbonyl, or mono(di(alkoxycarbonyl)alkyl)aminocarbonyl. These compounds compounds can be further treated under standard hydrolysis conditions to form compounds of formula (Iy) wherein $R^4$ is mono(carboxyalkyl)aminocarbonyl, mono((alkoxycarbonyl)(carboxy)alkyl)aminocarbonyl or mono(dicarboxyalkyl)aminocarbonyl.

N. Preparation of Compounds of Formula (Iz)

Compounds of formula (Iz) are compounds of formula (I) wherein A is =N— and $R^6$ is —N($R^7$)—C(O)— and are prepared as described below in Reaction Scheme 14 wherein a, b, $R^1$, $R^2$, $R^4$, and $R^5$ are as described above in the Summary of the Invention; $R^{7a}$ is hydrogen or alkyl; $R^8$ is alkyl or aralkyl; and X is halo:

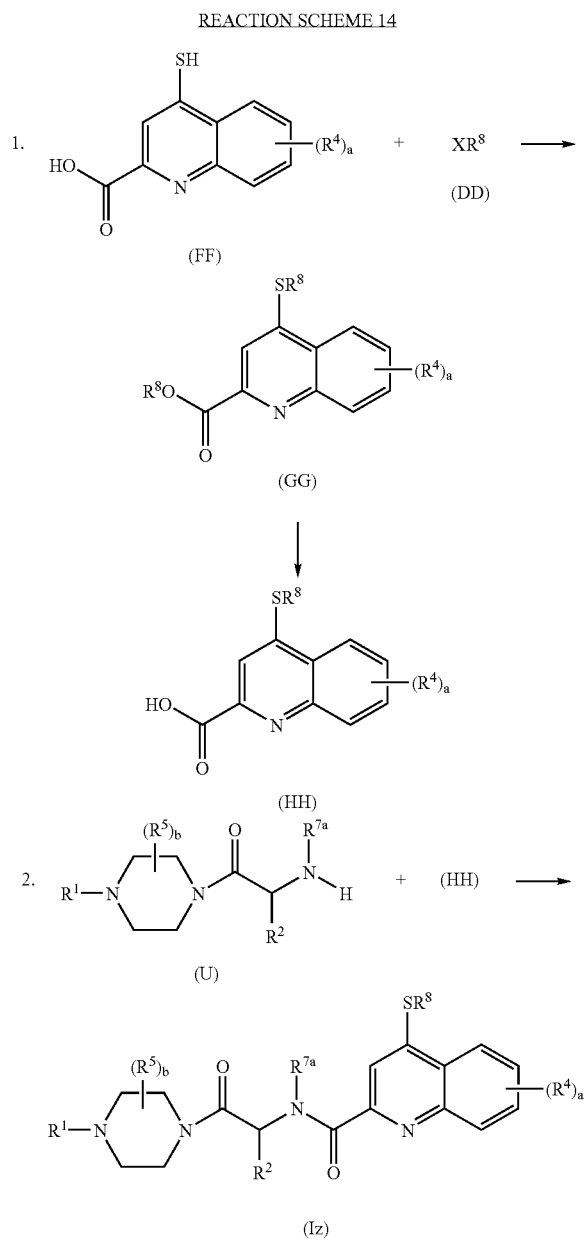

Compounds of formula (FF) and formula (DD) are commercially available or may be prepared according to methods known to those skilled in the art. Compounds of formula (U) are prepared by methods disclosed herein or by methods known to those of ordinary skill in the art.

In general, compounds of formula (Iz) are prepared by first treating a compound of formula (FF) in an aprotic solvent, such as DMF, with an excess equimolar amount of an alkyl halide, preferably methyl iodide, in the presence of a base, preferably cesium carbonate. The reaction mixture is stirred at a temperature between about 60° C. and about 100° C., preferably at about 70° C., from about 6 hours to about 18 hours, preferably for about 12 hours. The compound of formula (GG) is isolated from the reaction mixture by standard isolation techniques, such as organic solvent extraction, evaporation and purification by flash column chromatography.

The compound of formula (GG) is hydrolyzed under standard hydrolysis conditions to form a compound of formula (HH). The compound of formula (HH) in an aprotic solvent, such as THF and/or DMF, is then treated with a slightly excess equimolar amount of a compound of formula (U) in the presence of a slightly excess equimolar amount of a peptide coupling agent, such as HOBT and/or EDCI. The resulting mixture is stirred at ambient temperature from about 6 hours to about 18 hours, preferably for about 12 hours. The compound of formula (Iz) is isolated from the reaction mixture by standard isolation techniques, such as concentration, organic solvent extraction, evaporation of solvents and purification by flash column chromatography. The compound of formula (Iz) may be further treated under standard hydrolysis conditions to form compounds of the invention having the corresponding acid substituents.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques.

The following specific preparations and examples are provided as a guide to assist in the practice of the invention, and are not intended as a limitation on the scope of the invention. Where one or more NMR's are given for a particular compound, each NMR may represent a single stereoisomer, a non-racemic mixture of stereoisomers or a racemic mixture of the stereoisomers of the compound.

PREPARATION 1

Compounds of Formula (D)

A. To a solution of N-carbobenzyloxy-L-glutamic acid gamma t-butyl ester (24.4 g, 72.3 mmol) in tetrahydrofuran ("THF") (400 mL) and $CH_2Cl_2$ (100 mL) was added 1-hydroxybenzotriazole ("HOBT") (10.7 g, 79.5 mmol) and 1-(3-dimethylaminopropyl)-3-ethylcarbodiimide ("EDCI") (15.3 g, 79.5 mmol). After 5 minutes, 1-ethoxycarbonylpiperazine (11.7 mL, 79.5 mmol) was added and the reaction was stirred overnight. The reaction mixture was evaporated in vacuo to afford an oil, which was dissolved in ethyl acetate, and washed with saturated $NaHCO_3$, 1M $HaHSO_4$ and brine. The organic layer was evaporated in vacuo to 4-ethoxycarbonyl-1-(1-amino-3-(1,1-dimethylethoxycarbonyl)propyl)carbonylpiperazine (40.7 g), as an oil that was used without further purification. To 4-ethoxycarbonyl-1-(1-(benzyloxycarbonyl)amino-3 -(1,1-dimethylethoxycarbonyl)propyl)carbonylpiperazine in MeOH (100 mL) was added 10% Pd/C (1 g) and the mixture was shaken under 50 psi $H_2$ overnight. The reaction was filtered and stripped to 4-ethoxycarbonyl-1-(1-amino-3-(1,1-dimethylethoxycarbonyl)propyl)carbonylpiperazine (25 g, 99%) and used without further purification; NMR (CDCl$_3$) 1.25 (t, 3), 1.43 (s, 9), 2.55 (m, 1), 1.90 (m, 1), 2.37 (m, 1), 2.55 (m, 1), 3.40–3.70 (m, 8), 3.80 (m, 1), 4.18 (q, 2) ppm.

B. In a similar manner, other compounds of formula (D) were prepared.

4-ethoxycarbonyl-1-(aminomethyl)carbonylpiperazine;
4-ethoxycarbonyl-1-(1-amino-3-carboxypropyl)carbonylpiperazine;
4-ethoxycarbonyl-2-methyl-1-(aminomethyl)carbonylpiperazine;
4-ethoxycarbonyl-3-methyl-1-(aminomethyl)carbonylpiperazine;
4-ethoxycarbonyl-1-(1-amino-5-((2-chlorobenzyloxy)carbonylamino)pentyl)carbonylpiperazine;
4-ethoxycarbonyl-1-(1-amino-2-(benzyloxycarbonyl)ethyl)carbonylpiperazine;
4-ethoxycarbonyl-1-(1-amino-2-phenylethyl)carbonylpiperazine;
4-ethoxycarbonyl-1-(1-amino-2-methylpropyl)carbonylpiperazine;
4-ethoxycarbonyl-1-(1-amino-2-carboxyethyl)carbonylpiperazine; and
4-ethoxycarbonyl-1-(1,5-diaminopentyl)carbonylpiperazine.

PREPARATION 2

Compounds of Formula (G)

A. To a solution of m-toludine (20.0 g, 0.186 mol) in methanol (300 mL), dimethyl acetylenedicarboxylate (26.42 g, 0.186 mol) was added drop-wise and the reaction mixture was stirred at ambient temperature for 30 minutes. The solvent was removed by evaporation and the residue was added to stirred diphenyl ether (150 ml), which has been preheated to 250° C. After 30 minutes, the mixture was cooled to ambient temperture and the resulting precipitate was collected and washed with hot petroleum ether (1.5 L) to give a mixture (27.0 g) of 5-methyl-4-hydroxy-2-methoxycarbonylquinoline and 7-methyl-4-hydroxy-2-methoxycarbonylquinoline. The mixture was dissolved in boiling methanol (1.3 L) and kept at ambient temperature for two days to afford (6.45 g, 16%) of 7-methyl-4-hydroxy-2-methoxycarbonylquinoline, NMR (DMSO-d$_6$) 2.40 (s, 3), 3.92 (s, 3), 6.56 (s, 1), 7.16 (d, 1), 7.68 (s, 1), 7.94 (d, 1) ppm.

B. In a similar manner, other compounds of formula (G) were prepared as follows:

8-methoxy-4-hydroxy-2-methoxycarbonylquinoline;
5-amino-4-hydroxy-2-methoxycarbonylquinoline;
5-nitro-4-hydroxy-2-methoxycarbonylquinoline;
5-carboxymethylamino-4-hydroxy-2-methoxycarbonylquinoline;
7-chloro-4-hydroxy-2-methoxycarbonylquinoline;
5-di(acetyl)amino-4-hydroxy-2-methoxycarbonylquinoline;
5-acetylamino-4-hydroxy-2-methoxycarbonylquinoline;
5,7-dichloro-4-hydroxy-2-methoxycarbonylquinoline;
6-chloro-4-hydroxy-2-methoxycarbonylquinoline;
6-nitro-4-hydroxy-2-methoxycarbonylquinoline;
6-amino-4-hydroxy-2-methoxycarbonylquinoline;
7-benzyloxy-4-hydroxy-2-methoxycarbonylquinoline;
4,7-dihydroxy-2-methoxycarbonylquinoline;
7-prop-1-oxy-4-hydroxy-2-methoxycarbonylquinoline;
7-carboxymethoxy-4-hydroxy-2-methoxycarbonylquinoline;
7-diethylaminoethoxy-4-hydroxy-2-methoxycarbonylquinoline;
7-methoxy-4-hydroxy-2-methoxycarbonylquinoline;
7-(2-(4-hydroxy-2-carboxypyrrolidinyl)ethoxy)-4-hydroxy-2-methoxycarbonylquinoline;
8-methyl-4-hydroxy-2-methoxycarbonylquinoline;
6-diethylaminomethyl-4-hydroxy-2-methoxycarbonylquinoline;
6-benzyloxy-4-hydroxy-2-methoxycarbonylquinoline;
4,6-dihydoxy-2-methoxycarbonylquinoline;
6-carboxymethoxy-4-hydroxy-2-methoxycarbonylquinoline;
6-ethoxy-4-hydroxy-2-methoxycarbonylquinoline;
6-methoxy-4-hydroxy-2-methoxycarbonylquinoline;
6-prop-2-oxy-4-hydroxy-2-methoxycarbonylquinoline;
7-fluoro-4-hydroxy-2-methoxycarbonylquinoline;
7-trifluoromethyl-4-hydroxy-2-methoxycarbonylquinoline;
7-hydroxymethyl-4-hydroxy-2-methoxycarbonylquinoline;
7-cyano-4-hydroxy-2-methoxycarbonylquinoline;
7-nitro-4-hydroxy-2-methoxycarbonylquinoline;
6-carboxy-4-hydroxy-2-methoxycarbonylquinoline;
7-trifluoromethoxy-4-hydroxy-2-methoxycarbonylquinoline;
6-trifluoromethoxy-4-hydroxy-2-methoxycarbonylquinoline;
7-acetyl-4-hydroxy-2-methoxycarbonylquinoline;
5-ethoxycarbonyl-4-hydroxy-2-methoxycarbonylquinoline;
6-ethyl-4-hydroxy-2-methoxycarbonylquinoline;
7-carboxy-4-hydroxy-2-methoxycarbonylquinoline;
6-aminocarbonyl-4-hydroxy-2-methoxycarbonylquinoline;
6,7-dimethoxy-4-hydroxy-2-methoxycarbonylquinoline;
6-chloro-7-methyl-4-hydroxy-2-methoxycarbonylquinoline;
6-fluoro-7-methyl-4-hydroxy-2-methoxycarbonylquinoline;
6-fluoro-4-hydroxy-2-methoxycarbonylquinoline;
6-fluoro-7-chloro-4-hydroxy-2-methoxycarbonylquinoline;
7-bromo-4-hydroxy-2-methoxycarbonylquinoline;
6,7-dimethyl-4-hydroxy-2-methoxycarbonylquinoline;
6-methoxy-7-methyl-4-hydroxy-2-methoxycarbonylquinoline;
6-methoxy-7-chloro-4-hydroxy-2-methoxycarbonylquinoline;
6-chloro-8-fluoro-4-hydroxy-2-methoxycarbonylquinoline;
6,7-dichloro-4-hydroxy-2-methoxycarbonylquinoline;
6,8-difluoro-4-hydroxy-2-methoxycarbonylquinoline;
6,7-difluoro-4-hydroxy-2-methoxycarbonylquinoline;
6-dimethylamino-4-hydroxy-2-methoxycarbonylquinoline;
5-fluoro-6-methyl-4-hydroxy-2-methoxycarbonylquinoline;
6-methyl-7-chloro-4-hydroxy-2-methoxycarbonylquinoline;
6-acetyl-4-hydroxy-2-methoxycarbonylquinoline;
6-methylthio-4-hydroxy-2-methoxycarbonylquinoline;
4,5-dihydroxy-2-methoxycarbonylquinoline;
7-ethyl-4-hydroxy-2-methoxycarbonylquinoline;
5-methyl-4-hydroxy-2-methoxycarbonylquinoline;
5-hydroxymethoxy-4-hydroxy-2-methoxycarbonylquinoline;
5-(3-ethoxycarbonylpropoxy)-4-hydroxy-2-methoxycarbonylquinoline; and
5-(3-carboxypropoxy)-4-hydroxy-2-methoxycarbonylquinoline.

PREPARATION 3

Compounds of Formula (H)

A. 7-methyl-4-hydroxy-2-methoxycarbonylquinoline (6.45 g, 30.14 mmol) was suspended in MeOH (150 mL) and water (100 mL), and LiOH (3.08 g, 75.5 mmol) was added and stirred at ambient temperature for 2 hours. The methanol was evaporated in vacuo and residue was crystallized by addition of 2N hydrochloric acid. The resulting solid was filtered, washed with water and dried to afford 7-methyl-4-hydroxy-2-carboxyquinoline (6.0 g, 98%), NMR (DMSO-$d_6$) 2.40 (s, 3), 6.68 (s, 1), 7.22 (d, 1), 7.68 (s, 1), 7.96 (d, 1).

B. In a similar manner, the following compounds of formula (H) were prepared:
8-methoxy-4-hydroxy-2-carboxyquinoline;
5-amino-4-hydroxy-2-carboxyquinoline;
5-nitro-4-hydroxy-2-carboxyquinoline;
5-carboxymethylamino-4-hydroxy-2-carboxyquinoline;
7-chloro-4-hydroxy-2-carboxyquinoline;
5-di(acetyl)amino-4-hydroxy-2-carboxyquinoline;
5-acetylamino-4-hydroxy-2-carboxyquinoline;
5,7-dichloro-4-hydroxy-2-carboxyquinoline;
6-chloro-4-hydroxy-2-carboxyquinoline;
6-nitro-4-hydroxy-2-carboxyquinoline;
6-amino-4-hydroxy-2-carboxyquinoline;
7-benzyloxy-4-hydroxy-2-carboxyquinoline;
4,7-dihydroxy-2-carboxyquinoline;
7-prop-1-oxy-4-hydroxy-2-carboxyquinoline;
7-carboxymethoxy-4-hydroxy-2-carboxyquinoline;
7-diethylaminoethoxy-4-hydroxy-2-carboxyquinoline;
7-methoxy-4-hydroxy-2-carboxyquinoline;
7-(2-(4-hydroxy-2-carboxypyrrolidinyl)ethoxy)-4-hydroxy-2-carboxyquinoline;
8-methyl-4-hydroxy-2-carboxyquinoline;
6-diethylaminomethyl-4-hydroxy-2-carboxyquinoline;
3-methyl-4-hydroxy-2-carboxyquinoline;
6-benzyloxy-4-hydroxy-2-carboxyquinoline;
4,6-dihydoxy-2-carboxyquinoline;
6-carboxymethoxy-4-hydroxy-2-carboxyquinoline;
6-ethoxy-4-hydroxy-2-carboxyquinoline;
6-methoxy-4-hydroxy-2-carboxyquinoline;
6-prop-2-oxy-4-hydroxy-2-carboxyquinoline;
7-fluoro-4-hydroxy-2-carboxyquinoline;
7-trifluoromethyl-4-hydroxy-2-carboxyquinoline;
7-hydroxymethyl-4-hydroxy-2-carboxyquinoline;
7-cyano-4-hydroxy-2-carboxyquinoline;
7-nitro-4-hydroxy-2-carboxyquinoline;
2,6-dicarboxy-4-hydroxyquinoline;
7-trifluoromethoxy-4-hydroxy-2-carboxyquinoline;
6-trifluoromethoxy-4-hydroxy-2-carboxyquinoline;
7-acetyl-4-hydroxy-2-carboxyquinoline;
5-ethoxycarbonyl-4-hydroxy-2-carboxyquinoline;
6-ethyl-4-hydroxy-2-carboxyquinoline;
2,7-dicarboxy-4-hydroxyquinoline;
6-aminocarbonyl-4-hydroxy-2-carboxyquinoline;
6,7-dimethoxy-4-hydroxy-2-carboxyquinoline;
6-methyl-7-chloro-4-hydroxy-2-carboxyquinoline;
6-chloro-7-methyl-4-hydroxy-2-carboxyquinoline;
6-fluoro-7-methyl-4-hydroxy-2-carboxyquinoline;
6-fluoro-4-hydroxy-2-carboxyquinoline;
6-fluoro-7-chloro-4-hydroxy-2-carboxyquinoline;
7-bromo-4-hydroxy-2-carboxyquinoline;
6,7-dimethyl-4-hydroxy-2-carboxyquinoline;
6-methoxy-7-methyl-4-hydroxy-2-carboxyquinoline;
6-methoxy-7-chloro-4-hydroxy-2-carboxyquinoline;
6-chloro-8-fluoro-4-hydroxy-2-carboxyquinoline;
6,7-dichloro-4-hydroxy-2-carboxyquinoline;
6,8-difluoro-4-hydroxy-2-carboxyquinoline;
6,7-difluoro-4-hydroxy-2-carboxyquinoline;
6-dimethylamino-4-hydroxy-2-carboxyquinoline;
5-fluoro-6-methyl-4-hydroxy-2-carboxyquinoline;
6-acetyl-4-hydroxy-2-carboxyquinoline;
6-methylthio-4-hydroxy-2-carboxyquinoline;
4,5-dihydroxy-2-carboxyquinoline;
5-hydroxymethoxy-4-hydroxy-2-carboxyquinoline;
7-methyl-4-hydroxy-2-carboxyquinoline;
5-methyl-4-hydroxy-2-carboxyquinoline;
5-(3-ethoxycarbonylpropoxy)-4-hydroxy-2-carboxyquinoline; and
5-(3-carboxypropoxy)-4-hydroxy-2-carboxyquinoline.

PREPARATION 4

Compounds of Formulae (Fb), (Ga) and (Gb)

A. To a solution of $SnCl_2H_2O$ (140 g, 0.62 mol) in ethanol (350 mL) was added a solution of 2,6-dichloro-3-nitrotoluene (25 g, 0.12 mol) in ethanol (50 mL). The reaction mixture was refluxed for 1 hour. The reaction mixture was concentrated under reduced pressure. The residue was dissolved in water (100 mL), pH was adjusted to approximately pH 12 with 1N NaOH solution and extracted with ethyl acetate. The ethyl acetate layer was washed with brine, dried over sodium sulfate, and concentrated to afford 2,6-dichloro-3-aminotoluene (21 g, 98%); NMR ($CDCl_3$) 2.42 (s, 3), 6.62 (d, 1), 7.14 (d, 1) ppm.

B. To a solution of 2,6-dichloro-3-aminotoluene (20.5 g, 0.11 mol) in methanol (300 mL) was added dimethyl acetylenedicarboxylate (15 mL, 0.12 mol) and the reaction mixture was refluxed for 2 hours. The reaction mixture was concentrated under reduced pressure to a yellow solid. Diphenyl ether (350 mL) was heated to 230–240° C., and the yellow solid was added to it. The temperature was maintained at 230–240° C. for 20 minutes and the reaction mixture was cooled slowly to ambient temperature and diluted with petroleum ether (1 L). The solid was filtered and washed with hot ethyl acetate to afford a brown solid, 2-(methoxycarbonyl)-4-oxo-6,8-dichloro-7-methylquinoline (28.5 g, 85%); NMR ($CDCl_3$) 2.62 (s, 3), 4.04 (s, 3), 7.02 (s, 1), 8.24 (s, 1) ppm.

C. 2-(Methoxycarbonyl)-4-oxo-6,8-dichloro-7-methylquinoline (28.5 g, 99.6 mmol) was suspended in methanol (1 L) and a solution of $LiOH.H_2O$ (20.5 g, 0.5 mol) in water (200 mL) was added to the solution. The resulting reaction mixture was stirred at ambient temperature for 0.5 hours. Pd/C (5.8 g) was added to the reaction mixture and the resulting reaction mixture was shaken under 50 Psi hydrogen overnight. The reaction mixture was filtered, concentrated under reduced pressure to remove methanol, diluted with water (300 mL) and the pH was adjusted to between pH 3 and pH 4 by 2N HCl. The precipitate was collected by filtration, washed with water and dried to afford a white solid, 2-carboxy-4-oxo-7-methylquinoline (20 g, 90%); NMR (DMSO-$d_6$) 2.40 (s, 3), 6.60 (s, 1), 7.20 (d, 1), 7.68 (s, 1), 7.96 (d, 1) ppm.

PREPARATION 5

Compounds of Formulae (M) and (N)

A. To a solution of 2-aminonaphthalene (1.43 g, 10 mmol) in $CH_2Cl_2$ (15 mL) and triethylamine (1 mL) was added a solution of ethyl malonyl chloride (1.4 mL, 11 mmol) in CH$_2$Cl$_2$ (10 mL) dropwise at 5° C. The reaction mixture was stirred at 10° C. After 1 hour the reaction was diluted with 100 mL CH$_2$Cl$_2$, washed with 2N NaHSO$_4$ and water, brine. The organic layer was evaporated in vacuo to afford 2-((ethoxycarbonyl)methylcarbonylamino)naphthalene (2.3 g, 8.9 mmol) as a solid that was used without further purification.

B. To a solution of 2-((ethoxycarbonyl)methylcarbonylamino)naphthalene (2.3 g, 8.9 mmol) in MeOH (40 mL) was added a solution of LiOH (1.18 g, 27 mmol) in water (40 mL). The reaction mixture was stirred at ambient temperature. After 3 hours, the reaction mixture was acidified to pH 2–3 by 2N NaHSO$_4$, then extracted with ethyl acetate (3×50 mL). The organic layer was dried over Na$_2$SO$_4$ and evaporated in vacuo to afford 2-((carboxy)methylcarbonylamino)naphthalene (2.0 g, 8.7 mmol) as a solid that was used in further preparations without further purification.

PREPARATION 6

Compounds of formula (S) and formula (U)

A. To a solution of 1-ethoxycarbonylpiperazine (1.5 mL, 10 mmol) in 40 mL CH$_2$Cl$_2$, was added triethylamine (2 mL, 14 mmol) and chloroacetyl chloride (0.8 mL, 5.0 mmol) at 0° C. The resulting reaction mixture was stirred at amibent temperature for 2 hours. The reaction mixture was washed with water, 2N NaHSO$_4$ and brine, and dried over sodium sulfate. The solvent was evaporated in vacuo to afford 1-ethoxycarbonyl-4-chloromethylcarbonylpiperazine (4.5 g) as an yellow oil, which was used without further purification.

B. To a solution of 1-ethoxycarbonyl-4-chloromethylcarbonylpiperazine (520 mg, 2.21 mmol) in DMF (40 mL) was added cesium carbonate (2.0 g, 6.20 mmol) and glycine ethyl ester hydrochloride (310 mg, 2.21 mmol). The resulting reaction mixture was stirred at 50° C. After 1 hour, the reaction mixture was diluted with ethyl acetate (200 mL), washed with water (3×150 mL) and brine, and concentrated in vacuo to afford 1-ethoxycarbonyl-4-(ethoxycarbonylmethyl)aminomethylcarbonylpiperazine as an oil (520 mg), which was used without purification.

C. In a similar manner, other compounds of formula (S) and formula (U) are prepared.

PREPARATION 7

Compounds of Formula (X), Formula (Z) and Formula (AA)

A. To a solution of 2-aminonaphthalene (985 mg, 6.8 mmol) in N,N-dimethylformamide (DMF) (50 mL) was added potassium carbonate (1.806 g, 13.6 mmol) and tert-butyl bromoacetate (1.4 mL, 9.9 mmol). The resulting reaction mixture was stirred at ambient temperature. After 24 hours, the reaction mixture was diluted with water (200 mL), then extracted by ethyl acetate (150 mL). The organic layer was separated and washed with water (3×100 mL), then dried over sodium sulfate. The solvent was evaporated in vacuo to afford a product as ann yellow oil. Purification of product by flash column on silica gel afforded 2-((1,1-dimethylethoxycarbonyl)methyl)aminonaphthalene (1.2 g).

B. To a solution of 2-((1,1-dimethylethoxycarbonyl)methyl)aminonaphthalene (926 mg, 3.6 mmol) in CH$_2$Cl$_2$ (40 mL) was added triethylamine (3 mL, 21.5 mmol) and ethyl 3-chloro-3-oxapropionate (1.3 mL, 10.1 mmol). The resulting reaction mixture was stirred at ambient temperature for 2 days. The reaction mixture was washed with water and brine, and dried over sodium sulfate. The solvent was evaporated in vacuo to afford a product as an yellow oil. Purification of the product by flash column on silica gel afforded 2-[ethoxycarbonylmethylcarbonyl][(1,1-dimethylethoxycarbonyl)methyl]aminonaphthalene (730 mg) as a clear oil.

C. To-a solution of 2-[ethoxycarbonylmethylcarbonyl][(1,1-dimethylethoxycarbonyl)methyl]aminonaphthalene (730 mg, 1.95 mmol) in methanol (5.0 mL) was added a solution of LiOH (123 mg, 2.91 mmol) in water (3.0 mL). The resulting reaction mixture was stirred at ambient temperature for 1 hour. The reaction mixture was acidified by 2N NaHSO$_4$ to pH 3, then extracted by ethyl acetate (3×10 mL). The organic layer was evaporated in vacuo to afford 2-[carboxymethylcarbonyl][(1,1-dimethylethoxycarbonyl)methyl]aminonaphthalene (270 mg) as a white solid.

D. In a similar manner, other compounds of formula (X), formula (Z) and formula (M) are prepared.

EXAMPLE 1

Compounds of Formula (Ia)

A. To a suspension of 7-methyl-4-hydroxy-2-carboxyquinoline (0.81 g, 4 mmol) in methylene chloride:DMF (4:1, 25 mL) was added 1-hydoxybenzotriazole (HOBT) (0.64 g, 4.8 mmol) and 1-(3-dimethylaminopropyl)-3-ethylcarbodiimide (EDCI) (1.09 g, 4.8 mmol) and the reaction mixture was stirred for 10 minutes. A solution of 4-ethoxycarbonyl-1-(1-amino-3-(1,1-dimethylethoxycarbonyl)propyl)carbonylpiperazine (1.37 g, 4 mmol) in methylene chloride (10 mL) was added to the reaction mixture and the resulting mixture was stirred at ambient temperature for 6 hours. The solvent was evaporated in vacuo and the resulting residue was partitioned in ethyl acetate and water. The organic layers were combined and washed with water, brine and concentrated to afford an off-white foam, 2-[1-(4-(ethoxycarbonyl)piperazin-1-yl)carbonyl-3-(1,1-dimethylethoxycarbonyl)propyl]aminocarbonyl-4-hydroxyquinoline; (1.44 g, 68%).

B. In a similar manner, other compounds of formula (Ia) are prepared.

EXAMPLE 2

Compounds of Formula (Ib)

A. 1-Ethoxycarbonyl-1-bromocyclobutane (0.62 g, 3.03 mmol) was added to a solution of 2-[1-(4-(ethoxycarbonyl)piperazin-1-yl)carbonyl-3-(1,1-dimethylethoxycarbonyl)propyl]aminocarbonyl-4-hydroxyquinoline (0.8 g, 1.52 mmol) and cesium carbonate (1.00 g, 3.03 mmol) in N,N-dimethylformamide (DMF) (15 mL) and stirred at 90–100° C. At every 2 hours, excess equimolar amounts of 1-ethoxycarbonyl-1-bromocyclobutane and cesium carbonate were added to the solution to a total of 8 equivalents of each reagent. After 10 hours, the reaction mixture was filtered, the solvent was evaporated and the residue was purified by preparative HPLC to afford 2-[1-(4-(ethoxycarbonyl)piperazin-1-yl)carbonyl-3-(1,1-dimethylethoxycarbonyl)propyl]aminocarbonyl-7-methyl-4-(1-(ethoxycarbonyl)cyclobut-1-oxy)quinoline (0.45 g , 38%) as a white solid (TFA salt); NMR (DMSO-d$_6$) 1.04 (t, 3), 1.14 (t, 3), 1.32 (s, 9), 1.82 (m, 1), 2.00 (m, 3), 2.26 (m, 2), 2.52 (s, 3), 2.58 (m, 2), 2.78 (m, 2), 3.5 (m, 8), 4.04 (q, 2), 4.15 (q, 2), 5.00 (m, 1), 6.94 (s, 1), 7.52 (d, 1), 7.88 (s, 1), 8.14 (d, 1), 8.84 (d, 1) ppm.

B. A solution of 2-[1-(4-(ethoxycarbonyl)piperazin-1-yl)carbonyl-3-(1,1-dimethylethoxycarbonyl)propyl]aminocarbonyl-7-methyl-4-(1-(ethoxycarbonyl)cyclobut-1-oxy)quinoline (75 mg, 0.09 mmol) in 50% trifluoroacetic acid-methylene chloride (2 ml) was stirred at ambient temperature for 1 hour. The solvent was evaporated in vacuo and the resulting residue was purified by preparative HPLC to afford 2-[1-(4-(ethoxycarbonyl)piperazin-1-yl)carbonyl-3-carboxypropyl] aminocarbonyl-7-methyl-4-(1-(ethoxycarbonyl)cyclobut-1-oxy)quinoline as a white solid (60 mg, 93%, trifluoroacetic acid salt); NMR (DMSO-$d_6$) 1.03 (t, 3), 1.16 (t, 3), 1.82 (m, 1), 2.00 (m, 3), 2.26 (m, 2), 2.55 (s, 3), 2.59 (m, 2), 2.77 (m, 2), 3.38 (m, 6), 3.60 (m, 2), 4.02 (q, 2), 4.12 (q, 2), 4.98 (m, 1), 6.92 (s, 1), 7.52 (d, 1), 7.88 (s, 1), 8.14 (d, 1), 8.85 (d, 1) ppm.

C. A solution of 2-[1-(4-(ethoxycarbonyl)piperazin-1-yl)carbonyl-3-carboxypropyl]aminocarbonyl-7-methyl-4-(1-(ethoxycarbonyl)cyclobut-1-oxy)quinoline (220 mg, 0.29 mmol) in 50% trifluoroacetic acid-methylene chloride (6 mL) was stirred at ambient temperature for 1 hour. The solvent was evaporated in vacuo and the residue was dissolved in methanol (5 ml). LiOH (5 mL, 0.025 M) was added and the reaction stirred for 3 hours. The solvent was evaporated and the residue was purified by preparative HPLC to afford 2-[1-(4-(ethoxycarbonyl)piperazin-1-yl)carbonyl-3-carboxypropyl]aminocarbonyl-7-methyl-4-(1-carboxycyclobut-1-oxy)quinoline, as a white solid (190 mg, 95%, trifluoroacetic acid salt); NMR (DMSO-$d_6$) 1.15 (t, 3), 1.82 (m, 1), 2.00 (m, 3), 2.30 (m, 2), 2.51 (s, 3), 2.56 (m, 2), 2.68 (m, 2), 3.40 (m, 6), 3.62 (m, 2), 4.00 (q, 2), 4.98 (m, 1), 6.98 (s, 1), 7.52 (dd, 1), 7.88 (s, 1), 8.14 (d, 1), 8.85 (d, 1) ppm.

D. In a similar manner as described above in Paragraphs A-C, the following compounds were made:

2-[(4-(1,1-dimethylethoxycarbonyl)piperazin-1-yl)carbonylmethyl]aminocarbonyl-4-methoxyquinoline; NMR (DMSO-$d_6$) 1.40 (s, 9), 3.30–3.50 (m, 8), 4.10 (S, 3), 4.24 (d, 2), 7.60 (S, 3), 7.64 (t, 1), 7.82 (t, 1), 8.03 (d, 1), 8.20 (d, 1), 8.94 (t, 1) ppm;

2-[(piperazin-1-yl)carbonylmethyl]aminocarbonyl-4-methoxyquinoline; NMR (DMSO-$d_6$) 2.60–2.70 (m, 4), 3.35–3.41 (m, 4), 7.58 (s, 3), 7.63 (t, 1), 7.82 (t, 1), 8.03 (d, 1), 8.18 (d, 1), 8.93 (t, 1) ppm;

2-[(2-methyl-4-(4-fluorobenzyl)piperazin-1-yl)carbonylmethyl]aminocarbonyl-4-methoxyquinoline; NMR (DMSO-$d_6$) 1.16–1.34 (m, 3), 1.80–2.20 (m, 2), 2.60–2.90 (m, 3), 3.40–3.70 (m, 3), 4.12 (m, 5), 4.20–4.50 (m, 1), 7.16 (m, 2), 7.34 (m, 2), 7.60 (s, 1), 7.63 (t, 1), 7.83 (t, 1), 8.03 (d, 1), 8.20 (d, 1), 8.93 (m, 1) ppm;

2-[(3-methyl-4-(ethoxycarbonyl)piperazin-1-yl)carbonylmethyl]aminocarbonyl-4-methoxyquinoline; NMR (DMSO-$d_6$) 1.02–1.21 (m, 6), 2.60–3.20 (m, 3), 3.70–3.90 (m, 2), 4.05 (m, 2), 4.13 (s, 3), 4.17–4.40 (m, 4), 7.60 (s, 2), 7.63 (t, 1), 7.83 (t, 1), 8.04 (d, 1), 8.18 (d, 1), 8.97 (m, 1) ppm, and NMR (CDCl$_3$) 1.30 (m, 6), 2.80–3.20 (m, 3), 3.40 (m, 1), 3.60 (m, 1), 4.00–4.40 (m, 9), 7.55 (m, 1), 7.65 (s, 1), 7.70 (t, 1), 8.10 (d, 1), 8.20 (d, 1), 9.10 (m, 1) ppm;

2-[(2-methyl-4-(ethoxycarbonyl)piperazin-1-yl)carbonylmethyl]aminocarbonyl-4-methoxyquinoline; NMR (DMSO-$d_6$) 1.03–1.15 (d, 3), 1.18 (t, 3), 2.8–3.2 (m, 3), 3.7–4.0 (m, 2), 4.06 (q, 2), 4.10 (s, 3), 4.15–4.60 (m, 4), 7.6 (s, 1), 7.63 (t, 1), 7.83 (t, 1), 8.04 (d, 1), 8.19 (d, 1), 8.96 (m, 1) ppm;

2-[(4-(2-methylpropoxycarbonyl)piperazin-1-yl)carbonylmethyl]aminocarbonyl-4-methoxyquinoline; NMR (DMSO-$d_6$) 0.88 (d, 6), 1.86 (m, 1), 3.30–3.50 (m, 8), 3.78 (d, 2), 4.12 (s, 3), 4.25 (d, 2), 7.58 (s, 1), 7.65 (t, 1), 7.84 (t, 1), 8.06 (d, 1), 8.18 (d, 1), 8.95 (t, 1) ppm;

2-[(4-(trichloromethoxycarbonyl)piperazin-1-yl)carbonylmethyl]aminocarbonyl-4-methoxyquinoline; NMR (DMSO-$d_6$) 3.50–3.75 (m, 8), 4.10 (s, 3), 4.26 (d, 2), 7.58 (s, 1), 7.64 (t, 1), 7.83 (t, 1), 8.05 (d, 1), 8.18 (d, 1), 8.94 (t, 1) ppm;

2-[(4-(benzyloxycarbonyl)piperazin-1-yl)carbonylmethyl]aminocarbonyl-4-methoxyquinoline; NMR (DMSO-$d_6$) 3.35–3.54 (m, 8), 4.10 (s, 3), 4.26 (d, 2), 5.07 (s, 2), 7.10–7.20 (m, 5), 7.58 (s, 1), 7.64 (t, 1), 7.83 (t, 1), 8.05 (d, 1), 8.18 (d, 1), 8.94 (t, 1) ppm;

2-[(4-(1-chloroethoxycarbonyl)piperazin-1-yl)carbonylmethyl]aminocarbonyl-4-methoxyquinoline; NMR (DMSO-$d_6$) 1.78 (d, 3), 3.40–3.60 (m, 8), 4.10 (s, 3), 4.26 (d, 2), 6.58 (q, 1), 7.60 (s, 1), 7.64 (t, 1), 7.84 (t, 1), 8.06 (d, 1), 8.19 (d, 1), 8.95 (t, 1) ppm;

2-[(4-(methoxycarbonyl)piperazin-1-yl)carbonylmethyl]aminocarbonyl-4-methoxyquinoline; NMR (DMSO-$d_6$) 3.30–3.52 (m, 8), 3.60 (s, 3), 4.10 (s, 3), 4.26 (d, 2), 7.60 (s, 1), 7.65 (t, 1), 7.83 (t, 1), 8.06 (d, 1), 8.18 (d, 1), 8.94 (t, 1) ppm;

2-[(4-(phenoxycarbonyl)piperazin-1-yl)carbonylmethyl]aminocarbonyl-4-methoxyquinoline; NMR (DMSO-$d_6$) 3.40–3.70 (m, 8), 4.10 (s, 3), 4.30 (d, 2), 7.13 (d, 1), 7.22 (t, 1), 7.38 (t, 1), 7.60 (s, 1), 7.64 (t, 1), 7.83 (t, 1), 8.06 (d, 1), 8.18 (d, 1), 8.94 (t, 1) ppm;

2-[(2-methyl-4-benzylpiperazin-1-yl)carbonylmethyl]aminocarbonyl-4-methoxyquinoline; NMR (DMSO-$d_6$) 1.16–1.34 (m, 3), 1.80–2.20 (m, 2), 2.60–2.90 (m, 3), 3.40–3.70 (m, 3), 4.12 (m, 5), 4.20–4.50 (m, 1), 7.16 (m, 2), 7.34 (m, 2), 7.60 (s, 1), 7.63 (t, 1), 7.83 (t, 1), 8.03 (d, 1), 8.20 (d, 1), 8.93 (m, 1) ppm, and NMR (CDCl$_3$) 1.40 (m, 3), 2.10 (m, 1), 2.20 (m, 1), 2.70 (m, 1), 2.90 (m, 1), 3.40–3.60 (m, 3), 4.0 (m, 1), 4.10 (s, 3), 4.20–4.40 (m, 3), 7.20–7.40 (m, 5), 7.60 (m, 1), 7.65 (s, 1), 7.70 (m, 1), 8.10 (d, 1), 8.20 (d, 1), 9.15 (m, 1) ppm;

2-[1-(4-(ethoxycarbonyl)piperazin-1-yl)carbonylethyl]aminocarbonyl-4-methoxyquinoline; NMR (CDCl$_3$) 1.26 (t, 3), 1.52 (d, 3), 3.60 (m, 8H), 3.36 (m, 4), 4.12 (s, 3), 4.18 (q, 2), 5.16 (m, 1), 7.56 (t, 1), 7.66 (s, 1), 7.72 (t, 1), 8.08 (d, 1), 8.20 (d, 1H), 9.06 (d, 1) ppm, and NMR (CDCl$_3$) 1.28 (t, 3), 1.52 (d, 3), 3.40–3.96 (m, 8), 4.12 (s, 3), 4.18 (q, 2), 5.16 (m, 1), 7.56 (t, 1), 7.66 (s, 1), 7.74 (t, 1), 8.10 (d, 1), 8.20 (d, 1H), 9.06 (d, 1) ppm;

2-[(2-methyl-4-(ethoxycarbonyl)piperazin-1-yl)carbonylmethyl]aminocarbonyl-4-methoxyquinoline; NMR (CDCl$_3$) 1.30 (m, 6), 2.80–3.10 (m, 3), 3.40 (m, 1), 3.60 (m, 1), 4.00–4.40 (m, 9), 7.55 (m, 1), 7.65 (s, 1), 7.78 (m, 1), 8.10 (d, 1), 8.20 (d, 1), 9.10 (m, 1) ppm;

2-[(4-(2-methyl-5-chlorophenyl)piperazin-1-yl)carbonylmethyl]aminocarbonyl-4-methoxyquinoline; NMR (DMSO-$d_6$) 2.20 (s, 3), 2.85 (m, 4), 3.60 (m, 4), 4.10 (s, 3), 4.30 (m, 2), 7.0 (m, 1), 7.20 (m, 1), 7.60 (s, 1), 7.65 (m, 1), 7.80 (m, 1), 8.05 (d, 1), 8.20 (d, 1), 8.95 (m, 1) ppm;

2-[(4-benzylpiperazin-1-yl)carbonylmethyl]aminocarbonyl-4-methoxyquinoline; NMR (DMSO-$d_6$) 2.30–2.43 (m, 4), 3.40–3.56 (m, 6), 4.10 (s, 3), 4.23 (d, 2), 7.20–7.16 (m, 5), 7.60 (s, 1), 7.65 (t, 1), 7.83 (t, 1), 8.06 (d, 1), 8.18 (d, 1), 8.94 (t, 1) ppm;

2-[(4-ethylpiperazin-1-yl)carbonylmethyl]aminocarbonyl-4-methoxyquinoline; NMR (DMSO-$d_6$) 0.98 (t, 3), 2.30–2.40 (m, 6), 3.48 (m, 4), 4.12 (s, 3), 4.22 (d, 2), 7.59 (s, 1), 7.64 (t, 1), 7.83 (t, 1), 8.04 (d, 1), 8.18 (d, 1), 8.96 (t, 1) ppm;

2-[1-(4-(ethoxycarbonyl)piperazin-1-yl)carbonyl-5-((2-chlorobenzyloxy)carbonyl)aminopentyl]aminocarbonyl-4-methoxyquinoline; NMR (CDCl$_3$) 1.25 (t, 3), 1.40–2.00 (m, 8), 3.20–3.80 (m, 8), 4.10 (s, 3), 4.15 (q, 2), 4.95 (m, 1), 5.20 (m, 2), 7.21 (m, 2), 7.38 (m, 2), 7.55 (m, 1), 7.63 (s, 1), 7.75 (m, 1), 8.05 (d, 1), 8.20 (d, 1), 8.95 (d, 1) ppm;

2-[1-(4-(ethoxycarbonyl)piperazin-1-yl)carbonyl-2-(benzyloxycarbonyl)ethyl]aminocarbonyl-4-methoxyquinoline; NMR (CDCl$_3$) 1.25 (t, 3), 2.81 (m, 1), 3.20 (m, 1), 3.40–3.65 (m, 8), 4.15 (m, 5), 5.15 (m, 2), 5.60 (m, 1), 7.30 (m, 5), 7.55 (m, 1), 7.75 (m, 1), 8.00 (d, 1), 8.20 (d, 1), 8.95 (d, 1) ppm;

2-[1-(4-(ethoxycarbonyl)piperazin-1-yl)carbonyl-3-(benzyloxycarbonyl)propyl]aminocarbonyl-4-methoxyquinoline; NMR (CDCl$_3$) 1.25 (t, 3), 2.05 (m, 1), 2.25 (m, 1), 2.45–2.65 (m, 2), 3.40–3.80 (m, 8), 4.10–4.20 (m, 5), 5.15 (m, 2), 5.23 (m, 1), 7.35 (m, 5), 7.55 (dd, 1), 7.63 (s, 1), 7.75 (dd, 1), 8.05 (dd, 1), 8.20 (dd, 1), 9.00 (dd, 1) ppm;

2-[1-(4-(ethoxycarbonyl)piperazin-1-yl)carbonyl-2-phenylethyl]aminocarbonyl-4-methoxyquinoline; NMR (CDCl$_3$) 1.23 (t, 3), 2.63 (m, 1), 3.05 (m, 2), 3.20 (m, 4), 3.30 (m, 2), 3.45 (m, 2), 3.62 (m, 1), 4.15 (m, 5), 5.38 (m, 1), 7.30 (m, 5), 7.56 (d, 1), 7.75 (dd, 1), 8.05 (d, 1), 8.20 (d, 1), 8.98 (m, 1) ppm;

2-[1-(4-(ethoxycarbonyl)piperazin-1-yl)carbonyl-2-(benzyloxy)ethyl]aminocarbonyl-4-methoxyquinoline; NMR (CDCl$_3$) 1.23 (t, 3), 3.23 (m, 8), 3.80 (m, 2), 4.15 (m, 5), 4.58 (d, 2), 5.40 (m, 1), 7.24 (m, 5), 7.55 (dd, 1), 7.62 (s, 3), 7.75 (dd, 1), 8.05 (dd, 1), 8.20 (dd, 1), 8.98 (d, 1) ppm;

2-[1-(4-(ethoxycarbonyl)piperazin-1-yl)carbonyl-2-methylpropyl]aminocarbonyl-4-methoxyquinoline; NMR (CDCl$_3$) 1.05 (m, 6), 1.30 (m, 3), 2.20 (m, 1), 3.40–3.80 (m, 8), 4.15–4.20 (m, 5), 5.0 (m, 1), 7.58 (m, 1), 7.65 (s, 1), 7.78 (m, 1), 8.05 (d, 1), 8.20 (d, 1), 8.90 (m, 1) ppm;

2-[(4-(1,1-dimethylethoxy)carbonylmethylpiperazin-1-yl)carbonylmethyl]aminocarbonyl-4-methoxyquinoline; NMR (DMSO-d$_6$) 1.39 (s, 9), 2.50–2.60 (m, 4), 3.16 (s, 2), 3.47 (m, 4), 4.12 (s, 3), 4.22 (d, 2), 7.59 (s, 1), 7.64 (t, 1), 7.83 (t, 1), 8.04 (d, 1), 8.18 (d, 1), 8.96 (t, 1) ppm;

2-[(4-(methoxycarbonyl)piperazin-1-yl)carbonylmethyl]aminocarbonyl-4-methoxyquinoline; NMR (DMSO-d$_6$) 2.50–2.60 (m, 4), 3.26 (m, 2), 3.47 (m, 4), 3.60 (s, 3), 4.14 (s, 3), 4.23 (d, 2), 7.59 (s, 1), 7.64 (t, 1), 7.83 (t, 1), 8.04 (d, 1), 8.18 (d, 1), 8.96 (t, 1) ppm;

2-[1-(4-(ethoxycarbonyl)piperazin-1-yl)carbonyl-2-carboxyethyl]aminocarbonyl-4-methoxyquinoline; NMR (CDCl$_3$) 1.23 (t, 3), 2.82 (dd, 1), 3.18 (dd, 1), 3.40–3.75 (m, 8), 4.14 (m, 5), 5.58 (m, 1), 7.58 (dd, 1), 7.80 (s, 1), 7.73 (dd, 1), 8.01 (d, 1), 8.20 (d, 1), 8.98 (d, 1) ppm;

2-[1-(4-(ethoxycarbonyl)piperazin-1-yl)carbonyl-3-carboxypropyl]aminocarbonyl-4-methoxyquinoline; NMR (CDCl$_3$) 1.23 (t, 3), 1.99 (m, 1), 2.23 (m, 1), 2.41–2.63 (m, 2), 3.40–3.82 (m, 8), 4.10 (s, 3), 4.15 (q, 2), 5.35 (m, 1), 7.58 (dd, 1), 7.62 (s, 1), 7.73 (dd, 1), 8.08 (d, 1), 8.19 (d, 1), 9.15 (d, 1) ppm;

2-[1-(4-(ethoxycarbonyl)piperazin-1-yl)carbonyl-5-aminopentyl]aminocarbonyl-4-methoxyquinoline; NMR (CDCl$_3$) 1.22 (t, 3), 2.85 (dd, 1), 3.17 (dd, 1), 3.40–3.75 (m, 8), 4.15 (m, 5), 5.58 (m, 1), 7.56 (dd, 1), 7.61 (s, 1), 7.75 (dd, 1), 8.05 (d, 1), 8.20 (d, 1), 8.98 (d, 1) ppm;

2-[1-(4-(ethoxycarbonyl)piperazin-1-yl)carbonyl-2-hydroxyethyl]aminocarbonyl-4-methoxyquinoline; NMR (CDCl$_3$) 1.23 (t, 3), 3.40–3.80 (m, 8), 3.92 (m, 1), 4.03 (m, 1), 4.15 (m, 5), 5.20 (m, 1), 7.58 (d, 1), 7.63 (s, 1), 7.75 (dd, 1), 8.05 (d, 1), 8.21 (d, 1), 9.15 (d, 1) ppm;

2-[(4-(carboxymethyl)piperazin-1-yl)carbonylmethyl]aminocarbonyl-4-methoxyquinoline; NMR (DMSO-d$_6$) 2.48–2.60 (m, 4), 3.17 (s, 2), 3.46 (m, 4), 4.08 (s, 3), 4.18 (d, 2), 7.56 (s, 1), 7.62 (t, 1), 7.80 (t, 1), 8.01 (d, 1), 8.16 (d, 1), 8.92 (t, 1) ppm;

2-[(4-(ethoxycarbonyl)piperazin-1-yl)carbonylmethyl]aminocarbonyl-4-(ethoxycarbonyl)methoxyquinoline; NMR (DMSO-d$_6$) 1.20 (m, 6), 3.3–3.5 (m, 8), 4.04 (q, 2), 4.2–4.3 (m, 4), 5.3 (s, 2), 7.5 (s, 1), 7.7 (t, 1), 7.8 (t, 1), 8.1 (d, 1), 8.13 (d, 1), 8.98 (m, 1) ppm;

2-[(4-(ethoxycarbonyl)piperazin-1-yl)carbonylmethyl]aminocarbonyl-4-(carboxy)methoxyquinoline; NMR (DMSO-d$_6$) 1.18 (t, 3), 3.3–3.5 (m, 8), 4.04 (q, 2), 4.25 (d, 2), 5.1 (s, 2), 7.5 (s, 1), 7.7 (t, 1), 7.85 (t, 1), 8.03 (d, 1), 8.13 (d, 1), 8.95 (m, 1) ppm;

2-[(4-methylpiperazin-1-yl)carbonylmethyl]aminocarbonyl4-methoxyquinoline; NMR (DMSO-d$_6$) 2.58 (s, 3), 2.71–7.93 (m, 4), 3.67 (m, 4), 4.13 (s, 3), 4.26 (d, 2), 7.60 (s, 1), 7.66 (t, 1), 7.84 (t, 1), 8.06 (d, 1), 8.21 (d, 1), 8.94 (t, 1) ppm;

2-[(4-(ethoxycarbonyl)piperazin-1-yl)carbonylmethyl]aminocarbonyl-4-ethoxyquinoline; NMR (DMSO-d$_6$) 1.21 (t, 3), 1.48 (t, 3), 3.30–3.60 (m, 8), 4.06 (q, 2), 4.28 (d, 2), 4.42 (q, 2), 7.57 (s, 1), 7.66 (t, 1), 7.85 (t, 1), 8.07 (d, 1), 8.21 (d, 1), 8.95 (t, 1) ppm;

2-[(4-(ethoxycarbonyl)piperazin-1-yl)carbonylmethyl]aminocarbonyl-4-(aminocarbonyl)methoxyquinoline; NMR (DMSO-d$_6$) 1.20 (t, 3), 3.30–3.50 (m, 8), 4.05 (q, 2), 4.25 (d, 2), 4.90 (s, 2), 7.50 (s, 1), 7.70 (t, 1), 7.86 (t, 1), 8.03 (d, 1), 8.40 (d, 1), 8.95 (m, 1) ppm;

2-[1-(4-(ethoxycarbonyl)piperazin-1-yl)carbonyl-2-(aminocarbonyl)ethyl]aminocarbonyl-4-methoxyquinoline; NMR (CDCl$_3$) 1.30 (t, 3), 2.80 (dd, 1), 3.00 (dd, 1), 3.40–3.80 (m, 8), 4.15 (m, 5), 5.60 (m, 2), 6.15 (m, 1), 7.60 (m, 2), 7.75 (m, 1), 8.0 (d, 1), 8.20 (d, 1), 9.0 (d, 1) ppm;

2-[1-(4-(ethoxycarbonyl)piperazin-1-yl)carbonyl-3-(aminocarbonyl)propyl]aminocarbonyl-4-methoxyquinoline; NMR (CDCl$_3$) 1.30 (t, 3), 2.0 (m, 1), 2.20–2.50 (m, 3), 3.40–3.80 (m, 8), 4.15 (m, 5), 5.20 (m, 1), 5.50 (m, 1), 6.25 (m, 1), 7.60 (m, 2), 7.75 (m, 1), 8.10 (d, 1), 8.20 (d, 1), 9.20 (d, 1) ppm;

2-[1-(4-(ethoxycarbonyl)piperazin-1-yl)carbonyl-2-(imidazol-4-yl)ethyl]aminocarbonyl-4-methoxyquinoline; NMR (CDCl$_3$) 1.25 (t, 3), 3.10–3.30 (m, 2), 3.20–3.65 (m, 8), 4.10 (m, 5), 5.40 (m, 1), 6.90 (s, 1), 7.55–7.60 (m, 3), 7.70 (t, 1), 8.02 (d, 1), 8.20 (d, 1), 9.0 (d, 1) ppm;

2-[1-(4-(ethoxycarbonyl)piperazin-1-yl)carbonyl-2-(indol-3-yl)ethyl]aminocarbonyl-4-methoxyquinoline; NMR (CDCl$_3$) 1.20 (t, 3), 2.25 (m, 1), 2.90 (m, 2), 3.20 (m, 2), 3.40 (m, 4), 3.60 (m, 1), 4.05 (q, 2), 4.15 (s, 3), 5.50 (m, 1), 7.20 (m, 3), 7.35 (d, 1), 7.55 (m, 1), 7.70 (s, 1), 7.80 (m, 2), 8.10 (d, 1), 8.20 (m, 2), 9.10 (d, 1) ppm;

2-[(3-(benzyloxy)carbonyl-4-(ethoxycarbonyl)piperazin-1-yl)carbonylmethyl]aminocarbonyl-4-methoxyquinoline; NMR (CDCl$_3$) 1.28 (m, 3), 2.82 (m, 1), 3.28 (m, 3), 3.88 (m, 1), 4.18 (s, 3), 4.22 (m, 4), 4.60 (m, 3), 5.20 (m, 2), 7.42 (m, 1), 7.22 (m, 2), 7.28 (m, 3), 7.60 (t, 1), 7.64 (s, 1), 7.68 (t, 1), 8.12 (d, 1), 8.22 (d, 1H), 9.18 (s, 1) ppm;

2-[(3-carboxy-4-(ethoxycarbonyl)piperazin-1-yl)carbonylmethyl]aminocarbonyl-4-methoxyquinoline; NMR (CDCl$_3$) 1.28 (m, 3), 2.82 (m, 1), 3.26 (m, 4H), 3.88 (m, 1), 4.12 (s, 3), 4.46 (m, 5), 7.42 (m, 1), 7.56 (s, 1), 7.64 (t, 1), 8.00 (d, 1), 8.20 (d, 1), 9.18 (s, 1) ppm;

2-[1-(4-(ethoxycarbonyl)piperazin-1-yl)carbonyl-2-(benzyloxycarbonyl)ethyl]aminocarbonyl-4-methoxyquinoline; NMR (CDCl$_3$) 1.23 (m, 3), 2.85 (dd, 1), 3.20 (m, 1), 3.40–3.80 (m, 8), 4.15 (m, 5), 5.15 (m, 2), 5.60 (m, 1), 7.35 (m, 5), 7.59 (m, 1), 7.62 (m, 1), 7.75 (m, 1), 8.05 (m, 1), 8.21 (m, 1), 8.90 (m, 1) ppm;

2-[1-(4-(ethoxycarbonyl)piperazin-1-yl)carbonyl-4-(1,1-dimethylethoxy)carbonylbutyl]aminocarbonyl-4-methoxyquinoline; NMR (CDCl$_3$) 1.25 (t, 3), 1.22 (s, 9), 1.70–2.00 (m, 6), 2.30 (dd, 1), 3.40–3.80 (m, 8), 4.15 (m, 5), 5.18 (m, 1), 7.55 (d, 1), 7.62 (s, 1), 7.75 (dd, 1), 8.05 (d, 1), 8.20 (d, 1), 8.95 (d, 1) ppm;

2-[1-(4-(ethoxycarbonyl)piperazin-1-yl)carbonyl-4-carboxybutyl]aminocarbonyl-4-methoxyquinoline; NMR (DMSO-d$_6$) 1.20 (t, 3), 1.30–1.90 (m, 6), 2.25 (m, 2), 3.25–3.63 (m, 8), 4.05 (m, 2), 4.15 (s, 3), 5.05 (m, 1), 7.61 (s, 1), 7.65 (dd, 1), 7.85 (dd, 1), 8.10 (d, 1), 8.20 (d, 1), 8.95 (d, 1) ppm;

2-[1-(4-(ethoxycarbonyl)piperazin-1-yl)carbonyl-2-carboxyethyl]aminocarbonyl-4-methoxyquinoline; NMR (DMSO-d$_6$) 1.20 (t, 3), 1.30–1.90 (m, 6), 2.25 (m, 2), 3.25–3.63 (m, 8), 4.05 (m, 2), 4.15 (s, 3), 5.05 (m, 1), 7.61 (s, 1), 7.65 (dd, 1), 7.85 (dd, 1), 8.10 (d, 1), 8.20 (d, 1), 8.95 (d, 1) ppm;

2-[1-(4-(ethoxycarbonyl)piperazin-1-yl)carbonyl-3-carboxypropyl]aminocarbonyl-4-hydroxyquinoline; NMR (DMSO-d$_6$) 1.17 (t, 3), 1.83 (m, 1), 1.92 (m, 1), 2.24 (m, 2), 3.30–3.70 (m, 8), 4.03 (q, 2), 4.93 (m, 1), 6.94 (s, 1), 7.35 (t, 1), 7.64 (t, 1), 7.86 (d, 1), 8.09 (d, 1) ppm;

2-[1-(4-(ethoxycarbonyl)piperazin-1-yl)carbonyl-3-(benzyloxycarbonyl)propyl]aminocarbonyl-4-ethoxyquinoline; NMR (DMSO-d$_6$) 1.16 (t, 3), 1.46 (t, 3), 1.85 (m, 1), 2.10 (m, 1), 2.45 (m, 2), 3.3–3.6 (m, 8), 4.02 (q, 2), 4.37 (q, 2), 5.00 (s, 2), 5.05 (m, 1), 7.30 (m, 5), 7.53 (s, 1), 7.63 (t, 1), 7.80 (t, 1), 8.04 (d, 1), 8.17 (d, 1), 9.90 (m, 1) ppm;

2-[1-(4-(ethoxycarbonyl)piperazin-1-yl)carbonyl-3-carboxypropyl]aminocarbonyl-4-ethoxyquinoline; NMR (DMSO-d$_6$) 1.15 (t, 3), 1.46 (t, 3), 1.82 (m, 1), 2.00 (m, 1), 2.30 (m, 2), 3.3–3.7 (m, 8), 4.00 (q, 2), 4.40 (q, 2), 5.04 (m, 1), 7.53 (s, 1), 7.63 (t, 1), 7.80 (t, 1), 8.04 (d, 1), 8.20 (d, 1), 9.90 (m, 1) ppm;

2-[1-(4-(ethoxycarbonyl)piperazin-1-yl)carbonyl-3-(benzyloxycarbonyl)propyl]aminocarbonyl-4-methoxyquinoline; NMR (CDCl$_3$) 1.23 (t, 3), 2.05 (m, 1), 2.23 (m, 1), 2.58 (m, 2), 3.40–3.80 (m, 8), 4.15 (s, 3), 4.16 (q, 2), 5.17 (m, 1), 5.25 (m, 1), 7.15 (m, 5), 7.56 (dd, 1), 7.62 (s, 1), 7.75 (dd, 1), 8.0 (d, 1), 8.21 (d, 1), 9.05 (d, 1) ppm;

2-[1-(4-(ethoxycarbonyl)piperazin-1-yl)carbonyl-3-carboxypropyl]aminocarbonyl-4-methoxyquinoline; NMR (CDCl$_3$) 1.23 (t, 3), 2.00 (m, 1), 2.23 (m, 1), 2.41–2.63 (m, 2), 3.40–3.82 (m, 8), 4.12 (s, 3), 4.15 (q, 2), 5.35 (m, 1), 7.58 (dd, 1), 7.60 (s, 1), 7.75 (dd, 1), 8.10 (d, 1), 8.20 (d, 1), 9.19 (d, 1) ppm;

2-[1-(4-(ethoxycarbonyl)piperazin-1-yl)carbonyl-2-((1,1-dimethylethoxy)carbonyl)ethyl]aminocarbonyl-4-methoxyquinoline; NMR (CDCl$_3$) 1.23 (t, 3), 1.45 (s, 9), 2.78 (dd, 1), 2.99 (s, 3), 3.10 (m, 1), 3.40–3.82 (m, 8), 4.18 (q, 2), 4.20 (s, 3), 5.95 (m, 1), 7.05 (m, 1), 7.65 (dd, 1), 7.90 (dd, 1), 8.30 (m, 2) ppm;

2-[1-(4-(ethoxycarbonyl)piperazin-1-yl)carbonyl-3-(benzyloxycarbonyl)propyl]aminocarbonyl-4-methoxyquinoline; NMR (CDCl$_3$) 1.23 (t, 3), 2.20–2.40 (m, 2), 2.50–2.82 (m, 2), 3.02 (s, 3), 3.30–3.80 (m, 8), 4.03 (s, 3), 4.15 (q, 2), 5.15 (m, 2), 5.63 (m, 1), 7.00 (s, 1), 7.35 (m, 5), 7.55 (dd, 1), 7.75 (dd, 1), 7.98 (d, 1), 8.20 (d, 1) ppm;

2-[1-(4-(ethoxycarbonyl)piperazin-1-yl)carbonyl-3-carboxypropyl][methyl]aminocarbonyl-4-methoxyquinoline; NMR (CDCl$_3$) 1.23 (t, 3), 2.17–2.35 (m, 2), 2.52 (m, 1), 3.03 (s, 3), 3.35 (m, 8), 4.05 (s, 3), 4.15 (q, 2), 5.62 (m, 1), 7.00 (s, 1), 7.5 (dd, 1), 7.73 (dd, 1), 8.05 (d, 1), 8.20 (d, 1) ppm;

2-[1-(4-(1,1-dimethylethoxycarbonyl)piperazin-1-yl)carbonyl-3-(methoxycarbonyl)propyl]aminocarbonyl-4-methoxyquinoline; NMR (CDCl$_3$) 1.45 (s, 9), 2.01 (m, 1), 2.22 (m, 1), 2.40–2.60 (m, 2), 3.20–3.80 (m, 11), 4.12 (s, 3), 5.25 (m, 1), 7.58 (dd, 1), 7.62 (s, 1), 7.75 (dd, 1), 8.10 (d, 1), 8.21 (d, 1), 9.05 (d, 1) ppm;

2-[(4-(2-carboxyethyl)carbonylpiperazin-1-yl)carbonylmethyl]aminocarbonyl-4-methoxyquinoline; NMR (DMSO-d$_6$) 2.40–2.60 (m, 4), 3.41–3.60 (m, 8), 4.13 (s, 3), 4.27 (d, 2), 7.61 (s, 1), 7.64 (t, 1), 7.83 (t, 1), 8.05 (d, 1), 8.23 (d, 1), 8.97 (t, 1) ppm;

2-[(4-(5-(ethoxycarbonyl)pentyl)carbonylpiperazin-1-yl)carbonylmethyl]aminocarbonyl-4-methoxyquinoline; NMR (CDCl$_3$) 1.25 (t, 3), 1.38 (m, 2), 1.60–1.78 (m, 6), 2.36 (m, 4), 3.51–3.78 (m, 8), 4.11 (m, 5), 4.27 (d, 2), 7.57 (t, 1), 7.65 (s, 1), 7.76 (t, 1), 8.09 (d, 1), 8.23 (d, 1), 9.12 (m, 1) ppm;

2-[(4-(5-carboxypentyl)carbonylpiperazin-1-yl)carbonylmethyl]aminocarbonyl-4-methoxyquinoline; NMR (DMSO-d$_6$) 1.24 (m, 2), 1.43 (m, 4), 2.13 (m, 2), 2.27 (m, 2), 3.40–3.52 (m, 8), 4.08 (s, 3), 4.24 (d, 2), 7.56 (s, 1), 7.63 (t, 1), 7.79 (t, 1), 8.01 (d, 1), 8.17 (d, 1), 8.92 (m, 1) ppm;

2-[(2,4-di(ethoxycarbonyl)piperazin-1-yl)carbonylmethyl]aminocarbonyl-4-methoxyquinoline;

2-[(2-carboxy-4-(ethoxycarbonyl)piperazin-1-yl)carbonylmethyl]aminocarbonyl-4-methoxyquinoline;

2-[1-(4-(ethoxycarbonyl)piperazin-1-yl)carbonyl-3-carboxypropyl]aminocarbonyl-4-(carboxy)methoxyquinoline; NMR (DMSO-d$_6$) 1.17 (t, 3), 1.84 (m, 1), 2.04 (m, 1), 2.30 (m, 2), 3.31–3.71 (m, 8), 4.03 (q, 2), 5.05 (m, 1), 5.13 (s, 2), 7.47 (s, 1), 7.68 (t, 1), 7.85 (t, 1), 8.09 (d, 1), 8.23 (d, 1), 8.95 (d, 1) ppm;

2-[(4-(ethoxycarbonyl)piperazin-1-yl)carbonylmethyl]aminocarbonyl-4-n-propoxyquinoline; NMR (DMSO-d$_6$) 1.06 (t, 3), 1.17 (t, 3), 1.90 (m, 2), 3.30–3.55 (m, 8), 4.04 (q, 2), 4.25 (d, 2), 4.30 (q, 2), 7.57 (s, 1), 7.64 (t, 1), 7.84 (t, 1), 8.03 (d, 1), 8.20 (d, 1), 8.93 (m, 1) ppm;

2-[1-(piperazin-1-yl)carbonyl-3-(methoxycarbonyl)propyl]aminocarbonyl-4-methoxyquinoline; NMR (CDCl$_3$) 2.00 (m, 1), 2.25 (m, 1), 2.40–2.60 (m, 2), 2.90 (m, 1), 2.95 (m, 1), 3.60–3.75 (m, 7), 4.12 (s, 3), 5.22 (m, 1), 7.55 (dd, 1), 7.63 (s, 1), 7.75 (dd, 1), 8.0 (d, 1), 8.21 (d, 1), 9.05 (d, 1) ppm;

2-[1-(4-(pyrimidin-2-yl)piperazin-1-yl)carbonyl-3-(methoxycarbonyl)propyl]aminocarbonyl-4-methoxyquinoline; NMR (CDCl$_3$) 2.02 (m, 1), 2.30 (m, 1), 2.40–2.62 (m, 2), 3.70 (s, 3), 3.80–5.04 (m, 8), 4.14 (s, 3), 5.30 (m, 1), 6.55 (m, 1), 7.55 (dd, 1), 7.62 (s, 1), 7.75 (dd, 1), 8.10 (d, 1), 8.21 (d, 1), 8.35 (d, 2), 9.05 (d, 1) ppm;

2-[1-(4-((1,1-dimethylethyl)aminocarbonyl)piperazin-1-yl)carbonyl-3-(methoxycarbonyl)propyl]aminocarbonyl-4-methoxyquinoline; NMR (CDCl$_3$) 1.38 (s, 9), 2.00 (m, 1), 2.23 (m, 1), 2.40–2.61 (m, 2), 3.25–3.80 (m, 11), 4.12 (s, 3), 2.25 (m, 1), 7.5 (dd, 1), 7.62 (s, 1), 7.75 (dd, 1), 8.07 (d, 1), 8.21 (d, 1), 9.01 (d, 1) ppm;

2-[1-(4-(ethoxycarbonyl)piperazin-1-yl)carbonyl-3-(methoxycarbonyl)propyl]aminocarbonyl-4-methoxyquinoline; NMR (CDCl$_3$) 1.25 (t, 3), 2.00 (m, 1), 2.22 (m, 1), 2.40–2.61 (m, 2), 3.40–3.80 (m, 11), 4.11 (s, 3), 4.17 (q, 2), 5.23 (m, 1), 7.56 (dd, 1), 7.62 (s, 1), 7.75 (dd, 1), 8.10 (d, 1), 8.21 (d, 1), 9.02 (d, 1) ppm;

2-[1-(4-((1,1-dimethylethyl)aminocarbonyl)piperazin-1-yl)carbonyl-3-carboxypropyl]aminocarbonyl-4-methoxyquinoline; NMR (CDCl$_3$) 1.38 (s, 9), 1.98 (m, 1), 2.22 (m, 1), 2.41–2.62 (m, 2), 3.33–3.90 (m, 8), 4.09 (s, 3), 4.11 (q, 2), 5.30 (m, 1), 7.5 (dd, 1), 7.58 (s, 1), 7.73 (dd, 1), 8.05 (d, 1), 8.11 (d, 1), 9.07 (d, 1) ppm;

2-[1-(4-(aminocarbonyl)piperazin-1-yl)carbonyl-3-(methoxycarbonyl)propyl]aminocarbonyl-4-methoxyquinoline; NMR (CDCl$_3$) 2.00 (m, 1), 2.2 (m, 1), 2.40–2.61 (m, 2), 3.40–3.90 (m, 11), 4.13 (s, 3), 5.22 (m, 1), 7.58 (dd, 1), 7.61 (s, 1), 7.75 (dd, 1), 8.09 (d, 1), 8.21 (d, 1), 9.00 (d, 1) ppm;

2-[1-(4-(benzoxazol-2-yl)piperazin-1-yl)carbonyl-3-(methoxycarbonyl)propyl]aminocarbonyl-4-methoxyquinoline; NMR (CDCl$_3$) 2.01 (m, 1), 2.23 (m, 1), 2.41–2.62 (m, 2), 3.63–3.98 (m, 11), 4.13 (s, 3), 5.21 (m, 1), 7.04 (dd, 1), 7.18 (dd, 1), 7.25 (d, 1), 7.38 (d, 1), 7.57 (dd, 1), 7.62 (s, 1), 7.75 (dd, 1), 8.09 (d, 1), 8.11 (d, 1), 9.02 (d, 1) ppm;

2-[1-(4-(benzthiazol-2-yl)piperazin-1-yl)carbonyl-3-(methoxycarbonyl)propyl]aminocarbonyl-4-methoxyquinoline; NMR (CDCl$_3$) 2.02 (m, 1), 2.30 (m, 1), 2.41–2.65 (m, 1), 3.60–3.95 (m, 11), 4.12 (s, 3), 5.31 (m, 1), 7.10 (dd, 1), 7.35 (dd, 1), 7.57 (m, 2), 7.61 (m, 1), 7.75 (dd, 1), 8.08 (d, 1), 8.21 (d, 1), 9.02 (d, 1) ppm;

2-[1-(4-(pyrimidin-2-yl)piperazin-1-yl)carbonyl-3-carboxypropyl]aminocarbonyl-4-methoxyquinoline; NMR (CDCl$_3$) 2.02 (m, 1), 2.25 (m, 1), 2.42–2.70 (m, 2), 3.63–4.08 (m, 8), 4.1 (s, 3), 5.40 (m, 1), 6.50 (m, 1), 7.55 (dd, 1), 7.62 (s, 1), 7.75 (dd, 1), 8.10 (d, 1), 8.19 (d, 1), 8.31 (d, 2), 9.21 (d, 1) ppm;

2-[1-(4-(aminocarbonyl)piperazin-1-yl)carbonyl-3-carboxypropyl]aminocarbonyl-4-methoxyquinoline; NMR (DMSO-d$_6$) 1.85 (m, 1), 2.05 (m, 1), 2.35 (m, 2), 3.20–3.63 (m, 11), 4.13 (s, 3), 5.08 (m, 1), 6.08 (br s, 1), 7.61 (s, 1), 7.65 (dd, 1), 7.86 (dd, 1), 8.08 (d, 1), 8.20 (d, 1), 8.98 (d, 1) ppm;

2-[1-(4-(benzoxazol-2-yl)piperazin-1-yl)carbonyl-3-carboxypropyl]aminocarbonyl-4-methoxyquinoline; NMR (DMSO-d$_6$) 1.96 (m, 1), 2.13 (m, 1), 2.38 (m, 2), 3.58–3.85 (m, 8), 4.16 (s, 3), 5.18 (m, 1), 7.02 (dd, 1), 7.79 (dd, 1), 7.31 (d, 1), 7.41 (d, 1), 7.61 (s, 1), 7.65 (dd, 1), 8.85 (dd, 1), 8.12 (d, 1), 8.20 (d, 1), 8.99 (d, 1) ppm;

2-[1-(4-(benzthiazol-2-yl)piperazin-1-yl)carbonyl-3-carboxypropyl]aminocarbonyl-4-methoxyquinoline; NMR (DMSO-d$_6$) 1.96 (m, 1), 2.15 (m, 1), 2.38 (m, 2), 3.58–3.90 (m, 8), 4.16 (s, 3), 5.15 (m, 1), 7.05 (dd, 1), 7.28 (dd, 1), 7.46 (d, 1), 7.81 (s, 1), 7.65 (dd, 1), 7.78 (d, 1), 7.82 (d, 1), 8.10 (d, 1), 8.19 (d, 1), 8.98 (d, 1) ppm;

2-[(4-(ethoxycarbonyl)piperazin-1-yl)carbonylmethyl]aminocarbonyl-4-(3-(ethoxycarbonyl)propoxy)quinoline; NMR (DMSO-d$_6$) 1.14 (t, 3), 1.18 (t, 3), 2.14 (m, 2), 2.47 (q, 2), 3.30–3.55 (m, 8), 4.04 (q, 2), 4.25 (d, 2), 4.36 (q, 2), 7.56 (s, 1), 7.64 (t, 1), 7.83 (t, 1), 8.03 (d, 1), 8.19 (d, 1), 8.93 (m, 1) ppm;

2-[(4-(ethoxycarbonyl)piperazin-1-yl)carbonylmethyl]aminocarbonyl-4-(3-carboxypropoxy)quinoline; NMR (DMSO-d$_6$) 1.17 (t, 3), 2.11 (m, 2), 2.47 (q, 2), 3.30–3.55 (m, 8), 4.04 (q, 2), 4.25 (d, 2), 4.37 (q, 2), 7.56 (s, 1), 7.64 (t, 1), 7.83 (t, 1), 8.03 (d, 1), 8.20 (d, 1), 8.93 (m, 1) ppm;

2-[(4-(ethoxycarbonyl)piperazin-1-yl)carbonylmethyl]aminocarbonyl-4-(3-(ethoxycarbonyl)prop-2-en-1-oxy)quinoline; NMR (DMSO-d$_6$) 1.18 (t, 3), 1.20 (t, 3), 3.30–3.55 (m, 8), 4.04 (q, 2), 4.15 (q, 2), 4.25 (d, 2), 5.20 (s, 1), 6.23 (d, 1), 7.14 (d, 1), 7.60 (s, 1), 7.68 (t, 1), 7.83 (t, 1), 8.03 (d, 1), 8.30 (d, 1), 8.93 (m, 1) ppm;

2-[1-(4-(ethoxycarbonyl)piperazin-1-yl)carbonyl-2-((methoxycarbonyl)methyl)thioethyl]aminocarbonyl-4-methoxyquinoline; NMR (CDCl$_3$) 1.30 (t, 3), 3.0 (m, 1), 3.30 (m, 1), 3.30–3.45 (m, 2), 3.50–3.80 (m, 8), 3.75 (s, 3), 4.15 (m, 5), 5.45 (m, 1), 7.60 (t, 1), 7.65 (s, 1), 7.75 (t, 1), 8.10 (d, 1), 8.20 (d, 1), 9.0 (d, 1) ppm;

2-[1-(4-(ethoxycarbonyl)piperazin-1-yl)carbonyl-2-(carboxymethyl)thioethyl]aminocarbonyl-4-methoxyquinoline; NMR (CDCl$_3$) 1.30 (t, 3), 3.0 (m, 1), 3.30 (m, 1), 3.30–3.50 (m, 2), 3.50–3.80 (m, 8), 4.10 (m, 5), 5.45 (m, 1), 7.55 (m, 1), 7.65 (s, 1), 7.75 (t, 1), 8.10 (d, 1), 8.20 (d, 1), 9.0 (d, 1) ppm;

2-[(4-(ethoxycarbonyl)piperazin-1-yl)carbonylmethyl]aminocarbonyl4-(tetrahydro-2-oxofuran-3-yl)oxyquinoline; NMR (CDCl$_3$) 1.28 (t, 3), 2.58 (m, 1), 3.00 (m, 1), 3.55 (m, 6), 3.70 (m, 2), 4.18 (q, 2), 4.37 (m, 2), 4.47 (m, 1), 4.60 (m, 1), 5.40 (t, 1), 7.60 (q, 1), 7.75 (s, 1), 7.80 (t, 1), 8.12 (d, 1), 8.26 (d, 1), 9.10 (m, 1) ppm;

2-[(4-(ethoxycarbonyl)piperazin-1-yl)carbonylmethyl]aminocarbonyl-4-(1-carboxy-3-hydroxypropoxy)quinoline; NMR (DMSO-d$_6$) 1.18 (t, 3), 2.20 (m, 2), 3.30–3.55 (m, 6), 3.68 (m, 2), 4.04 (q, 2), 4.25 (d, 2), 5.20 (t, 1), 7.40 (s, 1), 7.70 (t, 1), 7.85 (t, 1), 8.03 (d, 1), 8.24 (d, 1), 8.96 (m, 1) ppm;

2-[(4-(ethoxycarbonyl)piperazin-1-yl)carbonylmethyl]aminocarbonyl-4-(1,1-di(ethoxycarbonyl)methoxy)quinoline; NMR (CDCl$_3$) 1.28–1.40 (m, 9), 3.55 (m, 6), 3.70 (m, 2), 4.18 (q, 2), 4.38 (m, 6), 5.60 (s, 1), 7.57 (s, 1), 7.65 (t, 1), 7.80 (t, 1), 8.13 (d, 1), 8.42 (d, 1), 9.06 (m, 1) ppm;

2-[(4-(ethoxycarbonyl)piperazin-1-yl)carbonylmethyl]aminocarbonyl-4-(1,1-di(carboxy)methoxy)quinoline; NMR (DMSO-d$_6$) 1.20 (t, 3), 3.20–3.60 (m, 8), 4.08 (q, 2), 4.30 (d, 6), 5.90 (s, 1), 7.54 (s, 1), 7.75 (t, 1), 7.90 (t, 1), 8.10 (d, 1), 8.30 (d, 1), 8.98 (m, 1) ppm;

2-[(4-(ethoxycarbonyl)piperazin-1-yl)carbonylmethyl]aminocarbonyl-4-(1-(ethoxycarbonyl)ethoxy)quinoline; NMR (CDCl$_3$) 1.28 (t, 6), 1.8 (d, 3), 3.52 (m, 6), 3.70 (m, 2), 4.17–4.36 (m, 6), 5.16 (q, 1), 7.52 (s, 1), 7.60 (t, 1), 7.76 (t, 1), 8.10 (d, 1), 8.34 (d, 1), 9.06 (m, 1) ppm;

2-[(4-(ethoxycarbonyl)piperazin-1-yl)carbonylmethyl]aminocarbonyl-4-(1-carboxyethoxy)quinoline; NMR (CDCl$_3$) 1.25 (t, 3), 1.83 (d, 3), 3.50 (m, 6), 3.65 (m, 2), 4.17 (q, 2), 4.35 (m, 2), 5.23 (q, 1), 7.58 (m, 2), 7.70 (t, 1), 8.02 (d, 1), 8.32 (d, 1), 9.16 (m, 1) ppm;

2-[(3-(methoxycarbonyl)methyl-4-(ethoxycarbonyl)piperazin-1-yl)carbonylmethyl]aminocarbonyl-4-methoxyquinoline; NMR (CDCl$_3$) 1.18 (t, 3), 2.22–2.42 (m, 2), 2.74 (m, 1), 2.96 (m, 1), 3.16 (d, 1), 3.68 (s, 3), 3.80 (m, 2), 4.08 (q, 2), 4.12 (s, 3), 4.34 (m, 6), 7.58 (t, 1), 7.62 (s, 1), 7.68 (t, 1), 8.08 (d, 1), 8.22 (d, 1), 8.96 (d, 1) ppm;

2-[(3-(carboxy)methyl-4-(ethoxycarbonyl)piperazin-1-yl)carbonylmethyl]aminocarbonyl-4-methoxyquinoline; NMR (DMSO-d$_6$) 1.18 (t, 3), 2.22–2.42 (m, 2), 2.74 (m, 1), 2.96 (m, 1), 3.16 (d, 1), 3.80 (m, 2), 4.06 (q, 2), 4.12 (s, 3), 4.34 (m, 6), 7.60 (s, 1), 7.62 (t, 1), 7.84 (t, 1), 8.06 (d, 1), 8.19 (d, 1), 9.06 (m, 1) ppm;

2-[1-(4-(ethoxycarbonyl)piperazin-1-yl)carbonyl-5-(methoxycarbonyl)pentyl]aminocarbonyl-4-methoxyquinoline; NMR (CDCl$_3$) 1.30 (t, 3), 1.50 (m, 2), 1.70 (m, 2), 1.80 (m, 1), 1.90 (m, 1), 2.30 (m, 2), 3.40–3.80 (m, 8), 3.65 (s, 3), 4.15 (m, 5), 5.18 (m, 1), 7.60 (m, 1), 7.65 (s, 1), 7.75 (m, 1), 8.10 (d, 1), 8.20 (d, 1), 8.95 (d, 1) ppm;

2-[1-(4-(ethoxycarbonyl)piperazin-1-yl)carbonyl-5-(carboxy)pentyl]aminocarbonyl-4-methoxyquinoline; NMR (CDCl$_3$) 1.30 (t, 3), 1.50 (m, 2), 1.65–1.95 (m, 4), 2.18 (m, 2), 3.40–3.80 (m, 8), 4.15 (m, 5), 5.20 (m, 1), 7.55 (m, 1), 7.65 (s, 1), 7.75 (m, 1), 8.05 (d, 1), 8.20 (d, 1), 9.0 (d, 1) ppm;

2-[1-(4-(ethoxycarbonyl)piperazin-1-yl)carbonyl-1-(4-hydroxyphenyl)methyl]aminocarbonyl-4-methoxyquinoline;

2-[(4-(ethoxycarbonyl)piperazin-1-yl)carbonylmethyl]aminocarbonyl-4-(3-(carboxy)prop-1-en-1-oxy)quinoline;

NMR (DMSO-d$_6$) 1.18 (t, 3), 3.25 (d, 2), 3.30–3.55 (m, 8), 4.02 (q, 2), 4.25 (d, 2), 5.20–5.40 (m, 1), 7.13 (d, 1), 7.64 (s, 1), 7.75 (t, 1), 7.90 (t, 1), 8.10 (d, 1), 8.30 (d, 1), 9.00 (m, 1) ppm;

2-[1-(4-(ethoxycarbonyl)piperazin-1-yl)carbonyl-3-carboxypropyl]aminocarbonyl-8-methoxy-4-hydroxyquinoline; NMR (DMSO-d$_6$) 1.17 (t, 3), 1.84–2.12 (m, 2), 2.37–2.48 (m, 2), 3.31–3.72 (m, 8), 4.04 (m, 5), 4.98 (m, 1), 7.25 (s, 1), 7.28 (d, 1), 7.42 (t, 1), 7.66 (d, 1) ppm;

2-[(2-(methoxycarbonyl)methyl-4-(ethoxycarbonyl)piperazin-1-yl)carbonylmethyl]aminocarbonyl-4-methoxyquinoline; NMR (CDCl$_3$) 1.26 (t, 3), 2.60–3.22 (m, 4), 3.38–4.22 (m, 1), 3.64 (s, 3), 3.76 (m, 2), 4.06 (m, 4), 4.18 (s, 3), 4.34 (m, 3), 7.62 (t, 1), 7.66 (s, 1), 7.94 (t, 1), 8.06 (d, 1), 8.18 (d, 1), 9.12 (m, 1) ppm;

2-[(2-(carboxy)methyl-4-(ethoxycarbonyl)piperazin-1-yl)carbonylmethyl]aminocarbonyl-4-methoxyquinoline; NMR (DMSO-d$_6$) 1.16 (t, 3), 2.24 (dd, 1), 2.58 (m, 1), 2.62 (d, 1), 2.80 (m, 1), 3.16 (m, 2), 3.76 (d, 1), 4.06 (m, 4), 4.18 (s, 3), 4.34 (m, 6), 7.60 (s, 1), 7.62 (t, 1), 7.84 (t, 1), 8.06 (d, 1), 8.18 (d, 1), 8.98 (m, 1) ppm;

2-[1-(4-(ethoxycarbonyl)piperazin-1-yl)carbonyl-3-(methoxycarbonyl)propyl]aminocarbonyl-4-(tetrahydro-2-oxofuran-3-yl)oxyquinoline; NMR (CDCl$_3$) 1.26 (t, 3), 2.00 (m, 1), 2.24 (m, 1), 2.40–2.60 (m, 3), 3.00 (m, 1), 3.40–3.80 (m, 11), 4.16 (q, 2), 4.44 (m, 1), 4.60 (m, 1), 5.25 (m, 1), 5.38 (q, 1), 7.60 (t, 1), 7.72 (s, 1), 7.78 (t, 1), 8.12 (d, 1), 8.24 (d, 1), 9.00 (m, 1) ppm;

2-[(4-(ethoxycarbonyl)piperazin-1-yl)carbonylmethyl]aminocarbonyl-4-(1-(methoxycarbonyl)propoxy)quinoline; NMR (CDCl$_3$) 1.20 (t, 3), 1.30 (t, 3), 2.20 (m, 2), 3.55 (m, 6), 3.70 (m, 2), 3.80 (s, 3), 4.20 (q, 2), 4.39 (d, 2), 5.04 (t, 1), 7.50 (s, 1), 7.60 (t, 1), 7.77 (t, 1), 8.10 (d, 1), 8.35 (d, 1), 9.06 (m, 1) ppm;

2-[(4-(ethoxycarbonyl)piperazin-1-yl)carbonylmethyl]aminocarbonyl-4-(1-(carboxy)propoxy)quinoline; NMR (DMSO-d$_6$) 1.10 (t, 3), 1.20 (t, 3), 2.10 (m, 2), 3.30–3.60 (m, 8), 4.06 (q, 2), 4.26 (d, 2), 5.20 (t, 1), 7.45 (s, 1), 7.70 (t, 1), 7.90 (t, 1), 8.08 (d, 1), 8.30 (d, 1), 8.96 (m, 1) ppm;

2-[(4-(ethoxycarbonyl)piperazin-1-yl)carbonylmethyl]aminocarbonyl-4-(1-methyl-1-(ethoxycarbonyl)ethoxy)quinoline; NMR (CDCl$_3$) 1.20–1.30 (m, 6), 1.80 (s, 6), 3.55 (m, 6), 3.70 (m, 2), 4.16 (q, 2), 4.25 (q, 2), 4.34 (d, 2), 7.38 (s, 1), 7.57 (t, 1), 7.74 (t, 1), 8.08 (d, 1), 8.28 (d, 1), 9.02 (m, 1) ppm;

2-[1-(4-(ethoxycarbonyl)piperazin-1-yl)carbonyl-3-carboxypropyl]aminocarbonyl-4-(3-hydroxy-1-carboxypropoxy)quinoline; NMR (DMSO-d$_6$) 1.20 (m, 3), 1.86 (m, 1), 2.05 (m, 1), 2.20 (m, 2), 2.30 (m, 2), 3.30–3.60 (m, 6), 3.68 (m, 4), 4.06 (q, 2), 5.05 (m, 1), 5.22 (q, 1), 7.43 (s, 1), 7.70 (t, 1), 7.90 (t, 1), 8.10 (d, 1), 8.26 (d, 1), 8.95 (m, 1) ppm;

2-[(4-(ethoxycarbonyl)piperazin-1-yl)carbonylmethyl]aminocarbonyl-4-(1-methyl-1-(carboxy)ethoxy)quinoline; NMR (CDCl$_3$) 1.26 (t, 3), 1.90 (s, 6), 3.55 (m, 6), 3.70 (m, 2), 4.16 (q, 2), 4.42 (d, 2), 7.43 (s, 1), 7.55 (t, 1), 7.60 (t, 1), 7.90 (d, 1), 8.24 (d, 1), 9.03 (m, 1) ppm;

2-[1-(4-(ethoxycarbonyl)piperazin-1-yl)carbonyl-3-(methoxycarbonyl)propyl]aminocarbonyl-4-(methoxycarbonyl)methoxyquinoline; NMR (DMSO-d$_6$) 1.17 (t, 3), 1.90 (m, 1), 2.06 (m, 1), 2.38 (m, 2), 3.30–3.50 (m, 6), 3.52 (s, 3), 3.62 (m, 2), 3.72 (s, 3), 4.03 (q, 2), 5.03 (m, 1), 5.24 (s, 2), 7.50 (s, 1), 7.70 (t, 1), 7.87 (t, 1), 8.10 (d, 1), 8.23 (d, 1), 8.95 (m, 1) ppm;

2-[1-(2-methyl-4-(benzyl)piperazin-1-yl)carbonyl-3-(1,1-dimethylethoxycarbonyl)propyl]aminocarbonyl-4-methoxyquinoline; NMR (CDCl$_3$) 1.24–1.36 (m, 6), 1.43 (s, 9), 1.92–2.52 (m, 8), 2.67–3.14 (m, 4), 3.40–3.63 (m, 3), 4.13 (s, 3), 4.24–4.80 (m, 2), 5.18 (m, 1), 7.34 (m, 5), 7.57 (t, 1), 7.65 (s, 1), 7.73 (t, 1), 8.10 (d, 1), 8.23 (d, 1), 9.03 (m, 1) ppm;

2-[1-(2-methyl-4-(ethoxycarbonyl)piperazin-1-yl)carbonyl-3-(methoxycarbonyl)propyl]aminocarbonyl-4-methoxyquinoline; NMR (CDCl$_3$) 1.17–1.40 (m, 6), 2.00 (m, 1), 2.20 (m, 1), 2.40–2.60 (m, 2), 3.30–3.40 (m, 3), 3.70 (s, 3), 4.00–4.24 (m, 7), 4.40–4.80 (m, 2), 5.20 (m, 1), 7.57 (t, 1), 7.65 (s, 1), 7.75 (t, 1), 8.10 (d, 1), 8.23 (d, 1), 9.03 (m, 1) ppm;

2-[1-(2-methyl-4-(ethoxycarbonyl)piperazin-1-yl)carbonyl-3-carboxypropyl]aminocarbonyl-4-methoxyquinoline; NMR (CDCl$_3$) 1.17–1.40 (m, 6), 2.00 (m, 1), 2.20 (m, 1), 2.45–2.64 (m, 2), 3.00–3.40 (m, 3), 4.00–4.24 (m, 8), 4.40–4.50 (m, 1), 5.25 (m, 1), 7.56 (t, 1), 7.65 (s, 1), 7.75 (t, 1), 8.10 (d, 1), 8.21 (d, 1), 9.20 (m, 1) ppm;

2-[1-(4-(ethoxycarbonyl)piperazin-1-yl)carbonyl-3-(methoxycarbonyl)propyl]aminocarbonyl-4-(1-methyl-1-(methoxycarbonyl)ethoxy)quinoline; NMR (CDCl$_3$) 1.28 (t, 3), 1.80 (d, 6), 2.00 (m, 1), 2.22 (m, 1), 2.51 (m, 2), 3.40–3.80 (m, 14), 4.17 (q, 2), 5.23 (m, 1), 7.35 (s, 1), 7.57 (t, 1), 7.75 (t, 1), 8.10 (d, 1), 8.26 (d, 1), 8.96 (d, 1) ppm;

2-[1-(4-(ethoxycarbonyl)piperazin-1-yl)carbonyl-3-carboxypropyl]aminocarbonyl-4-(1-methyl-1-carboxyethoxy)quinoline;

2-[1-(4-(ethoxycarbonyl)piperazin-1-yl)carbonyl-3-(benzyloxycarbonyl)propyl]aminocarbonylnaphthalene; NMR (CDCl$_3$) 1.30 (t, 3), 1.90 (m, 1), 2.25 (m, 1), 2.50–2.70 (m, 2), 3.40–3.75 (m, 8), 4.18 (q, 2), 5.20 (m, 2), 5.30 (m, 1), 7.40 (m, 6), 7.55 (m, 2), 7.90 (m, 4), 8.35 (s, 1) ppm;

2-[1-(4-(ethoxycarbonyl)piperazin-1-yl)carbonyl-3-carboxypropyl]aminocarbonylnaphthalene; NMR (CDCl$_3$) 1.30 (t, 3), 1.80 (m, 1), 2.20 (m, 1), 2.50 (m, 2), 3.40–3.80 (m, 8), 4.10 (q, 2), 5.30 (m, 1), 7.50 (m, 2), 7.65 (m, 1), 7.80 (m, 4), 8.30 (s, 1) ppm;

2-[(4-(ethoxycarbonyl)piperazin-1-yl)carbonylmethyl]aminocarbonylnaphthalene; NMR (CDCl$_3$) 1.30 (t, 3), 3.40–3.80 (m, 8), 4.18 (q, 2), 4.35 (d, 2), 7.40–7.60 (m, 3), 7.92 (m, 3), 8.40 (s, 1) ppm;

2-[1-(4-(ethoxycarbonyl)piperazin-1-yl)carbonyl-2-(2-hydroxyphenyl)ethyl]aminocarbonyl-4-methoxyquinoline; NMR (DMSO-d$_6$) 1.18 (t, 3), 2.82 (m, 1), 3.36 (m, 5), 3.64 (m, 6), 3.06 (m, 2), 4.02 (s, 3), 4.12 (m, 2), 5.38 (m, 1), 6.80 (t, 1), 6.98 (d, 1), 7.18 (m, 3), 7.58 (t, 1), 7.62 (s, 1), 7.68 (t, 1), 8.16 (d, 1), 8.22 (d, 1), 8.32 (s, 1), 9.08 (d, 1) ppm;

2-[(4-(2-hydroxy-3-chloropyridin-5-yl)carbonylpiperazin-1-yl)carbonylmethyl]aminocarbonyl-4-methoxyquinoline;

2-[(4-(4-acetamidophenyl)carbonylpiperazin-1-yl)carbonylmethyl]aminocarbonyl-4-methoxyquinoline;

2-[(4-((2-methoxyethoxy)methyl)carbonylpiperazin-1-yl)carbonylmethyl]aminocarbonyl-4-methoxyquinoline;

2-[(4-(2-methoxycarbonylphenyl)carbonylpiperazin-1-yl)carbonylmethyl]aminocarbonyl-4-methoxyquinoline;

2-[1-(4-(ethoxycarbonyl)piperazin-1-yl)carbonyl-3-carboxypropyl]aminocarbonyl-5-aminoquinoline; NMR (DMSO-d$_6$) 1.20 (t, 3), 1.85 (m, 1), 2.05 (m, 1), 2.30 (m, 2), 3.25–3.65 (m, 8), 4.0 (q, 2), 5.05 (m, 1), 6.10 (m, 1), 6.80 (d, 1), 7.25 (d, 1), 7.50 (t, 1), 7.90 (d, 1), 8.70 (d, 1), 8.90 (d, 1) ppm;

2-[1-(4-(ethoxycarbonyl)piperazin-1-yl)carbonyl-3-(1,1-dimethylethoxycarbonylpropyl]aminocarbonyl-4-(1-(ethoxycarbonyl)ethoxy)quinoline; NMR (CDCl$_3$) 1.22–1.35 (m, 6), 1.48 (s, 9), 1.80 (d, 3), 1.97 (m, 1), 2.17 (m, 1), 2.40 (m, 2), 3.40–3.80 (m, 8), 4.18 (q, 2), 4.26 (m, 2), 5.10–5.30 (m, 2), 7.30 (d, 1), 7.60 (t, 1), 7.78 (t, 1), 8.10 (d, 1), 8.32 (d, 1), 8.96 (d, 1) ppm;

2-[1-(4-(ethoxycarbonyl)piperazin-1-yl)carbonyl-3-carboxypropyl]aminocarbonyl-4-(1-(ethoxycarbonyl)ethoxy)quinoline; NMR (CDCl$_3$) 1.28 (m, 6), 1.80 (d, 3), 1.97 (m, 1), 2.23 (m, 1), 2.57 (m, 2), 3.40–3.80 (m, 8), 4.17 (q, 2), 4.27 (m, 2), 5.07 (q, 2), 5.31 (m, 1), 7.50 (d, 1), 7.62 (t, 1), 7.78 (t, 1), 8.10 (d, 1), 8.34 (d, 1), 9.16 (d, 1) ppm;

2-[1-(4-(ethoxycarbonyl)piperazin-1-yl)carbonyl-3-(methoxycarbonyl)propyl]aminocarbonyl-4-(1-(ethoxycarbonyl)ethoxy)quinoline; NMR (CDCl$_3$) 1.26 (m, 6), 1.78 (d, 3), 1.97 (m, 1), 2.23 (m, 1), 2.52 (m, 2), 3.40–3.80 (m, 11), 4.18 (q, 2), 4.24 (m, 2), 5.10–5.30 (m, 2), 7.50 (d, 1), 7.58 (t, 1), 7.76 (t, 1), 8.10 (d, 1), 8.35 (d, 1), 8.97 (d, 1) ppm;

2-[1-(4-(ethoxycarbonyl)piperazin-1-yl)carbonyl-3-(methoxycarbonyl)propyl]aminocarbonyl-4-(1-(ethoxycarbonyl)-2-methylpropoxy)quinoline; NMR (CDCl$_3$) 1.17–1.34 (m, 9), 2.00 (m, 1), 2.23 (m, 1), 2.51 (m, 2), 3.40–3.80 (m, 11), 4.18 (q, 2), 4.25 (m, 2), 4.84 (m, 1), 5.23 (m, 1), 7.48 (d, 1), 7.60 (t, 1), 7.77 (t, 1), 8.10 (d, 1), 8.26 (d, 1), 8.98 (m, 1) ppm;

2-[1-(4-(ethoxycarbonyl)piperazin-1-yl)carbonyl-3-carboxypropyl]aminocarbonyl-4-(1-carboxy-2,2-dimethylpropoxy)quinoline; NMR (CDCl$_3$) 1.17–1.30 (m, 9), 1.90 (m, 1), 2.16 (m, 1), 2.34–2.60 (m, 2), 3.40–3.80 (m, 8), 4.15 (q, 2), 4.87 (m, 1), 5.35 (m, 1), 7.50 (d, 1), 7.58 (t, 1), 7.71 (m, 1), 8.07 (m, 1), 8.26 (m, 1), 9.10 (m, 1) ppm;

2-[1-(4-(ethoxycarbonyl)piperazin-1-yl)carbonyl-3-(methoxycarbonyl)propyl]aminocarbonyl-4-(cyanomethoxy)quinoline; NMR (CDCl$_3$) 1.27 (t, 3), 1.98 (m, 1), 2.23 (m, 1), 2.53 (m, 2), 3.40–3.80 (m, 11), 4.17 (q, 2), 5.10 (s, 2), 5.24 (m, 1), 7.66 (t, 1), 7.71 (s, 1), 7.80 (t, 1), 8.18 (d, 1), 8.21 (d, 1), 9.01 (d, 1) ppm;

2-[1-(4-(ethoxycarbonyl)piperazin-1-yl)carbonyl-3-(1,1-dimethylethoxycarbonyl)propyl]aminocarbonyl-4-(1-methyl-1-(methoxycarbonyl)ethoxy)quinoline; NMR (CDCl$_3$) 1.26 (t, 3), 1.43 (s, 9), 1.83 (d, 6), 1.97 (m, 1), 2.17 (m, 1), 2.40 (m, 2), 3.40–3.80 (m, 11), 4.18 (q, 2), 5.23 (m, 1), 7.35 (s, 1), 7.57 (t, 1), 7.75 (t, 1), 8.10 (d, 1), 8.26 (d, 1), 8.96 (d, 1) ppm;

2-[1-(4-(ethoxycarbonyl)piperazin-1-yl)carbonyl-3-carboxypropyl]aminocarbonyl-4-(1-methyl-1-(methoxycarbonyl)ethoxy)quinoline; NMR (CDCl$_3$) 1.26 (t, 3), 1.82 (d, 6), 1.97 (m, 1), 2.21 (m, 1), 2.56 (m, 2), 3.40–3.80 (m, 11), 4.18 (q, 2), 5.33 (m, 1), 7.30 (s, 1), 7.60 (t, 1), 7.80 (t, 1), 8.14 (d, 1), 8.29 (d, 1), 9.19 (d, 1) ppm;

2-[1-(4-(ethoxycarbonyl)piperazin-1-yl)carbonyl-3-(1,1-dimethylethoxycarbonyl)propyl]aminocarbonyl-4-(1-(ethoxycarbonyl)cyclobut-1-oxy)quinoline; NMR (CDCl$_3$) 1.22 (t, 3), 1.23 (t, 3), 1.90–2.23 (m, 4), 2.38 (m, 2), 2.64 (m, 2), 2.94 (m, 2), 3.40–3.80 (m, 8), 4.17 (q, 2), 4.22 (q, 2), 5.23 (m, 1), 7.28 (s, 1), 7.58 (t, 1), 7.76 (t, 1), 8.10 (d, 1), 8.32 (d, 1), 8.96 (d, 1) ppm;

2-[1-(4-(ethoxycarbonyl)piperazin-1-yl)carbonyl-3-carboxypropyl]aminocarbonyl-4-(1-(ethoxycarbonyl)cyclobut-1-oxy)quinoline; NMR (DMSO-d$_6$) 1.04 (t, 3), 1.18 (t, 3), 1.84 (m, 1), 1.95–2.01 (m, 3), 2.31 (m, 2), 2.62 (m, 2), 2.81 (m, 2), 3.30–3.66 (m, 8), 4.03 (q, 2), 4.14 (q, 2), 5.01 (m, 1), 6.99 (s, 1), 7.68 (t, 1), 7.86 (t, 1), 8.08 (d, 1), 8.28 (d, 1), 8.89 (d, 1) ppm;

2-[1-(4-(ethoxycarbonyl)piperazin-1-yl)carbonyl-3-carboxypropyl]aminocarbonyl-4-(1-carboxyethoxy)quinoline; NMR (DMSO-d$_6$) 1.07 (t, 3), 1.867 (d, 3), 1.85 (m, 1), 2.04 (m, 1), 2.30 (m, 2), 3.30–3.70 (m, 8), 4.06 (q, 2), 5.03 (m, 1), 5.30 (m, 1), 7.42 (s, 1), 7.67 (t, 1), 7.86 (t, 1), 7.78 (t, 1), 8.08 (d, 1), 8.24 (d, 1), 8.96 (d, 1) ppm;

2-[1-(4-(ethoxycarbonyl)piperazin-1-yl)carbonyl-3-carboxypropyl]aminocarbonyl-4-(1-carboxycyclobut-1-oxy)quinoline; NMR (DMSO-d$_6$) 1.19 (t, 3), 1.85 (m, 1), 2.04 (m, 3), 2.33 (m, 2), 2.60 (m, 2), 2.83 (m, 2), 3.30–3.70 (m, 8), 4.06 (q, 2), 5.03 (m, 1), 7.08 (s, 1), 7.70 (t, 1), 7.90 (t, 1), 8.10 (d, 1), 8.32 (d, 1), 9.15 (d, 1) ppm;

2-[1-(4-(ethoxycarbonyl)piperazin-1-yl)carbonyl-3-(methoxycarbonyl)propyl]aminocarbonyl-4-(dimethylaminocarbonyl)methoxyquinoline; NMR (CDCl$_3$) 1.26 (t, 3), 1.98 (m, 1), 2.24 (m, 1), 2.53 (m, 2), 3.05 (s, 3), 3.13 (s, 3), 3.40–3.80 (m, 11), 4.17 (q, 2), 5.02 (q, 2), 5.24 (m, 1), 7.56 (s, 1), 7.59 (t, 1), 7.76 (t, 1), 8.12 (d, 1), 8.35 (d, 1), 9.01 (d, 1) ppm;

2-[1-(4-(ethoxycarbonyl)piperazin-1-yl)carbonyl-3-carboxypropyl]aminocarbonyl-4-(dimethylaminocarbonyl)methoxyquinoline; NMR (CDCl$_3$) 1.26 (t, 3), 1.98 (m, 1), 2.22 (m, 1), 2.53 (m, 2), 3.04 (s, 3), 3.13 (s, 3), 3.40–3.80 (m, 8), 4.17 (q, 2), 5.03 (s, 2), 5.33 (m, 1), 7.56 (s, 1), 7.59 (t, 1), 7.76 (t, 1), 8.08 (d, 1), 8.32 (d, 1), 9.11 (d, 1) ppm;

2-[1-(4-(ethoxycarbonyl)piperazin-1-yl)carbonyl-3-(methoxycarbonyl)propyl]aminocarbonyl-4-(oxiranyl)methoxyquinoline; NMR (DMSO-d$_6$) 1.27 (t, 3), 1.98 (m, 1), 2.24 (m, 1), 2.40–2.60 (m, 2), 2.85 (m, 1), 3.00 (m, 1), 3.40–3.80 (m, 11), 4.16 (q, 2), 4.21 (m, 1), 4.62 (m, 1), 7.59 (t, 1), 7.63 (s, 1), 7.76 (t, 1), 8.10 (d, 1), 8.27 (d, 1), 9.02 (d, 1) ppm;

2-[1-(4-(ethoxycarbonyl)piperazin-1-yl)carbonyl-2-(3-hydroxyphenyl)ethyl]aminocarbonyl-4-methoxyquinoline; NMR (DMSO-d$_6$) 1.18 (t, 3), 2.62 (m, 1), 3.20 (m, 3), 3.36 (m, 2), 3.46 (m, 2), 3.64 (m, 1), 4.12 (s, 3), 3.06 (m, 2), 5.38 (m, 1), 6.78 (dd, 1), 6.82 (d, 1), 6.92 (s, 1), 7.18 (t, 1), 7.52 (t, 1), 7.62 (s, 1), 7.68 (t, 1), 8.16 (d, 1), 8.20 (d, 1), 8.90 (d, 1) ppm;

2-[1-(4-(ethoxycarbonyl)piperazin-1-yl)carbonyl-3-(benzyloxycarbonyl)propyl]aminocarbonyl-5-nitroquinoline; NMR (CDCl$_3$) 1.30 (m, 3), 2.0 (m, 1), 2.25 (m, 1), 2.55 (m, 2), 3.40–3.80 (m, 8), 4.15 (m, 2), 5.15 (m, 2), 5.30 (m, 1), 7.30 (m, 5), 7.85 (m, 1), 8.45 (m, 3), 8.90 (m, 1), 9.15 (m, 1) ppm;

2-[1-(4-(ethoxycarbonyl)piperazin-1-yl)carbonyl-3-methoxycarbonylpropyl]aminocarbonyl-5-nitroquinoline; NMR (CDCl$_3$) 1.30 (t, 3), 1.95 (m, 1), 2.25 (m, 1), 2.45 (m, 2), 3.40–3.80 (m, 8), 4.20 (q, 2), 5.40 (m, 1), 7.90 (m, 1), 8.40–8.50 (m, 3), 9.00 (m, 1), 9.20 (m, 1) ppm;

2-[1-(4-(ethoxycarbonyl)piperazin-1-yl)carbonyl-3-((ethoxycarbonyl)methoxycarbonyl)propyl]aminocarbonyl-5-aminoquinoline; NMR (CDCl$_3$) 1.30 (t, 6), 2.10 (m, 1), 2.30 (m, 1), 2.65 (m, 2), 3.40–3.80 (m, 8), 4.20 (m, 4), 4.60 (m, 2), 5.30 (m, 1), 6.90 (d, 1), 7.55 (m, 1), 7.65 (m, 1), 8.20 (d, 1), 8.30 (d, 1), 9.0 (d, 1) ppm;

2-[1-(4-(ethoxycarbonyl)piperazin-1-yl)carbonyl-3-(methoxycarbonyl)propyl]aminocarbonyl-4-(2,2,2-trifluoroethoxy)quinoline; NMR (CDCl$_3$) 1.27 (t, 3), 2.00 (m, 1), 2.24 (m, 1), 2.51 (m, 2), 3.40–3.78 (m, 11), 4.16 (q, 2), 4.64 (m, 2), 5.26 (m, 1), 7.60–7.78 (m, 2), 7.85 (t, 1), 8.15–8.35 (m, 2), 9.01 (m, 1) ppm;

2-[1-(4-(ethoxycarbonyl)piperazin-1-yl)carbonyl-3-carboxypropyl]aminocarbonyl-4-(oxiranyl)methoxyquinoline; NMR (DMSO-d$_6$) 1.17 (t, 3), 1.85 (m, 1), 2.03 (m, 1), 2.33 (m, 2), 3.30–3.57 (m, 6), 3.64 (m, 2), 4.04 (q, 2), 4.37 (m, 1), 4.58 (m, 1), 5.07 (m, 1), 7.63 (s, 1), 7.72 (t, 1), 7.86 (t, 1), 8.10 (d, 1), 8.32 (d, 1), 9.02 (d, 1) ppm;

2-[1-(4-(ethoxycarbonyl)piperazin-1-yl)carbonyl-3-(methylsulfonyl)propyl]aminocarbonyl-4-methoxyquinoline;

2-[1-(4-(ethoxycarbonyl)piperazin-1-yl)carbonyl-2-(1,2,4-triazol-3-yl)ethyl]aminocarbonyl-4-methoxyquinoline; NMR (DMSO-d$_6$) 1.15 (t, 3), 3.15 (m, 1), 3.23–3.40 (m, 8), 4.01 (q, 2), 4.10 (s, 3), 5.38 (m, 1), 7.55 (s, 1), 7.63 (dd, 1), 7.81 (dd, 1), 8.05 (d, 1), 8.18 (d, 1), 8.36 (br s, 1), 9.15 (d, 1) ppm;

2-[1-(4-(ethoxycarbonyl)piperazin-1-yl)carbonyl-3-(methoxycarbonyl)propyl]aminocarbonyl-4-(carboxy)methoxyquinoline; NMR (CDCl$_3$) 1.26 (t, 3), 1.97 (m, 1), 2.18 (m, 1), 2.48 (m, 2), 3.40–3.80 (m, 11), 4.16 (q, 2), 5.07 (q, 2), 5.24 (m, 1), 7.61 (t, 1), 7.65 (s, 1), 7.78 (t, 1), 8.09 (d, 1), 8.26 (d, 1), 9.05 (d, 1) ppm;

2-[1-(4-(ethoxycarbonyl)piperazin-1-yl)carbonyl-3-(methoxycarbonyl)propyl]aminocarbonyl-4-(ethoxycarbonylmethylaminocarbonyl)methoxyquinoline; NMR (CDCl$_3$) 1.28 (m, 6), 1.97 (m, 1), 2.24 (m, 1), 2.43–2.58 (m, 2), 3.43–3.78 (m, 11), 4.16 (m, 4), 4.28 (q, 2), 4.86 (s, 2), 5.27 (m, 1), 7.13 (m, 1), 7.65 (m, 2), 7.80 (t, 1), 8.17 (d, 1), 8.27 (d, 1), 8.98 (d, 1) ppm;

2-[1-(4-(ethoxycarbonyl)piperazin-1-yl)carbonyl-3-(methoxycarbonyl)propyl]aminocarbonyl-4-(3,3,3-trifluoropropoxy)quinoline; NMR (CDCl$_3$) 1.27 (t, 3), 1.97 (m, 1), 2.23 (m, 1), 2.51 (m, 2), 2.79 (m, 2), 3.41–3.80 (m, 11), 4.17 (q, 2), 4.57 (t, 2), 5.26 (m, 1), 7.58 (t, 1), 7.63 (s, 1), 7.77 (t, 1), 8.12 (d, 1), 8.22 (d, 1), 9.02 (d, 1) ppm;

2-[1-(4-(ethoxycarbonyl)piperazin-1-yl)carbonyl-3-carboxypropyl]aminocarbonyl-4-(3,3,3-trifluoropropoxy)quinoline; NMR (CDCl$_3$) 1.27 (t, 3), 1.99 (m, 1), 2.23 (m, 1), 2.54 (m, 2), 2.79 (m, 2), 3.41–3.80 (m, 8), 4.18 (q, 2), 4.56 (t, 2), 5.26 (m, 1), 7.58 (t, 1), 7.64 (s, 1), 7.77 (t, 1), 8.13 (d, 1), 8.21 (d, 1), 9.013 (d, 1) ppm;

2-[1-(4-(ethoxycarbonyl)piperazin-1-yl)carbonyl-3-(methoxycarbonyl)propyl]aminocarbonyl-4-(1-cyanoethoxy)quinoline; NMR (CDCl$_3$) 1.27 (t, 3), 1.98 (d, 3), 2.00 (m, 1), 2.24 (m, 1), 2.54 (m, 2), 3.40–3.80 (m, 11), 4.17 (q, 2), 5.20–5.40 (m, 2), 7.64 (t, 1), 7.80 (m, 2), 8.18 (m, 2), 8.98 (d, 1) ppm;

2-[1-(4-(ethoxycarbonyl)piperazin-1-yl)carbonyl-3-(methoxycarbonyl)propyl]aminocarbonyl-4-(benzylaminocarbonyl)methoxyquinoline; NMR (CDCl$_3$) 1.27 (t, 3), 1.98 (m, 1), 2.23 (m, 1), 2.53 (m, 2), 3.40–3.80 (m, 11), 4.16 (q, 2), 4.61 (d, 2), 4.88 (s, 2), 5.26 (m, 1), 7.78 (t, 1), 7.28–7.40 (m, 5), 7.61 (t, 1), 7.65 (s, 1), 7.77 (t, 1), 8.14 (d, 1), 8.16 (d, 1), 9.01 (d, 1) ppm;

2-[1-(4-(ethoxycarbonyl)piperazin-1-yl)carbonyl-3-carboxypropyl]aminocarbonyl-4-(1-tetrazol-5-ylethoxy)quinoline; NMR (DMSO-d$_6$) 1.18 (t, 3), 1.85 (m, 3), 2.03 (m, 1), 2.31 (m, 2), 3.30–3.70 (m, 8), 4.05 (q, 2), 5.03 (m, 1), 6.47 (m, 1), 7.71 (m, 2), 7.84 (t, 1), 8.08 (d, 1), 8.27 (d, 1), 8.92 (m, 1) ppm;

2-[1-(4-(ethoxycarbonyl)piperazin-1-yl)carbonyl-3-carboxypropyl]aminocarbonyl-4-(benzylaminocarbonyl)methoxyquinoline; NMR (DMSO-d$_6$) 1.19 (t, 3), 1.90 (m, 1), 2.07 (m, 1), 2.37 (m, 2), 3.30–3.73 (m, 8), 4.04 (q, 2), 4.39 (d, 2), 5.01 (s, 2), 5.08 (m, 1), 7.20–7.38 (m, 5), 7.58 (s, 1), 7.71 (t, 1), 7.88 (t, 1), 8.10 (d, 1), 8.43 (d, 1), 8.86 (m, 1), 8.97 (d, 1) ppm;

2-[1-(4-(ethoxycarbonyl)piperazin-1-yl)carbonyl-3-carboxypropyl]aminocarbonyl-4-((carboxy)methylamino)carbonylmethoxyquinoline; NMR (CDCl$_3$) 1.24 (t, 3), 1.91 (m, 1), 2.16 (m, 1), 2.43–2.58 (m, 2), 3.41–3.78 (m, 8), 4.12 (m, 4), 4.77 (s, 2), 5.27 (m, 1), 7.45 (m, 1), 7.55 (m, 1), 7.64 (t, 1), 7.94 (d, 1), 8.04 (d, 1), 9.04 (d, 1) ppm;

2-[1-(3-(2-methylpropyl)-4-(furan-2-ylcarbonyl)piperazin-1-yl)carbonyl-3-carboxypropyl]aminocarbonyl-4-methoxyquinoline;

2-[1-(3-(1-methylethyl)-4-(furan-2-ylcarbonyl)piperazin-1-yl)carbonyl-3-carboxypropyl]aminocarbonyl-4-methoxyquinoline;

2-[1-(3-benzyl-4-(furan-2-ylcarbonyl)piperazin-1-yl)carbonyl-3-carboxypropyl]aminocarbonyl-4-methoxyquinoline;

2-[1-(3-(4-hydroxybenzyl)-4-(furan-2-ylcarbonyl)piperazin-1-yl)carbonyl-3-carboxypropyl]aminocarbonyl-4-methoxyquinoline;

2-[1-(4-(furan-2-ylcarbonyl)piperazin-1-yl)carbonyl-3-carboxypropyl]aminocarbonyl-4-methoxyquinoline;

2-[1-(4-(3-methylphenyl)piperazin-1-yl)carbonyl-3-(1,1-dimethylethoxycarbonyl)propyl]aminocarbonyl-4-methoxyquinoline; NMR (CDCl$_3$) 1.47 (s, 9), 2.01 (m, 1), 2.24 (m, 1), 2.34 (s, 3), 2.42 (m, 2), 3.14–3.34 (m, 4), 3.74–3.93 (m, 4), 4.13 (s, 3), 5.31 (m, 1), 6.75 (m, 3), 7.16 (t, 1), 7.57 (t, 1), 7.66 (s, 1), 7.74 (t, 1), 8.10 (d, 1), 8.23 (d, 1), 9.03 (d, 1) ppm;

2-[1-(4-(pyridin-2-yl)piperazin-1-yl)carbonyl-3-(1,1-dimethylethoxycarbonyl)propyl]aminocarbonyl-4-methoxyquinoline; NMR (CDCl$_3$) 1.44 (s, 9), 1.98 (m, 1), 2.23 (m, 1), 2.43 (m, 2), 3.51–3.90 (m, 8), 4.13 (s, 3), 5.30 (m, 1), 6.66 (m, 2), 7.57 (m, 2), 7.65 (s, 1), 7.75 (t, 1), 8.10 (d, 1), 8.23 (m, 2), 9.04 (d, 1) ppm;

2-[1-(4-(3-methylphenyl)piperazin-1-yl)carbonyl-3-carboxypropyl]aminocarbonyl-4-methoxyquinoline; NMR (DMSO-d$_6$) 1.89 (m, 1), 2.08 (m, 1), 2.24 (s, 3), 2.32 (m, 2), 3.10–3.26 (m, 4), 3.65 (m, 2), 3.79 (m, 2), 4.13 (s, 3), 5.07 (m, 1), 6.64 (d, 1), 6.80 (m, 2), 7.12 (t, 1), 7.61 (s, 1), 7.66 (t, 1), 7.85 (t, 1), 8.10 (d, 1), 8.18 (d, 1), 8.97 (d, 1) ppm;

2-[1-(4-(pyridin-2-yl)piperazin-1-yl)carbonyl-3-carboxypropyl]aminocarbonyl-4-methoxyquinoline; NMR (DMSO-d$_6$) 1.88 (m, 1), 2.08 (m, 1), 2.34 (m, 2), 3.51–3.72 (m, 6), 3.78 (m, 2), 4.13 (s, 3), 5.16 (m, 1), 6.66 (m, 1), 6.85 (d, 1), 7.56 (t, 1), 7.61 (s, 1), 7.67 (t, 1), 7.85 (t, 1), 8.08–8.21 (m, 3), 8.97 (d, 1) ppm;

2-[1-(4-(ethoxycarbonyl)piperazin-1-yl)carbonyl-3-(methoxycarbonyl)propyl]aminocarbonyl-4-(3,4,4-trifluorobut-3-en-1-oxy)quinoline; NMR (CDCl$_3$) 1.26 (t, 3), 1.98 (m, 1), 2.24 (m, 1), 2.52 (m, 2), 2.92 (m, 2), 2.97 (m, 2), 3.41–3.78 (m, 11), 4.16 (q, 2), 4.45 (t, 2), 5.24 (m, 1), 7.58 (t, 1), 7.63 (s, 1), 7.74 (t, 1), 8.10 (d, 1), 8.17 (d, 1), 9.01 (d, 1) ppm;

2-[1-(4-(ethoxycarbonyl)piperazin-1-yl)carbonyl-3-carboxypropyl]aminocarbonyl-4-(3,4,4-trifluorobut-3-en-1-oxy)quinoline; NMR (CDCl$_3$) 1.25 (t, 3), 1.98 (m, 1), 2.24 (m, 1), 2.56 (m, 2), 2.92 (m, 2), 2.97 (m, 2), 3.41–3.78 (m, 8), 4.16 (q, 2), 4.44 (t, 2), 5.31 (m, 1), 7.58 (t, 1), 7.63 (s, 1), 7.74 (t, 1), 8.10 (d, 1), 8.17 (d, 1), 9.17 (d, 1) ppm;

2-[(4-(ethoxycarbonyl)piperazin-1-yl)carbonylmethyl]aminocarbonyl-4-(1-(ethoxycarbonyl)cyclobut-1-oxy)quinoline; NMR (CDCl$_3$) 1.22 (t, 3), 1.31 (t, 3), 2.13 (m, 2), 2.63 (m, 2), 2.94 (m, 2), 3.57 (m, 6), 3.68 (m, 2), 4.17 (q, 2), 4.24 (q, 2), 4.35 (d, 2), 7.16 (s, 1), 7.60 (t, 1), 7.76 (t, 1), 8.10 (d, 1), 8.34 (d, 1), 9.03 (t, 1) ppm;

2-[(4-(ethoxycarbonyl)piperazin-1-yl)carbonylmethyl]aminocarbonyl-4-(1-(carboxy)cyclobut-1-oxy)quinoline; NMR (DMSO-d$_6$) 1.22 (t, 3), 2.03 (m, 2), 2.59 (m, 2), 2.82 (m, 2), 3.30–3.60 (m, 8), 4.04 (q, 2), 4.23 (d, 2), 7.08 (s, 1), 7.71 (t, 1), 7.90 (t, 1), 8.07 (d, 1), 8.28 (d, 1), 8.94 (t, 1) ppm;

2-[1-(4-(ethoxycarbonyl)piperazin-1-yl)carbonyl-3-carboxypropyl]aminocarbonyl-4-(tetrazol-5-yl)methoxyquinoline; NMR (DMSO-d$_6$) 1.18 (t, 3), 1.86 (m, 1), 2.08 (m, 1), 2.26 (m, 2), 3.44 (m, 6), 3.64 (m, 2), 4.04 (q, 2), 5.06 (m, 1), 5.88 (s, 1), 7.70 (t, 3), 7.78 (s, 1), 7.84 (t, 1), 8.10 (d, 1), 8.26 (d, 1), 8.90 (d, 1) ppm;

2-[1-(4-(ethoxycarbonyl)piperazin-1-yl)carbonyl-3-carboxypropyl]aminocarbonyl-4-(2-hydroxyethoxy)quinoline;

NMR (DMSO-d$_6$) 1.18 (t, 3), 1.84 (m, 1), 2.14 (m, 1), 2.14 (m, 2), 3.40 (m, 6), 3.64 (m, 2), 3.86 (m, 2), 4.04 (q, 2), 4.36 (m, 2), 5.08 (m, 1), 7.58 (s, 1), 7.68 (t, 3), 7.84 (t, 1), 8.08 (d, 1), 8.18 (d, 1), 8.90 (d, 1) ppm;

2-[1-(4-(ethoxycarbonyl)piperazin-1-yl)carbonyl-3-carboxypropyl]aminocarbonyl-5-(carboxymethyl)aminoquinoline; NMR (DMSO-d$_6$) 1.10 (t, 3), 1.80 (m, 1), 2.0 (m, 1), 2.25 (m, 2), 3.20–3.60 (m, 8), 4.0 (m, 4), 5.0 (m, 1), 6.40 (d, 1), 7.30 (d, 1), 7.50 (m, 1), 7.95 (d, 1), 8.70 (d, 1), 8.85 (d, 1) ppm;

2-[1-(4-(ethoxycarbonyl)piperazin-1-yl)carbonyl-3-(methoxycarbonyl)propyl]aminocarbonyl-4-(1-(methoxycarbonyl)ethoxy)quinoline; NMR (CDCl$_3$) 1.27 (t, 3), 1.77 (d, 3), 1.98 (m, 1), 2.23 (m, 1), 2.48 (m, 2), 3.40–3.80 (m, 14), 4.16 (q, 2), 5.14–5.30 (m, 2), 7.48 (s, 1), 7.60 (t, 1), 7.76 (t, 1), 8.10 (d, 1), 8.32 (d, 1), 8.98 (t, 1) ppm and NMR (CDCl$_3$) 1.27 (t, 3), 1.78 (d, 3), 1.98 (m, 1), 2.23 (m, 1), 2.48 (m, 2), 3.40–3.80 (m, 14), 4.16 (q, 2), 5.14–5.30 (m, 2), 7.48 (s, 1), 7.60 (t, 1), 7.76 (t, 1), 8.10 (d, 1), 8.32 (d, 1), 8.98 (t, 1) ppm;

2-[1-(4-(ethoxycarbonyl)piperazin-1-yl)carbonyl-3-carboxypropyl]aminocarbonyl-4-(1-(carboxy)ethoxy)quinoline; NMR (DMSO) 1.24 (t, 3), 1.71 (d, 3), 1.85 (m, 1), 2.03 (m, 1), 2.32 (m, 2), 3.30–3.71 (m, 8), 4.06 (q, 2), 5.06 (m, 1), 5.34 (m, 1), 7.46 (s, 1), 7.71 (t, 1), 7.89 (t, 1), 8.10 (d, 1), 8.27 (d, 1), 8.98 (m, 1) ppm and NMR (DMSO) 1.18 (t, 3), 1.71 (d, 3), 1.86 (m, 1), 2.03 (m, 1), 2.32 (m, 2), 3.30–3.73 (m, 8), 4.06 (q, 2), 5.06 (m, 1), 5.34 (m, 1), 7.46 (s, 1), 7.71 (t, 1), 7.89 (t, 1), 8.10 (d, 1), 8.27 (d, 1), 8.98 (m, 1) ppm;

2-[1-(3-(1-methylethyl)-4-(ethoxycarbonyl)piperazin-1-yl)carbonyl-3-(1,1-dimethylethoxycarbonyl)propyl]aminocarbonyl-4-methoxyquinoline; NMR (CDCL$_3$) 0.76–0.98 (m, 6), 1.26 (m, 3), 1.38–1.70 (m, 12), 1.96 (m, 1), 2.24 (m, 1), 2.32–2.50 (m, 2), 2.71–3.47 (m, 3), 4.01–4.31 (m, 7), 4.32–4.60 (m, 2), 5.15–5.33 (m, 1), 7.56 (t, 1), 7.64 (s, 1), 7.75 (t, 1), 8.10 (d, 1), 8.24 (d, 1), 9.03 (m, 1) ppm and NMR (CDCL$_3$) 0.77–0.98 (m, 6), 1.26 (m, 3), 1.38–1.70 (m, 12), 1.96 (m, 1), 2.24 (m, 1), 2.32–2.50 (m, 2), 2.71–3.45 (m, 3), 4.01–4.27 (m, 7), 4.32–4.60 (m, 2), 5.15–5.33 (m, 1), 7.56 (t, 1), 7.64 (s, 1), 7.75 (t, 1), 8.10 (d, 1), 8.24 (d, 1), 9.03 (m, 1) ppm;

2-[1-(3-(2-methylpropyl)-4-(ethoxycarbonyl)piperazin-1-yl)carbonyl-3-carboxypropyl]aminocarbonyl-4-methoxyquinoline; NMR (DMSO) 0.73–0.98 (m, 6), 1.15–1.57 (m, 6), 1.78–2.20 (m, 2), 2.34 (m, 2), 2.65–3.44 (m, 3), 3.80–4.38 (m, 9), 5.01–5.18 (m, 1), 7.61 (s, 1), 7.66 (t, 1), 7.87 (t, 1), 8.10 (d, 1), 8.22 (d, 1), 8.96 (m, 1) ppm and NMR (DMSO) 0.73–0.98 (m, 6), 1.16–1.60 (m, 6), 1.82–2.17 (m, 2), 2.34 (m, 2), 2.67–3.42 (m, 3), 3.80–4.36 (m, 9), 5.01–5.18 (m, 1), 7.61 (s, 1), 7.66 (t, 1), 7.87 (t, 1), 8.10 (d, 1), 8.22 (d, 1), 8.96 (m, 1) ppm;

2-[1-(4-(ethoxycarbonyl)piperazin-1-yl)carbonyl-3-(1,1-dimethylethoxycarbonyl)propyl]aminocarbonyl-7-chloro-4-methoxyquinoline; NMR (CDCl$_3$) 1.30 (t, 3), 1.45 (s, 9), 2.0 (m, 1), 2.20 (m, 1), 2.40 (m, 2), 3.40–3.80 (m, 8), 4.10 (s, 3), 4.20 (q, 2), 5.20 (m, 1), 7.50 (d, 1), 7.65 (s, 1), 8.15 (m, 2), 8.95 (d, 1) ppm;

2-[1-(4-(ethoxycarbonyl)piperazin-1-yl)carbonyl-3-carboxypropyl]aminocarbonyl-7-chloro-4-methoxyquinoline; NMR (CDCl$_3$) 1.30 (t, 3), 2.0 (m, 1), 2.20 (m, 1), 2.60 (m, 2), 3.40–3.90 (m, 8), 4.20 (m, 5), 5.35 (m, 1), 7.60 (m, 1), 7.70 (m, 1), 8.20 (m, 2), 9.20 (m, 1) ppm;

2-[1-(2-(2-methylpropyl)-4-(ethoxycarbonyl)piperazin-1-yl)carbonyl-3-(1,1-dimethylethoxycarbonyl)propyl]aminocarbonyl-4-methoxyquinoline; NMR (CDCl$_3$) 0.88–1.10 (m, 6), 1.26 (m, 3), 1.38–1.62 (m, 12), 1.96 (m, 1), 2.21 (m, 1), 2.32–2.50 (m, 2), 2.61–3.42 (m, 3), 3.92–4.80 (m, 9), 5.15–5.30 (m, 1), 7.57 (t, 1), 7.65 (s, 1), 7.75 (t, 1), 8.10 (d, 1), 8.24 (d, 1), 8.92 (m, 1) ppm;

2-[1-(2-(2-methylpropyl)-4-(ethoxycarbonyl)piperazin-1-yl)carbonyl-3-carboxypropyl]aminocarbonyl-4-methoxyquinoline; NMR (CDCl$_3$) 0.88–1.10 (m, 6), 1.27 (m, 3), 1.35–1.60 (m, 3), 1.80–2.24 (m, 2), 2.48–2.65 (m, 2), 2.84–3.11 (m, 2), 3.37 (m, 1), 3.94–4.80 (m, 9), 5.25 (m, 1), 7.59 (t, 1), 7.64 (s, 1), 7.80 (t, 1), 8.14 (d, 1), 8.23 (d, 1), 9.16 (m, 1) ppm and NMR (CDCl$_3$) 0.88–1.08 (m, 6), 1.25 (m, 3), 1.35–1.62 (m, 3), 1.78–2.26 (m, 2), 2.41–2.62 (m, 2), 2.80–3.42 (m, 3), 3.92–4.85 (m, 9), 5.18–5.33 (m, 1), 7.56 (t, 1), 7.63 (s, 1), 7.74 (t, 1), 8.10 (d, 1), 8.21 (d, 1), 9.12 (m, 1) ppm;

2-[1-(3-(1-methylethyl)-4-(ethoxycarbonyl)piperazin-1-yl)carbonyl-3-carboxypropyl]aminocarbonyl-4-methoxyquinoline; NMR (DMSO-d$_6$) 0.67–1.23 (m, 9), 1.73–2.11 (m, 3), 2.32 (m, 2), 2.74–2.98 (m, 2), 3.10–3.37 (m, 2), 3.72 (m, 1), 3.80–4.53 (m, 8), 5.07 (m, 1), 7.58 (s, 1), 7.64 (t, 1), 7.83 (t, 1), 8.07 (d, 1), 8.18 (d, 1), 8.88 (m, 1) ppm;

2-[1-(4-(ethoxycarbonyl)piperazin-1-yl)carbonyl-3-(methoxycarbonyl)propyl]aminocarbonyl-4-(1-(ethoxycarbonyl)cyclobut-1-oxy)quinoline; NMR (CDCl$_3$) 1.19 (t, 3), 1.28 (t, 3), 1.95–2.25 (m, 4), 2.40–2.70 (m, 4), 2.96 (m, 2), 3.40–3.80 (m, 11), 4.17 (q, 2), 4.23 (q, 2), 5.24 (m, 1), 7.14 (s, 1), 7.60 (t, 1), 7.87 (t, 1), 8.10 (d, 1), 8.32 (d, 1), 8.94 (d, 1) ppm;

2-[1-(4-(3-chlorophenyl)piperazin-1-yl)carbonyl-3-(1,1-dimethylethoxycarbonyl)propyl]aminocarbonyl-4-methoxyquinoline; NMR (DMSO-d$_6$) 1.35 (s, 9), 1.84 (m, 1), 2.03 (m, 1), 2.31 (m, 2), 3.12–3.34 (m, 4), 3.63 (m, 2), 3.75 (m, 2), 4.12 (s, 3), 5.07 (m, 1), 6.78 (d, 1), 6.92 (d, 1), 6.96 (s, 1), 7.21 (t, 1), 7.57 (s, 1), 7.65 (t, 1), 7.84 (t, 1), 8.07 (d, 1), 8.17 (d, 1), 8.92 (d, 1) ppm;

2-[1-(4-(3-methylphenyl)-3-methylpiperazin-1-yl)carbonyl-3-(1,1-dimethylethoxycarbonyl)propyl]aminocarbonyl-4-methoxyquinoline; NMR (CDCl$_3$) 0.95–1.13 (m, 3), 1.47 (s, 9), 2.02 (m, 1), 2.21–2.57 (m, 5), 3.08–4.45 (m, 10), 5.27 (m, 1), 6.74 (m, 3), 7.16 (m, 1), 7.57 (m, 1), 7.65 (s, 1), 7.75 (t, 1), 8.12 (d, 1), 8.22 (d, 1), 9.04 (m, 1) ppm;

2-[1-(4-(3-chlorophenyl)piperazin-1-yl)carbonyl-3-carboxypropyl]aminocarbonyl-4-methoxyquinoline; NMR (CDCl$_3$) 2.02 (m, 1), 2.24 (m, 1), 2.57 (m, 2), 3.18–3.32 (m, 4), 3.77–3.91 (m, 4), 4.15 (s, 3), 5.33 (m, 1), 6.79 (d, 1), 7.87 (m, 2), 7.18 (t, 1), 7.57 (s, 1), 7.66 (s, 1), 7.77 (t, 1), 8.12 (d, 1), 8.24 (d, 1), 9.25 (d, 1) ppm;

2-[1-(piperazin-1-yl)carbonyl-3-carboxypropyl]aminocarbonyl-4-methoxyquinoline;

2-[1-(4-(piperidin-4-ylcarbonyl)piperazin-1-yl)carbonyl-3-carboxypropyl]aminocarbonyl-4-methoxyquinoline;

2-[1-(4-(ethoxycarbonyl)piperazin-1-yl)carbonyl-3-carboxypropyl]aminocarbonyl-5-di(acetyl)aminoquinoline; NMR (CDCl$_3$) 1.30 (t, 3), 2.0 (m, 1), 2.30 (m, 1), 2.35 (s, 3), 2.40 (s, 3), 2.60 (m, 2), 3.40–3.85 (m, 8), 4.20 (q, 2), 5.35 (m, 1), 7.50 (d, 1), 7.85 (m, 1), 8.15 (d, 1), 8.35 (m, 1), 8.65 (m, 2), 9.15 (m, 1) ppm;

2-[1-(3-methyl-4-(3-methylphenyl)piperazin-1-yl)carbonyl-3-carboxypropyl]aminocarbonyl-4-methoxyquinoline; NMR (DMSO-d$_6$) 0.82–0.91 (m, 3), 1.78 (m, 1), 2.02 (m, 1), 2.18–2.56 (m, 5), 3.07–3.35 (m, 1), 3.40–3.95 (m, 4), 4.02–4.41 (m, 5), 5.03 (m, 1), 7.08 (m, 1), 7.26 (m, 3), 7.57 (m, 2), 7.76 (m, 1), 8.01–8.13 (m, 2), 9.18 (m, 1) ppm;

2-[1-(4-(ethoxycarbonyl)piperazin-1-yl)carbonyl-3-carboxypropyl]aminocarbonyl-5-acetamidoquinoline; NMR (CDCl$_3$) 1.30 (m, 3), 2.0 (m, 1), 2.20 (m, 1), 2.40 (s, 3), 2.60 (m, 2), 3.40–3.85 (m, 8), 4.20 (m, 2), 5.35 (m, 1), 7.60–7.80 (m, 3), 8.40 (m, 1), 9.0 (m, 2) ppm;

2-[1-(3-(1-hydroxyethyl)-4-(ethoxycarbonyl)piperazin-1-yl)carbonyl-3-(1,1-dimethylethoxycarbonyl)propyl]aminocarbonyl-4-methoxyquinoline; NMR (CDCl$_3$) 1.27–1.38 (m, 6), 1.46 (s, 9), 1.94 (m, 1), 2.17 (m, 1), 2.44 (m, 2), 2.92 (m, 1), 3.27–3.60 (m, 2), 3.90–4.63 (m, 9), 5.26 (m, 1), 7.56 (t, 1), 7.63 (s, 1), 7.73 (t, 1), 8.09 (d, 1), 8.22 (d, 1), 8.93 (m, 1) ppm;

2-[1-(4-(ethoxycarbonyl)piperazin-1-yl)carbonyl-3-(ethoxycarbonyl)propyl]aminocarbonyl-4-(1-tetrazol-5-ylethoxy)quinoline; NMR (DMSO-d$_6$) 1.07–1.18 (m, 6), 1.87 (m, 4), 2.05 (m, 1), 2.37 (m, 2), 3.32–3.68 (m, 8), 3.95–4.06 (m, 4), 5.03 (m, 1), 6.47 (m, 1), 7.67 (m, 2), 7.85 (t, 1), 8.07 (d, 1), 8.27 (d, 1), 8.93 (d, 1) ppm;

2-[1-(3-(1-hydroxyethyl)-4-(ethoxycarbonyl)piperazin-1-yl)carbonyl-3-carboxypropyl]aminocarbonyl-4-methoxyquinoline; NMR (DMSO-d$_6$) 1.18 (m, 6), 1.78 (m, 1), 2.01 (m, 1), 2.32 (m, 2), 2.77 (m, 1), 3.27–3.43 (m, 2), 3.80–4.41 (m, 9), 5.06 (m, 1), 7.56 (m, 1), 7.63 (t, 1), 7.83 (t, 1), 8.08 (m, 1), 8.18 (m, 1), 8.93 (m, 1) ppm and NMR (DMSO-d$_6$) 1.05–1.23 (m, 6), 1.82 (m, 1), 2.01 (m, 1), 2.30 (m, 2), 2.84 (m, 1), 3.03–3.23 (m, 2), 3.40–4.41 (m, 9), 5.04 (m, 1), 7.56 (s, 1), 7.63 (t, 1), 7.83 (t, 1), 8.08 (d, 1), 8.18 (d, 1), 8.93 (m, 1) ppm;

2-[1-(4-(3-methylphenyl)piperazin-1-yl)carbonyl-3-carboxypropyl]aminocarbonyl-4-(1-(carboxy)cyclobut-1-oxy)quinoline; NMR (DMSO-d$_6$) 1.84 (m, 1), 2.03 (m, 3), 2.25 (s, 3), 2.35 (m, 2), 2.58 (m, 2), 2.83 (m, 2), 3.10–3.24 (m, 4), 3.62–3.85 (m, 4), 5.11 (m, 1), 6.64 (d, 1), 6.77 (m, 2), 7.08 (s, 1), 7.12 (d, 1), 7.71 (t, 1), 7.88 (t, 1), 8.11 (d, 1), 8.27 (d, 1), 8.92 (d, 1) ppm;

2-[1-(4-(ethoxycarbonyl)piperazin-1-yl)carbonyl-3-(1,1-dimethylethoxycarbonyl)propyl]aminocarbonyl-7-chloro-4-(1-(ethoxycarbonyl)cyclobut-1-oxy)quinoline; NMR (CDCl$_3$) 1.23 (t, 3), 1.27 (t, 3), 1.46 (s, 9), 1.96 (m, 1), 2.16 (m, 3), 2.37 (m, 2), 2.94 (m, 2), 3.41–3.79 (m, 8), 4.17 (q, 2), 4.24 (q, 2), 5.19 (m, 1), 7.13 (s, 1), 7.54 (d, 1), 8.13 (s, 1), 8.25 (d, 1), 8.87 (d, 1) ppm;

2-[1-(4-(ethoxycarbonyl)piperazin-1-yl)carbonyl-3-carboxypropyl]aminocarbonyl-7-chloro-4-(1-(ethoxycarbonyl)cyclobut-1-oxy)quinoline; NMR (DMSO-d$_6$) 1.05 (t, 3), 1.18 (t, 3), 1.82 (m, 1), 2.00 (m, 3), 2.30 (m, 2), 2.60 (m, 2), 2.79 (m, 2), 3.35–3.65 (m, 8), 4.05 (q, 2), 4.16 (q, 2), 5.00 (m, 1), 6.99 (s, 1), 7.72 (d, 1), 8.15 (s, 1), 8.30 (d, 1), 8.88 (d, 1) ppm;

2-[1-(4-(ethoxycarbonyl)piperazin-1-yl)carbonyl-3-(ethoxycarbonyl)propyl]aminocarbonyl-4-(1-(ethoxycarbonyl)cyclobut-1-oxy)quinoline; NMR (CDCl$_3$) 1.18 (t, 3), 1.25 (m, 6), 1.97 (m, 1), 2.09 (m, 1), 2.21 (m, 2), 2.48 (m, 2), 2.62 (m, 2), 2.94 (m, 2), 3.42–3.78 (m, 8), 4.12–4.26 (m, 6), 5.23 (m, 1), 7.13 (s, 1), 7.60 (t, 1), 7.75 (t, 1), 8.07 (d, 1), 8.33 (d, 1), 8.92 (d, 1) ppm;

2-[1-(4-(ethoxycarbonyl)piperazin-1-yl)carbonyl-3-carboxypropyl]aminocarbonyl-7-chloro-4-(1-carboxycyclobut-1-oxy)quinoline; NMR (DMSO-d$_6$) 1.18 (t, 3), 1.85 (m, 1), 1.98 (m, 3), 2.30 (m, 2), 2.58 (m, 2), 2.78 (m, 2), 3.35–3.62 (m, 8), 4.05 (q, 2), 4.96 (m, 1), 7.03 (s, 1), 7.70 (d, 1), 8.15 (s, 1), 8.25 (d, 1), 8.88 (d, 1) ppm;

2-[1-(4-(ethoxycarbonyl)piperazin-1-yl)carbonyl-3-carboxypropyl]aminocarbonyl-5,7-dichloro-4-methoxyquinoline; NMR (CDCl$_3$) 1.30 (t, 3), 2.0 (m, 1), 2.20 (m, 1), 2.60 (m, 2), 3.40–3.85 (m, 8), 4.10 (s, 3), 4.20 (q, 2), 5.30 (m, 1), 7.60 (m, 2), 8.0 (s, 1), 9.10 (m, 1) ppm;

2-[1-(4-(ethoxycarbonyl)piperazin-1-yl)carbonyl-3-carboxypropyl]aminocarbonyl-4-(1-carboxy-3-(diethylamino)propoxy)quinoline; NMR (DMSO-d$_6$) 1.18 (m, 9), 1.83 (m, 1), 2.02 (m, 1), 2.31 (m, 2), 2.48 (m, 2), 3.22–3.68 (m, 14), 4.04 (q, 2), 5.03 (m, 1), 5.46 (m, 1), 7.47 (s, 1), 7.71 (t, 1), 7.88 (t, 1), 8.10 (d, 1), 8.31 (d, 1), 8.94 (m, 1) ppm;

2-[1-(4-(ethoxycarbonyl)piperazin-1-yl)carbonyl-3-carboxypropyl]aminocarbonyl-5,7-dichloro-4-(1-carboxycyclobut-1-oxy)quinoline; NMR (CD$_3$OD) 1.15 (t, 3), 1.90 (m, 1), 2.10 (m, 3), 2.40 (m, 2), 2.60 (m, 2), 2.80 (m, 2), 3.40–3.70 (m, 8), 4.05 (q, 2), 5.10 (m, 1), 7.0 (s, 1), 7.60 (s, 1), 8.0 (s, 1) ppm;

2-[1-(4-(ethoxycarbonyl)piperazin-1-yl)carbonyl-3-carboxypropyl]aminocarbonyl-6-chloro-4-(1-carboxycyclobut-1-oxy)quinoline; NMR (DMSO-d$_6$) 1.15 (t, 3), 1.80–1.95 (m, 1), 2.00 (m, 2), 2.30 (m, 2), 2.60 (m, 2), 2.80 (m, 2), 3.30–3.75 (m, 8), 4.05 (q, 2), 5.00 (m, 1), 7.15 (s, 1), 7.85 (d, 1), 8.10 (d, 1), 8.25 (s, 1), 8.85 (d, 1) ppm;

2-[1-(4-(ethoxycarbonyl)piperazin-1-yl)carbonyl-2-carboxyethyl]aminocarbonyl-4-(1-carboxycyclobut-1-oxy)quinoline; NMR (DMSO-d$_6$) 1.10 (t, 3), 1.98 (m, 2), 2.30–2.63 (m, 3), 2.75–2.87 (m, 3), 3.28–3.50 (m, 8), 3.94 (q, 2), 5.17 (m, 1), 7.64 (t, 1), 7.80 (t, 1), 8.01 (d, 1), 8.22 (d, 1), 9.10 (d, 1) ppm;

2-[1-(4-(ethoxycarbonyl)piperazin-1-yl)carbonyl-3-(methoxycarbonyl)propyl]aminocarbonyl-4-(1,1-di(ethoxycarbonyl)methoxy)quinoline; NMR (CDCl$_3$) 1.04–1.18 (m, 9), 1.96 (m, 1), 2.23 (m, 1), 2.53 (m, 2), 3.40–3.80 (m, 8), 4.15 (q, 2), 4.37 (m, 4), 5.24 (m, 1), 5.57 (s, 1), 7.53 (s, 1), 7.63 (t, 1), 7.78 (t, 1), 8.11 (d, 1), 8.41 (d, 1), 8.98 (d, 1) ppm;

2-[1-(4-(ethoxycarbonyl)piperazin-1-yl)carbonyl-3-carboxypropyl]aminocarbonyl-4-(1,1-di(carboxy)methoxy)quinoline; NMR (DMSO-d$_6$) 1.18 (t, 3), 1.84 (m, 1), 2.00 (m, 1), 2.30 (m, 2), 3.35–3.65 (m, 8), 4.01 (q, 2), 5.02 (m, 1), 5.88 (s, 1), 7.47 (s 1), 7.70 (t, 1), 7.90 (t, 1), 8.10 (d, 1), 8.27 (d, 1), 8.94 (d, 1) ppm;

2-[1-(4-(ethoxycarbonyl)piperazin-1-yl)carbonyl-3-carboxypropyl]aminocarbonyl-6-methyl-4-(1-carboxycyclobut-1-oxy)quinoline; NMR (DMSO-d$_6$) 1.14 (t, 3), 1.83 (m, 1), 2.02 (m, 3), 2.28 (m, 2), 2.54 (s, 3), 2.56 (m, 2), 2.78 (m, 2), 3.40 (m, 6), 3.62 (m, 2), 4.03 (q, 2), 5.00 (m, 1), 7.02 (s, 1), 7.68 (dd, 1), 7.95 (d, 1), 8.14 (s, 1), 8.85 (d, 1) ppm;

2-[1-(4-(ethoxycarbonyl)piperazin-1-yl)carbonyl-3-carboxypropyl]aminocarbonyl-6-nitro-4-(1-carboxycyclobut-1-oxy)quinoline; NMR (DMSO-d$_6$) 1.20 (t, 3), 1.88 (m, 1), 2.06 (m, 3), 2.30 (m, 2), 2.69 (m, 2), 2.83 (m, 2), 3.30–3.65 (m, 8), 4.05 (q, 2), 5.02 (m, 1), 7.19 (s, 1), 8.32 (d, 1), 8.59 (d, 1), 8.64 (s, 1), 9.02 (d, 1), 9.06 (s, 1) ppm;

2-[1-(4-(ethoxycarbonyl)piperazin-1-yl)carbonyl-3-carboxypropyl]aminocarbonyl-6-amino-4-(1-carboxycyclobut-1-oxy)quinoline; NMR (DMSO-d$_6$) 1.20 (t, 3), 1.84 (m, 1), 2.01 (m, 3), 2.30 (m, 2), 2.65 (m, 2), 2.78 (m, 2), 3.30–3.65 (m, 8), 4.05 (q, 2), 5.00 (m, 1), 6.92 (s, 1), 7.19 (m, 2), 7.92 (d, 1), 8.79 (m, 1) ppm;

2-[1-(4-(ethoxycarbonyl)piperazin-1-yl)carbonyl-3-carboxypropyl]aminocarbonyl-5-methyl-4-(1-carboxycyclobut-1-oxy)quinoline; NMR (DMSO-d$_6$) 1.17 (t, 3), 1.82 (m, 1), 2.00 (m, 3), 2.30 (m, 2), 2.55 (m, 2), 2.77 (m, 2), 2.88 (s, 3), 3.40 (m, 6), 3.62 (m, 2), 4.03 (q, 2), 4.98 (m, 1), 6.93 (s, 1), 7.42 (d, 1), 7.65 (t, 1), 7.86 (d, 1), 8.85 (d, 1) ppm;

2-[1-(4-(ethoxycarbonyl)piperazin-1-yl)carbonyl-3-(1,1-dimethylethoxycarbonyl)propyl]aminocarbonyl-7-(benzyloxy)-4-(1-(ethoxycarbonyl)cyclobut-1-oxy)quinoline; NMR (CDCl$_3$) 1.22 (t, 3), 1.28 (t, 3), 1.46 (s, 9), 1.95 (m, 1), 1.99–2.24 (m, 3), 2.38 (m, 2), 2.62 (m, 2), 2.94 (m, 2), 3.41–3.80 (m, 8), 4.20 (m, 4), 5.22 (m, 1), 5.25 (s, 2), 7.06 (s, 1), 7.18–7.58 (m, 7), 8.13 (d, 1), 8.92 (d, 1) ppm;

2-[1-(4-(ethoxycarbonyl)piperazin-1-yl)carbonyl-3-(1,1-dimethylethoxycarbonyl)propyl]aminocarbonyl-7-hydroxy-4-(1-(ethoxycarbonyl)cyclobut-1-oxy)quinoline; NMR (CDCl$_3$) 1.22 (t, 3), 1.28 (t, 3), 1.46 (s, 9), 1.77 (m, 1), 1.95–2.24 (m, 3), 2.42 (m, 2), 2.59 (m, 2), 2.94 (m, 2), 3.46–3.83 (m, 8), 4.21 (m, 4), 5.22 (m, 1), 6.95 (s, 1), 7.07 (d, 1), 7.34 (s, 1), 8.04 (d, 1), 8.85 (d, 1) ppm;

2-[1-(4-(ethoxycarbonyl)piperazin-1-yl)carbonyl-3-carboxypropyl]aminocarbonyl-7-(benzyloxy)-4-(1-carboxycyclobut-1-oxy)quinoline; NMR (DMSO-d$_6$) 1.18 (t, 3), 1.85 (m, 1), 1.94–2.17 (m, 3), 2.32 (m, 2), 2.57 (m, 2), 2.81 (m, 2), 3.31–3.72 (m, 8), 4.05 (q, 4), 5.05 (m, 1), 5.26 (s, 2), 6.96 (s, 1), 7.35–7.61 (m, 7), 8.19 (d, 1), 8.88 (d, 1) ppm;

2-[1-(4-(ethoxycarbonyl)piperazin-1-yl)carbonyl-3-carboxypropyl]aminocarbonyl-7-hydroxy-4-(1-carboxycyclobut-1-oxy)quinoline; NMR (DMSO-d$_6$) 1.20 (t, 3), 1.85 (m, 1), 2.02 (m, 3), 2.30 (m, 2), 2.55 (m, 2), 2.80 (m, 2), 3.35–3.65 (m, 8), 4.05 (q, 2), 5.00 (m, 1), 6.90 (s, 1), 7.20 (d, 1), 7.30 (s, 1), 8.10 (d, 1), 8.85 (d, 1), 10.40 (s, 1) ppm;

2-[1-(4-(ethoxycarbonyl)piperazin-1-yl)carbonyl-3-carboxypropyl]aminocarbonyl-7-n-propoxy-4-(1-carboxycyclobut-1-oxy)quinoline; NMR (DMSO-d$_6$) 1.03 (t, 3), 1.18 (t, 3), 1.82 (m, 3), 2.03 (m, 3), 2.31 (m, 2), 2.57 (m, 2), 2.77 (m, 2), 3.34–3.68 (m, 8), 4.06 (q, 2), 2.13 (q, 2), 5.03 (m, 1), 6.84 (s, 1), 7.33 (d, 1), 7.43 (d, 1), 8.14 (d, 1), 8.87 (d, 1) ppm;

2-[1-(4-(ethoxycarbonyl)piperazin-1-yl)carbonyl-3-carboxypropyl]aminocarbonyl-7-(carboxy)methoxy-4-(1-carboxycyclobut-1-oxy)quinoline; NMR (DMSO-d$_6$) 1.18 (t, 3), 1.82 (m, 1), 2.00 (m, 3), 2.30 (m, 2), 2.60 (m, 2), 2.80 (m, 2), 3.30–3.62 (m, 8), 4.05 (q, 2), 4.94 (s, 2), 5.02 (m, 1), 6.93 (s, 1), 7.40 (m, 2), 8.20 (d, 1), 8.90 (d, 1) ppm;

2-[1-(4-(ethoxycarbonyl)piperazin-1-yl)carbonyl-3-carboxybutyl]aminocarbonyl-4-(1-carboxycyclobut-1-oxy)quinoline; NMR (DMSO-d$_6$) 1.05 (d, 3), 1.19 (t, 3), 1.65 (m 1), 2.0 (m, 3), 2.40–2.60 (m, 2), 2.80 (m, 2), 3.30–3.75 (m, 8), 4.05 (q, 2), 4.99 (m, 1), 7.02 (s, 1), 7.70 (t, 1), 7.85 (t, 3), 8.10 (d, 1), 8.25 (d, 1), 8.95 (d, 1) ppm;

2-[1-(4-(ethoxycarbonyl)piperazin-1-yl)carbonyl-3-carboxypropyl]aminocarbonyl-7-(diethylamino)ethoxy-4-(1-carboxycyclobut-1-oxy)quinoline; NMR (DMSO-d$_6$) 1.18–1.33 m, 9), 1.82 (m, 1), 2.03 (m, 3), 2.31 (m, 2), 2.57 (m, 2), 2.80 (m, 2), 3.24–3.71 (m, 14), 4.06 (q, 2), 4.57 (m, 2), 5.07 (m, 1), 6.97 (s, 1), 7.37 (d, 1), 7.56 (s, 1), 8.23 (d, 1), 8.86 (d, 1) ppm;

2-[1-(4-(ethoxycarbonyl)piperazin-1-yl)carbonyl-3-carboxypropyl]aminocarbonyl-7-methoxy-4-(1-carboxycyclobut-1-oxy)quinoline; NMR (DMSO-d$_6$) 1.15 (t, 3), 1.82 (m, 1), 2.00 (m, 3), 2.30 (m, 2), 2.56 (m, 2), 2.79 (m, 2), 3.35–3.65 (m, 8), 3.92 (s, 3), 4.02 (q, 2), 5.00 (m, 1), 6.95 (s, 1), 7.30 (d, 1), 7.42 (s, 1), 8.15 (d, 1), 8.85 (d, 1) ppm;

2-[1-(4-(ethoxycarbonyl)piperazin-1-yl)carbonyl-3-carboxypropyl]aminocarbonyl-7-(2-carboxy-4-hydroxypyrrolidin-1-yl)ethoxy-4-(1-carboxycyclobut-1-oxy)quinoline; NMR (DMSO-d$_6$) 1.19 (t, 3), 1.82–2.18 (m, 6), 2.31 (m, 2), 2.57 (m, 2), 2.81 (m, 2), 3.31–3.83 (m, 10), 4.04 (q, 2), 4.21–4.42 (m, 6), 5.05 (m, 1), 6.96 (s, 1), 7.36 (t, 1), 7.46 (d, 1), 8.17 (d, 1), 8.88 (d, 1) ppm;

2-[1-(4-(ethoxycarbonyl)piperazin-1-yl)carbonyl-3-carboxypropyl]aminocarbonyl-8-methyl-4-(1-carboxycyclobut-1-oxy)quinoline; NMR (DMSO-d$_6$) 1.15 (t, 3), 1.72 (m, 1), 1.85 (m, 1), 1.92 (m, 2), 2.12 (m, 2), 2.30 (m, 2), 2.70 (s, 3), 2.72 (m, 2), 3.40 (m, 8), 3.62 (m, 2), 4.02 (q, 2), 4.98 (m, 1), 7.10 (s, 1), 7.46 (t, 1), 7.60 (6, 1), 8.04 (d, 1), 8.95 (d, 1) ppm;

2-[1-(4-(ethoxycarbonyl)piperazin-1-yl)carbonyl-3-carboxypropyl]aminocarbonyl-6-(diethylamino)methyl-4-(1-carboxycyclobut-1-oxy)quinoline; NMR (DMSO-d$_6$) 1.16 (t, 3), 2.18 (t, 6), 1.83 (m, 1), 2.04 (m, 3), 2.28 (m, 2), 2.58 (m, 2), 2.84 (m, 2), 3.18 (m, 4), 3.40 (m, 6), 3.62 (m, 2), 4.04 (q, 2), 4.58 (s, 2), 5.00 (m, 1), 7.06 (s, 1), 7.98 (d, 1), 87.82 (d, 1), 8.42 (s, 1), 8.90 (d, 1) ppm;

2-[1-(4-(ethoxycarbonyl)piperazin-1-yl)carbonyl-3-carboxypropyl]aminocarbonyl-7-(diethylamino)methyl-4-(1-carboxycyclobut-1-oxy)quinoline; NMR (DMSO-d$_6$) 1.14 (t, 3), 1.18 (t, 6), 1.83 (m, 1), 2.04 (m, 3), 2.28 (m, 2), 2.58 (m, 2), 2.80 (m, 2), 3.18 (m, 4), 3.40 (m, 6), 3.62 (m, 2), 4.04 (q, 2), 4.58 (s, 2), 5.00 (m, 1), 7.06 (s, 1), 7.78 (d, 1), 8.34 (s, 1), 8.38 (d, 1), 8.85 (d, 1) ppm;

2-[1-(4-(ethoxycarbonyl)piperazin-1-yl)carbonyl-3-carboxypropyl]aminocarbonyl-6-(benzyloxy)-4-(1-carboxycyclobut-1-oxy)quinoline; NMR (DMSO-d$_6$) 1.18 (t, 3), 1.83 (m, 1), 1.94–2.08 (m, 3), 2.29 (m, 2), 2.57 (m, 2), 2.80 (m, 2), 3.31–3.67 (m, 8), 4.02 (q, 4), 4.98 (m, 1), 5.27 (s, 2), 7.00 (s, 1), 7.35–7.64 (m, 7), 8.01 (d, 1), 8.81 (d, 1) ppm;

2-[1-(4-(ethoxycarbonyl)piperazin-1-yl)carbonyl-3-carboxypropyl]aminocarbonyl-6-hydroxy-4-(1-carboxycyclobut-1-oxy)quinoline;

2-[1-(4-(ethoxycarbonyl)piperazin-1-yl)carbonyl-3-carboxypropyl]aminocarbonyl-6-(carboxy)methoxy-4-(1-carboxycyclobut-1-oxy)quinoline; NMR (DMSO-d$_6$) 1.18 (t, 3), 1.83 (m, 1), 2.02 (m, 3), 2.28 (m, 2), 2.56 (m, 2), 2.78 (m, 2), 3.30–3.70 (m, 8), 4.03 (q, 2), 4.86 (s, 2), 4.98 (m, 1), 7.01 (s, 1), 7.44 (s, 1), 7.56 (d, 1), 8.03 (d, 1), 8.82 (d, 1) ppm;

2-[1-(4-(ethoxycarbonyl)piperazin-1-yl)carbonyl-3-carboxypropyl]aminocarbonyl-6-ethoxy-4-(1-carboxycyclobut-1-oxy)quinoline; NMR (DMSO-d$_6$) 1.15 (t, 3), 1.29 (t, 3), 1.80 (m, 1), 1.98 (m, 3), 2.30 (m, 2), 2.58 (m, 2), 2.78 (m, 2), 3.30–3.63 (m, 8), 4.02 (q, 2), 4.19 (q, 2), 4.98 (m, 1), 7.00 (s, 1), 7.47 (m, 2), 7.98 (d, 1), 8.80 (d, 1) ppm;

2-[1-(4-(ethoxycarbonyl)piperazin-1-yl)carbonyl-3-carboxypropyl]aminocarbonyl-6-methoxy-4-(1-carboxycyclobut-1-oxy)quinoline; NMR (DMSO-d$_6$) 1.15 (t, 3), 1.82 (m, 1), 1.98 (m, 3), 2.30 (m, 2), 2.58 (m, 2), 2.79 (m, 2), 3.35–3.65 (m, 8), 3.91 (s, 3), 4.02 (q, 2), 4.98 (m, 1), 7.01 (s, 1), 7.30 (m, 1), 7.98 (d, 1), 8.80 (d, 1) ppm;

2-[1-(4-(ethoxycarbonyl)piperazin-1-yl)carbonyl-3-carboxypropyl]aminocarbonyl-6-(1-methylethoxy)-4-(1-carboxycyclobut-1-oxy)quinoline; NMR (DMSO-d$_6$) 1.18 (t, 3), 1.35 (d, 6), 1.83 (m, 1), 2.01 (m, 3), 2.28 (m, 2), 2.57 (m, 2), 2.78 (m, 2), 3.30–3.70 (m, 8), 4.04 (q, 2), 4.84 (m, 1), 4.98 (m, 1), 7.00 (s, 1), 7.47 (d, 1), 7.51 (s, 1), 7.97 (d, 1), 8.82 (d, 1) ppm;

2-[1-(4-(ethoxycarbonyl)piperazin-1-yl)carbonyl-3-carboxypropyl]aminocarbonyl-7-fluoro-4-(1-carboxycyclobut-1-oxy)quinoline; NMR (CD$_3$OD) 1.2 (t, 3), 1.9 (m, 3), 2.0–2.15 (m, 3), 2.4 (m, 2), 2.6 (m, 2), 2.9 (m, 2), 3.3–3.75 (m, 8), 5.1 (m, 1), 7.0 (s, 1), 7.4 (t, 1), 7.7 (d, 1), 8.3 (m, 1) ppm;

2-[1-(4-(ethoxycarbonyl)piperazin-1-yl)carbonyl-3-carboxypropyl]aminocarbonyl-7-(trifluoromethyl)-4-(1-carboxycyclobut-1-oxy)quinoline; NMR (DMSO-d$_6$) 1.18 (t, 3), 1.84 (m, 1), 2.04 (m, 3), 2.28 (m, 2), 2.60 (m, 2), 2.80 (m, 2), 2.86 (m, 3), 3.44 (m, 6), 3.62 (m, 2), 4.03 (q, 2), 5.00 (m, 1), 7.18 (s, 1), 7.96 (d, 1), 8.42 (s, 1), 8.46 (d, 1), 8.94 (d, 1) ppm;

2-[1-(4-(ethoxycarbonyl)piperazin-1-yl)carbonyl-3-(tetrazol-1-yl)propyl]aminocarbonyl-4-(1-carboxycyclobut-1-oxy)quinoline; NMR (DMSO-$d_6$) 1.19 (t, 3), 2.00 (m, 1), 2.15 (m, 1), 2.35 (m, 1), 2.60 (m, 2), 2.80 (m, 2), 2.90–3.05 (m, 2), 3.30–3.65 (m, 8), 4.05 (q, 2), 5.10 (m, 1), 7.05 (s, 1), 7.70 (t, 1), 7.90 (t, 1), 7.95 (s, 1), 8.10 (d, 1), 8.30 (d, 1), 9.05 (d, 1) ppm;

2-[1-(4-(ethoxycarbonyl)piperazin-1-yl)carbonyl-3-carboxypropyl]aminocarbonyl-7-chloro-4-(1-(aminocarbonyl)cyclobut-1-oxy)quinoline; NMR (CDCl$_3$) 1.25 (t, 3), 1.80 (m, 1), 2.00 (m, 2), 2.30 (m, 2), 2.15 (m, 1), 2.30–2.50 (m, 3), 2.60 (m, 1), 2.80 (m, 1), 3.00 (m, 1), 3.40–3.75 (m, 8), 4.15 (q, 2), 5.24 (m, 1), 6.20 (s, 1), 6.90 (s, 1), 7.15 (s, 1), 7.55 (d, 1), 8.10 (s, 1), 8.20 (d, 1), 9.00 (d, 1) ppm;

2-[1-(4-(ethoxycarbonyl)piperazin-1-yl)carbonyl-3-carboxypropyl]aminocarbonyl-7-(hydroxymethyl)-4-(1-carboxycyclobut-1-oxy)quinoline; NMR (DMSO-$d_6$) 1.17 (t, 3), 1.82 (m, 1), 3.00 (m, 3), 2.30 (m, 2), 2.58 (m, 2), 2.78 (m, 2), 3.30–3.65 (m, 8), 4.02 (q, 2), 4.70 (s, 2), 5.00 (m, 1), 7.00 (s, 1), 7.60 (d, 1), 8.00 (s, 1), 8.20 (d, 1), 8.92 (d, 1) ppm;

2-[1-(4-(ethoxycarbonyl)piperazin-1-yl)carbonyl-3-carboxypropyl]aminocarbonyl-7-ethyl-4-(1-carboxycyclobut-1-oxy)quinoline; NMR (DMSO-$d_6$) 1.15 (t, 3), 1.25 (t, 2), 1.82 (m, 1), 2.00 (m, 3), 2.28 (m, 2), 2.56 (m, 2), 2.82 (m, 4), 3.40 (m, 6), 3.62 (m, 2), 4.00 (q, 2), 5.00 (m, 1), 6.98 (s, 1), 7.55 (dd, 1), 7.85 (s, 1), 8.15 (d, 1), 8.85 (d, 1) ppm;

2-[1-(4-(ethoxycarbonyl)piperazin-1-yl)carbonyl-3-carboxypropyl]aminocarbonyl-7-cyano-4-(1-carboxycyclobut-1-oxy)quinoline; NMR (DMSO-$d_6$) 1.18 (t, 3), 1.83 (m, 1), 2.00 (m, 3), 2.30 (m, 2), 2.60 (m, 2), 2.80 (m, 2), 3.30–3.62 (m, 8), 4.05 (q, 2), 5.00 (m, 1), 7.14 (s, 1), 7.98 (d, 1), 8.40 (d, 1), 8.64 (s, 1), 8.90 (d, 1) ppm;

2-[1-(4-(ethoxycarbonyl)piperazin-1-yl)carbonyl-3-carboxypropyl]aminocarbonyl-5-cyano-4-(1-carboxycyclobut-1-oxy)quinoline; NMR (DMSO-$d_6$) 1.18 (t, 3), 1.84 (m, 1), 2.02 (m, 3), 2.28 (m, 2), 2.67 (m, 2), 2.78 (m, 2), 3.30–3.70 (m, 8), 4.03 (q, 2), 5.02 (m, 1), 7.12 (s, 1), 7.96 (t, 1), 8.25 (d, 1), 8.40 (d, 1), 8.92 (d, 1) ppm;

2-[1-(4-(ethoxycarbonyl)piperazin-1-yl)carbonyl-3-carboxypropyl]aminocarbonyl-7-nitro-4-(1-carboxycyclobut-1-oxy)quinoline; NMR (CD$_3$OD) 1.30 (t, 3), 1.90 (m, 1), 2.0–2.30 (m, 4), 2.50 (m, 2), 2.70 (m, 1), 2.95 (m, 2), 3.40–3.85 (m, 8), 4.10 (q, 2), 5.20 (m, 1), 7.10 (s, 1), 8.25 (m, 1), 8.45 (d, 1), 8.80 (s, 1) ppm;

2-[1-(4-(ethoxycarbonyl)piperazin-1-yl)carbonyl-3-carboxypropyl]aminocarbonyl-6-carboxy-4-(1-carboxycyclobut-1-oxy)quinoline; NMR (CD$_3$OD) 1.30 (t, 3), 1.90 (m, 1), 2.15 (m, 3), 2.45 (m, 3), 2.50 (m, 1), 2.99 (m, 2), 3.40–3.80 (m, 8), 4.15 (q, 2), 5.20 (m, 1), 7.20 (s, 1), 8.10 (d, 1), 8.30 (d, 1), 9.0 (s, 1) ppm;

2-[1-(4-(ethoxycarbonyl)piperazin-1-yl)carbonyl-3-carboxypropyl]aminocarbonyl-7-amino-4-(1-carboxycyclobut-1-oxy)quinoline; NMR (CD$_3$OD) 1.25 (t, 3), 1.9–2.25 (m, 4), 2.45 (m, 2), 2.6 (m, 2), 2.95 (m, 2), 3.4–3.8 (m, 8), 4.10 (q, 2), 5.15 (m, 1), 6.8 (s, 1), 7.0 (s, 1), 7.1 (d, 1), 8.05 (d, 1) ppm;

2-[1-(4-(ethoxycarbonyl)piperazin-1-yl)carbonyl-3-carboxypropyl]aminocarbonyl-7-(trifluoromethoxy)-4-(1-carboxycyclobut-1-oxy)quinoline; NMR (DMSO-$d_6$) 1.15 (t, 3), 1.85 (m, 1), 2.02 (m, 3), 2.28 (m, 2), 2.58 (m, 2), 2.78 (m, 2), 3.36 (m, 4), 3.48 (m, 2), 3.63 (m, 2), 4.02 (q, 2), 5.00 (m, 1), 7.06 (s, 1), 7.68 (dd, 1), 7.98 (s, 1), 8.38 (d, 1), 8.92 (d, 1) ppm;

2-[1-(4-(ethoxycarbonyl)piperazin-1-yl)carbonyl-3-(tetrazol-1-yl)propyl]aminocarbonyl-4-(1-(ethoxycarbonyl)cyclobut-1-oxy)quinoline; NMR (DMSO-$d_6$) 1.05 (t, 3), 1.15 (t, 3), 2.00 (m, 2), 2.15 (m, 1), 2.25 (m, 1), 2.60 (m, 2), 2.75–3.00 (m, 4), 3.25–3.61 (m, 8), 4.03 (q, 2), 4.15 (q, 2), 5.05 (m, 1), 6.95 (s, 1), 7.65 (t, 2), 7.85 (t, 2), 8.05 (d, 2), 8.25 (d, 2), 9.05 (d, 1) ppm;

2-[1-(4-(ethoxycarbonyl)piperazin-1-yl)carbonyl-3-(tetrazol-1-yl)propyl]aminocarbonyl-7-methyl-4-(1-carboxycyclobut-1-oxy)quinoline; NMR (DMSO-$d_6$) 1.15 (t, 3), 2.00 (m, 2), 2.15 (m, 1), 2.25 (m, 1), 2.55 (s, 3), 2.60 (m, 2), 2.75–3.00 (m, 4), 3.25–3.61 (m, 8), 4.03 (q, 2), 4.15 (q, 2), 5.05 (m, 1), 6.95 (s, 1), 7.50 (d, 1), 7.88 (s, 1), 8.15 (d, 2), 9.05 (d, 2) ppm;

2-[1-(4-(ethoxycarbonyl)piperazin-1-yl)carbonyl-3-((trifluoromethyl)sulfonylamino)propyl]aminocarbonyl-7-methyl-4-(1-(ethoxycarbonyl)cyclobut-1-oxy)quinoline; NMR (DMSO-$d_6$) 1.05 (t, 3), 1.15 (t, 3), 1.90–2.10 (m, 4), 2.5 (s, 3), 2.60 (m, 2), 2.80 (m, 2), 3.15–3.60 (m, 10), 4.00 (q, 2), 4.15 (q, 2), 5.05 (m, 1), 6.95 (s, 1), 7.55 (d, 2), 7.85 (s, 1), 8.17 (d, 2), 9.03 (d, 2), 9.41 (br t, 1) ppm;

2-[1-(4-(ethoxycarbonyl)piperazin-1-yl)carbonyl-3-((trifluoromethyl)sulfonylamino)propyl]aminocarbonyl-7-methyl-4-(1-carboxycyclobut-1-oxy)quinoline; NMR (DMSO-$d_6$) 1.15 (t, 3), 1.90–2.10 (m, 4), 2.5 (s, 3), 2.60 (m, 2), 2.80 (m, 2), 3.15–3.60 (m, 10), 4.00 (q, 2), 4.15 (q, 2), 5.05 (m, 1), 6.95 (s, 1), 7.55 (d, 2), 7.85 (s, 1), 8.17 (d, 2), 9.03 (d, 2), 9.41 (br t, 1) ppm;

2-[1-(4-(ethoxycarbonyl)piperazin-1-yl)carbonyl-3-carboxypropyl]aminocarbonyl-6-trifluoromethoxy-4-(1-carboxycyclobut-1-oxy)quinoline; NMR (DMSO-$d_6$) 1.17 (t, 3), 1.85 (m, 1), 2.02 (m, 3), 2.28 (m, 2), 2.60 (m, 2), 2.68 (m, 2), 3.40 (m, 6), 3.63 (m, 2), 4.02 (q, 2), 4.98 (m, 1), 7.08 (s, 1), 7.85 (dd, 1), 8.10 (s, 1), 8.22 (d, 1), 8.90 (d, 1) ppm;

2-[1-(4-(ethoxycarbonyl)piperazin-1-yl)carbonyl-3-carboxypropyl]aminocarbonyl-7-methyl-4-(1-tetrazol-5-ylethoxy)quinoline; NMR (DMSO-$d_6$) 1.18 (t, 3), 1.80–1.88 (m, 4), 2.00 (m, 1), 2.30 (m, 2), 2.55 (s, 3), 3.35–3.65 (m, 8), 4.02 (q, 2), 5.01 (m, 1), 6.42 (q, 1), 7.55 (d, 1), 7.60 (d, 1), 7.88 (s, 1), 8.16 (d, 1), 8.88 (m, 1) ppm; and NMR (DMSO-$d_6$) 1.18 (t, 3), 1.78–1.82 (m, 4), 2.00 (m, 1), 2.30 (m, 2), 2.55 (s, 3), 3.35–3.62 (m, 8), 4.05 (q, 2), 5.04 (m, 1), 6.44 (m, 1), 7.55 (d, 1), 7.60 (s, 1), 7.88 (s, 1), 8.16 (d, 1), 8.88 (d, 1), 12.16 (s, 1) ppm; and NMR (DMSO-$d_6$) 1.18 (t, 3), 1.78–1.90 (m, 4), 2.00 (m, 1), 2.30 (m, 2), 2.55 (s, 3), 3.35–3.65 (m, 8), 4.02 (q, 2), 5.00 (m, 1), 6.45 (q, 1), 7.55 (d, 1), 7.62 (s, 1), 7.88 (s, 1), 8.16 (d, 1), 8.88 (d, 1) ppm;

2-[1-(4-(ethoxycarbonyl)piperazin-1-yl)carbonyl-3-carboxypropyl]aminocarbonyl-7-acetyl-4-(1-carboxycyclobut-1-oxy)quinoline; NMR (DMSO-$d_6$) 1.18 (t, 3), 1.85 (m, 2), 2.00 (m, 3), 2.30 (m, 2), 2.60 (m, 2), 2.75 (s, 3), 2.80 (m, 2), 3.40 (m, 6), 3.65 (m, 2), 4.05 (m, 2), 5.05 (m, 1), 7.15 (s, 1), 8.10 (d, 1), 8.35 (d, 1), 8.70 (s, 1), 8.92 (d, 1) ppm;

2-[1-(4-(ethoxycarbonyl)piperazin-1-yl)carbonyl-3-carboxypropyl]aminocarbonyl-5-ethoxycarbonyl-4-(1-carboxycyclobut-1-oxy)quinoline; NMR (CD$_3$OD) 1.25 (t, 3), 1.35 (t, 3), 2.0 (m, 2), 2.20 (m, 2), 2.45 (m, 2), 2.60 (m, 2), 2.90 (m, 2), 3.40–3.80 (m, 8), 4.10 (q, 2), 4.40 (q, 2), 5.20 (m, 1), 7.20 (s, 1), 7.60 (d, 1), 7.85 (m, 1), 8.20 (d, 1) ppm;

2-[1-(4-(ethoxycarbonyl)piperazin-1-yl)carbonyl-3-carboxypropyl]aminocarbonyl-7-methyl-4-(tetrazol-5-yl)methoxyquinoline; NMR (DMSO-$d_6$) 1.13 (t, 3), 1.81 (m, 1), 1.98 (m, 2), 2.37 (m, 2), 2.50 (s, 3), 2.56 (m, 2), 3.40 (m, 6), 3.62 (m, 2), 4.00 (q, 2), 5.00 (m, 1), 5.85 (s, 1), 7.50 (dd, 1), 7.67 (s, 1), 7.85 (s, 1), 8.14 (d, 1), 8.90 (d, 1) ppm;

2-[1-(4-(ethoxycarbonyl)piperazin-1-yl)carbonyl-3-carboxypropyl]aminocarbonyl-6-ethyl-4-(1-carboxycyclobut-1-oxy)quinoline; NMR (DMSO-d$_6$) 1.16 (t, 3), 1.27 (t, 2), 1.82 (m, 1), 2.00 (m, 3), 2.28 (m, 2), 2.56 (m, 2), 2.84 (m, 4), 3.40 (m, 6), 3.64 (m, 2), 4.03 (q, 2), 4.98 (m, 1), 7.02 (s, 1), 7.72 (dd, 1), 8.00 (d, 1), 8.02 (d, 1), 8.85 (d, 1) ppm;

2-[1-(4-(ethoxycarbonyl)piperazin-1-yl)carbonyl-3-carboxypropyl]aminocarbonyl-6-acetyl-4-(1-carboxycyclobut-1-oxy)quinoline;

2-[1-(4-(ethoxycarbonyl)piperazin-1-yl)carbonyl-3-carboxypropyl]aminocarbonyl-7-carboxy-4-(1-carboxycyclobut-1-oxy)quinoline; NMR (CD$_3$OD) 1.30 (t, 3), 2.20 (m, 4), 2.50 (m, 2), 2.70 (m, 2), 2.95 (m, 2), 3.40–3.80 (m, 8), 4.15 (q, 2), 5.20 (m, 1), 7.20 (s, 1), 8.20 (d, 1), 8.40 (d, 1), 8.75 (s, 1) ppm;

2-[1-(4-(ethoxycarbonyl)piperazin-1-yl)carbonyl-3-carboxypropyl]aminocarbonyl-6-aminocarbonyl-4-(1-carboxycyclobut-1-oxy)quinoline; NMR (DMSO-d$_6$) 1.19 (t, 3), 1.85 (m, 2), 2.00 (m, 3), 2.30 (m, 2), 2.58 (m, 2), 2.80 (m, 2), 3.40 (m, 6), 3.60 (m, 2), 4.05 (m, 2), 5.00 (m, 1), 7.05 (s, 1), 7.60 (br s, 1), 8.15 (d, 1), 8.30 (d, 1), 8.38 (br s, 1), 8.80 (s, 1), 8.94 (d, 1) ppm;

2-[1-(4-(ethoxycarbonyl)piperazin-1-yl)carbonyl-3-carboxypropyl]aminocarbonyl-7-methyl-4-(1-methyl-1-carboxyethoxy)quinoline; NMR (DMSO-d$_6$) 1.15 (t, 3), 1.61 (s, 3), 1.63 (s, 3), 1.75 (m, 1), 2.00 (m, 1), 2.5 (s, 4), 3.15–3.63 (m, 8), 4.02 (q, 2), 5.05 (m, 1), 7.30 (s, 1), 7.50 (d, 2), 7.85 (s, 1), 8.10 (d, 1), 8.95 (d, 1) ppm;

2-[1-(4-(ethoxycarbonyl)piperazin-1-yl)carbonyl-3-carboxypropyl]aminocarbonyl-6,7-dimethoxy-4-(1-carboxycyclobut-1-oxy)quinoline; NMR (CD$_3$OD) 1.30 (t, 3), 2.20 (m, 4), 2.45 (m, 2), 2.65 (m, 2), 2.90 (m, 2), 3.40–3.80 (m, 8), 4.0 (s, 6), 4.10 (q, 2), 5.20 (m, 1), 7.05 (s, 1), 7.45 (s, 1), 7.55 (s, 1) ppm;

2-[1-(4-(ethoxycarbonyl)piperazin-1-yl)carbonyl-3-carboxypropyl]aminocarbonyl-7-chloro-6-methyl-4-(1-(ethoxycarbonyl)cyclobut-1-oxy)quinoline; NMR (DMSO-d$_6$) 1.04 (t, 3), 1.15 (t, 3), 1.82 (m, 1), 2.00 (m, 3), 2.28 (m, 2), 2.55 (s, 3), 2.60 (m, 2), 2.67 (m, 2), 3.40 (m, 6), 3.62 (m, 2), 4.02 (q, 2), 4.15 (q, 2), 4.98 (m, 1), 6.95 (s, 1), 8.15 (s, 1), 8.22 (s, 1), 8.83 (d, 1) ppm;

2-[1-(4-(ethoxycarbonyl)piperazin-1-yl)carbonyl-3-carboxypropyl]aminocarbonyl-7-chloro-6-methyl-4-(1-carboxycyclobut-1-oxy)quinoline; NMR (DMSO-d$_6$) 1.15 (t, 3), 1.85 (m, 1), 2.00 (m, 3), 2.28 (m, 2), 2.55 (s, 3), 2.57 (m, 2), 2.67 (m, 2), 3.40 (m, 6), 3.62 (m, 2), 4.0 (q, 2), 4.98 (m, 1), 7.00 (s, 1), 8.12 (s, 1), 8.20 (s, 1), 8.83 (d, 1) ppm;

2-[1-(4-(ethoxycarbonyl)piperazin-1-yl)carbonyl-3-carboxypropyl]aminocarbonyl-6-chloro-7-methyl-4-(1-carboxycyclobut-1-oxy)quinoline; NMR (DMSO-d$_6$) 1.15 (t, 3), 1.82 (m, 1), 2.00 (m, 3), 2.30 (m, 2), 2.52 (s, 3), 2.57 (m, 2), 2.67 (m, 2), 3.40 (m, 6), 3.62 (m, 2), 4.02 (q, 2), 4.98 (m, 1), 7.00 (s, 1), 8.09 (s, 1), 8.21 (s, 1), 8.85 (d, 1) ppm;

2-[1-(4-(ethoxycarbonyl)piperazin-1-yl)carbonyl-3-carboxypropyl]aminocarbonyl-6,7-dimethoxy-4-(1-(ethoxycarbonyl)cyclobut-1-oxy)quinoline; NMR (CD$_3$OD) 1.20 (t, 3), 1.30 (t, 3), 2.20 (m, 4), 2.45 (m, 2), 2.70 (m, 2), 3.0 (m, 2), 3.40–3.80 (m, 8), 4.0 (s, 6), 4.15 (q, 2), 4.25 (q, 2), 5.20 (m, 1), 7.05 (s, 1), 7.50 (s, 1), 7.60 (s, 1) ppm;

2-[1-(4-(ethoxycarbonyl)piperazin-1-yl)carbonyl-3-carboxypropyl]aminocarbonyl-7-methyl-4-(1-(carboxy)ethoxy)quinoline; NMR (DMSO-d$_6$) 1.20 (t, 3), 1.65 (d, 3), 1.83 (m, 1), 2.04 (m, 1), 2.32 (m, 2), 2.56 (s, 3), 3.35–3.70 (m, 8), 4.05 (q, 2), 5.04 (m, 1), 5.28 (m, 1), 7.37 (s, 1), 7.55 (d, 1), 7.88 (s, 1), 8.13 (d, 1), 8.90 (d, 1) ppm; and NMR (DMSO-d$_6$) 1.18 (t, 3), 1.65 (d, 3), 1.84 (m, 1), 2.00 (m, 1), 2.30 (m, 2), 2.55 (s, 3), 3.35–3.65 (m, 8), 4.02 (q, 2), 5.01 (m, 1), 6.28 (q, 1), 7.38 (s, 1), 7.50 (d, 1), 7.87 (s, 1), 8.12 (d, 1), 8.90 (m, 1) ppm; and NMR (DMSO-d$_6$) 1.18 (t, 3), 1.65 (d, 3), 1.84 (m, 1), 2.00 (m, 1), 2.30 (m, 2), 2.55 (s, 3), 3.35–3.65 (m, 8), 4.02 (q, 2), 5.01 (m, 1), 6.35 (q, 1), 7.36 (s, 1), 7.50 (d, 1), 7.86 (s, 1), 8.12 (d, 1), 8.90 (m, 1) ppm;

2-[1-(4-(ethoxycarbonyl)piperazin-1-yl)carbonyl-3-carboxypropyl]aminocarbonyl-6-fluoro-7-methyl-4-(1-(ethoxycarbonyl)cyclobut-1-oxy)quinoline; NMR (DMSO-d$_6$) 1.02 (t, 3), 1.18 (t, 3), 1.81 (m, 1), 2.00 (m, 3), 2.30 (m, 2), 2.48 (s, 3), 2.60 (m, 2), 2.79 (m, 2), 3.35–3.65 (m, 8), 4.02 (q, 2), 4.15 (q, 2), 5.00 (m, 1), 6.85 (s, 1), 7.85 (d, 1), 8.05 (d, 1), 8.82 (d, 1) ppm;

2-[1-(4-(ethoxycarbonyl)piperazin-1-yl)carbonyl-3-carboxypropyl]aminocarbonyl-6-fluoro-7-methyl-4-(1-carboxycyclobut-1-oxy)quinoline; NMR (DMSO-d$_6$) 1.18 (t, 3), 1.81 (m, 1), 2.00 (m, 3), 2.30 (m, 2), 2.48 (s, 3), 2.58 (m, 2), 2.79 (m, 2), 3.35–3.62 (m, 8), 4.05 (q, 2), 5.00 (m, 1), 7.03 (s, 1), 7.84 (d, 1), 8.05 (d, 1), 8.84 (d, 1) ppm;

2-[1-(4-(ethoxycarbonyl)piperazin-1-yl)carbonyl-3-carboxypropyl]aminocarbonyl-6-fluoro-4-(1-carboxycyclobut-1-oxy)quinoline; NMR (DMSO-d$_6$) 1.17 (t, 3), 1.87 (m, 1), 2.00 (m, 4), 2.30 (m, 2), 2.58 (m, 2), 2.80 (m, 2), 3.40 (m, 6), 3.60 (m, 2), 4.05 (m, 2), 5.00 (m, 1), 7.08 (s, 1), 7.78 (m, 1), 7.92 (d, 1), 8.38 (m, 1), 8.90 (d, 1) ppm;

2-[1-(4-(ethoxycarbonyl)piperazin-1-yl)carbonyl-3-carboxypropyl]aminocarbonyl-6-chloro-7-methyl-4-(1-(ethoxycarbonyl)cyclobut-1-oxy)quinoline; NMR (DMSO-d$_6$) 1.02 (t, 3), 1.15 (t, 3), 1.85 (m, 1), 2.00 (m, 3), 2.28 (m, 2), 2.54 (s, 3), 2.53 (m, 2), 2.67 (m, 2), 3.40 (m, 6), 3.62 (m, 2), 4.02 (q, 2), 4.15 (q, 2), 4.98 (m, 1), 6.97 (s, 1), 8.10 (s, 1), 8.23 (s, 1), 8.85 (d, 1) ppm;

2-[1-(4-(ethoxycarbonyl)piperazin-1-yl)carbonyl-3-carboxypropyl]aminocarbonyl-7-chloro-6-fluoro-4-(1-(ethoxycarbonyl)cyclobut-1-oxy)quinoline; NMR (DMSO-d$_6$) 1.04 (t, 3), 1.18 (t, 3), 1.83 (m, 1), 2.00 (m, 3), 2.30 (m, 2), 2.62 (m, 2), 2.78 (m, 2), 3.35–3.65 (m, 8), 4.03 (q, 2), 4.16 (q, 2), 5.00 (m, 1), 7.00 (s, 1), 8.17 (d, 1), 8.37 (d, 1), 8.82 (d, 1) ppm;

2-[1-(4-(ethoxycarbonyl)piperazin-1-yl)carbonyl-3-carboxypropyl]aminocarbonyl-7-chloro-6-fluoro-4-(1-carboxycyclobut-1-oxy)quinoline; NMR (DMSO-d$_6$) 1.15 (t, 3), 1.82 (m, 1), 2.00 (m, 3), 2.30 (m, 2), 2.58 (m, 2), 2.79 (m, 2), 3.35–3.65 (m, 8), 4.05 (q, 2), 5.00 (m, 1), 7.05 (s, 1), 8.15 (d, 1), 8.35 (d, 1), 8.84 (d, 1) ppm;

2-[1-(4-(ethoxycarbonyl)piperazin-1-yl)carbonyl-3-carboxypropyl]aminocarbonyl-7-bromo-4-(1-carboxycyclobut-1-oxy)quinoline; NMR (DMSO-d$_6$) 1.19 (t, 3), 1.85 (m, 1), 2.00 (m, 3), 2.28 (m, 2), 2.55 (m, 2), 2.80 (m, 2), 3.38 (m, 6), 3.62 (m, 2), 4.05 (m, 2), 4.95 (m, 1), 7.05 (s, 1), 7.82 (d, 1), 8.20 (d, 1), 8.30 (s, 1), 8.90 (d, 1) ppm;

2-[1-(4-(ethoxycarbonyl)piperazin-1-yl)carbonyl-2-(tetrazol-5-yl)ethyl]aminocarbonyl-7-methyl-4-(1-carboxycyclobut-1-oxy)quinoline; NMR (DMSO-d$_6$) 1.19 (t, 3), 2.00 (m, 2), 2.50 (s, 3), 2.50–2.60 (m, 2), 2.80 (m, 2), 3.30–3.60 (m, 8), 4.00 (q, 2), 5.40 (m, 1), 6.95 (s, 1), 7.0 (d, 2), 7.88 (s, 1), 8.15 (d, 1), 9.25 (d, 1) ppm;

2-[1-(4-(ethoxycarbonyl)piperazin-1-yl)carbonyl-3-carboxypropyl]aminocarbonyl-7-methoxy-4-(1-(ethoxycarbonyl)cyclobut-1-oxy)quinoline; NMR (DMSO-d$_6$) 1.02 (t, 3), 1.18 (t, 3), 1.82 (m, 1), 2.00 (m, 3), 2.30 (m, 2), 2.58 (m, 2), 2.79 (m, 2), 3.35–3.65 (m, 8), 3.93 (s, 3), 4.05 (q, 2), 4.13 (q, 2), 5.00 (m, 1), 6.88 (s, 1), 7.30 (d, 1), 7.43 (s, 1), 8.16 (d, 1), 8.84 (d, 1) ppm;

2-[1-(4-(ethoxycarbonyl)piperazin-1-yl)carbonyl-3-carboxypropyl]aminocarbonyl-7-hydroxy-4-(1-(ethoxycarbonyl)cyclobut-1-oxy)quinoline; NMR (DMSO-d$_6$) 1.02 (t, 3), 1.15 (t, 3), 1.82 (m, 1), 2.00 (m, 3), 2.28 (m, 2), 2.55 (m, 2), 2.77 (m, 2), 3.30–3.65 (m, 8), 4.02 (q, 2), 4.15 (q, 2), 4.96 (m, 1), 6.80 (s, 1), 7.20 (d, 1), 7.27 (s, 1), 8.10 (d, 1), 8.84 (d, 1) ppm;

2-[1-(4-(ethoxycarbonyl)piperazin-1-yl)carbonyl-3-carboxypropyl]aminocarbonyl-7-hydroxy-4-(1-carboxycyclobut-1-oxy)quinoline; NMR (DMSO-$d_6$) 1.15 (t, 3), 1.82 (m, 1), 2.00 (m, 3), 2.28 (m, 2), 2.55 (m, 2), 2.76 (m, 2), 3.35–3.65 (m, 8), 4.02 (q, 2), 4.96 (m, 1), 6.86 (s, 1), 7.20 (d, 1), 7.28 (s, 1), 8.09 (d, 1), 8.85 (d, 1) ppm;

2-[1-(4-(ethoxycarbonyl)piperazin-1-yl)carbonyl-3-carboxypropyl]aminocarbonyl-6,7-dimethyl-4-(1-(ethoxycarbonyl)cyclobut-1-oxy)quinoline; NMR (DMSO-$d_6$) 1.05 (t, 3), 1.15 (t, 3), 1.82 (m, 1), 2.00 (m, 3), 2.28 (m, 2), 2.46 (s, 6), 2.57 (m, 2), 2.79 (m, 2), 3.40 (m, 6), 3.62 (m, 2), 4.05 (q, 2), 4.12 (q, 2), 4.98 (m, 1), 6.92 (s, 1), 7.92 (s, 1), 8.02 (s, 1), 8.92 (d, 1) ppm;

2-[1-(4-(ethoxycarbonyl)piperazin-1-yl)carbonyl-3-carboxypropyl]aminocarbonyl-6,7-dimethyl-4-(1-carboxycyclobut-1-oxy)quinoline; NMR (DMSO-$d_6$) 1.15 (t, 3), 1.81 (m, 1), 2.00 (m, 3), 2.28 (m, 2), 2.45 (s, 6), 2.55 (m, 2), 2.75 (m, 2), 3.40 (m, 6), 3.62 (m, 2), 4.05 (q, 2), 5.00 (m, 1), 6.98 (s, 1), 7.98 (s, 1), 8.14 (s, 1), 8.84 (d, 1) ppm;

2-[1-(4-(ethoxycarbonyl)piperazin-1-yl)carbonyl-3-carboxypropyl]aminocarbonyl-7-chloro-6-methoxy-4-(1-(ethoxycarbonyl)cyclobut-1-oxy)quinoline; NMR (DMSO-$d_6$) 1.08 (t, 3), 1.17 (t, 3), 1.82 (m, 1), 2.00 (m, 3), 2.28 (m, 2), 2.62 (m, 2), 2.70 (m, 2), 3.40 (m, 6), 3.60 (m, 2), 4.02 (q, 2), 4.04 (s, 3), 4.15 (q, 2), 4.98 (m, 1), 6.95 (s, 1), 7.58 (s, 1), 8.18 (s, 1), 8.78 (d, 1) ppm;

2-[1-(4-(ethoxycarbonyl)piperazin-1-yl)carbonyl-3-carboxypropyl]aminocarbonyl-7-chloro-6-methoxy-4-(1-carboxycyclobut-1-oxy)quinoline; NMR (DMSO-$d_6$) 1.17 (t, 3), 1.82 (m, 1), 2.00 (m, 3), 2.28 (m, 2), 2.58 (m, 2), 2.76 (m, 2), 3.38 (m, 6), 3.62 (m, 2), 4.02 (q, 2), 4.04 (s, 3), 4.98 (m, 1), 7.02 (s, 1), 7.60 (s, 1), 8.18 (s, 1), 8.80 (d, 1) ppm;

2-[1-(4-(ethoxycarbonyl)piperazin-1-yl)carbonyl-3-carboxypropyl]aminocarbonyl-6,7-dichloro-4-(1-carboxycyclobut-1-oxy)quinoline; NMR (CD$_3$OD) 1.26 (t, 3), 2.0 (s, 3), 2.1–2.2 (m, 4), 2.4 (m, 2), 2.6 (m, 2), 2.9 (m, 2), 3.5–3.8 (m, 8), 4.10 (q, 2), 5.18 (m, 1), 7.2 (s, 1), 8.25 (s, 1), 8.42 (s, 1) ppm;

2-[1-(4-(ethoxycarbonyl)piperazin-1-yl)carbonyl-3-carboxypropyl]aminocarbonyl-7-methyl-4-(1-(ethoxycarbonyl)propoxy)quinoline; NMR (DMSO-$d_6$) 1.05 (t, 3), 1.15 (m, 6), 1.82 (m, 1), 2.04 (m, 3), 2.28 (m, 2), 2.53 (s, 3), 3.38 (m, 6), 3.64 (m, 2), 4.05 (q, 2), 4.18 (q, 2), 5.00 (m, 1), 5.28 (m, 1), 7.36 (s, 1), 7.52 (dd, 1), 7.88 (s, 1), 8.15 (d, 1), 8.90 (d, 1) ppm;

2-[1-(4-(ethoxycarbonyl)piperazin-1-yl)carbonyl-3-carboxypropyl]aminocarbonyl-7-methyl-4-(1-carboxypropoxy)quinoline; NMR (DMSO-$d_6$) 1.15 (t, 3), 1.25 (t, 3), 1.82 (m, 1), 2.05 (m, 3), 2.30 (m, 2), 2.53 (s, 3), 3.42 (m, 6), 3.64 (m, 2), 4.05 (q, 2), 5.02 (m, 1), 5.12 (m, 1), 7.35 (s, 1), 7.52 (dd, 1), 7.88 (s, 1), 8.14 (d, 1), 8.90 (d, 1) ppm;

2-[1-(4-(ethoxycarbonyl)piperazin-1-yl)carbonyl-3-carboxypropyl]aminocarbonyl-7-methyl-4-(1-(ethoxycarbonyl)-2-methylpropoxy)quinoline; NMR (DMSO-$d_6$) 1.05 (m, 9), 1.82 (m, 1), 1.85 (m, 1), 2.05 (m, 1), 2.25 (m, 2), 2.35 (m, 1), 2.52 (s, 3), 3.42 (m, 6), 3.64 (m, 2), 4.04 (q, 2), 4.15 (q, 2), 5.02 (m, 1), 5.13 (m, 1), 7.33 (s, 1), 7.55 (d, 1), 7.88 (s, 1), 8.15 (d, 1), 8.88 (d, 1) ppm;

2-[1-(4-(ethoxycarbonyl)piperazin-1-yl)carbonyl-3-carboxypropyl]aminocarbonyl-7-methyl-4-(1-carboxy-2-methylpropoxy)quinoline; NMR (DMSO-$d_6$) 1.10 (t, 6), 1.15 (t, 3), 1.82 (m, 1), 1.85 (m, 1), 2.05 (m, 1), 2.30 (m, 2), 2.35 (m, 1), 2.53 (s, 3), 3.40 (m, 6), 3.64 (m, 2), 4.03 (q, 2), 5.00 (m, 2), 7.35 (s, 1), 7.52 (d, 1), 7.88 (s, 1), 8.1 (d, 1), 8.92 (d, 1) ppm;

2-[1-(4-(ethoxycarbonyl)piperazin-1-yl)carbonyl-3-carboxypropyl]aminocarbonyl-6,7-difluoro-4-(1-carboxycyclobut-1-oxy)quinoline; NMR (CD$_3$OD) 1.26 (t, 3), 2.0 (s, 3), 2.1–2.25 (m, 4), 2.45 (m, 2), 2.65 (m, 2), 2.95 (m, 2), 3.45–3.80 (m, 8), 4.15 (q, 2), 5.2 (m, 1), 7.2 (s, 1), 7.96 (dd, 1), 8.10 (dd, 1) ppm;

2-[1-(4-(ethoxycarbonyl)piperazin-1-yl)carbonyl-3-carboxypropyl]aminocarbonyl-5-fluoro-6-methyl-4-(1-carboxycyclobut-1-oxy)quinoline; NMR (CD$_3$OD) 1.25 (t, 3), 2.0 (m, 1), 2.05–2.20 (m, 4), 2.45 (m, 2), 2.5 (s, 3), 2.65 (m, 2), 2.95 (m, 2), 3.4–3.8 (m, 8), 4.15 (q, 2), 5.1 (m, 1), 7.1 (s, 1), 7.65 (d, 1), 8.18 (d, 1) ppm;

2-[1-(4-(ethoxycarbonyl)piperazin-1-yl)carbonyl-3-carboxypropyl]aminocarbonyl-5-fluoro-6-methyl-4-(1-(ethoxycarbonyl)cyclobut-1-oxy)quinoline; NMR (CD$_3$OD) 1.15 (t, 3), 1.3 (t, 3), 2.0 (m, 1), 2.05–2.25 (m, 3), 2.45 (m, 2), 2.55 (s, 3), 2.65 (m, 2), 2.90 (m, 2), 3.4–3.8 (m, 8), 4.15 (q, 2), 4.21 (q, 2), 5.2 (m, 1), 7.06 (s, 1), 7.7 (d, 1), 8.2 (d, 1) ppm;

2-[1-(4-(ethoxycarbonyl)piperazin-1-yl)carbonyl-3-(ethoxycarbonyl)propyl]aminocarbonyl-7-methyl-4-(1-(ethoxycarbonyl)cyclobut-1-oxy)quinoline; NMR (CDCl$_3$) 1.18 (t, 3), 1.25 (m, 6), 1.90–2.25 (m, 4), 2.93–2.65 (m, 7), 2.90–3.00 (m, 2), 3.40–3.80 (m, 8), 4.10–4.23 (m, 6), 5.21 (m, 1), 7.03 (s, 3), 7.40 (d, 1), 7.85 (s, 1), 8.18 (d, 1), 8.93 (d, 1) ppm;

2-[1-(4-(ethoxycarbonyl)piperazin-1-yl)carbonyl-3-(1-methylethoxycarbonyl)propyl]aminocarbonyl-7-methyl-4-(1-(ethoxycarbonyl)cyclobut-1-oxy)quinoline;

2-[1-(4-(ethoxycarbonyl)piperazin-1-yl)carbonyl-3-carboxypropyl]aminocarbonyl-6,7-dichloro-4-(1-(ethoxycarbonyl)cyclobut-1-oxy)quinoline; NMR (CD$_3$OD) 1.16 (t, 3), 1.25 (t, 3), 2.0 (m, 1), 2.18 (m, 3), 2.46 (m, 2), 2.70 (m, 2), 2.95 (m, 2), 3.4–3.8 (m, 8), 4.15 (q, 2), 4.25 (q, 2), 5.2 (m, 1), 7.1 (s, 1), 8.3 (s, 1), 8.4 (s, 1) ppm;

2-[1-(4-(ethoxycarbonyl)piperazin-1-yl)carbonyl-3-(ethoxycarbonyl)propyl]aminocarbonyl-6-fluoro-7-methyl-4-(1-(ethoxycarbonyl)cyclobut-1-oxy)quinoline; NMR (CDCl$_3$) 1.18 (t, 3), 1.25 (m, 6), 1.94 (m, 1), 2.03–2.24 (m, 3), 2.41–2.52 (m, 5), 2.62 (m, 2), 2.93 (m, 2), 3.41–3.78 (m, 8), 4.11–4.26 (m, 6), 5.21 (m, 1), 7.07 (s, 1), 7.82 (d, 1), 7.93 (d, 1), 8.86 (d, 1) ppm;

2-[1-(4-(ethoxycarbonyl)piperazin-1-yl)carbonyl-3-(ethoxycarbonyl)propyl]aminocarbonyl-6-fluoro-7-methyl-4-(1-carboxycyclobut-1-oxy)quinoline; NMR (DMSO-$d_6$) 1.09 (t, 3), 1.17 (t, 3), 1.84 (m, 1), 2.94–2.07 (m, 3), 2.36 (m, 2), 2.48 (s, 3), 2.56 (m, 2), 2.77 (m, 2), 3.28–3.64 (m, 8), 3.98 (q, 2), 4.02 (q, 2), 4.98 (m, 1), 7.01 (s, 1), 7.84 (d, 1), 8.05 (d, 1), 8.83 (d, 1) ppm;

2-[1-(4-(ethoxycarbonyl)piperazin-1-yl)carbonyl-3-(1-methylethoxycarbonyl)propyl]aminocarbonyl-6-fluoro-7-methyl-4-(1-carboxycyclobut-1-oxy)quinoline; NMR (DMSO-$d_6$) 1.06–1.18 (m, 9), 1.84 (m, 1), 2.94–2.07 (m, 3), 2.36 (m, 2), 2.48 (s, 3), 2.57 (m, 2), 2.77 (m, 2), 3.28–3.64 (m, 8), 4.02 (q, 2), 4.83 (m, 1), 4.98 (m, 1), 7.01 (s, 1), 7.84 (d, 1), 8.05 (d, 1), 8.82 (d, 1) ppm;

2-[1-(4-(ethoxycarbonyl)piperazin-1-yl)carbonyl-3-(ethoxycarbonyl)propyl]aminocarbonyl-7-methyl-4-(1-carboxycyclobut-1-oxy)quinoline; NMR (DMSO-$d_6$) 1.10 (t, 3), 1.18 (t, 3), 1.85 (m, 1), 2.00 (m, 3), 2.35 (m, 2), 2.41–2.60 (m, 2), 2.78 (m, 2), 3.30–3.62 (m, 8), 4.00 (m, 4), 5.00 (m, 1), 6.98 (s, 3), 7.50 (d, 1), 7.83 (s, 1), 8.15 (d, 1), 8.82 (d, 1) ppm;

2-[1-(4-(ethoxycarbonyl)piperazin-1-yl)carbonyl-3-(1-methylethoxycarbonyl)propyl]aminocarbonyl-7-methyl-4-(1-carboxycyclobut-1-oxy)quinoline; NMR (DMSO-d$_6$) 1.05–1.20 (m, 9), 1.79–1.93 (m, 1), 2.00 (m, 3), 2.30 (m, 2), 2.51 (m, 4), 2.78 (m, 2), 3.23–3.61 (m, 10), 4.02 (q, 2), 4.82 (m, 1), 4.98 (m, 1), 6.98 (s, 1), 7.53 (d, 1), 7.85 (d, 1), 8.82 (d, 1) ppm;

2-[1-(4-(ethoxycarbonyl)piperazin-1-yl)carbonyl-3-(ethoxycarbonyl)propyl]aminocarbonyl-6-chloro-7-methyl-4-(1-(ethoxycarbonyl)cyclobut-1-oxy)quinoline; NMR (DMSO-d$_6$) 1.12 (t, 3), 1.16 (t, 3), 1.18 (t, 3), 1.86 (m, 1), 1.96 (m, 2), 2.32 (m, 2), 2.56 (s, 3), 2.60 (m, 2), 2.80 (m, 2), 3.40 (m, 10), 3.98 (q, 2), 4.00 (q, 2), 4.16 (q, 2), 5.00 (m, 1), 6.96 (s, 1), 8.12 (s, 1), 8.22 (s, 1), 8.82 (d, 1) ppm;

2-[1-(4-(ethoxycarbonyl)piperazin-1-yl)carbonyl-3-(ethoxycarbonyl)propyl]aminocarbonyl-6-chloro-7-methyl-4-(1-carboxycyclobut-1-oxy)quinoline; NMR (DMSO-d$_6$) 1.12 (t, 3), 1.16 (t, 3), 1.86 (m, 1), 1.96 (m, 2), 2.02 (m, 3), 2.36 (m, 2), 2.56 (s, 3), 2.58 (m, 2), 3.40 (m, 10), 4.02 (q, 2), 4.08 (m, 2), 5.00 (m, 1), 7.00 (s, 1), 8.18 (s, 1), 8.22 (s, 1), 8.84 (d, 1) ppm;

2-[1-(4-(ethoxycarbonyl)piperazin-1-yl)carbonyl-3-(1-methylethoxycarbonyl)propyl]aminocarbonyl-6-chloro-7-methyl-4-(1-carboxycyclobut-1-oxy)quinoline; NMR (DMSO-d$_6$) 1.12 (d, 6), 1.20 (m, 5), 1.96 (m, 1), 2.56 (s, 3), 2.64 (m, 2), 2.76 (m, 2), 3.40 (m, 9), 2.75 (m, 2), 3.64 (m, 2), 4.05 (q, 2), 4.82 (m, 1), 5.00 (m, 1), 7.00 (s, 1), 8.18 (s, 1), 8.24 (s, 1), 8.84 (d, 1) ppm;

2-[1-(4-(ethoxycarbonyl)piperazin-1-yl)carbonyl-3-(ethoxycarbonyl)propyl]aminocarbonyl-7-chloro-4-(1-(ethoxycarbonyl)cyclobut-1-oxy)quinoline;

2-[1-(4-(ethoxycarbonyl)piperazin-1-yl)carbonyl-3-(ethoxycarbonyl)propyl]aminocarbonyl-7-chloro-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-6,7-dimethyl-4-(1-(ethoxycarbonyl)cyclobut-1-oxy)quinoline; NMR (DMSO-d$_6$) 1.02 (t, 3), 1.09 (t, 3), 1.18 (t, 3), 1.85 (m, 1), 2.02 (m, 3), 2.35 (m, 2), 2.42 (br s, 6), 2.58 (m, 2), 2.80 (m, 2), 3.23–3.62 (m, 8), 3.95–4.05 (m, 4), 4.15 (q, 2), 5.00 (m, 1), 6.92 (s, 1), 7.83 (s, 1), 7.99 (s, 1), 8.80 (d, 1) ppm;

2-[1-(4-(ethoxycarbonyl)piperazin-1-yl)carbonyl-3-(ethoxycarbonyl)propyl]aminocarbonyl-6,7-dimethyl-4-(1-carboxycyclobut-1-oxy)quinoline; NMR (DMSO-d$_6$) 1.08–1.20 (m, 6), 1.81 (m, 1), 2.00 (m, 2), 2.25–2.40 (m, 12), 2.78 (m, 2), 3.25–3.80 (m, 8), 4.00 (m, 4), 5.00 (m, 1), 8.97 (s, 1), 7.82 (s, 1), 7.98 (s, 1), 8.82 (d, 1) ppm;

2-[1-(4-(ethoxycarbonyl)piperazin-1-yl)carbonyl-3-(1-methylethoxycarbonyl)propyl]aminocarbonyl-6,7-dimethyl-4-(1-carboxycyclobut-1-oxy)quinoline; NMR (DMSO-d$_6$) 1.03–1.20 (m, 9), 1.81 (m, 1), 2.00 (m, 2), 2.30–2.40 (m, 12), 2.78 (m, 2), 3.20–3.40 (m, 8), 4.02 (m, 2), 4.83 (m, 1), 5.00 (m, 1), 8.97 (s, 1), 7.82 (s, 1), 7.98 (s, 1), 8.80 (d, 1) ppm;

2-[1-(4-(ethoxycarbonyl)piperazin-1-yl)carbonyl-3-(1-methylethoxycarbonyl)propyl]aminocarbonyl-7-chloro-4-(1-carboxycyclobut-1-oxy)quinoline;

2-[1-(4-(ethoxycarbonyl)piperazin-1-yl)carbonyl-3-(ethoxycarbonyl)propyl]aminocarbonyl-6,7-dichloro-4-(1-carboxycyclobut-1-oxy)quinoline; NMR (CD$_3$OD) 1.20 (t, 3), 1.30 (t, 3), 2.0 (m, 1), 2.20 (m, 3), 2.45 (m, 2), 2.70 (m, 2), 2.95 (m, 2), 3.40–3.80 (m, 8), 4.10 (m, 4), 5.20 (m, 1), 7.20 (s, 1), 8.30 (s, 1), 8.40 (s, 1) ppm;

2-[1-(4-(ethoxycarbonyl)piperazin-1-yl)carbonyl-3-(1-methylethoxycarbonyl)propyl]aminocarbonyl-6,7-dichloro-4-(1-carboxycyclobut-1-oxy)quinoline; NMR (CD$_3$OD) 1.25 (m, 9), 2.0 (m, 1), 2.20 (m, 3), 2.40 (m, 2), 2.65 (m, 2), 2.95 (m, 2), 3.40–3.80 (m, 8), 4.10 (q, 2), 4.95 (m, 1), 5.15 (m, 1), 7.20 (s, 1), 8.25 (s, 1), 8.40 (s, 1) ppm;

2-[1-(4-(ethoxycarbonyl)piperazin-1-yl)carbonyl-3-(ethoxycarbonyl)propyl]aminocarbonyl-6,7-dichloro-4-(1-(ethoxycarbonyl)cyclobut-1-oxy)quinoline; NMR (CDCl$_3$) 1.20 (t, 3), 1.30 (t, 6), 1.95 (m, 1), 2.05–2.25 (m, 3), 2.45 (m, 2), 2.65 (m, 2), 2.95 (m, 2), 3.40–3.80 (m, 8), 4.20 (q, 4), 4.25 (q, 2), 5.20 (m, 1), 7.10 (s, 1), 8.25 (s, 1), 8.40 (s, 1), 8.85 (d, 1) ppm;

2-[1-(4-(ethoxycarbonyl)piperazin-1-yl)carbonyl-3-carboxypropyl]aminocarbonyl-7-methyl-4-(1-methyl-1-(ethoxycarbonyl)ethoxy)quinoline; NMR (DMSO-d$_6$) 1.08 (t, 3), 1.16 (t, 3), 1.74 (s, 6), 1.82 (m, 1), 2.00 (m, 1), 2.28 (m, 2), 2.52 (s, 3), 3.40 (m, 2), 3.62 (m, 2), 4.04 (q, 2), 4.14 (q, 2), 5.02 (m, 1), 7.18 (s, 1), 7.50 (dd, 1), 7.86 (s, 1), 8.08 (d, 1), 8.86 (d, 1) ppm;

2-[1-(4-(ethoxycarbonyl)piperazin-1-yl)carbonyl-3-(ethoxycarbonyl)propyl]aminocarbonyl-7-methyl-4-(1-methyl-1-carboxyethoxy)quinoline; NMR (DMSO-d$_6$) 1.98 (t, 3), 1.22 (t, 3), 1.80 (br s, 6), 1.98 (m, 1), 2.15 (m, 1), 2.42 (m, 2), 2.61 (s, 3), 3.38–3.70 (m, 8), 4.08 (m, 4), 5.10 (m, 1), 7.18 (s, 1), 7.59 (d, 1), 7.97 (s, 1), 8.19 (d, 1), 8.99 (d, 1) ppm;

2-[1-(4-(ethoxycarbonyl)piperazin-1-yl)carbonyl-3-carboxypropyl]aminocarbonyl-6-methylthio-4-(1-(ethoxycarbonyl)cyclobut-1-oxy)quinoline; NMR (CD$_3$OD) 1.20 (t, 3), 1.25 (t, 3), 1.95 (m, 1), 2.20 (m, 3), 2.40 (m, 2), 2.65 (s, 3), 2.70 (m, 2), 2.95 (m, 2), 3.40–3.80 (m, 8), 4.10 (q, 2), 4.20 (q, 2), 5.20 (m, 1), 7.10 (s, 1), 7.70 (m, 1), 8.0 (m, 2) ppm;

2-[1-(4-(ethoxycarbonyl)piperazin-1-yl)carbonyl-3-carboxypropyl]aminocarbonyl-6-methylthio-4-(1-carboxycyclobut-1-oxy)quinoline; NMR (CD$_3$OD) 1.30 (t, 3), 2.0 (m, 1), 2.20 (m, 3), 2.40 (m, 2), 2.60 (s, 3), 2.70 (m, 2), 2.95 (m, 2), 3.40–3.80 (m, 8), 4.10 (q, 2), 5.20 (m, 1), 7.20 (s, 1), 7.70 (d, 1), 8.0 (m, 2) ppm;

2-[1-(4-(ethoxycarbonyl)piperazin-1-yl)carbonyl-3-carboxypropyl]aminocarbonyl-7-methyl-4-(1-cyclohexyl-1-carboxymethoxy)quinoline; NMR (CD$_3$OD) 1.25 (t, 3), 1.30–1.40 (m, 4), 1.55 (m, 1), 1.75 (m, 1), 1.85–2.00 (m, 5), 2.20 (m, 2), 2.50 (m, 2), 2.60 (s, 3), 3.40–3.80 (m, 8), 4.15 (q, 2), 4.95 (m, 1), 5.20 (m, 1), 7.45 (s, 1), 7.55 (d, 1), 7.90 (s, 1), 8.25 (d, 1) ppm and NMR (CD$_3$OD) 1.25 (t, 3), 1.30–1.40 (m, 4), 1.55 (m, 1), 1.75 (m, 1), 1.90–2.00 (m, 5), 2.20 (m, 2), 2.45 (m, 2), 2.60 (s, 3), 3.40–3.80 (m, 8), 4.15 (q, 2), 4.95 (m, 1), 5.20 (m, 1), 7.45 (s, 1), 7.55 (m, 1), 7.90 (s, 1), 8.20 (m, 1) ppm;

2-[1-(4-(ethoxycarbonyl)piperazin-1-yl)carbonyl-3-carboxypropyl]aminocarbonyl-7-methyl-4-(1-cyclohexyl-1-(methoxycarbonyl)methoxy)quinoline; NMR (CD$_3$OD) 1.20 (t, 3), 1.25 (m, 4), 1.50 (m, 1), 1.70 (m, 1), 1.80 (m, 4), 1.90 (m, 1), 2.10 (m, 2), 2.40 (m, 2), 2.55 (s, 3), 3.40–3.80 (m, 8), 3.70 (s, 3), 4.05 (q, 2), 5.05 (m, 1), 5.15 (m, 1), 7.45 (s, 1), 7.55 (d, 1), 7.85 (s, 1), 8.20 (d, 1) ppm and NMR (CD$_3$OD) 1.22 (t, 3), 1.25 (m, 4), 1.45 (m, 1), 1.70 (m, 1), 1.90 (m, 4), 2.0 (m, 1), 2.20 (m, 2), 2.45 (m, 2), 2.60 (s, 3), 3.40–3.80 (m, 8), 3.78 (s, 3), 4.10 (q, 2), 5.10 (m, 1), 5.25 (m, 1), 7.50 (s, 1), 7.60 (d, 1), 7.90 (s, 1), 8.25 (d, 1) ppm;

2-[1-(4-(ethoxycarbonyl)piperazin-1-yl)carbonyl-3-carboxypropyl]aminocarbonyl-7-methyl-4-(1-(methoxycarbonyl)cyclobut-1-oxy)quinoline; NMR (DMSO-d$_6$) 1.18 (t, 3), 1.82 (m, 1), 2.00 (m, 3), 2.30 (m, 2), 2.56 (s, 3), 2.59 (m, 3), 2,80 (m, 2), 3.30–3.50 (m, 6), 3.60 (m, 2), 3.64 (s, 3), 4.04 (q, 2), 4.98 (m, 1), 6.92 (s, 1), 7.55 (d, 1), 7.90 (s, 1), 8.17 (d, 1), 8.87 (d, 1) ppm;

2-[1-(4-(ethoxycarbonyl)piperazin-1-yl)carbonyl-3-carboxypropyl]aminocarbonyl-7-methyl-4-(1-(1-methylethoxycarbonyl)cyclobut-1-oxy)quinoline;

2-[1-(4-(ethoxycarbonyl)piperazin-1-yl)carbonyl-3-carboxypropyl]aminocarbonyl-6-chloro-7-methyl-4-(1-methyl-1-(ethoxycarbonyl)ethoxy)quinoline; NMR (DMSO-$d_6$) 1.18 (t, 3), 1.26 (t, 3), 1.74 (s, 6), 1.82 (m, 1), 2.00 (m, 1), 2.30 (m, 2), 2.54 (s, 3), 3.40 (m, 2), 3.62 (m, 2), 4.04 (q, 2), 4.16 (q, 2), 5.52 (m, 1), 7.10 (s, 1), 8.1 (s, 1), 8.18 (s, 1), 8.82 (d, 1) ppm;

2-[1-(4-(ethoxycarbonyl)piperazin-1-yl)carbonyl-3-carboxypropyl]aminocarbonyl-6-chloro-7-methyl-4-(1-methyl-1-carboxyethoxy)quinoline; NMR (DMSO-$d_6$) 1.18 (t, 3), 1.72 (2s, 6), 1.84 (m, 1), 2.00 (m, 1), 2.30 (m, 2), 2.54 (s, 3), 3.36 (m, 1), 3.40 (m, 1), 3.48 (m, 1), 3.64 (m, 1), 4.06 (q, 2), 5.02 (m, 1), 7.30 (s, 1), 8.08 (s, 1), 8.16 (s, 1), 8.86 (d, 1) ppm;

2-[(4-(ethoxycarbonyl)piperazin-1-yl)carbonylmethyl]aminocarbonylquinoline; NMR (DMSO-$d_6$) 1.17 (t, 3), 3.34–3.57 (m, 8), 4.06 (q, 3), 4.28 (d, 2), 7.74 (t, 1), 7.90 (t, 1), 8.06–18 (m, 3), 8.60 (d, 1), 8.98 (t, 1) ppm;

2-[(4-(ethoxycarbonyl)piperazin-1-yl)carbonylmethyl]aminocarbonyl-4-hydroxyquinoline; NMR (DMSO-$d_6$) 1.18 (t, 3), 3.30–3.48 (m, 8), 4.04 (q, 2), 4.20 (d, 2), 6.75 (m, 1), 7.40 (m, 1), 7.70 (t, 1), 7.92 (d, 1), 8.06 (d, 1) ppm;

2-[(4-(ethoxycarbonyl)piperazin-1-yl)carbonylmethyl]aminocarbonyl-4-methoxyquinoline;

2-[(4-(n-propylsulfonyl)piperazin-1-yl)carbonylmethyl]aminocarbonyl-4methoxyquinoline; NMR (DMSO-$d_6$) 0.94 (t, 3), 1.67 (m, 2), 3.02 (t, 2), 3.10–3.35 (m, 4), 3.57 (m, 4), 4.13 (s, 3), 4.26 (d, 2), 7.60 (s, 1), 7.66 (t, 1), 7.84 (t, 1), 8.04 (d, 1), 8.19 (d, 1), 8.96 (t, 1) ppm;

2-[(4-(2,5-dibromophenyl)sulfonylpiperazin-1-yl)carbonylmethyl]aminocarbonyl-4-methoxyquinoline; NMR (DMSO-$d_6$) 3.20–3.30 (m, 4), 3.58 (m, 4), 4.10 (s, 3), 4.25 (d, 2), 7.57 (s, 1), 7.64 (t, 1), 7.80 (m, 3), 8.02 (d, 1), 8.06 (s, 1), 8.18 (d, 1), 8.94 (t, 1) ppm;

2-[(4-(2,6-difluorophenyl)sulfonylpiperazin-1-yl)carbonylmethyl]aminocarbonyl-4-methoxyquinoline; NMR (DMSO-$d_6$) 3.10–3.20 (m, 4), 3.60 (m, 4), 4.10 (s, 3), 4.23 (d, 2), 7.34 (t, 1), 7.58 (s, 1), 7.64 (t, 1), 7.75–7.82 (m, 2), 8.02 (d, 1), 8.18 (d, 1), 8.88 (t, 1) ppm;

2-[(4-(3-bromophenyl)carbonylpiperazin-1-yl)carbonylmethyl]aminocarbonyl-4-methoxyquinoline;

2-[(4-(4-ethylphenyl)carbonylpiperazin-1-yl)carbonylmethyl]aminocarbonyl-4-methoxyquinoline; NMR (DMSO-$d_6$) 1.18 (t, 3), 2.60 (m, 2), 3.30–3.65 (m, 8), 4.12 (s, 3), 4.24 (d, 2), 7.26 (d, 2), 7.35 (d, 2), 7.60 (s, 1), 7.64 (t, 1), 7.83 (t, 1), 8.04 (d, 1), 8.18 (d, 1), 8.94 (t, 1) ppm;

2-[(4-(4-n-propylphenyl)carbonylpiperazin-1-yl)carbonylmethyl]aminocarbonyl-4-methoxyquinoline; NMR (CDCl$_3$) 0.94 (t, 3), 1.65 (m, 2), 2.62 (t, 2), 3.50–3.80 (m, 8), 4.15 (s, 3), 4.38 (d, 2), 7.24 (d, 2), 7.36 (d, 2), 7.56 (t, 1), 7.65 (s, 1), 7.75 (t, 1), 8.08 (d, 1), 8.23 (d, 1), 9.08 (t, 1) ppm;

2-[(4-(4-n-butylphenyl)carbonylpiperazin-1-yl)carbonylmethyl]aminocarbonyl-4-methoxyquinoline;

2-[(4-(phenoxymethyl)carbonylpiperazin-1-yl)carbonylmethyl]aminocarbonyl-4-methoxyquinoline; NMR (DMSO-$d_6$) 3.40–3.60 (m, 8), 4.13 (s, 3), 4.26 (d, 2), 4.84 (s, 2), 6.93 (m, 3), 7.26 (m, 2), 7.60 (s, 1), 7.64 (t, 1), 7.83 (t, 1), 8.06 (d, 1), 8.18 (d, 1), 8.94 (t, 1) ppm;

2-[(4-(2,2-dimethylpropyl)carbonylpiperazin-1-yl)carbonylmethyl]aminocarbonyl-4-methoxyquinoline; NMR (CDCl$_3$) 1.07 (s, 9), 2.32 (s, 2), 3.53–3.77 (m, 8), 4.15 (s, 3), 4.38 (d, 2), 7.57 (t, 1), 7.65 (s, 1), 7.74 (t, 1), 8.09 (d, 1), 8.13 (d, 1), 9.09 (t, 1) ppm;

2-[(4-(2-ethoxycarbonylethyl)carbonylpiperazin-1-yl)carbonylmethyl]aminocarbonyl-4-methoxyquinoline; NMR (DMSO-$d_6$) 1.15 (t, 3), 2.51 (m, 2), 2.60 (m, 2), 3.44–3.56 (m, 8), 4.01 (q, 2), 4.11 (s, 3), 4.27 (d, 2), 7.57 (s, 1), 7.64 (t, 1), 7.83 (t, 1), 8.04 (d, 1), 8.18 (d, 1), 8.94 (t, 1) ppm;

2-[(4-(n-propyl)carbonylpiperazin-1-yl)carbonylmethyl]aminocarbonyl-4-methoxyquinoline; NMR (DMSO-$d_6$) 0.86 (t, 3), 1.51 (m, 2), 2.30 (m, 2), 3.40–3.58 (m, 8), 4.14 (s, 3), 4.27 (d, 2), 7.60 (s, 1), 7.64 (t, 1), 7.83 (t, 1), 8.04 (d, 1), 8.18 (d, 1), 8.96 (t, 1) ppm;

2-[(4-(n-pentyl)carbonylpiperazin-1-yl)carbonylmethyl]aminocarbonyl-4-methoxyquinoline; NMR (DMSO-$d_6$) 0.82 (t, 3), 1.23 (m, 6), 1.44 (m, 2), 2.30 (m, 2), 3.40–3.56 (m, 8), 4.12 (s, 3), 4.25 (d, 2), 7.60 (s, 1), 7.64 (t, 1), 7.83 (t, 1), 8.04 (d, 1), 8.18 (d, 1), 8.94 (t, 1) ppm;

2-[(4-(furan-2-yl)carbonylpiperazin-1-yl)carbonylmethyl]aminocarbonyl-4-methoxyquinoline; NMR (CDCl$_3$) 3.63 (m, 2), 3.83 (m, 6), 4.14 (s, 3), 4.39 (d, 1), 6.53 (m, 1), 7.08 (d, 1), 7.53 (d, 1), 7.57 (t, 1), 7.65 (s, 1), 7.74 (t, 1), 8.09 (d, 1), 8.13 (d, 1), 9.10 (t, 1) ppm;

2-[(4-(thien-2-yl)carbonylpiperazin-1-yl)carbonylmethyl]aminocarbonyl-4-methoxyquinoline; NMR (CDCl$_3$) 3.63 (m, 2), 3.83 (m, 6), 4.14 (s, 3), 4.38 (d, 1), 7.08 (m, 1), 7.35 (d, 1), 7.52 (d, 1), 7.58 (t, 1), 7.66 (s, 1), 7.74 (t, 1), 8.09 (d, 1), 8.13 (d, 1), 9.08 (t, 1) ppm;

2-[(4-(2-phenylcyclopropyl)carbonylpiperazin-1-yl)carbonylmethyl]aminocarbonyl-4-methoxyquinoline;

2-[(4-(2-bromo-5-methoxyphenyl)carbonylpiperazin-1-yl)carbonylmethyl]aminocarbonyl-4-methoxyquinoline; NMR (DMSO-$d_6$) 3.10–3.20 (m, 2), 3.48–3.72 (m, 6), 3.75 (s, 3), 4.10 (s, 3), 4.25 (d, 2), 6.85 (m, 2), 7.57–7.66 (m, 3), 7.83 (m, 1), 8.02 (d, 1), 8.18 (d, 1), 8.96 (t, 1) ppm;

2-[(4-(n-butyl)carbonylpiperazin-1-yl)carbonylmethyl]aminocarbonyl-4-methoxyquinoline; NMR (DMSO-$d_6$) 0.82 (t, 3), 1.23 (m, 4), 1.44 (m, 2), 2.30 (m, 2), 3.40–3.60 (m, 8), 4.12 (s, 3), 4.25 (d, 2), 7.60 (s, 1), 7.64 (t, 1), 7.83 (t, 1), 8.04 (d, 1), 8.18 (d, 1), 8.94 (t, 1) ppm;

2-[(4-(3-trifluoromethoxyphenyl)carbonylpiperazin-1-yl)carbonylmethyl]aminocarbonyl-4-methoxyquinoline; NMR (CDCl$_3$) 3.52–3.94 (m, 8), 4.15 (s, 3), 4.39 (d, 2), 7.25–7.41 (m, 3), 7.48 (d, 1), 7.58 (t, 1), 7.64 (s, 1), 7.75 (t, 1), 8.08 (d, 1), 8.13 (d, 1), 9.08 (t, 1) ppm;

2-[(4-((1,1-dimethylethyl)aminocarbonyl)piperazin-1-yl)carbonylmethyl]aminocarbonyl-4-methoxyquinoline; NMR (DMSO-$d_6$) 1.23 (s, 9), 3.24–3.33 (m, 4), 3.44 (m, 4), 4.12 (s, 3), 4.14 (d, 2), 5.88 (s, 1), 7.57 (s, 1), 7.64 (t, 1), 7.83 (t, 1), 8.03 (d, 1), 8.17 (d, 1), 8.92 (t, 1) ppm;

2-[(4-((1-methylethyl)aminocarbonyl)piperazin-1-yl)carbonylmethyl]aminocarbonyl-4-methoxyquinoline; NMR (CDCl$_3$) 1.17 (d, 6), 3.36–3.78 (m, 8), 3.98 (m, 1), 4.12 (s, 3), 4.36 (d, 3), 7.58 (t, 1), 7.66 (s, 1), 7.75 (t, 1) ppm;

2-[(4-((n-propyl)aminocarbonyl)piperazin-1-yl)carbonylmethyl]aminocarbonyl-4-methoxyquinoline; NMR (DMSO-$d_6$) 0.80 (t, 3), 1.39 (m, 2), 2.95 (m, 2), 3.30–3.46 (m, 8), 4.13 (s, 3), 4.25 (d, 2), 6.57 (t, 1), 7.60 (s, 1), 7.64 (t, 1), 7.83 (t, 1), 8.04 (d, 1), 8.18 (d, 1), 8.96 (t, 1) ppm;

2-[(4-((n-butyl)aminocarbonyl)piperazin-1-yl)carbonylmethyl]aminocarbonyl-4-methoxyquinoline; NMR (CDCl$_3$) 0.92 (t, 3), 1.37 (m, 2), 1.52 (m, 2), 3.26 (m, 2), 3.40 (m, 2), 3.56 (m, 4), 3.64 (m, 2), 4.14 (s, 3), 4.26 (d, 2), 7.56 (t, 1), 7.66 (s, 1), 7.73 (t, 1), 8.10 (d, 1), 8.24 (d, 1), 9.10 (t, 1) ppm;

2-[(4-((n-hexyl)aminocarbonyl)piperazin-1-yl)carbonylmethyl]aminocarbonyl-4-methoxyquinoline; NMR (DMSO-$d_6$) 0.82 (t, 3), 1.23 (m, 6), 1.38 (m, 2), 2.97 (m, 2), 3.30–3.48 (m, 8), 4.12 (s, 3), 4.25 (d, 2), 6.54 (t, 1), 7.60 (s, 1), 7.64 (t, 1), 7.83 (t, 1), 8.04 (d, 1), 8.18 (d, 1), 8.94 (t, 1) ppm;

2-[(4-((n-pentyl)aminocarbonyl)piperazin-1-yl)carbonylmethyl]aminocarbonyl-4-methoxyquinoline; NMR (DMSO-d$_6$) 0.82 (t, 3), 1.23 (m, 4), 1.38 (m, 2), 2.97 (m, 2), 3.28–3.48 (m, 8), 4.12 (s, 3), 4.26 (d, 2), 6.53 (t, 1), 7.60 (s, 1), 7.64 (t, 1), 7.83 (t, 1), 8.04 (d, 1), 8.18 (d, 1), 8.94 (t, 1) ppm;

2-[(4-((ethoxycarbonyl)aminocarbonyl)piperazin-1-yl)carbonylmethyl]aminocarbonyl-4-methoxyquinoline; NMR (DMSO-d$_6$) 1.18 (t, 3), 3.30–3.48 (m, 8), 4.06 (q, 2), 4.12 (s, 3), 4.25 (d, 2), 6.57 (t, 1), 7.59 (s, 1), 7.64 (t, 1), 7.83 (t, 1), 8.04 (d, 1), 8.18 (d, 1), 8.96 (t, 1) ppm;

2-[(4-(morpholin-4-yl)carbonylpiperazin-1-yl)carbonylmethyl]aminocarbonyl-4-methoxyquinoline; NMR (CDCl$_3$) 3.35 (m, 8), 3.58 (m, 2), 3.71 (m, 6), 4.14 (s, 3), 4.37 (d, 2), 7.56 (t, 1), 7.65 (s, 1), 7.74 (t, 1), 8.07 (d, 1), 8.13 (d, 1), 9.09 (t, 1) ppm;

2-[(4-(pyridin-2-yl)piperazin-1-yl)carbonylmethyl]aminocarbonyl-4-methoxyquinoline; NMR (CDCl$_3$) 3.57 (m, 2), 3.69 (m, 4), 3.84 (m, 2), 4.15 (s, 3), 4.41 (d, 2), 6.70 (m, 2), 7.56 (m, 2), 7.67 (s, 1), 7.76 (t, 1), 8.10 (d, 1), 8.22 (d, 1), 9.15 (t, 1) ppm;

2-[(4-(3-chlorophenyl)piperazin-1-yl)carbonylmethyl]aminocarbonyl-4-methoxyquinoline; NMR (CDCl$_3$) 3.25 (m, 4), 3.67 (m, 2), 3.86 (m, 2), 4.15 (s, 3), 4.19 (d, 2), 6.81 (d, 1), 6.91 (m, 2), 7.22 (t, 1), 7.57 (t, 1), 7.68 (s, 1), 7.74 (t, 1), 8.11 (d, 1), 8.23 (d, 1), 9.14 (t, 1) ppm;

2-[(3-methyl-4-(3-methylphenyl)piperazin-1-yl)carbonylmethyl]aminocarbonyl-4-methoxyquinoline; NMR (DMSO-d$_6$) 0.83–0.95 (dd, 3), 2.23 (s, 3), 2.85–3.18 (m, 2), 3.30–4.42 (m, 10), 6.57 (d, 1), 6.68 (m, 2), 7.08 (t, 1), 7.60 (s, 1), 7.65 (t, 1), 7.84 (t, 1), 8.07 (d, 1), 8.18 (d, 1), 8.96 (t, 1) ppm; and 2-[(4-(3-methylphenyl)piperazin-1-yl)carbonylmethyl]aminocarbonyl-4-methoxyquinoline; NMR (CDCl$_3$) 2.35 (s, 3), 3.22 (m, 4), 3.66 (m, 2), 3.87 (m, 2), 4.15 (s, 3), 4.38 (d, 2), 6.77 (m, 3), 7.18 (t, 1), 7.57 (t, 1), 7.69 (s, 1), 7.75 (t, 1), 8.11 (d, 1), 8.22 (d, 1), 9.17 (t, 1) ppm.

EXAMPLE 3

Compounds of Formula (Ic)

A. To a solution of 2-((carboxy)methylcarbonylamino)naphthalene (1.2 g, 5.2 mmol) in CH$_2$Cl$_2$ (40 mL) was added triethylamine (2.2 mL, 15.6 mmol) and 1-hydroxybenzotriazole (HOBT) (0.84 g, 6.2 mmol) and 1-(3-dimethylaminopropyl)-3-ethylcarbodiimide (EDCI) (1.2 g, 6.2 mmol). After 5 minutes, 1-ethoxycarbonylpiperazine (0.84 mL, 5.3 mmol) was added and the reaction was stirred overnight. The reaction mixture was evaporated in vacuo to afford an oil, which was dissolved in ethyl acetate, and washed with saturated NaHCO$_3$, 1M NaHSO$_4$ and brine. The organic layer was evaporated in vacuo to afford 2-[((4-(ethoxycarbonyl)piperazin-1-yl)carbonylmethyl)carbonyl]aminonaphthalene (1.2 g), as a solid that was used without further purification.

B. In a similar manner, the following compounds of formula (Ic) were prepared:

2-[((4-(ethoxycarbonyl)piperazin-1-yl)carbonylmethyl)carbonyl]amino-5-hydroxynaphthalene; NMR (DMSO-d$_6$) 1.17 (t, 3), 3.28–3.60 (m, 10), 4.04 (q, 2), 6.72 (d, 1), 7.22 (m, 2), 7.24 (d, 1), 8.02 (d, 1), 8.17 (s, 1) ppm;

2-[((4-(ethoxycarbonyl)piperazin-1-yl)carbonylmethyl)carbonyl]amino-4-methoxynaphthalene; NMR (DMSO-d$_6$) 1.17 (t, 3), 3.30–3.60 (m, 10), 3.93 (s, 3), 4.03 (q, 2), 7.03 (s, 1), 7.34 (t, 1), 7.43 (t, 1), 7.73 (d, 1), 7.82 (s, 1), 8.01 (d, 1) ppm;

2-[((4-(ethoxycarbonyl)piperazin-1-yl)carbonylmethyl)carbonyl]amino-5-(carboxymethoxy)naphthalene; NMR (DMSO-d$_6$) 1.17 (t, 3), 3.30–3.60 (m, 10), 4.03 (q, 2), 6.73 (d, 1), 7.36 (m, 2), 7.52 (d, 1), 8.13 (d, 1), 8.21 (s, 1) ppm;

2-[((4-(ethoxycarbonyl)piperazin-1-yl)carbonylmethyl)carbonyl]amino-5-(3-(ethoxycarbonyl)propoxy)naphthalene; NMR (CDCl$_3$) 1.25 (m, 6), 2.24 (m, 2), 2.61 (t, 2), 3.52–3.71 (m, 10), 4.17 (m, 6), 6.73 (d, 1), 7.36 (m, 2), 7.45 (d, 1), 8.21 (m, 2), 9.93 (s, 1) ppm;

2-[((4-(ethoxycarbonyl)piperazin-1-yl)carbonylmethyl)carbonyl]amino-5-(3-carboxypropoxy)naphthalene; NMR (DMSO-d$_6$) 1.17 (t, 3), 2.04 (m, 2), 3.30–3.60 (m, 10), 4.03 (q, 2), 4.12 (t, 2), 6.79 (m, 1), 7.34 (m, 2), 7.47 (d, 1), 8.07 (d, 1), 8.21 (s, 1), 10.29 (s, 1) ppm and;

2-[((4-(ethoxycarbonyl)piperazin-1-yl)carbonylmethyl)carbonyl]amino-4-(carboxymethoxy)naphthalene.

EXAMPLE 4

Compounds of Formula (Id)

A. NaH 95% (15 mg, 0.6 mmol) was suspended in DMF (5 mL). A solution of 2-[((4-(ethoxycarbonyl)piperazin-1-yl)carbonylmethyl)carbonyl]aminonaphthalene (160 mg, 0.43 mmol) in DMF (1 mL) was added dropwise. The reaction mixture was stirred at ambient temperature. After 5 minutes, a solution of methyl 3-(bromomethyl) benzoate (99 mg, 0.43 mmol) in DMF (0.5 mL) was added. The reaction was quenched by water (100 mL) after 15 minutes, then extracted with ethyl acetate (80 mL). The organic layer was evaporated in vacuo. Purification by flash column on silica gel afforded a solid, 2-[(1-(4-(ethoxycarbonyl)piperazin-1-yl)carbonyl-2 -(3-(methoxycarbonyl)phenyl)ethyl)carbonyl]-aminonaphthalene (195 mg, 0.38 mmol).

B. In a similar manner, the following compounds of formula (Id) were prepared:

2-[(1-(4-(ethoxycarbonyl)piperazin-1-yl)carbonyl-1-(tetrahydro-2-oxofuran-3-yl)methyl)carbonyl]aminonaphthalene; NMR (CDCl$_3$) 1.24 (t, 3), 2.31–2.78 (m, 2), 3.41–3.90 (m, 10), 4.16 (q, 2), 4.28 (m, 1), 4.44 (m, 1), 7.42–7.56 (m, 3), 7.80 (m, 3), 8.23 (s, 1) ppm;

2-[(1-(4-(ethoxycarbonyl)piperazin-1-yl)carbonyl-2-carboxy-4-hydroxybutyl)carbonyl]aminonaphthalene; NMR (CDCl$_3$) 1.25 (t, 3), 2.02 (m, 2), 2.34 (m, 1), 3.37 (m, 2), 3.57 (m, 2), 3.71–3.90 (m, 4), 3.95–4.12 (m, 2), 4.17 (q, 2), 4.25 (d, 1), 7.36 (d, 1), 7.56 (m, 2), 7.80 (s, 1), 7.91 (m, 2), 7.97 (d, 1) ppm;

2-[(1-(4-(ethoxycarbonyl)piperazin-1-yl)carbonyl-2-(ethoxycarbonyl)ethyl)carbonyl]aminonaphthalene; NMR (DMSO-d$_6$) 1.27 (m, 6), 2.87 (m, 2), 3.32–3.62 (m, 8), 4.03 (m, 4), 4.18 (m, 1), 7.38 (t, 1), 7.43 (t, 1), 7.56 (d, 1), 7.83 (m, 3), 8.22 (s, 1) ppm; and 2-[(1-(4-(ethoxycarbonyl)piperazin-1-yl)carbonyl-2-(4-(methoxycarbonyl)phenyl)ethyl)carbonyl]aminonaphthalene. NMR (DMSO-d$_6$) 1.16 (t, 3), 3.17–3.36 (m, 6), 3.42–3.58 (m, 4), 3.79 (s, 3), 3.98 (q, 2), 4.17 (m, 1), 7.42 (m, 5), 7.80 (m, 5), 8.17 (s, 1) ppm.

C. To a solution of 2-[(1-(4-(ethoxycarbonyl)piperazin-1-yl)carbonyl-2-(3-(methoxycarbonyl)phenyl)ethyl)carbonyl] aminonaphthalene (110 mg, 0.2 mmol) in THF (8 mL) was added a solution of LiOH (27 mg, 0.6 mmol) in water (6 mL). The reaction mixture was stirred at ambient temperature. After 5 hours, the reaction mixture was acidified to pH 2–3 by 2N NaHSO$_4$, then extracted with ethyl acetate (3×10 mL). The organic layer was dried over Na$_2$SO$_4$ and evaporated in vacuo to afford 2-[(1-(4-(ethoxycarbonyl)piperazin-1-yl)carbonyl-2-(3-carboxyphenyl)ethyl)carbonyl]aminonaphthalene (90 mg, 0.18 mmol); NMR (DMSO-d$_6$) 1.25 (t, 3), 3.10–3.30 (m, 6), 3.40–3.60 (m, 4), 3.97 (q, 2), 4.14 (t, 1), 7.35–7.55 (m, 5), 7.70–7.87 (m, 5), 8.14 (s, 1), 10.12 (s, 1) ppm.

D. In a similar manner, the following compounds were made:

2-[(1-(4-(ethoxycarbonyl)piperazin-1-yl)carbonyl-2-carboxyethyl)carbonyl]aminonaphthalene; NMR (CDCl$_3$) 1.27 (t, 3), 3.01 (m, 1), 3.32 (m, 2), 3.54 (m, 2), 3.81 (m, 3), 4.06 (m, 2), 4.17 (q, 2), 4.25 (m, 1), 7.34 (d, 1), 7.57 (m, 2), 7.79 (s, 1), 7.88 (m, 2), 7.94 (d, 1) ppm;

2-[(1-(4-(ethoxycarbonyl)piperazin-1-yl)carbonyl-2-(4-carboxyphenyl)ethyl)carbonyl]aminonaphthalene; NMR (DMSO-d$_6$) 1.14 (t, 3), 3.17–3.33 (m, 6), 3.42–3.56 (m, 4), 3.98 (q, 2), 4.16 (m, 1), 7.37–7.47 (m, 5), 7.80 (m, 5), 8.16 (s, 1) ppm; and 2-[((4-(ethoxycarbonyl)piperazin-1-yl)carbonylmethyl)carbonyl]amino-4-hydroxyquinoline; NMR (CDCl$_3$) 1.26 (t, 3), 3.43–3.63 (m, 8), 1.17 (q, 2), 5.93 (s, 1), 7.24–7.35 (m, 3), 7.57 (t, 1), 8.23 (d, 1) ppm.

EXAMPLE 5

Compounds of Formulae (Q), (If) and (Ig)

A. To a solution of 2-[1-(4-(ethoxycarbonyl)piperazin-1-yl)carbonyl-2-(2-hydroxyphenyl)ethyl]aminocarbonyl-4-methoxyquinoline (380 mg, 0.75 mmol) in CH$_2$Cl$_2$ cooled to −30° C. was added triethylamine (0.12 mL, 1.12 mmol) and dimethylamino pyridine (20 mg, 1.6 mmol) and the reaction mixture was stirred for 10 minutes. Triflouromethanesulfonic anhydride (0.19 mL, 1.12 mmol) was added and the reaction mixture was slowly warmed to ambient temperature. The solvent was evaporated under reduced pressure and residue was purified by flash chromatography (ethyl acetate:hexane—30:70) to afford 2-[1-(4-(ethoxycarbonyl)piperazin-1-yl)carbonyl-2-(2-(trifluoromethylsulfonyl)oxyphenyl)ethyl]aminocarbonyl-4-methoxyquinoline as a yellow oil (320 mg).

B. In a similar manner, the following compounds were made:

2-[1-(4-(ethoxycarbonyl)piperazin-1-yl)carbonyl-2-(4-(trifluoromethylsulfonyl)oxyphenyl)ethyl]aminocarbonyl-4-methoxyquinoline;

2-[1-(4-(ethoxycarbonyl)piperazin-1-yl)carbonyl-2-(3-(trifluoromethylsulfonyl)oxyphenyl)ethyl]aminocarbonyl-4-methoxyquinoline; and 2-[1-(4-(ethoxycarbonyl)piperazin-1-yl)carbonyl-1-(4-(trifluoromethylsulfonyl)boxyphenyl)methyl]aminocarbonyl-4-methoxyquinoline.

C. Carbon monoxide was bubbled for 10 minutes to a solution of 2-[1-(4-(ethoxycarbonyl)piperazin-1-yl)carbonyl-2-(2-(trifluoromethylsulfonyl)oxyphenyl)ethyl]aminocarbonyl-4-methoxyquinoline (320 mg, 0.50 mmol) in a mixture of DMSO (3 mL), MeOH (2 mL) and triethylamine (0.2 mL). Palladium acetate (60 mg) and 2′,2′-bis(diphenylphosphino)-1,1-binaphthyl (200 mg) was added and reaction mixture was heated to 70° C. for 45 minutes. The reaction mixture was cooled to ambiemt temperature, filtered through celite and concentrated under reduced pressure. Flash column chromatography (methanol:CH$_2$Cl$_2$, 1:99) afforded 2-[1-(4-(ethoxycarbonyl)piperazin-1-yl)carbonyl-2-(2-methoxycarbonylphenyl)ethyl]aminocarbonyl-4-methoxyquinoline as an orange oil, 220 mg (80%); NMR (CDCl$_3$) 2.40 (t, 3), 3.4 (m, 10), 3.88 (s, 3), 3.16 (q, 2), 3.18 (s, 3), 5.62 (m, 1), 7.26 (m, 2), 7.48 (m, 2), 7.68 (m, 1). 7.92 (d, 1), 8.04 (d, 1), 8.20 (d, 1), 9.00 (d, 1) ppm.

D. In a similar manner, the following compound was made:

2-[1-(4-(ethoxycarbonyl)piperazin-1-yl)carbonyl-2-(4-(1,1-dimethylethoxy)carbonylphenyl)ethyl]aminocarbonyl-4-methoxyquinoline; NMR (CDCl$_3$) 1.23 (t, 3), 1.60 (s, 9), 3.02–3.60 (m, 10), 4.12 (m, 5), 5.40 (m, 1), 7.35 (d, 1), 7.58 (dd, 1), 7.82 (s, 1), 7.75 (dd, 1), 7.92 (d, 1), 8.05 (d, 1), 8.21 (d, 1), 8.99 (d, 1) ppm.

E. To a solution of 2-[1-(4-(ethoxycarbonyl)piperazin-1-yl)carbonyl-2-(2-methoxycarbonylphenyl)ethyl]aminocarbonyl-4-methoxyquinoline (220 mg, 0.4 mmol) in methanol was added a solution of LiOH (3 mL, 0.25 M) and the resulting reaction mixture was stirred at ambient temperature overnight. The product was purified by preparative HPLC and lyophilization to afford 2-[1-(4-(ethoxycarbonyl)piperazin-1-yl)carbonyl-2-(2-carboxyphenyl)ethyl]aminocarbonyl-4-methoxyquinoline as an orange solid, 140 mg (50%); NMR (DMSO-d$_6$), 1.08 (t, 3), 3.40 (m, 10), 4.00 (q, 2), 4.04 (s, 3), 5.28 (m, 1), 7.26 (t, 1), 7.34 (m; 2), 7.42 (s, 1), 7.82 (m, 2), 8.06 (d, 1), 8.14 (d, 1H), 8.88 (d, 1) ppm.

F. In a similar manner, the following compounds were made:

2-[1-(4-(ethoxycarbonyl)piperazin-1-yl)carbonyl-2-(4-carboxyphenyl)ethyl]aminocarbonyl-4-methoxyquinoline; NMR (CDCl$_3$) 1.23 (t, 3), 3.20–4.80 (m, 8), 4.15 (q, 2), 4.30 (s, 3), 5.45 (m, 1), 7.32 (d, 2), 7.81 (dd, 1), 7.83 (s, 1), 7.95 (d, 1), 8.01 (dd, 1), 8.38 (d, 2) ppm;

2-[1-(4-(ethoxycarbonyl)piperazin-1-yl)carbonyl-2-(3-carboxyphenyl)ethyl]aminocarbonyl-4-methoxyquinoline; and 2-[1-(4-(ethoxycarbonyl)piperazin-1-yl)carbonyl-1-(4-carboxyphenyl)methyl]aminocarbonyl-4-methoxyquinoline.

EXAMPLE 6

Compounds of Formula (Ih)

A. To a solution of 2-[1-(4-(ethoxycarbonyl)piperazin-1-yl)carbonyl-2-(2-hydroxyphenyl)ethyl]aminocarbonyl-4-methoxyquinoline (200 mg, 0.39 mmol) in DMF (5 mL) was added CsCO$_3$ (260 mg, 0.8 mmol) and ethyl bromoacetate (120 mg, 0.7 mmol) and the reaction mixture was stirred at ambient temperature for 6 hours. The reaction mixture was partitioned in water and ethyl acetate and extracted with ethyl acetate. Combined organic layers were washed with water, brine, dried over sodium sulfate and concentrated. The residue was purified by preparative HPLC to afford 2-[1-(4-(ethoxycarbonyl)piperazin-1-yl)carbonyl-2-(2-(ethoxycarbonyl)methoxyphenyl)ethyl]aminocarbonyl-4-methoxyquinoline as a white solid 140 mg (60%); NMR (DMSO-d$_6$), 1.18 (m, 6), 3.26 (m, 10), 4.00 (q, 2), 4.04 (s, 3), 4.84 (s, 2), 5.26 (m, 1), 6.82 (q, 1), 7.88 (d, 1), 7.48 (s, 1), 7.64 (t, 1), 7.82 (t, 1), 8.06 (d, 1), 8.16 (d, 1), 8.86 (d, 1) ppm.

B. In a similar manner, the following compound was prepared:

2-[1-(4-(ethoxycarbonyl)piperazin-1-yl)carbonyl-2-(3-(ethoxycarbonyl)methoxyphenyl)ethyl]aminocarbonyl-4-methoxyquinoline.

C. The compounds prepared in Paragraph A and B and similar compounds were hydrolyzed under standard hydrolysis conditions to yield the following compounds:

2-[1-(4-(ethoxycarbonyl)piperazin-1-yl)carbonyl-1-(4-(carboxymethoxy)phenyl)methyl]aminocarbonyl-4-methoxyquinoline;

2-[1-(4-(ethoxycarbonyl)piperazin-1-yl)carbonyl-2-(2-(carboxy)methoxyphenyl)ethyl]aminocarbonyl-4-methoxyquinoline; and 2-[1-(4-(ethoxycarbonyl)piperazin-1-yl)carbonyl-2-(3-(carboxy)methoxyphenyl)ethyl]aminocarbonyl-4-methoxyquinoline.

EXAMPLE 7

Compounds of Formula (Ij)

A. To a solution of 2-[1-(4-(ethoxycarbonyl)piperazin-1-yl)carbonyl-2-hydroxyethyl]aminocarbonyl-4-methoxyquinoline (50 mg, 0.116 mmol) in tetrahydrofuran (THF) (2 mL) at 0° C. was added potassium hexamethyldisilazide (0.232 mL, 0.5 M in toluene, 0.122 mmol). After 5 minutes, ethyl bromoacetate (0.18 mg, 0.174 mmol) was added. The reaction mixture was stirred at 0° C. for 1 hour and the reaction was quenched with water. The resultant solution was partitioned between water and ethyl acetate. The organic layer was concentrated in vacuo to afford an oil (50 mg). The crude product was purified by elution through silica gel with 4:1 ethyl acetate-hexanes, dissolved in methanol and treated with 200 µL 0.25M lithium hydroxide. The reaction mixture was acidified with 10% HCl and extracted into ethyl acetate and concentrated in vacuo to afford 2-[1-(4-(ethoxycarbonyl)piperazin-1-yl)carbonyl-2-(carboxy)methoxyethyl]aminocarbonyl-4-methoxyquinoline (20 mg, 35%); NMR (CDCl$_3$) 1.25 (t, 6), 3.42–3.95 (m, 10), 4.11–4.23 (m, 9), 5.45 (m, 1), 7.55 (t, 1), 7.63 (s, 1), 7.76 (t, 1), 8.05 (d, 1), 8.20 (d, 1), 9.05 (d, 1) ppm.

B. In a similar manner, other compounds of formula (Ij) are prepared.

C. The compounds prepared above in Paragraph A and B may be further hydrolyzed under standard hydrolysis conditions to yield the following compounds:

EXAMPLE 8

Compounds of Formulae (Il) and (Im)

A. To a solution of 2-[(1-(4-(ethoxycarbonyl)piperazin-1-yl)carbonyl-3-carboxypropyl]aminocarbonyl-4-hydroxyquinoline (80 mg, 0.17 mmol) in N,N-dimethylformamide (DMF) (25 mL) was added cesium carbonate (454 mg, 1.36 mmol) and tert-butyl bromoacetate (102 mg, 0.51 mmol). The reaction mixture was heated at 50° C. After half hour, the reaction was diluted with 200 mL water, then extracted by ethyl acetate (80 mL). The organic layer was separated and dried over sodium sulfate. The solvent was evaporated in vacuo to afford an yellow oil. Purification by flash column on silica gel afforded 2-[1-(4-(ethoxycarbonyl)piperazin-1-yl)carbonyl-3-(((1,1-dimethylethoxy)carbonyl)methoxy)carbonylpropyl]aminocarbonyl-4-((1,1-dimethylethoxy)carbonyl)methoxyquinoline NMR (DMSO-d$_6$) 1.17 (t, 3), 1.37 (s, 9), 1.42 (s, 9), 1.93 (m, 1), 2.08 (m, 1), 2.48 (m, 2), 3.31–3.71 (m, 8), 4.03 (q, 2), 4.46 (q, 2), 5.07 (m, 3), 7.46 (s, 1), 7.68 (t, 1), 7.85 (t, 1), 8.09 (d, 1), 8.23 (d, 1), 8.95 (d, 1) ppm as a solid (110 mg).

B. To a solution of 2-[1-(4-(ethoxycarbonyl)piperazin-1-yl)carbonyl-3-(((1,1-dimethylethoxy)carbonyl)methoxy)carbonylpropyl]aminocarbonyl-4-((1,1-dimethylethoxy)carbonyl)methoxyquinoline (38 mg, 0.05 mmol) in 1 mL CH$_2$Cl$_2$, was added 2 mL trifluoroacetic acid, then the reaction mixture was stirred at ambient temperature for 3 hours. The reaction mixture was evaporated in vacuo to afford an oil. The oil was diluted in water (5 mL), adjusted to pH 4.5 by saturated NaHCO$_3$, then extracted by ethyl acetate (3×10 mL). The organic layer was evaporated in vacuo to afford 2-[1-(4-(ethoxycarbonyl)piperazin-1-yl)carbonyl-3-(((carboxy)methoxycarbonyl)propyl]aminocarbonyl-4-(carboxy)methoxyquinoline as a white solid (30 mg); NMR (DMSO-d$_6$), 1.16 (t, 3), 1.90 (m, 1), 2.10 (m, 1), 2.45 (m, 2), 3.3–3.9 (m, 8), 4.02 (q, 2), 4.52 (q, 2), 5.04 (m, 1), 5.13 (s, 2), 7.46 (s, 1), 7.68 (t, 1), 7.84 (t, 1), 8.08 (d, 1), 8.23 (d, 1), 9.95 (m, 1) ppm.

C. In a similar manner, similar compounds of the invention are prepared.

EXAMPLE 9

Compounds of Formula (In)

A. To a solution of 2-[1-(4-(ethoxycarbonyl)piperazin-1-yl)carbonyl-3-carboxypropyl]aminocarbonyl-4-methoxyquinoline (142 mg, 0.30 mmol) in tetrahydrofuran (THF) (5 mL) was added glycine t-butyl ester hydrochloride (44 mg, 0.33 mmol), 1-(3-dimethylaminopropyl)-3-ethylcarbodiimide (EDCI) (64 mg, 0.33 mmol), 1-hydroxybenzotriazole (HOBT) (45 mg, 0.33 mmol) and diisopropylethylamine (DIEA) (0.43 g, 0.33 mmol). The reaction was stirred at ambient temperature overnight. The resultant solution was partitioned between water and ethyl acetate. The organic layer was concentrated in vacuo to afford an oil. The crude product was purified by elution through silica gel with 20:1 methylene chloride-methanol to afford 2-[1-(4-(ethoxycarbonyl)piperazin-1-yl)carbonyl-3-(((1,1-dimethylethoxycarbonyl)methyl)aminocarbonyl)propyl]aminocarbonyl-4-methoxyquinoline (62 mg, 35%); NMR (CDCl$_3$) 1.25 (t, 3), 1.50 (s, 9), 2.00 (m, 1), 2.15–2.50 (m, 3), 3.31–3.95 (m, 9), 4.10–4.32 (m, 7), 5.40 (m, 1), 759 (t, 1), 7.63 (s, 1), 7.75 (t, 1), 8.14 (d, 1), 8.22 (d, 1), 9.41 (d, 1) ppm.

B. The compound prepared above is hydrolyzed under standard conditions to yield the compound 2-[1-(4-(ethoxycarbonyl)piperazin-1-yl)carbonyl-3-((carboxymethyl)aminocarbonyl)propyl]aminocarbonyl-4-methoxyquinoline.

C. In a similar manner, similiar compounds of the invention are prepared.

EXAMPLE 10

Compounds of Formula (Ip)

A. To a solution of 2-[1-(4-(ethoxycarbonyl)piperazin-1-yl)carbonyl-2-carboxyethyl]aminocarbonyl-4-methoxyquinoline (50 mg, 0.11 mmol) in tetrahydrofuran (THF) (2 mL) was added glycine t-butyl ester hydrochloride (20 mg, 0.12 mmol), 1-(3-dimethylaminopropyl)-3-ethylcarbodiimide (EDCI) (23 mg, 0.12 mmol), 1-hydroxybenzotriazole (HOBT) (16 mg, 0.12 mmol) and diisopropylethylamine (DIEA) (0.16 g, 0.12 mmol). The reaction was stirred at ambient temperature overnight. The resultant solution was partitioned between water and ethyl acetate. The organic layer was concentrated in vacuo to afford 2-[1-(4-(ethoxycarbonyl)piperazin-1-yl)carbonyl-2-(((carboxy)methyl)aminocarbonyl)ethyl]aminocarbonyl-4-methoxyquinoline as an oil.

B. In a similar manner, the following compounds were prepared:

2-[1-(4-(ethoxycarbonyl)piperazin-1-yl)carbonyl-2-(((carboxy)methyl)(methyl)aminocarbonyl)ethyl]aminocarbonyl-4-methoxyquinoline; NMR (DMSO-$d_6$) 1.20 (t, 3), 2.70–3.85 (m, 13), 3.95–4.21 (m, 4), 4.35 (s, 3), 5.45 (m, 1), 7.83 (dd, 1), 7.98 (s, 1), 8.04 (dd, 1), 8.35 (d, 1), 8.41 (d, 1), 9.78 (m, 1) ppm; and 2-[1-(4-(ethoxycarbonyl)piperazin-1-yl)carbonyl-2-(((1,1-dimethylethoxycarbonyl)methyl)(methyl)aminocarbonyl) ethyl]aminocarbonyl-4-methoxyquinoline; NMR (CDCl$_3$) 1.23 (t, 3), 1.42 (s, 9), 2.80 (m, 1), 3.07 (s, 3), 3.40–3.80 (m, 8), 4.12 (s, 3), 5.65 (m, 1), 7.58 (dd, 1), 7.63 (s, 1), 7.75 (dd, 1), 8.02 (d, 1), 8.21 (d, 1), 8.75 (m, 1) ppm.

EXAMPLE 11

Compounds of Formulae (Iq), (Ir) and (Is)

A. To a solution of N-t-butoxycarbonylhistidine (2 g, 7.05 mmol) in THF (30 mL) was added 1-ethoxycarbonylpiperazine (1.36 mL, 1.3 eq.), EDCI (1.65 g, 1.2 eq. ), HOBt (1.2 g, 1.1 eq.) and the reaction mixture was stirred overnight. The reaction mixture was evaporated in vacuo to afford a crude product, which was dissolved in ethyl acetate, washed with saturated NaHCO$_3$, 1M NaHSO$_4$ and brine. The organic layer was evaporated. Flash column chromatography with 2%–6% MeOH in CH$_2$Cl$_2$ afforded 4-ethoxycarbonyl-1-(1-(t-butoxycarbonyl)amino-2-(imidazol-4-yl) ethyl)carbonylpiperazine (820 mg). 4-Ethoxycarbonyl-1-(1-(t-butoxycarbonyl)amino-2-(imidazol-4-yl)ethyl) carbonylpiperazine (200 mg, 0.5 mmol) was treated with trifluoroacetic acid/methylene chloride (1:1, 2.0 mL) with stirring at ambient temperture for 1 hour. Evaporation gave 4-ethoxycarbonyl-1-(1-amino-2-(imidazol-4-yl)ethyl)carbonylpiperazine, which was treated with methylene chloride and triethylamine (0.5 mL), and the solvents evaporated to again afford 4-ethoxycarbonyl-1-(1-amino-2-(imidazol-4-yl)ethyl)carbonylpiperazine. To a solution of 2-carboxy-4-methoxyquinoline (124 mg, 0.61 mmol) in THF (4 mL) was added a mixture of 4-ethoxycarbonyl-1-(1-amino-2-(imidazol-4-yl)ethyl)carbonylpiperazine, THF (2 mL), and triethylamine (0.1 mL), followed by addition of EDCI (136 mg, 1.4 eq.), HOBt (98 mg, 1.4 eq.). The resulting mixture was stirred overnight. The crude product (245 mg, foam) was isolated from the reaction mixture by the same methods employed above. Flash column chromatography with 25%–6% MeOH in methylene chloride afforded 2-[1-(4-(ethoxycarbonyl)piperazin-1-yl)carbonyl-2-(imidazol-4-yl) ethyl]aminocarbonyl-4-methoxyquinoline; NMR (CDCl$_3$) 1.25 (t, 3), 3.10–3.30 (m, 2), 3.20–3.65 (m, 9), 4.10 (m, 5), 5.40 (m, 1), 6.90 (s, 1), 7.55–7.60 (m, 3), 7.70 (t, 1), 8.02 (d, 1), 8.20 (d, 1), 9.0 (d, 1) ppm.

B. To a solution of 2-[1-(4-(ethoxycarbonyl)piperazin-1-yl)carbonyl-2-(imidazol-4-yl)ethyl]aminocarbonyl-4-methoxyquinoline (69 mg, 0.14 mmol) in DMF (2 mL) was added t-butyl bromo acetate (0.026 mL, 1.2 eq.), potassium carbonate (30 mg, 1.5 eq), NaI (2.0 mg, 0.1 eq.). The reaction mixture was heated at 50° C. for 1 hour. Evaporation followed by flash column chromatography with 2%–3% MeOH in methylene chloride afforded 2-[1-(4-(ethoxycarbonyl)piperazin-1-yl)carbonyl-2-(1-(t-butoxycarbonyl)methyl)imidazol-4-yl)ethyl]aminocarbonyl-4-methoxyquinoline (25 mg) which was treated with neat trifluoroacetic acid (0.5 mL) for 1.5 hours at ambient temperature. Repeated evaporation of the solvents and treatment with methylene chloride afforded 2-[1-(4-(ethoxycarbonyl)piperazin-1-yl) carbonyl-2-(1-(carboxymethyl)imidazol-4-yl)ethyl]-aminocarbonyl-4-methoxyquinoline (27 mg) as a trifluoroacetic acide salt: NMR (DMSO) 1.20 (t, 3), 3.2–3.6 (m, 11), 4.05 (q, 2), 4.1 (s, 3), 5.0 (s, 2), 5.3 (m, 1), 7.45 (s, 1), 7.5 (s, 1), 7.65 (t, 1), 7.8 (t, 1), 8.05 (d, 1), 8.16 (d, 1), 8.95 (s, 1) ppm.

C. In a similar manner, similar compounds of the invention are prepared.

EXAMPLE 12

Compounds of Formula (It)

A. To a solution of 4-methoxy-2-carboxyquinoline (102 mg, 0.50 mmol) in CH$_2$Cl$_2$ (15 mL) was added triethylamine (0.33 mL, 2.36 mmol) and 1-hydroxybenzotriazole (HOBT) (80 mg, 0.60 mmol) and 1-(3-dimethylaminopropyl)-3-ethylcarbodiimide (EDCI) (110 mg, 0.60 mmol). After 5 minutes, 1-ethoxycarbonyl-4-(ethoxycarbonylmethyl)aminomethylcarbonylpiperazine (150 mg, 0.50 mmol) was added and the reaction mixture was stirred overnight. The reaction mixture was evaporated in vacuo to afford an oil, which was dissolved in ethyl acetate, and washed with saturated NaHCO$_3$, 1M NaHSO$_4$ and brine. The organic layer was evaporated in vacuo and the crude product was purified by flash column to afford 2-[(4-(ethoxycarbonyl)piperazin-1-yl)carbonylmethyl](ethoxycarbonylmethyl)aminocarbonyl-4-methoxyquinoline (30 mg).

B. To a solution of 2-[(4-(ethoxycarbonyl)piperazin-1-yl) carbonylmethyl](ethoxycarbonylmethyl)aminocarbonyl-4-methoxyquinoline (30 mg, 0.06 mmol) in ethanol (1.0 mL), was added a solution of LiOH (6 mg, 0.12 mmol) in water (1.0 mL). The resulting reaction mixture was stirred at ambient temperature for 1 hour. The reaction mixture was acidified to pH 3 by 2N NaHSO$_4$, extracted by ethyl acetate (3×20 mL), dried over sodium sulfate, and concentrated in vacuo to afford 2-[(4-(ethoxycarbonyl)piperazin-1-yl)carbonylmethyl](carboxymethyl)aminocarbonyl-4-methoxyquinoline (25 mg) as a solid; NMR (DMSO-$d_6$), 1.20 (m, 3), 3.20–3.60 (m, 8), 4.00–4.14 (m, 5), 4.20 (s, 1), 4.35 (s, 1), 4.50 (s, 1), 4.70 (s, 1), 7.23 (d, 1), 7.65 (m, 1), 7.80–7.94 (m, 2), 8.17 (m, 1) ppm.

C. In a similar manner, other compounds of formula (It) are prepared.

EXAMPLE 13

Compounds of Formula (Iu)

A. To a solution of 2-[carboxymethylcarbonyl][(1,1-dimethylethoxycarbonyl)methyl]aminonaphthalene (270 mg, 0.78 mmol) in CH$_2$Cl$_2$ (50 mL) was added triethylamine (0.33 mL, 2.36 mmol) and 1-hydroxybenzotriazole (HOBT) (128 mg, 0.91 mmol) and 1-(3-dimethylaminopropyl)-3-ethylcarbodiimide (EDCI) (238 mg, 1.23 mmol). After 5 minutes, 1-ethoxycarbonylpiperazine (0.12 mL, 0.78 mmol) was added and the reaction mixture was stirred overnight. The reaction mixture was evaporated in vacuo to afford an oil, which was dissolved in ethyl acetate, and washed with saturated NaHCO$_3$, 1M NaHSO$_4$ and brine. The organic layer was evaporated in vacuo and the crude product was purified by flash column to afford 2-[((4-(ethoxycarbonyl) piperazin-1-yl)carbonylmethyl)carbonyl][(1,1-dimethylethoxycarbonyl)methyl]aminonaphthalene (147 mg).

B. To a solution of 2-[((4-(ethoxycarbonyl)piperazin-1-yl)carbonylmethyl)carbonyl][(1,1-dimethylethoxycarbonyl) methyl]aminonaphthalene (147 mg, 0.30 mmol) in CH$_2$Cl$_2$ (2.0 mL) was added TFA (3.0 mL). The resulting reaction mixture was stirred at ambient temperature for 3 hours. The reaction mixture was evaporated in vacuo to afford an oil, which was diluted with water (15 mL), adjusted to pH 4.5 by saturated NaHCO₃, then extracted by ethyl acetate (3×15 mL). The organic layer was evaporated in vacuo to afford 2-[((4-(ethoxycarbonyl)piperazin-1-yl)carbonylmethyl)carbonyl][carboxymethyl]aminonaphthalene (90 mg) as a solid; NMR (CDCl₃) 1.26 (t, 3), 3.24–3.30 (m, 2), 3.35–3.42 (m, 6), 3.57 (m, 2), 4.14 (q, 2), 4.52 (s, 2), 7.48 (d, 1), 7.58 (m, 2), 7.84–7.94 (m, 4) ppm.

C. In a similar manner, the following compound was made:

2-[((4-(ethoxycarbonyl)piperazin-1-yl)carbonylmethyl)carbonyl][carboxymethyl]amino-4-methoxynaphthalene; NMR (CDCl₃) 1.24 (t, 3), 3.32–3.60 (m, 8), 4.02 (s, 3), 4.13 (q, 2), 4.48 (s, 2), 6.82 (s, 1), 7.48 (s, 1), 7.57 (m, 2), 7.79 (d, 1), 8.26 (d, 1) ppm.

EXAMPLE 14

Compounds of Formula (Iv) and Formula (Iw)

A. A solution of 4-ethoxycarbonyl-1-(1-amino-3-(methoxycarbonyl)propyl)carbonylpiperazine (0.97 g, 3.23 mmol), 2-carboxy-4-chloroquinoline (0.67 g, 3.23 mmol), EDCI (0.68 g, 3.55 mmol) and HOBT (0.48 g, 3.55 mmol) was combined in 30 mL of THF. The reaction mixture was stirred overnight at ambient temperature. The reaction was diluted with ethyl acetate and washed with water. The organic layer was concentrated to give a dark oil (0.87 g) that was purified by flash chromatography through silica gel with 2:1 ethyl acetate-hexanes to provide 2-[1-(4-(ethoxycarbonyl)piperazin-1-yl)carbonyl-3-(methoxycarbonyl)propyl]aminocarbonyl-4-chloroquinoline (0.46 g). A solution of 2-[1-(4-(ethoxycarbonyl)piperazin-1-yl)carbonyl-3-(methoxycarbonyl)propyl]aminocarbonyl-4-chloroquinoline (0.15 g, 0.313 mmol) was dissolved in 5 mL THF and LiOH (0.25 M, 1.9 mL, 0.47 mmol) was added. The reaction mixture was stirred for 2 hours. The reaction mixture was concentrated to an oil, acidified with 10% HCl, extracted into ethyl acetate, and concentrated to provide pure 2-[1-(4-(ethoxycarbonyl)piperazin-1-yl)carbonyl-3-carboxypropyl]aminocarbonyl-4-chloroquinoline, (167 mg); NMR 1.20 (t, 3), 1.90 (m, 1), 2.05 (m, 1), 2.35 (m, 2), 3.35–3.60 (m, 8), 3.65 (m, 2), 4.05 (q, 2), 5.07 (m, 1), 7.95 (m, 1), 8.02 (m, 1), 8.23 (s, 1), 8.30 (m, 1), 8.98 (m, 1) ppm.

B. To a solution of 2-[1-(4-(ethoxycarbonyl)piperazin-1-yl)carbonyl-3-(methoxycarbonyl)propyl]aminocarbonyl-4-chloroquinoline (150 mg, 0.315 mmol) in DMSO (3.0 mL) was added (R)-3-hydroxypiperidine (68 mg, 0.5 mmol) and DIEA (65 mg, 0.5 mL). The mixture was heated at 110° C. for 18 hours. The crude reaction mixture was treated with lithium hydroxide (3.0 mL 0.25 M) for 4 hours. The reaction was purified by preparative HPLC to afford 2-[1-(4-(ethoxycarbonyl)piperazin-1-yl)carbonyl-3-carboxypropyl]aminocarbonyl-4-(3-hydroxypyrrolidin-1-yl)quinoline (41.0 mg); NMR (DMSO-d₆) 1.2 (t, 3), 2.00–2.20 (m, 4), 2.45 (m, 2), 3.30–3.75 (m, 8), 4.05 (q, 2), 4.60 (s, 1), 5.11 (m, 1), 7.39 (s, 1), 7.65 (m, 1), 7.95 (m, 1), 8.28 (m, 1), 8.58 (br s, 1), 9.75 (m, 1) ppm.

C. In a similar manner, the following compounds were made from the appropriate amine:

2-[1-(4-(ethoxycarbonyl)piperazin-1-yl)carbonyl-3-carboxypropyl]aminocarbonyl-4-(morpholin-4-yl)quinoline; NMR (CDCl₃) 1.23 (t, 3), 2.01 (m, 1), 2.20 (m, 1), 2.50–2.63 (m, 2), 3.40–3.80 (m, 8), 3.98 (m, 4), 4.15 (m, 2), 5.25 (m, 1), 7.55 (m, 1), 7.70 (s, 1), 7.75 (dd, 1), 8.00 (d, 1), 8.20 (d, 1), 9.21 (d, 1) ppm;

2-[1-(4-(ethoxycarbonyl)piperazin-1-yl)carbonyl-3-carboxypropyl]aminocarbonyl-4-(3-carboxypiperidin-1-yl)quinoline; NMR (DMSO-d₆) 1.22 (t, 3), 1.65 (m, 1), 1.75–1.98 (m, 3), 2.06 (m, 2), 2.35 (m, 2), 2.82 (m, 1), 2.96 (m, 1), 3.13 (m, 1), 3.38–3.77 (m, 10), 4.06 (q, 2), 5.06 (m, 1), 7.57 (s, 1), 7.64 (t, 1), 7.79 (t, 1), 8.11 (m, 2), 8.94 (d, 1) ppm;

2-[1-(4-(ethoxycarbonyl)piperazin-1-yl)carbonyl-3-carboxypropyl]aminocarbonyl-4-((dimethylamino)carbonylmethyl)(methyl)aminoquinoline; NMR (DMSO-d₆) 1.23 (t, 3), 1.95–2.15 (m, 2), 2.41 (dd, 1), 2.98 (s, 3), 3.05 (s, 3), 3.25–3.75 (m, 11), 4.05 (q, 2), 4.85 (m, 2), 5.05 (m, 1), 7.40 (s, 1), 7.65 (dd, 1), 7.99 (dd, 1), 8.25–8.35 (m, 2), 9.75 (d, 1) ppm;

2-[1-(4-(ethoxycarbonyl)piperazin-1-yl)carbonyl-3-carboxypropyl]aminocarbonyl-4-(carboxymethyl)(methyl)aminoquinoline; NMR (DMSO-d₆) 1.20 (t, 3), 1.85–2.05 (m, 2), 2.35 (m, 2), 3.20–3.63 (m, 11), 4.01 (q, 2), 4.65 (s, 2), 5.02 (m, 1), 7.55 (s, 1), 7.63 (dd, 1), 7.95 (dd, 1), 8.25 (dd, 1), 9.65 (d, 1) ppm;

2-[1-(4-(ethoxycarbonyl)piperazin-1-yl)carbonyl-3-carboxypropyl]aminocarbonyl-4-(4-methylpiperazin-1-yl)quinoline; NMR (DMSO-d₆) 1.18 (t, 3), 1.85 (m, 1), 2.05 (m, 1), 2.39 (dd, 2), 2.91 (s, 3), 3.25–3.70 (m, 16), 4.05 (m, 4), 5.15 (m, 1), 7.65 (m, 2), 7.95 (dd, 1), 8.15 (d, 1), 8.22 (d, 1), 9.35 (d, 1) ppm; 2-[1-(4-(ethoxycarbonyl)piperazin-1-yl)carbonyl-3-carboxypropyl]aminocarbonyl-4-(4-hydroxypiperidin-1-yl)quinoline; NMR (DMSO-d₆) 1.23 (t, 3), 1.78 (m, 2), 1.95–2.20 (m, 4), 2.42 (dd, 2), 3.34–3.82 (m, 10), 4.00 (m, 1), 4.05–4.20 (m, 3), 5.15 (m, 1), 7.70 (dd, 1), 7.78 (s, 1), 7.97 (dd, 1), 8.15 (d, 1), 8.35 (d, 1), 9.75 (d, 1) ppm;

2-[1-(4-(ethoxycarbonyl)piperazin-1-yl)carbonyl-3-carboxypropyl]aminocarbonyl-4-(4-(carboxymethyl)piperazin-1-yl)quinoline; NMR (DMSO-d₆) 1.20 (t, 3), 1.80–2.00 (m, 2), 2.35 (m, 2), 3.23–3.45 (m, 6), 3.63 (m, 6), 3.80–4.00 (m, 4), 4.02 (q, 2), 4.25 (s, 2), 5.05 (m, 1), 7.70 (m, 2), 7.93 (dd, 1), 8.10 (dd, 1), 8.24 (dd, 1), 9.39 (d, 1) ppm;

2-[1-(4-(ethoxycarbonyl)piperazin-1-yl)carbonyl-3-carboxypropyl]aminocarbonyl-4-(3-(carboxymethyl)piperazin-1-yl)quinoline; NMR (DMSO-d₆) 1.20 (t, 3), 1.82–2.10 (m, 2), 2.35 (m, 2), 2.75 (m, 2), 3.25–3.65 (m, 12), 3.90–4.10 (m, 6), 5.05 (m, 1), 7.63 (m, 2), 7.92 (dd, 1), 8.15–8.22 (m, 2), 9.38 (d, 1) ppm;

2-[1-(4-(ethoxycarbonyl)piperazin-1-yl)carbonyl-3-carboxypropyl]aminocarbonyl-4-(4-aminocarbonylpiperidin-1-yl)quinoline; NMR (DMSO-d₆) 1.23 (t, 3), 1.90–2.20 (m, 6), 2.43 (dd, 2), 2.65 (m, 1), 3.35–3.75 (m, 10), 4.05 (q, 2), 4.35 (m, 2), 5.18 (m, 1), 7.70 (dd, 1), 7.75 (s, 1), 7.98 (dd, 1), 8.18 (d, 1), 8.35 (d, 1), 8.78 (d, 1) ppm;

2-[1-(4-(ethoxycarbonyl)piperazin-1-yl)carbonyl-3-(methoxycarbonyl)propyl]aminocarbonyl-4-(3-ethoxycarbonylpiperidin-1-yl)quinoline; NMR (CDCl₃) 1.26 (m, 6), 1.74–2.08 (m, 4), 2.22 (m, 2), 2.57 (m, 2), 2.82–2.98 (m, 2), 3.16 (m, 1), 3.40–3.82 (m, 13), 4.18 (q, 2), 5.27 (m, 1), 7.55 (t, 1), 7.70 (s, 1), 7.76 (t, 1), 8.03 (d, 1), 8.11 (d, 1), 9.01 (d, 1) ppm;

2-[1-(4-(ethoxycarbonyl)piperazin-1-yl)carbonyl-3-carboxypropyl]aminocarbonyl-4-(3-ethoxycarbonylpiperidin-1-yl)quinoline; NMR (CDCl₃) 1.27 (m, 6), 1.78–2.08 (m, 4), 2.22 (m, 2), 2.57 (m, 2), 2.88 (m, 1), 3.07 (m, 1), 3.28 (m, 1), 3.40–3.82 (m, 10), 4.18 (q, 2), 5.29 (m, 1), 7.57 (t, 1), 7.73 (s, 1), 7.76 (t, 1), 8.05 (d, 1), 8.17 (d, 1), 9.24 (d, 1) ppm;

2-[1-(4-(ethoxycarbonyl)piperazin-1-yl)carbonyl-3-carboxypropyl]aminocarbonyl-4-(carboxymethyl)aminoquinoline; NMR (CD₃OD) 1.25 (t, 3), 2.0 (m, 1), 2.15 (m, 1), 2.45 (m, 2), 3.40–3.80 (m, 8), 3.90 (s, 2), 4.10 (q, 2), 5.20 (m, 1), 7.05 (s, 1), 7.50 (m, 1), 7.65 (m, 1), 7.85 (m, 1), 8.10 (m, 1) ppm;

2-[1-(4-(ethoxycarbonyl)piperazin-1-yl)carbonyl-3-carboxypropyl]aminocarbonyl-4-(methyl)(2-(dimethylamino)ethyl)aminoquinoline; NMR (DMSO-$d_6$) 1.21 (t, 3), 1.95–2.16 (m, 2), 2.45 (dd, 2), 2.95 (s, 3), 3.34–3.80 (m, 13), 4.09 (q, 2), 4.20 (m, 1), 5.15 (m, 1), 7.60 (s, 1), 7.75 (dd, 1), 8.02 (dd, 1), 8.30–8.40 (m, 2), 9.65 (d, 1) ppm; and 2-[1-(4-(ethoxycarbonyl)piperazin-1-yl)carbonyl-3-carboxypropyl]aminocarbonyl-4-(methyl)(2-hydroxyethyl)aminoquinoline. NMR (DMSO-$d_6$) 1.21 (t, 3), 1.95–2.15 (m, 2), 2.55 (s, 3), 3.30–3.75 (m, 11), 3.90 (m, 2), 4.10 (m, 3), 5.15 (m, 1), 7.61 (m, 2), 7.98 (dd, 1), 8.30 (d, 1), 8.55 (d, 1), 9.75 (d, 1) ppm.

D. To a solution of 4-ethoxycarbonyl-1-(1-amino-3-(1,1-dimethylethoxycarbonyl)propyl)carbonylpiperazine (100 mg, 0.173 mmol) in 4 mL of $CH_3CN$ was added methyl acrylate (20 μL, 0.217 mmol), palladium acetate (5 mg, 0.0173 mmol), palladium triphenylphosphine (10 mg, 0.035), and DIEA (30 μL, 0.017 mmol). The reaction was heated at 85° C. for 25 hours. Aqueous work-up afforded a crude product, which was dissolved in methylene chloride (5.0 mL). Trifluoroacetic acid (5.0 mL) was added to the solution. After 1 hour, the reaction mixture was concentrated in vacuo. The residue was dissolved in lithium hydroxide (5 mL, 0.25 M). After 6 hours, the desired product was purified by preparative HPLC to afford 2-[1-(4-(ethoxycarbonyl)piperazin-1-yl)carbonyl-3-carboxypropyl]aminocarbonyl-4-(2-carboxyethenyl)quinoline (34 mg); NMR (DMSO-$d_6$) 1.15 (t, 3), 1.80 (m, 1), 2.05 (m, 2), 3.15–3.63 (m, 8), 4.02 (q, 2), 5.05 (m, 1), 6.80 (d, 2), 7.75 (t, 1), 7.90 (t, 2), 8.20 (d, 1), 8.30–8.38 (m, 3), 8.99 (d, 1) ppm.

E. In a similar manner, other compounds of formula (Iv) and formula (Iw) are prepared.

EXAMPLE 15

Compounds of Formula (Ix) and Formula (Iy)

A. To a mixture of 2,4-dicarboxyquinoline (1.085 g, 5 mmol) in methanol (40 mL) was added chlorotrimethylsilane (TMSCl) (1.41 mL), and the reaction mixture was stirred overnight. The reaction mixture turned into a clear solution. The solvents were evaporated to yield a crude product, 2-carboxy-4-methoxycarbonylquinoline. To a solution of 2-carboxy-4-methoxycarbonylquinoline (151 mg, 0.65 mmol) in THF (10 mL) was added 4-ethoxycarbonyl-1-(1-amino-3-(1,1-dimethylethoxycarbonyl)propyl)carbonylpiperazine (181 mg, 1.05 eq.), EDCI (161 mg, 1.2 eq. ), and HOBt (75 mg, 1.1 eq.), and the resulting reaction mixture was stirred overnight. The reaction mixture was evaporated in vacuo to afford a crude product, which was dissolved in ethyl acetate, washed with saturated $NaHCO_3$, 1M $NaHSO_4$ and brine. The organic layer was evaporated. Flash column chromatography with 1%–3% MeOH in $CH_2Cl_2$ afforded 2-[1-(4-(ethoxycarbonyl)piperazin-1-yl)carbonyl-3-(1,1-dimethylethoxycarbonyl)propyl]aminocarbonyl-4-(methoxycarbonyl)quinoline (146 mg) which was treated with trifluoroacetic acid (TFA) and $CH_2Cl_2$ (TFA/$CH_2Cl_2$, 1:1, 1.5 mL) and the resulting reaction mixture was stirred at ambient temperature for 1 hour. Evaporation of the solvents gave 2-[1-(4-(ethoxycarbonyl)piperazin-1-yl)carbonyl-3-carboxypropyl]aminocarbonyl-4-(methoxycarbonyl)quinoline (74 mg). To this was added a mixture of THF:$H_2O$ (2:1, 2 mL) and LiOH (4 eq.). The resulting mixture was stirred at ambient temperature for 1.5 hours. The pH value was adjusted to between pH 3 and pH 4 with 1N HCl solution. Extraction of the organic layers with ethyl acetate was followed by evaporation of the solvents to yield 2-[1-(4-(ethoxycarbonyl)piperazin-1-yl)carbonyl-3-carboxypropyl]aminocarbonyl-4-carboxyquinoline (39 mg); NMR ($CD_3OD$) 1.25 (t, 3), 1.99 (m, 1), 2.2 (m, 1), 2.5 (m, 2), 3.4–3.9 (m, 8), 4.16 (q, 2), 5.25 (m, 1), 7.75 (m, 1), 7.86 (m, 1), 8.25 (m, 3) ppm.

B. Alternatively, 2-[1-(4-(ethoxycarbonyl)piperazin-1-yl)carbonyl-3-(1,1-dimethylethoxycarbonyl)propyl]aminocarbonyl-4-(methoxycarbonyl)quinoline (200 mg, 0.359 mmol) was treated with LiOH (2 eq.) in a solution of THF:$H_2O$ (3:1, 8 mL). The reaction mixturre was stirred at ambient temperature for 5 hours. The pH value was adjusted to between pH 3 and pH 4 with 1N HCl solution. Evaporation of the solvents, extraction with ethyl acetate, washing with $H_2O$ and brine, followed by evaporation and flash column chromatography with 100% ethyl acetate, 1–5% MeOH in ethyl acetate gave 2-[1-(4-(ethoxycarbonyl)piperazin-1-yl)carbonyl-3-(1,1-dimethylethoxycarbonyl)propyl]aminocarbonyl-4-carboxyquinoline (106 mg). To a solution of 2-[1-(4-(ethoxycarbonyl)piperazin-1-yl)carbonyl-3-(1,1-dimethylethoxycarbonyl)propyl]aminocarbonyl-4-carboxyquinoline (500 mg (two batches combined), 0.922 mmol) in THF (10 mL) was added 1-methyl 5-t-butyl ester glutamic acid (300 mg, 1.5 eq), EDCI (216 mg, 1.2eq.), HOBt (140 mg, 1.1 eq.), and the resulting mixture was stirred overnight. The reaction mixture was evaporated in vacuo to afford a crude product, which was dissolved in ethyl acetate, washed with saturated $NaHCO_3$, 1M $NaHSO_4$ and brine. The organic layer was evaporated. Flash column chromatography with 1%–3% MeOH in $CH_2Cl_2$ afforded 2-[1-(4-(ethoxycarbonyl)piperazin-1-yl)carbonyl-3-(1,1-dimethylethoxycarbonyl)propyl]aminocarbonyl-4-[(1-(methoxycarbonyl)-3-(1,1-dimethylethoxycarbonyl)propyl)aminocarbonyl]quinoline (387 mg); NMR ($CDCl_3$) 1.28 (t, 3), 1.40 (s, 9), 1.47 (s, 9), 1.83 (m, 1), 2.16 (m, 2), 2.35–2.50 (m, 5), 3.5–3.76 (m, 8), 3.8 (s, 3), 4.18 (q, 2), 4.85 (m, 1), 5.35 (m, 1), 7.15 (d, 1), 7.65 (m, 1), 7.80 (m, 1), 8.20 (d, 1), 8.30 (d, 1), 8.35 (s, 1), 8.70 (d, 1) ppm.

C. 2-[1-(4-(Ethoxycarbonyl)piperazin-1-yl)carbonyl-3-(1,1-dimethylethoxycarbonyl)propyl]aminocarbonyl-4-[(1-(methoxycarbonyl)-3-(1,1-dimethylethoxycarbonyl)propyl)aminocarbonyl]quinoline (170 mg, 0.229 mmol) was treated with LiOH (2.0 eq.) in a solution of THF:$H_2O$ (3:1, 12 mL). The reaction mixture was stirred at ambient temperature for 5 hours. The pH value of the reaction mixture was adjusted to between pH 3 and pH4 with 1N HCl solution. The reaction mixture was evaporated in vacuo to afford a crude product, which was dissolved in ethyl acetate, washed with $H_2O$ and brine. The solvent was evaporated to give 2-[1-(4-(ethoxycarbonyl)piperazin-1-yl)carbonyl-3-(1,1-dimethylethoxycarbonyl)propyl]aminocarbonyl-4-[(1-carboxy-3-(1,1-dimethylethoxycarbonyl)propyl)aminocarbonyl]quinoline (150 mg); NMR ($CD_3OD$) 1.30 (t, 3), 1.40 (s, 9), 1.50 (s, 9), 1.90 (m, 1), 2.15 (m, 2), 2.30–2.50 (m, 5), 3.45–3.90 (m, 8), 4.18 (q, 2), 4.75 (m, 1), 5.25 (m, 1), 7.75 (m, 1), 7.90 (m, 1), 8.25 (m, 3) ppm.

D. Alternatively, 2-[1-(4-(ethoxycarbonyl)piperazin-1-yl)carbonyl-3-(1,1-dimethylethoxycarbonyl)propyl]aminocarbonyl-4-[(1-(methoxycarbonyl)-3-(1,1-dimethylethoxycarbonyl)propyl)aminocarbonyl]quinoline (41 mg, 0.055 mmol) was treated with trifluoroacetic acid:methylene chloride (1:1, 0.6 mL) at ambient temperature for 2 hours.

Evaporation of the reaction mixture, followed by dilution with methylene chloride, and repeated evaporation of the solvent gave 2-[1-(4-(ethoxycarbonyl)piperazin-1-yl)carbonyl-3-carboxypropyl]aminocarbonyl-4-[(1-(methoxycarbonyl)-3-carboxypropyl)aminocarbonyl]quinoline (40 mg) as a trifluoroacetic acid salt; NMR (CD$_3$OD) 1.25 (t, 3), 1.95 (m, 1), 2.18 (m, 2), 2.40 (m, 1), 2.45–2.55 (m, 4), 3.45–3.92 (m, 11), 4.16 (q, 2), 4.80 (m, 1), 5.25 (m, 1), 7.72 (t, 1), 7.86 (t, 1), 8.21–8.26 (m, 3) ppm.

E. Alternatively, 2-[1-(4-(ethoxycarbonyl)piperazin-1-yl)carbonyl-3-(1,1-dimethylethoxycarbonyl)propyl]aminocarbonyl-4-[(1-carboxy-3-(1,1-dimethylethoxycarbonyl)propyl)aminocarbonyl]quinoline (136 mg, 0.187 mmol) was treated with trifluoroacetic acid:methylene chloride (1:1, 1.2 mL) at ambient temperature for 1 hour. The solvents were evaporate and resulting residue diluted with methylene chloride, followed by evaporation of the solvent gave 2-[1-(4-(ethoxycarbonyl)piperazin-1-yl)carbonyl-3-carboxypropyl]aminocarbonyl-4-[(1,3-dicarboxypropyl)aminocarbonyl]quinoline (112 mg); NMR (CD$_3$OD) 1.20 (m, 3), 1.90 (m, 1), 2.10 (m, 2), 2.30–2.50 (m, 5), 3.40–3.80 (m, 8), 4.10 (m, 2), 4.70 (m, 1), 5.18 (m, 1), 7.60 (m, 1), 7.80 (m, 1), 8.20 (m, 3) ppm.

F. In a similar manner as described above, the following compounds of the invention were made:

2-[1-(4-(ethoxycarbonyl)piperazin-1-yl)carbonyl-3-(1,1-dimethylethoxycarbonyl)propyl]aminocarbonyl-4-(methoxycarbonylmethyl)aminocarbonylquinoline; NMR (CDCl$_3$) 1.30 (t, 3), 1.50 (s, 9), 1.85 (m, 1), 2.20 (m, 1), 2.45 (m, 2), 3.55–3.80 (m, 8), 3.85 (s, 3), 4.20 (q, 2), 4.38 (d, 2), 5.35 (m, 1), 7.20 (d, 1), 7.70 (m, 1), 7.85 (m, 1), 8.20 (d, 1), 8.35 (d, 1), 8.38 (s, 1), 8.65 (m, 1) ppm;

2-[1-(4-(ethoxycarbonyl)piperazin-1-yl)carbonyl-3-(1,1-dimethylethoxycarbonyl)propyl]aminocarbonyl-4-(carboxymethyl)aminocarbonylquinoline; NMR (CD$_3$OD) 1.30 (t, 3), 1.50 (s, 9), 1.90 (m, 1), 2.20 (m, 1), 2.50 (m, 2), 3.45–3.92 (m, 8), 4.18 (q, 2), 4.25 (s, 2), 5.25 (m, 1), 7.75 (m, 1), 7.90 (m, 1), 8.25–8.32 (m, 3) ppm; and 2-[1-(4-(ethoxycarbonyl)piperazin-1-yl)carbonyl-3-carboxypropyl]aminocarbonyl-4-(carboxymethyl)aminocarbonylquinoline; NMR (CD$_3$OD) 1.30 (t, 3), 1.95 (m, 1), 2.20 (m, 1), 2.50 (m, 2), 3.45–3.90 (m, 8), 4.18 (q, 2), 4.22 (s, 2), 5.25 (m, 1), 7.75 (m, 1), 7.85 (m, 1), 8.25 (m, 3) ppm.

EXAMPLE 16

Compounds of Formula (Iz)

A. To a solution of 2-carboxy-7-chloro-4-mercaptoquinoline HCl salt (75 mg, 0.31 mmol) in DMF (3 mL) was added MeI (0.0425 mL, 2.5 eq.) and cesium carbonate (340 mg, 3.5 eq.). The resulting reaction mixture was stirred at 70° C. overnight. The reaction mixture was diluted with ethyl acetate and washed with water, brine, and dried over sodium sulfate. The solvent was evaporated. Flash column chromatograpgy with 1%–2% MeOH in methylene chloride afforded 2-(methoxycarbonyl)-7-chloro-4-methylthioquinoline (40 mg). To 2-(methoxycarbonyl)-7-chloro-4-methylthioquinoline (40 mg) was added THF:H$_2$O (2:1, 2 mL) and LiOH (10 mg, 1.5 eq.). The reaction mixture was stirred for 2 hours. The pH was adjusted to pH 4.5 with 1N HCl. Extraction with ethyl acetate, washing with brine, drying over sodium sulfate and evaporation gave 2-carboxy-7-chloro-4-methylthioquinoline (29 mg). To a solution of 2-carboxy-7-chloro-4-methylthioquinoline (29 mg) in THF (6 mL) and DMF (1 mL) was added 4-ethoxycarbonyl-1-(1-amino-3-(1,1-dimethylethoxycarbonyl)propyl)carbonylpiperazine (46 mg, 1.1 eq.), EDCI (28 mg, 1.2 eq.), and HOBt (18 mg, 1.1 eq.). The resulting reaction mixture was stirred at ambient temperature overnight. The reaction mixture was evaporated in vacuo to afford a crude product, which was dissolved in ethyl acetate, washed with saturated NaHCO$_3$, 1M NaHSO$_4$ and brine. The organic layer was evaporated. Flash column chromatography with 1%–3% MeOH in CH$_2$Cl$_2$ afforded the product, 2-[1-(4-(ethoxycarbonyl)piperazin-1-yl)carbonyl-3-(1,1-dimethylethoxycarbonyl)propyl]aminocarbonyl-7-chloro-4-(methylthio)quinoline (36 mg). The product (32 mg) was treated with TFA:CH$_2$Cl$_2$ (1:1, 1 mL) at ambient temperature for 2 hours. The solvents were then evaporated to afford the desired product, 2-[1-(4-(ethoxycarbonyl)piperazin-1-yl)carbonyl-3-carboxypropyl]aminocarbonyl-7-chloro-4-(methylthio)quinoline; NMR (CDCl$_3$) 1.35 (t, 3), 2.10 (m, 1), 2.25 (m, 1), 2.55 (m, 2), 2.7 (s, 3), 3.4–3.9 (m, 8), 4.2 (q, 2), 5.3 (m, 1), 7.55 (d, 1), 7.9 (s, 1), 8.02 (d, 1), 8.15 (s, 1) ppm.

B. In a similar manner, the following compound was made:

2-[1-(4-(ethoxycarbonyl)piperazin-1-yl)carbonyl-3-carboxypropyl]aminocarbonyl-5,7-dichloro-4-(methylthio)quinoline; NMR (CDCl$_3$) 1.30 (t, 3), 2.0 (m, 1), 2.20 (m, 1), 2.55 (m, 2), 2.60 (s, 3), 3.40–3.80 (m, 8), 4.15 (q, 2), 5.30 (m, 1), 7.60 (s, 1), 7.90 (s, 1), 8.05 (s, 1), 9.05 (m, 1) ppm.

EXAMPLE 17

Receptor Binding Studies

The ability of the compounds of the invention to bind to the platelet adenosine diphosphate ("ADP") receptor was tested using human washed platelets and rat washed platelets by displacement assays.

Methods:

One day old platelet concentrates were purchased from a local blood bank. The platelet concentrates were spun at 680 g for 10 minutes and the resulting pellets were resuspended in modified Tyrode's buffer (135 mM NaCl, 3.6 mL KCl, 1.8 mM MgCl$_2$, 9 mM HEPES, 0.18 mg/mL BSA, 4.5 mM glucose, pH 6.6) supplemented by 2% acid citrate dextrose (ACD). This platelet suspension was spun at 680 g for 10 minutes and the final pellet was resuspended in platelet binding buffer (20 mM Tris buffer, pH 7.5, 140 mM NaCl, 4 mM KCl, 2 mM MgCl$_2$, 1 mM EDTA, 0.1% BSA, 5 mM glucose, 2 μg/mL aprotinin, and 2 μg/mL leupeptin).

Platelets were isolated from rat whole blood as described in Example 13 with the final pellet resuspended in platelet binding buffer. The platelet number for binding to rat platelets (5×10$^6$ per well) was normalized to the number of platelets for binding to human platelet (4–6×10$^6$ per well).

Binding reactions were initiated by mixing [$^{33}$P]-2-methylthio-ADP (0.3–0.5 nM), test compounds and washed platelets in 96-well plates. The reactions were kept at ambient temperature for 60 minutes under constant shaking and were stopped by fast-filtration onto 96-well, glass-fiber (GFC) filter plates followed by washing 5 times with ice-cold 50 mM Tris buffer (pH 7.5). The amount of [$^{33}$P]-2-methylthio-ADP bound to the filters was measured by scintillation counting. Non-specific binding was determined in the presence of 10 μM unlabelled 2-methylthio-ADP. Competition studies were done using a single concentration of [$^{33}$P]-2-methylthio-ADP (0.3 nM) and varying concentrations of test compounds.

Results:

The compounds of the invention, when tested in this assay, demonstrated their ability to inhibitor the binding of [$^{33}$P]-2-methylthio-ADP binding to the human platelet ADP receptor and the rat platelet ADP receptor.

EXAMPLE 18

ADP-Induced Aggregation In Vitro Studies

The compounds of the invention were evaluated as functional antagonists of the platelet ADP receptor using both human and rat washed platelets.

Methods:

Human venous blood was collected from healthy, drug-free volunteers into 1/6 volume 3.2% acid/citrate/dextrose. Whole blood from Nembutal-anesthetized rats was collected from the abdominal aorta into 1/10 volume 3.8% acid/citrate/dextrose. Platelet rich plasma (PRP) was prepared by centrifugation at 800 g for 3–4 successive 1.5-minute intervals, with removal of the PRP after each spin. Alternatively, some PRP preps were performed by centrifugation at 100 g for 15 minutes. Washed platelets were prepared from the PRP by centrifugation at 680 g for 15 minutes and the platelet pellet resuspended in Tyrode's buffer (137 mM NaCl, 2.7 mM KCl, 12 mM NaHCO$_2$, 0.42 mM NaH$_2$PO, 1 mM MgCl$_2$, 2 mM CaCl$_2$, 0.35% BSA, 5.5 mM glucose, 5 mM HEPES, pH 7.35 supplemented with f.c. 10% ACD solution. The platelets were washed a total of two times under these acidic conditions and the platelet pellet collected by centrifugation at 680 g for 15 minutes at ambient temperature. The final platelet pellet was resuspended at 2×10$^8$ platelets/mL in Tyrode's buffer containing 0.02 units/mL apyrase. This platelet suspension was kept at 37° C. for at least 30 minutes prior to studies.

Inhibition of ADP-induced aggregation was measured at 37° C. in a 4-channel aggregometer. The platelet suspension (0.5 mL) was stirred at 1200 rpm. Human fibrinogen (400 µg) was added at time zero for 1 minute followed by 2 minute pre-incubation in the presence or absence of antagonist. Platelet aggregation was induced with the addition of 10 or 31.6 µM ADP (submaximal response) in human platelets or 3 or 10 µM ADP (submaximal response) in rat and monitored for 5 minutes. ADP-induced aggregation was quantified by measuring increase in light transmission (% T) compared to Tyrode's buffer control. IC$_{50}$ values were determined using the 4-parameter equation.

Results:

The compounds of the invention, when tested in this assay, demonstrated the ability to inhibit ADP-induced platelet aggregation in vitro in human and rat washed platelets.

EXAMPLE 19

Efficacy Assay

Inhibition of thrombus formation by compounds of the invention was evaluated in the rat arterio-venous (A-V) shunt model.

Methods:

Male Sprague-Dawley rats (350–400 g, 10–18 per group) were anesthetized with Nembutal (65 mg/kg, i.p). The left carotid artery and the right jugular vein were each cannulated with a piece of PE-50 tubing (8 cm, siliconized). Fifty minutes after anesthesia, the arterial and venous catheters were connected (A-V shunt) by a piece of shunt tubing (Tygon S-50-HL, 6 cm) that contained a silk thread (6–0 silk suture, 10 cm) coated with collagen (Horm, 100 µg/ml). Blood was allowed to flow through the A-V shunt for 10 minutes. The amount of thrombus deposited on the silk thread was measured as dry weight (24 hours at ambient temperature). A compound of the invention (1, 3 and 10 mg/kg) (as the appropriate salt form) or vehicle (15% DMSO in saline, 1 mL/kg) was injected via the jugular vein catheter 5 minutes before the A-V shunt. Blood samples (1 mL) were taken immediately before the dosing and at the end of the A-V shunt for measurements of ex vivo platelet aggregation and plasma levels of the compound of the invention.

Results:

When tested in this assay, compounds of the invention demonstrated the ability to dose-dependently inhibit platelet aggregation and thrombus formation in the rat A-V shunt model. Both the inhibition of platelet aggregation and thrombus formation were also parallel in relation to the changes in plasma drug concentrations. Thus, the inhibition of thrombus formation is correlated with the inhibition of platelet aggregation induced by the compound of the invention.

EXAMPLE 20

This example illustrates the preparation of representative pharmaceutical compositions for oral administration containing a compound of the invention, or a pharmaceutically acceptable salt thereof:

| A. Ingredients | % wt./wt. |
|---|---|
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
|---|---|
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
|---|---|
| Compound of the invention | 0.1 g |
| Propylene glycol | 20.0 g |
| Polyethylene glycol 400 | 20.0 g |

| -continued | |
|---|---|
| C. Ingredients | |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. Ingredients | % wt./wt. |
|---|---|
| Compound of the invention | 20.0% |
| Peanut Oil | 78.0% |
| Span 60 | 2.0% |

The above ingredients are melted, mixed and filled into soft elastic capsules.

| E. Ingredients | % wt./wt. |
|---|---|
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

EXAMPLE 21

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 22

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 23

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 24

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 25

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

All of the U.S. patents, U.S. patent application publications, U.S. patent applications, foreign patents, foreign patent applications and non-patent publications referred to in

The invention claimed is:
1. A compound of formula (I):

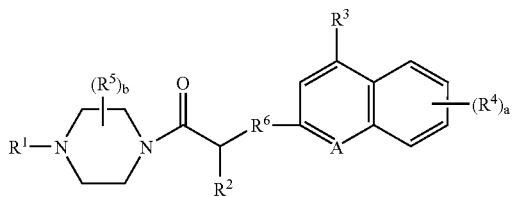

(I)

wherein:
a and b are independently 1 to 4;
A is =CH—;
$R^1$ is alkoxycarbonyl, aryloxycarbonyl, aralkoxycarbonyl, haloalkoxycarbonyl, or alkoxycarbonylaminocarbonyl;
$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, tetrahydrofuranonyl, or heterocyclylalkyl;
$R^3$ is hydrogen, alkyl, hydroxy, halo, carboxyalkenyl, alkoxy, alkoxycarbonyl, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono(alkoxycarbonylalkyl)aminocarbonyl, mono(carboxyalkyl)aminocarbonyl, mono(di(alkoxycarbonyl)alkyl)aminocarbonyl, mono((alkoxycarbonyl)(carboxy)alkyl)aminocarbonyl, mono(dicarboxyalkyl)aminocarbonyl, aminocarbonylalkoxy, dialkylaminocarbonylalkoxy, monoaralkylaminocarbonylalkoxy, mono(carboxyalkyl)aminocarbonylalkoxy, mono(alkoxycarbonylalkyl)aminocarbonylalkoxy, carboxycycloalkoxy, alkoxycarbonylcycloalkoxy, aminocarbonylcycloalkoxy, heterocyclyl, tetrahydrofuranonyloxy, or heterocyclylalkoxy;
each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, and heterocyclylalkoxy;
each $R^5$ is independently selected from the group consisting of hydrogen, alkyl, hydroxyalkyl, aralkyl, carboxy, alkoxycarbonyl, aralkoxycarbonyl, carboxyalkyl, and alkoxycarbonylalkyl;
$R^6$ is —N($R^7$)—C(O)— or —C(O)—N($R^7$)—;
$R^7$ is hydrogen, alkyl, carboxyalkyl, or alkoxycarbonylalkyl;
as a single stereoisomer, a mixture of individual stereoisomers, or a racemic mixture;
or a pharmaceutically acceptable salt thereof.

2. The compound of claim 1 wherein:
a is 1 or 2;
b is 1;
A is =CH—;
$R^1$ is alkoxycarbonyl;
$R^2$ is hydrogen, carboxyalkyl, or aralkoxycarbonylalkyl;
$R^3$ is hydrogen;
each $R^4$ is independently selected from the group consisting of hydrogen, alkyl, alkoxy, halo, haloalkyl, haloalkoxy, and hydroxy;
$R^5$ is hydrogen;
$R^6$ is —N($R^7$)—C(O)—; and
$R^7$ is hydrogen or alkyl.

3. The compound of claim 2 selected from the group consisting of the following:
2-[1-(4-(ethoxycarbonyl)piperazin-1-yl)carbonyl-3-(benzyloxycarbonyl)propyl]aminocarbonylnaphthalene;
2-[1-(4-(ethoxycarbonyl)piperazin-1-yl)carbonyl-3-carboxypropyl]aminocarbonylnaphthalene; and
2-[(4-(ethoxycarbonyl)piperazin-1-yl)carbonylmethyl] aminocarbonylnaphthalene.

4. The compound of claim 1 wherein:
a is 1;
b is 1;
A is =CH—;
$R^1$ is alkoxycarbonyl;
$R^2$ is hydrogen, aralkyl, carboxyalkyl, (carboxy)(hydroxy)alkyl, alkoxycarbonylalkyl, or tetrahydrofuranonyl;
$R^3$ is hydrogen, alkoxy, or carboxyalkoxy;
$R^4$ is hydrogen, hydroxy, carboxyalkoxy, or alkoxycarbonylalkoxy;
$R^5$ is hydrogen;
$R^6$ is —C(O)—N($R^7$)—; and
$R^7$ is hydrogen, alkyl or carboxyalkyl.

5. The compound of claim 4 selected from the group consisting of the following:
2-[((4-(ethoxycarbonyl)piperazin-1-yl)carbonylmethyl)carbonyl]aminonaphthalene;
2-[(1-(4-(ethoxycarbonyl)piperazin-1-yl)carbonyl-2-(ethoxycarbonyl)ethyl)carbonyl]aminonaphthalene;
2-[(1-(4-(ethoxycarbonyl)piperazin-1-yl)carbonyl-2-carboxyethyl)carbonyl]aminonaphthalene;
2-[(1-(4-(ethoxycarbonyl)piperazin-1-yl)carbonyl-2-(3-(methoxycarbonyl)phenyl)ethyl)carbonyl]-aminonaphthalene;
2-[(1-(4-(ethoxycarbonyl)piperazin-1-yl)carbonyl-2-(3-carboxyphenyl)ethyl)carbonyl]aminonaphthalene;

2-[(1-(4-(ethoxycarbonyl)piperazin-1-yl)carbonyl-2-(4-(methoxycarbonyl)phenyl)ethyl)carbonyl]aminonaphthalene;
2-[(1-(4-(ethoxycarbonyl)piperazin-1-yl)carbonyl-1-(tetrahydro-2-oxofuran-3-yl)methyl)carbonyl]aminonaphthalene;
2-[(1-(4-(ethoxycarbonyl)piperazin-1-yl)carbonyl-2-carboxy-4-hydroxybutyl)carbonyl]aminonaphthalene;
2-[(1-(4-(ethoxycarbonyl)piperazin-1-yl)carbonyl-2-(4-carboxyphenyl)ethyl)carbonyl]aminonaphthalene;
2-[((4-(ethoxycarbonyl)piperazin-1-yl)carbonylmethyl)carbonyl]amino-5-hydroxynaphthalene;
2-[((4-(ethoxycarbonyl)piperazin-1-yl)carbonylmethyl)carbonyl]amino-4-methoxynaphthalene;
2-[((4-(ethoxycarbonyl)piperazin-1-yl)carbonylmethyl)carbonyl]amino-5-(carboxymethoxy)naphthalene;
2-[((4-(ethoxycarbonyl)piperazin-1-yl)carbonylmethyl)carbonyl]amino-5-(3-(ethoxycarbonyl)propoxy)naphthalene;
2-[((4-(ethoxycarbonyl)piperazin-1-yl)carbonylmethyl)carbonyl]amino-5-(3-carboxypropoxy)naphthalene;
2-[((4-(ethoxycarbonyl)piperazin-1-yl)carbonylmethyl)carbonyl]amino-4-(carboxymethoxy)naphthalene;
2-[((4-(ethoxycarbonyl)piperazin-1-yl)carbonylmethyl)carbonyl][carboxymethyl]aminonaphthalene; and
2-[((4-(ethoxycarbonyl)piperazin-1-yl)carbonylmethyl)carbonyl][carboxymethyl]amino-4-methoxynaphthalene.

6. A pharmaceutical composition useful in treating a mammal having a disease-state characterized by thrombotic activity, which composition comprises a pharmaceutically acceptable excipient and a compound of formula (I):

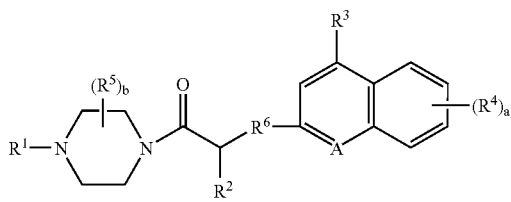

(I)

wherein:
a and b are independently 1 to 4;
A is =CH—;
$R^1$ is alkoxycarbonyl, aryloxycarbonyl, aralkoxycarbonyl, haloalkoxycarbonyl, aminocarbonyl, monoalkylaminocarbonyl, or alkoxycarbonylaminocarbonyl;
$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, tetrahydrofuranonyl, or heterocyclylalkyl;
$R^3$ is hydrogen, alkyl, hydroxy, halo, carboxyalkenyl, alkoxy, alkoxycarbonyl, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono(alkoxycarbonylalkyl)aminocarbonyl, mono(carboxyalkyl)aminocarbonyl, mono(di(alkoxycarbonyl)alkyl)aminocarbonyl, mono((alkoxycarbonyl)(carboxy)alkyl)aminocarbonyl, mono(dicarboxyalkyl)aminocarbonyl, aminocarbonylalkoxy, dialkylaminocarbonylalkoxy, monoaralkylaminocarbonylalkoxy, mono(carboxyalkyl)aminocarbonylalkoxy, mono(alkoxycarbonylalkyl)aminocarbonylalkoxy, carboxycycloalkoxy, alkoxycarbonylcycloalkoxy, aminocarbonylcycloalkoxy, heterocyclyl, tetrahydrofuranonyloxy, or heterocyclylalkoxy;
each $R^4$ is independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, or heterocyclylalkoxy;
each $R^5$ is independently selected from the group consisting of hydrogen, alkyl, hydroxyalkyl, aralkyl, carboxy, alkoxycarbonyl, aralkoxycarbonyl, carboxyalkyl, or alkoxycarbonylalkyl;
$R^6$ is —N($R^7$)— or —C(O)—N($R^7$)—;
$R^7$ is hydrogen, alkyl, carboxyalkyl, or alkoxycarbonylalkyl;
as a single stereoisomer, a mixture of individual stereoisomers, or a racemic mixture;
or a pharmaceutically acceptable salt thereof.

7. A method of treating a disease-state characterized by thrombotic activity, which method comprises administering to a mammal having a disease-state characterized by thrombotic activity a therapeutically effective amount of a compound of formula (I):

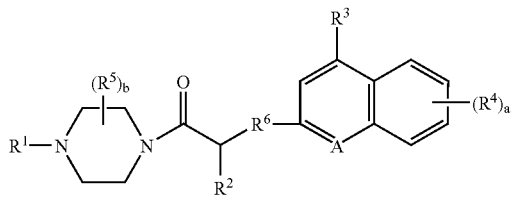

(I)

wherein:
a and b are independently 1 to 4;
A is =CH—;
$R^1$ is alkoxycarbonyl, aryloxycarbonyl, aralkoxycarbonyl, haloalkoxycarbonyl, aminocarbonyl, monoalkylaminocarbonyl, or alkoxycarbonylaminocarbonyl;
$R^2$ is hydrogen, alkyl, aryl, aralkyl, alkylsulfonylalkyl, aralkoxyalkyl, hydroxyalkyl, aminoalkyl, haloalkylsulfonylaminoalkyl, carboxyalkylthioalkyl, alkoxycarbonylalkylthioalkyl, carboxyalkyl, (carboxy)(hydroxy)alkyl, carboxyalkoxyalkyl, alkoxycarbonylalkyl, aralkoxycarbonylalkyl, carboxyalkoxycarbonylalkyl, alkoxycarbonylalkoxycarbonylalkyl, aminocarbonylalkyl, aralkoxycarbonylaminoalkyl, alkoxycarbonylalkylaminocarbonylalkyl, carboxyalkylaminocarbonylalkyl, (alkoxycarbonylalkyl)(alkyl)aminocarbonylalkyl, (carboxyalkyl)(alkyl)aminocarbonylalkyl, tetrahydrofuranonyl, or heterocyclylalkyl;

$R^3$ is hydrogen, alkyl, hydroxy, halo, carboxyalkenyl, alkoxy, alkoxycarbonyl, alkoxycarbonylalkoxy, di(alkoxycarbonyl)alkoxy, carboxyalkoxy, di(carboxy)alkoxy, (carboxy)(hydroxy)alkoxy, (dialkylamino)(carboxy)alkoxy, hydroxyalkoxy, cyanoalkoxy, haloalkoxy, haloalkenyloxy, carboxyalkenyloxy, alkoxycarbonylalkenyloxy, (cycloalkyl)(alkoxycarbonyl)alkoxy, (cycloalkyl)(carboxy)alkoxy, alkylthio, carboxy, (dialkylaminocarbonylalkyl)(alkyl)amino, (carboxyalkyl)(alkyl)amino, (hydroxyalkyl)(alkyl)amino, (dialkylaminoalkyl)(alkyl)amino, carboxyalkylamino, mono(alkoxycarbonylalkyl)aminocarbonyl, mono(carboxyalkyl)aminocarbonyl, mono(di(alkoxycarbonyl)alkyl)aminocarbonyl, mono((alkoxycarbonyl)(carboxy)alkyl)aminocarbonyl, mono(dicarboxyalkyl)aminocarbonyl, aminocarbonylalkoxy, dialkylaminocarbonylalkoxy, monoaralkylaminocarbonylalkoxy, mono(carboxyalkyl)aminocarbonylalkoxy, mono(alkoxycarbonylalkyl)aminocarbonylalkoxy, carboxycycloalkoxy, alkoxycarbonylcycloalkoxy, aminocarbonylcycloalkoxy, heterocyclyl, tetrahydrofuranonyloxy, or heterocyclylalkoxy;

each $R^4$ is-independently selected from the group consisting of hydrogen, alkyl, alkoxy, aralkoxy, halo, haloalkyl, haloalkoxy, hydroxy, cyano, alkylthio, carboxy, alkoxycarbonyl, aminocarbonyl, alkylcarbonyl, nitro, amino, monoalkylamino, dialkylamino, carboxyalkylamino, alkylcarbonylamino, di(alkylcarbonyl)amino, hydroxyalkyl, dialkylaminoalkyl, carboxyalkoxy, alkoxycarbonylalkoxy, dialkylaminoalkoxy, or heterocyclylalkoxy;

each $R^5$ is independently selected from the group consisting of hydrogen, alkyl, hydroxyalkyl, aralkyl, carboxy, alkoxycarbonyl, aralkoxycarbonyl, carboxyalkyl, or alkoxycarbonylalkyl;

$R^6$ is —N($R^7$)—C(O)— or —C(O)—N($R^7$)—;

$R^7$ is hydrogen, alkyl, carboxyalkyl, or alkoxycarbonylalkyl;

as a single stereoisomer, a mixture of individual stereoisomers, or a racemic mixture;

or a pharmaceutically acceptable salt thereof.

\* \* \* \* \*